United States Patent
Asher et al.

(10) Patent No.: US 11,602,364 B2
(45) Date of Patent: Mar. 14, 2023

(54) SURGICAL INSTRUMENT WITH REMOVABLE END EFFECTOR COMPONENTS

(71) Applicant: Ethicon LLC, Guaynabo, PR (US)

(72) Inventors: Ryan M. Asher, Cincinnati, OH (US); Gregory D. Bishop, Hamilton, OH (US); Brian D. Black, Loveland, OH (US); Chad P. Boudreaux, Cincinnati, OH (US); David J. Cagle, Cincinnati, OH (US); William E. Clem, Bozeman, MT (US); Joseph Dennis, Cincinnati, OH (US); Kristen G. Denzinger, Cincinnati, OH (US); Benjamin D. Dickerson, Cincinnati, OH (US); Kevin M. Fiebig, Cincinnati, OH (US); Ellen Burkart, Cincinnati, OH (US); Christina M. Hough, Cincinnati, OH (US); John V. Hunt, Cincinnati, OH (US); Cody R. Jackson, Cincinnati, OH (US); Cory G. Kimball, Hamilton, OH (US); Jeffrey D. Messerly, Cincinnati, OH (US); Gabriel I. Myers, Perryville, KY (US); Ion V. Nicolaescu, Carpentersville, IN (US); William A. Olson, Lebanon, OH (US); Candice Otrembiak, Loveland, OH (US); John K. Swain, St. Paul, MN (US); Gregory A. Trees, Loveland, OH (US); John A. Weed, III, Monroe, OH (US); William B. Weisenburgh, II, Maineville, OH (US); Eitan T. Wiener, Cincinnati, OH (US); Barry C. Worrell, Centerville, OH (US); David C. Yates, West Chester, OH (US); Monica L. Zeckel, Zionsville, IN (US)

(73) Assignee: Cilag GmbH International, Zug (CH)

( * ) Notice: Subject to any disclaimer, the term of this patent is extended or adjusted under 35 U.S.C. 154(b) by 1093 days.

(21) Appl. No.: 15/798,703

(22) Filed: Oct. 31, 2017

(65) Prior Publication Data

US 2018/0132887 A1 May 17, 2018

Related U.S. Application Data

(60) Provisional application No. 62/519,482, filed on Jun. 14, 2017, provisional application No. 62/508,720, (Continued)

(51) Int. Cl.
*A61B 17/32* (2006.01)
*A61B 17/28* (2006.01)
(Continued)

(52) U.S. Cl.
CPC ...... *A61B 17/2804* (2013.01); *A61B 18/1442* (2013.01); *A61B 18/1206* (2013.01);
(Continued)

(58) Field of Classification Search
CPC ............ A61B 17/2804; A61B 18/1206; A61B 18/1442; A61B 2017/00106;
(Continued)

(56) References Cited

U.S. PATENT DOCUMENTS 5,322,055 A 6/1994 Davison et al.
5,873,873 A 2/1999 Smith et al.
(Continued)

FOREIGN PATENT DOCUMENTS

CN 103027719 A 4/2013
CN 103379871 A 10/2013
(Continued)

OTHER PUBLICATIONS

U.S. Appl. No. 15/284,819.
(Continued)

*Primary Examiner* — Khadijeh A Vahdat
(74) *Attorney, Agent, or Firm* — Frost Brown Todd LLP

(57) ABSTRACT

A surgical instrument includes an ultrasonic waveguide extending through a body assembly. An ultrasonic blade
(Continued)

connects to the ultrasonic waveguide. A clamp arm assembly of the surgical instrument is able to move from an opened position for receiving a tissue toward a closed position for clamping the tissue. The clamp arm assembly includes a clamp body and a clamp pad facing the ultrasonic blade. A clamp arm actuator of the surgical instrument is able to move from a first position toward a second position to direct the clamp arm assembly from the opened position toward the closed position. A modular coupling of the surgical instrument connects to the clamp pad such that at least the clamp pad can be disconnected relative to the ultrasonic blade for replacement thereof.

20 Claims, 95 Drawing Sheets

Related U.S. Application Data filed on May 19, 2017, provisional application No. 62/422,698, filed on Nov. 16, 2016.

(51) Int. Cl.
  *A61B 18/14*   (2006.01)
  *A61B 18/00*   (2006.01)
  *A61B 90/00*   (2016.01)
  *A61B 17/00*   (2006.01)
  *A61B 18/12*   (2006.01)

(52) U.S. Cl.
  CPC .......... *A61B 2017/0046* (2013.01); *A61B 2017/00106* (2013.01); *A61B 2017/00424* (2013.01); *A61B 2017/00477* (2013.01); *A61B 2017/00876* (2013.01); *A61B 2017/2825* (2013.01); *A61B 2017/2845* (2013.01); *A61B 2017/320074* (2017.08); *A61B 2017/320082* (2017.08); *A61B 2017/320084* (2013.01); *A61B 2017/320088* (2013.01); *A61B 2017/320093* (2017.08); *A61B 2017/320094* (2017.08); *A61B 2017/320095* (2017.08); *A61B 2018/0063* (2013.01); *A61B 2018/0094* (2013.01); *A61B 2018/00642* (2013.01); *A61B 2018/00666* (2013.01); *A61B 2018/00672* (2013.01); *A61B 2018/00755* (2013.01); *A61B 2018/00875* (2013.01); *A61B 2018/00916* (2013.01); *A61B 2018/00958* (2013.01); *A61B 2018/00994* (2013.01); *A61B 2090/034* (2016.02); *A61B 2090/065* (2016.02); *A61B 2090/0811* (2016.02); *A61B 2090/0813* (2016.02)

(58) Field of Classification Search
  CPC .. A61B 2017/00424; A61B 2017/0046; A61B 2017/00477; A61B 2017/00526; A61B 2017/00876; A61B 2017/2825; A61B 2017/320074; A61B 2017/320082; A61B 2017/320084; A61B 2017/320088; A61B 2017/320093; A61B 2017/320094; A61B 2017/320095; A61B 2018/0063; A61B 2018/00642; A61B 2018/00666; A61B 2018/00672; A61B 2018/00755; A61B 2018/00875; A61B 2018/00916; A61B 2018/0094; A61B 2018/00958; A61B 2018/00994; A61B 2090/034; A61B 2090/065; A61B 2090/0811; A61B 2090/0813
  USPC ............. 606/51–52, 169, 205–207
  See application file for complete search history.

(56) References Cited

U.S. PATENT DOCUMENTS

| | | | |
|---|---|---|---|
| 5,935,144 | A | 8/1999 | Estabrook |
| 5,980,510 | A | 11/1999 | Tsonton et al. |
| 6,129,735 | A | 10/2000 | Okada et al. |
| 6,139,561 | A | 10/2000 | Shibata et al. |
| 6,325,811 | B1 | 12/2001 | Messerly |
| 6,461,368 | B2 | 10/2002 | Fogarty et al. |
| 6,773,444 | B2 | 8/2004 | Messerly |
| 6,783,524 | B2 | 8/2004 | Anderson et al. |
| 7,563,269 | B2 | 7/2009 | Hashiguchi |
| 8,048,074 | B2 | 11/2011 | Masuda |
| 8,461,744 | B2 | 6/2013 | Wiener et al. |
| 8,591,536 | B2 | 11/2013 | Robertson |
| 8,623,027 | B2 | 1/2014 | Price et al. |
| 8,768,435 | B2 | 7/2014 | Andrus et al. |
| 8,905,935 | B2 | 12/2014 | Akagane |
| 8,926,610 | B2 | 1/2015 | Hafner et al. |
| 8,986,302 | B2 | 3/2015 | Aldridge et al. |
| 9,023,071 | B2 | 5/2015 | Miller et al. |
| 9,050,120 | B2 | 6/2015 | Swarup et al. |
| 9,072,523 | B2 | 7/2015 | Houser et al. |
| 9,084,878 | B2 | 7/2015 | Kawaguchi et al. |
| 9,095,367 | B2 | 8/2015 | Olson et al. |
| 9,326,787 | B2 | 5/2016 | Sanai et al. |
| 9,351,753 | B2 | 5/2016 | Balanev et al. |
| 9,375,255 | B2 * | 6/2016 | Houser ............... G16H 20/40 |
| 9,381,058 | B2 | 7/2016 | Houser et al. |
| 9,393,037 | B2 | 7/2016 | Olson et al. |
| 9,510,891 | B2 | 12/2016 | Allen, IV et al. |
| 9,566,084 | B2 | 2/2017 | Katsumata |
| 9,572,622 | B2 | 2/2017 | Shelton, IV et al. |
| 9,901,360 | B2 | 2/2018 | Neurohr et al. |
| 9,949,785 | B2 | 4/2018 | Price et al. |
| 10,543,383 | B2 | 1/2020 | Kase |
| 10,568,682 | B2 | 2/2020 | Dycus et al. |
| 2006/0079874 | A1 * | 4/2006 | Faller ............ A61B 17/320092 606/40 |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2010/0331873 | A1 | 12/2010 | Dannaher et al. |
| 2012/0116265 | A1 | 5/2012 | Houser et al. |
| 2012/0203143 | A1 * | 8/2012 | Sanai ............ A61B 17/320092 601/3 |
| 2013/0303949 | A1 * | 11/2013 | Kawaguchi ......... A61B 17/282 601/2 |
| 2014/0135804 | A1 | 5/2014 | Weisenburgh, II et al. |
| 2014/0221994 | A1 | 8/2014 | Reschke |
| 2015/0080924 | A1 | 3/2015 | Stulen et al. |
| 2015/0080925 | A1 | 3/2015 | Schulte et al. |
| 2015/0142031 | A1 * | 5/2015 | Faller .................... A61B 90/70 606/169 |
| 2015/0148835 | A1 | 5/2015 | Faller et al. |
| 2015/0265305 | A1 | 9/2015 | Stulen et al. |
| 2016/0030076 | A1 | 2/2016 | Faller et al. |
| 2016/0175001 | A1 | 6/2016 | Hibner et al. |
| 2017/0105754 | A1 | 4/2017 | Boudreaux et al. |
| 2017/0105755 | A1 | 4/2017 | Boudreaux et al. |
| 2017/0105788 | A1 | 4/2017 | Boudreaux |
| 2018/0132883 | A1 | 5/2018 | Asher et al. |
| 2018/0132884 | A1 | 5/2018 | Denzinger et al. |
| 2018/0132888 | A1 | 5/2018 | Asher et al. |
| 2018/0132926 | A1 | 5/2018 | Asher et al. |
| 2018/0256245 | A1 | 9/2018 | Price et al. |

FOREIGN PATENT DOCUMENTS

| | | |
|---|---|---|
| JP | 2000-197640 A | 7/2000 |
| JP | 2003-199752 A | 7/2003 |
| JP | 2004-033565 A | 2/2004 |
| JP | 2005-073760 A | 3/2005 |
| JP | 2005-176905 A | 7/2005 |
| JP | 2005-253674 A | 9/2005 |
| JP | 2005-328881 A | 12/2005 |
| JP | 2006-288431 A | 10/2006 |

(56) References Cited

FOREIGN PATENT DOCUMENTS

| JP | 2009-261912 A | 11/2009 |
|---|---|---|
| JP | 2013-545536 A | 12/2013 |
| JP | 2016-504153 A | 2/2016 |
| WO | WO 2011/008672 A2 | 1/2011 |
| WO | WO 2013/062103 A1 | 4/2015 |
| WO | WO 2016/015233 A1 | 2/2016 |

OTHER PUBLICATIONS

U.S. Appl. No. 15/284,837.
U.S. Appl. No. 15/284,855.
U.S. Appl. No. 15/798,902.
U.S. Appl. No. 15/798,680, filed Oct. 31, 2017.
U.S. Appl. No. 15/798,720, filed Oct. 31, 2017.
U.S. Appl. No. 15/798,835, filed Oct. 31, 2017.
U.S. Appl. No. 15/798,902, filed Oct. 31, 2017.
U.S. Appl. No. 61/410,603, filed Nov. 5, 2010.
U.S. Appl. No. 62/363,411, filed Jul. 18, 2016.
U.S. Appl. No. 62/422,698, filed Nov. 16, 2016.
U.S. Appl. No. 62/508,720, filed May 19, 2017.
U.S. Appl. No. 62/519,482, filed Jun. 14, 2017.
European Examination Report dated Jun. 5, 2020 for Application No. EP 17812121.6, 4 pgs.
European Examination Report dated Jun. 5, 2020 for Application No. EP 17851837.9, 3 pgs.
European Examination Report dated Jun. 5, 2020 for Application No. EP 17811769.3, 3 pgs.
European Search Report, Extended, and Written Opinion dated Aug. 7, 2020 for Application No. EP 20163273.4, 7 pgs.
International Search Report and Written Opinion dated Jan. 30, 2018 for PCT/US2017/061995, 11 pgs.
International Search Report and Written Opinion dated Jun. 20, 2018 for PCT/US2017/062010, 16 pgs.
International Search Report and Written Opinion dated Apr. 13, 2018 for PCT/US2017/062016, 17 pgs.
International Search Report and Written Opinion dated Feb. 1, 2018 for PCT/US2017/062023, 13 pgs.
International Search Report and Written Opinion dated Apr. 3, 2018 for PCT/US2017/062025, 18 pgs.
U.S. Patent Pub. No. 2018/0132883.
U.S. Patent Pub. No. 2018/0132884.
U.S. Patent Pub. No. 2018/0132888.
U.S. Patent Pub. No. 2018/0132926.
Indian Office Action dated Jul. 23, 2021, for Application No. 201917019428, 6 pages.
Japanese Notification of Reasons for Refusal dated Sep. 27, 2021, for Application No. 2019-547241, 10 pages.
Japanese Notification of Reasons for Refusal dated Oct. 5, 2021, for Application No. 2019-547242, 10 pages.
Japanese Notification of Reasons for Refusal dated Oct. 5, 2021, for Application No. 2019-547243, 7 pages.
Japanese Notification of Reasons for Refusal dated Oct. 5, 2021, for Application No. 2019-547245, 7 pages.
Indian Office Action dated Jun. 30, 2021, for Application No. 201917019250, 5 pages.
Indian Office Action dated Jun. 30, 2021, for Application No. 201917019251, 6 pages.
Indian Office Action dated Jun. 25, 2021, for Application No. 201917019429, 5 pages.
Japanese Notification of Reasons for Refusal dated Oct. 5, 2021, for Application No. 2019-547244, 8 pages.
U.S. Appl. No. 15/798,680.
U.S. Appl. No. 15/798,720.
U.S. Appl. No. 15/798,835.
European Search Report, Extended, and Written Opinion dated Jan. 20, 2022 for Application No. 21189412.6, 8 pgs.
Indian Examination Report dated Jul. 12, 2021 for Application No. IN 20191701925.3. 6 pgs.
Chinese Search Report dated Apr. 22, 2022 for Application No. CN 201780083514.X, 1 pg.
Japanese Search Report by Registered Search Organization, dated Sep. 30, 2021 for Application No. JP 2019-547242, 18 pgs.
Japanese Decision to Grant a Patent dated May 31, 2022 for Application No. JP 2019-547242, 2 pgs.

* cited by examiner

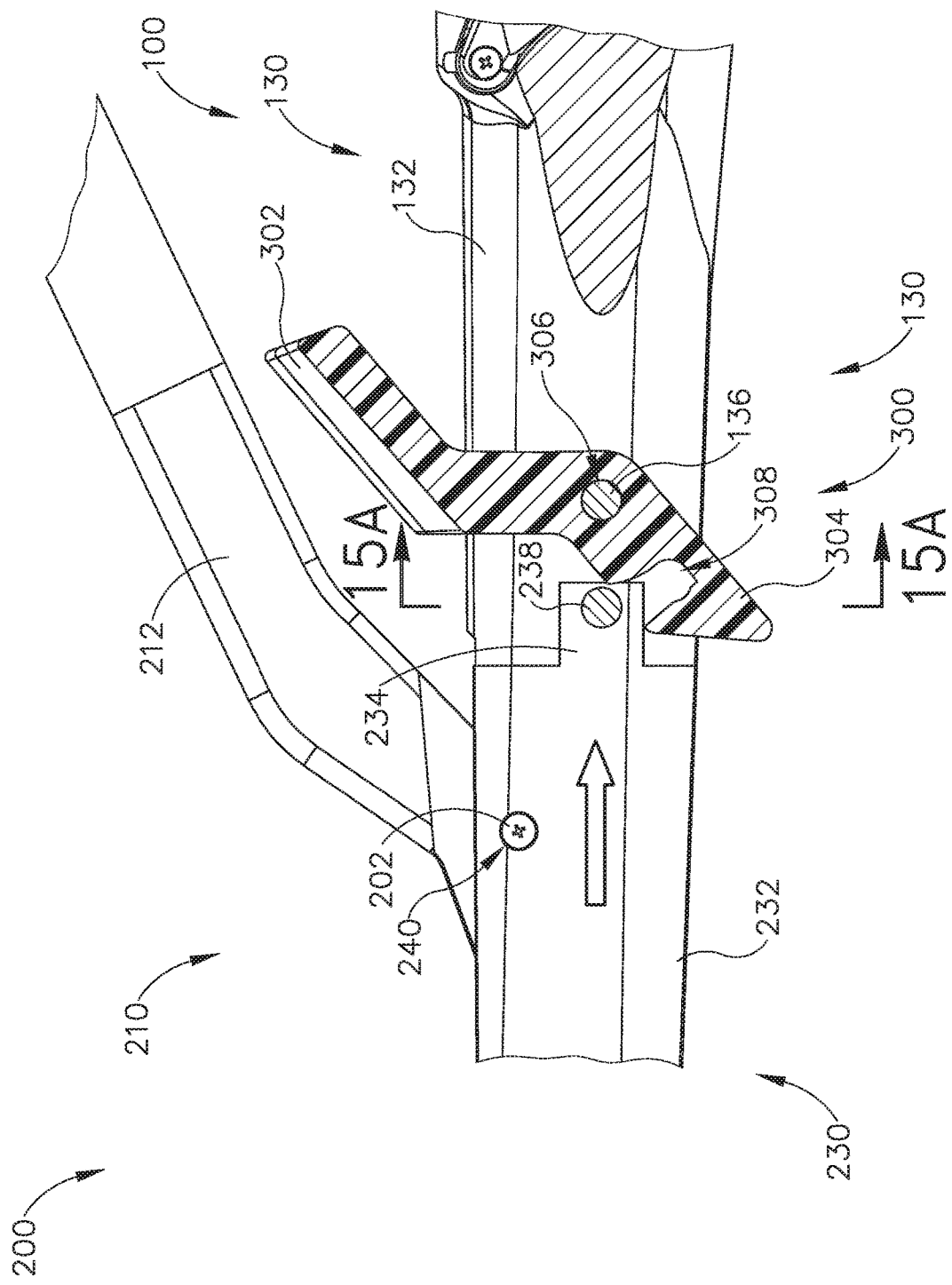

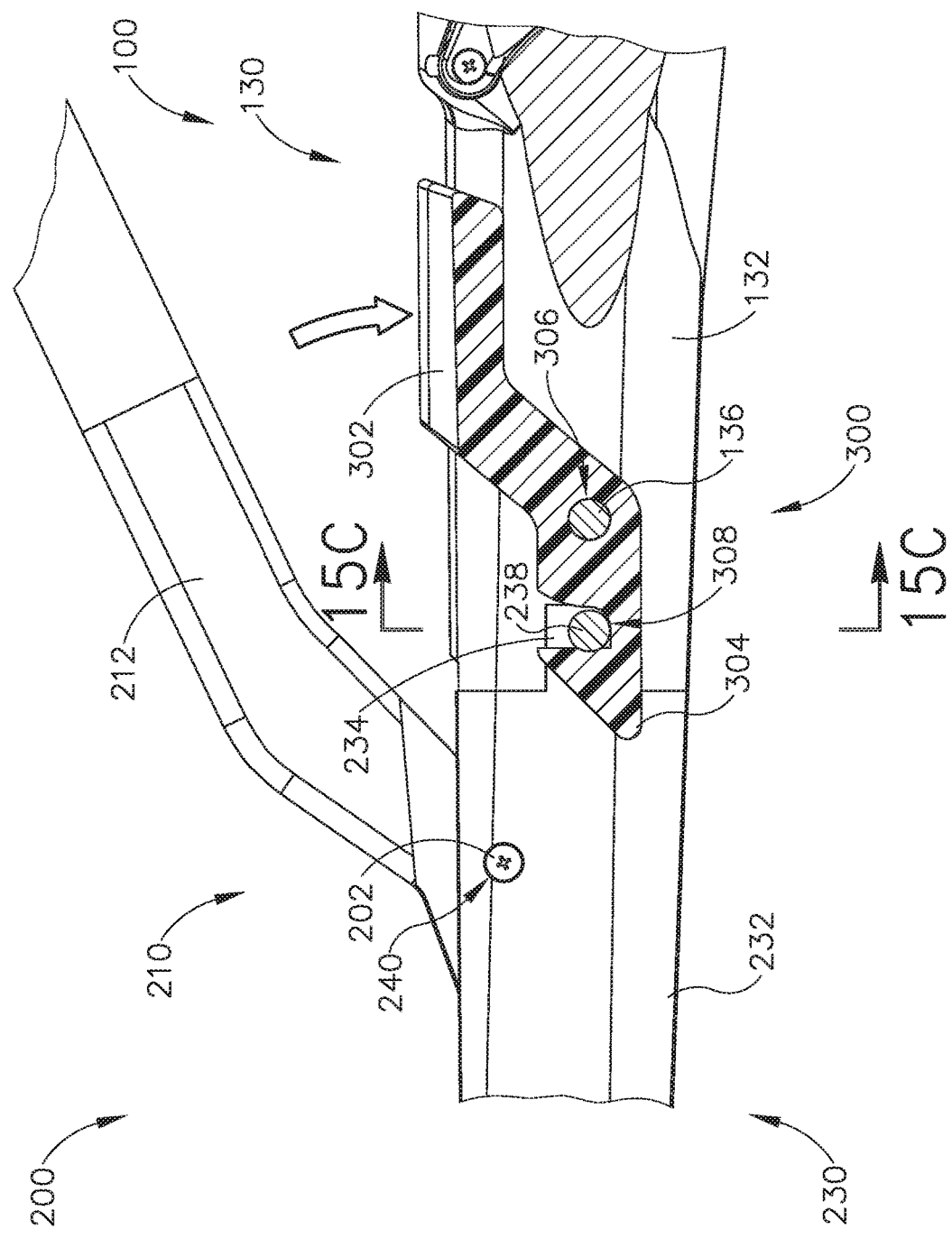

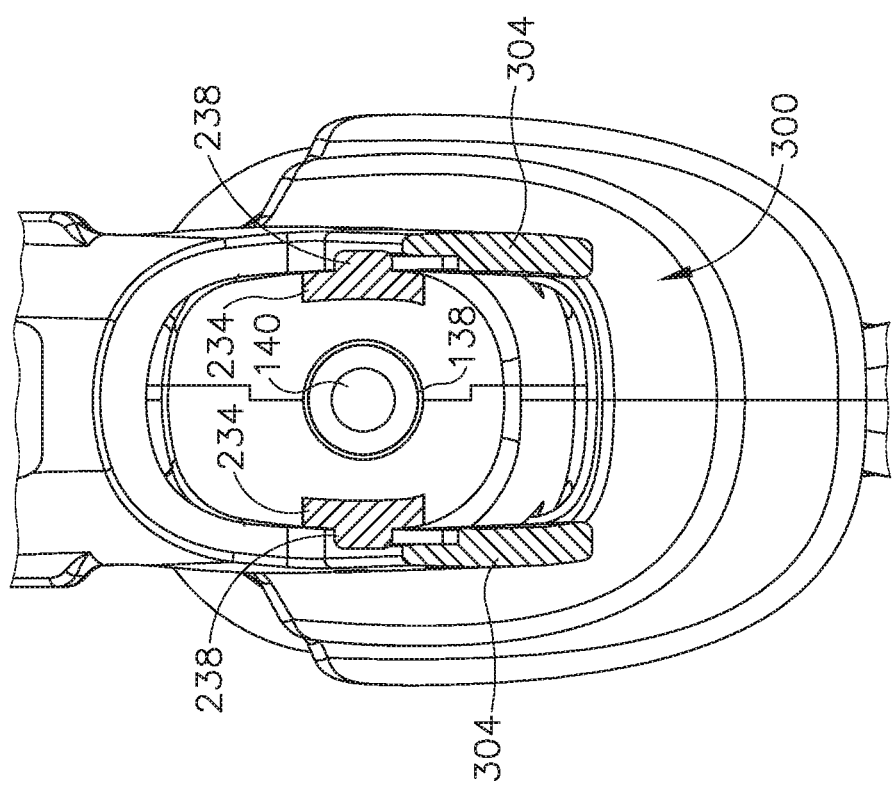

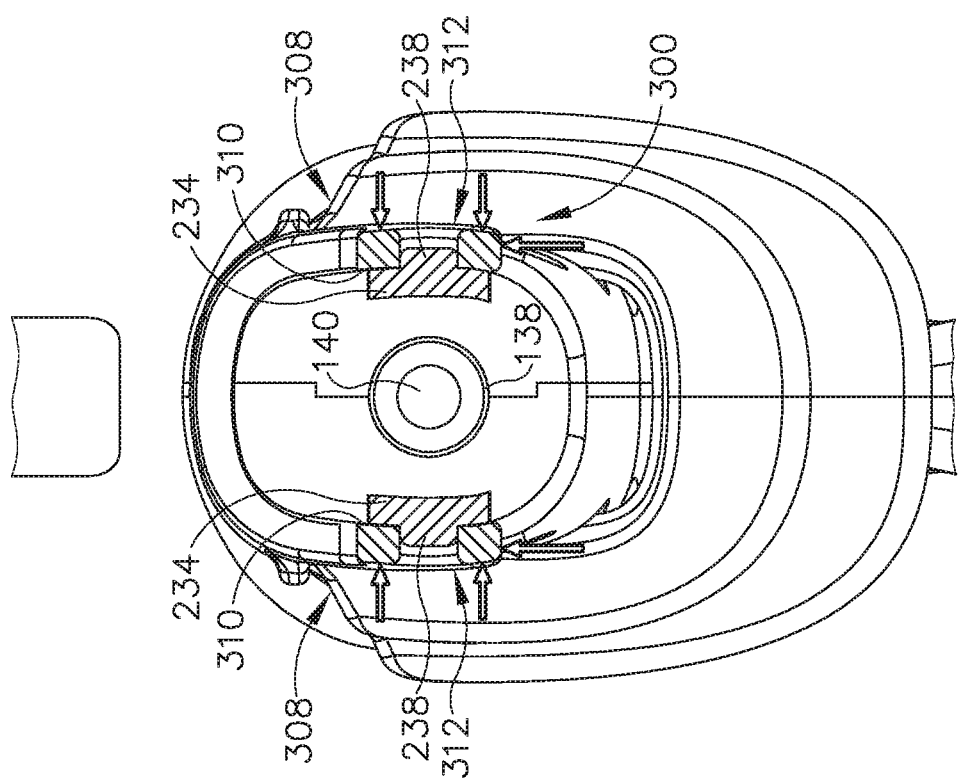

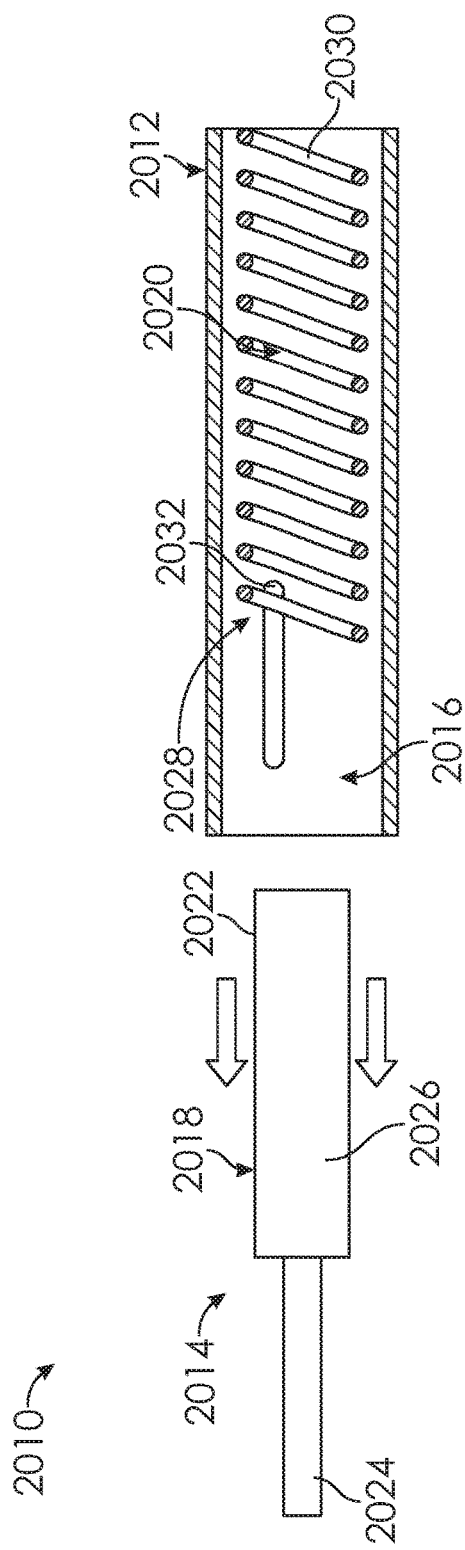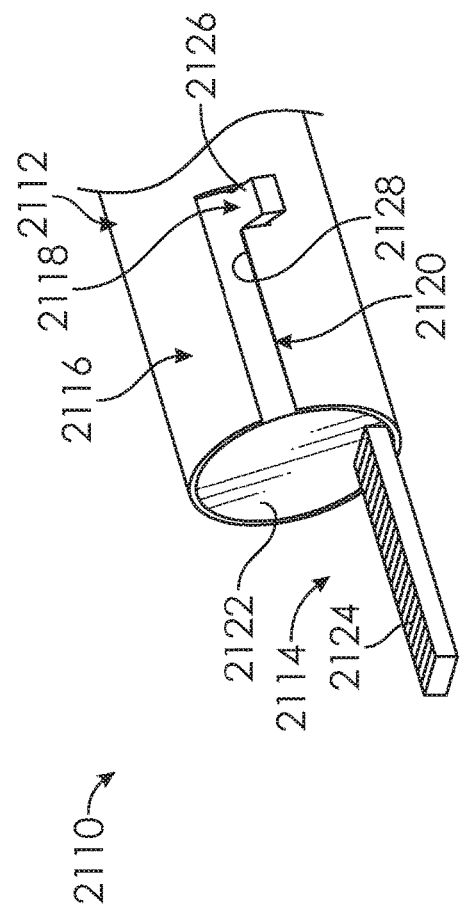

SURGICAL INSTRUMENT WITH REMOVABLE END EFFECTOR COMPONENTS

PRIORITY

This application claims priority to: (1) U.S. Provisional Patent Application Ser. No. 62/422,698, filed Nov. 16, 2016, entitled "Ultrasonic Surgical Shears with Contained Compound Lever Clamp Arm Actuator," the disclosure of which is incorporated by reference herein; (2) U.S. Provisional Patent Application Ser. No. 62/508,720, filed May 19, 2017, entitled "Ultrasonic and Electrosurgical Instrument with Replaceable End Effector Features," the disclosure of which is incorporated by reference herein; and (3) U.S. Provisional Patent Application Ser. No. 62/519,482, filed Jun. 14, 2017, entitled "Ultrasonic and Electrosurgical Instrument with Removable Features," the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,023,071, entitled "Ultrasonic Device for Fingertip Control," issued May 5, 2015, the disclosure of which is incorporated by reference herein; and U.S. Pat. No. 8,461,744, entitled "Rotating Transducer Mount for Ultrasonic Surgical Instruments," issued Jun. 11, 2013, the disclosure of which is incorporated by reference herein; and U.S. Pat. No. 8,591,536, entitled "Ultrasonic Surgical Instrument Blades," issued Nov. 26, 2013, the disclosure of which is incorporated by reference herein.

Some of ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, entitled "Surgical Instruments with Articulating Shafts," issued Jul. 19, 2016, the disclosure of which is incorporated by reference herein; and U.S. Pat. No. 9,095,367, entitled "Flexible Harmonic Waveguides/Blades for Surgical Instruments," issued Aug. 4, 2015 the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 14B depicts a cross-sectional side view of the second modular assembly of FIG. 8 further inserted over the shaft assembly of FIG. 5, taken along line 14-14 of FIG. 13B;

FIG. 14D depicts a cross-sectional side view of the coupling member of FIG. 7 connecting the second modular assembly of FIG. 8 and the shaft assembly of FIG. 5, taken along line 14-14 of FIG. 13B;

FIG. 15A depicts a cross-sectional front view of the second modular assembly of FIG. 8 inserted over the shaft assembly of FIG. 5, taken along line 15A-15A of FIG. 14B;

FIG. 15C depicts a cross-sectional front view of the coupling member of FIG. 7 connecting the second modular assembly of FIG. 8 and the shaft assembly of FIG. 5, taken along line 15C-15C of FIG. 14D;

FIG. 65C depicts the enlarged side sectional view of the surgical instrument similar to FIG. 65B, but showing the clamp arm assembly removed from the clamp arm actuator;

FIG. 66A depicts an enlarged perspective view of an eighteenth exemplary surgical instrument having a modular bayonet coupling associated with a clamp arm assembly;

FIG. 82 depicts an enlarged side view of a twenty-fourth exemplary surgical instrument having a modular inner release coupling associated with a clamp arm assembly;

FIG. 83 depicts an enlarged partially exploded side view of the surgical instrument of FIG. 82;

FIG. 84 depicts a perspective view of a third modular connection tool configured to disconnect the clamp arm assembly of FIG. 82 from a clamp arm actuator;

FIG. 85 depicts a perspective view of the clamp arm assembly of FIG. 82;

FIG. 86 depicts a cross-sectional view of the clamp arm assembly of FIG. 85 taken along section line 86-86 of FIG. 85;

FIG. 87 depicts a cross-sectional view of the clamp arm assembly of FIG. 85 taken along section line 87-87 of FIG. 85;

FIG. 88 depicts a perspective view of the surgical instrument of FIG. 82 receiving the modular connection tool of FIG. 84 for disconnecting a clamp arm assembly;

FIG. 89A depicts an enlarged cross-sectional view of the clamp arm actuator and the clamp arm assembly of FIG. 88 taken along section line 89A-89A of FIG. 88;

FIG. 89B depicts the enlarged cross-sectional view of the clamp arm actuator and the clamp arm assembly similar to FIG. 89A, but showing the clamp arm assembly being disconnected from the clamp arm actuator and removed therefrom;

FIG. 90A depicts an enlarged perspective view of a twenty-fifth exemplary surgical instrument having a modular helical coupling associated with a clamp arm assembly;

FIG. 90B depicts the enlarged perspective view of the surgical instrument similar to FIG. 90A, but showing the clamp arm assembly being removed from a clamp arm actuator in a closed configuration;

FIG. 91 depicts a distal end view of the clamp arm actuator of FIG. 90B;

Figure 1A:
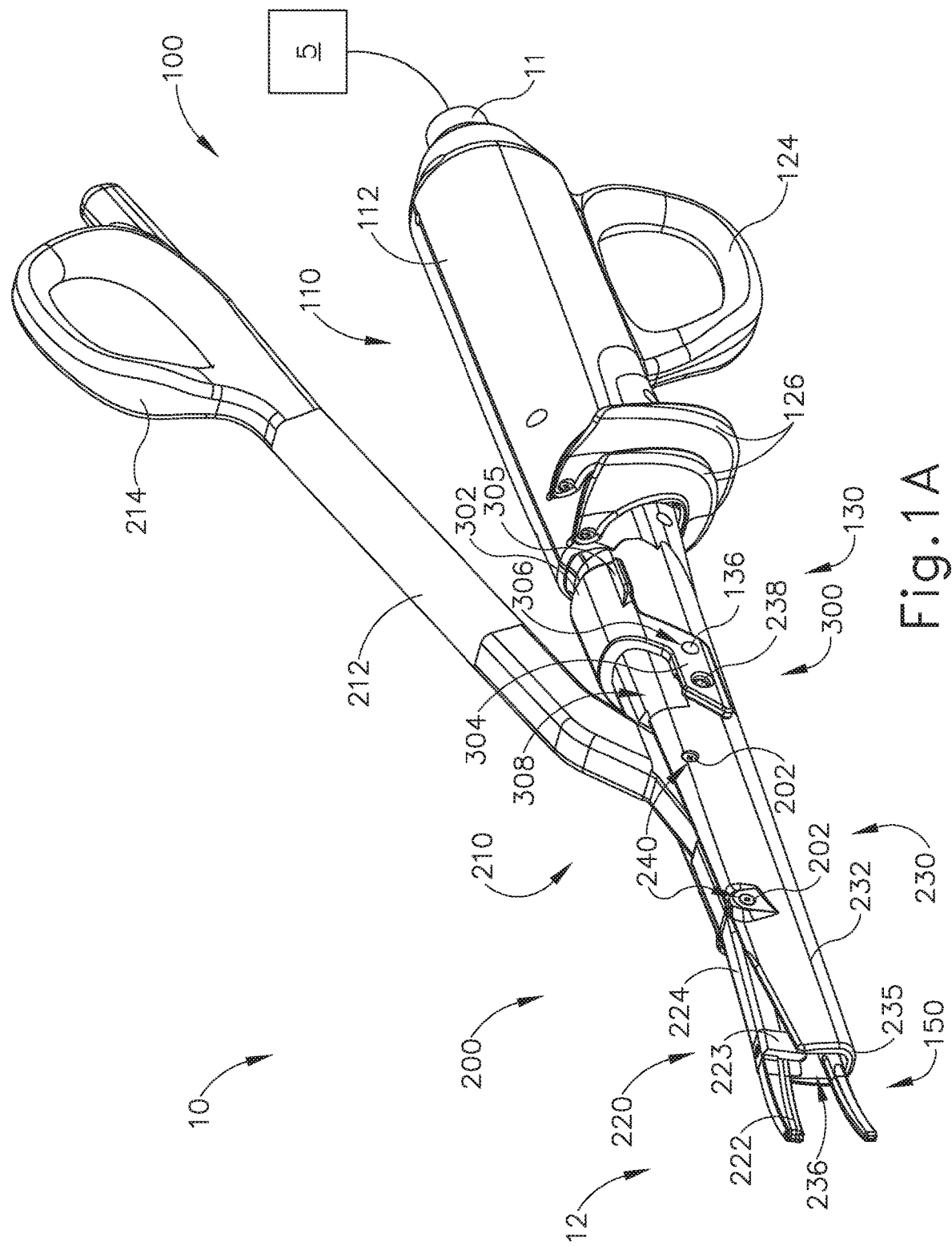
FIG. 1A depicts a perspective view of a first exemplary surgical instrument, with an end effector of the instrument in an open configuration.
Figure 90A:
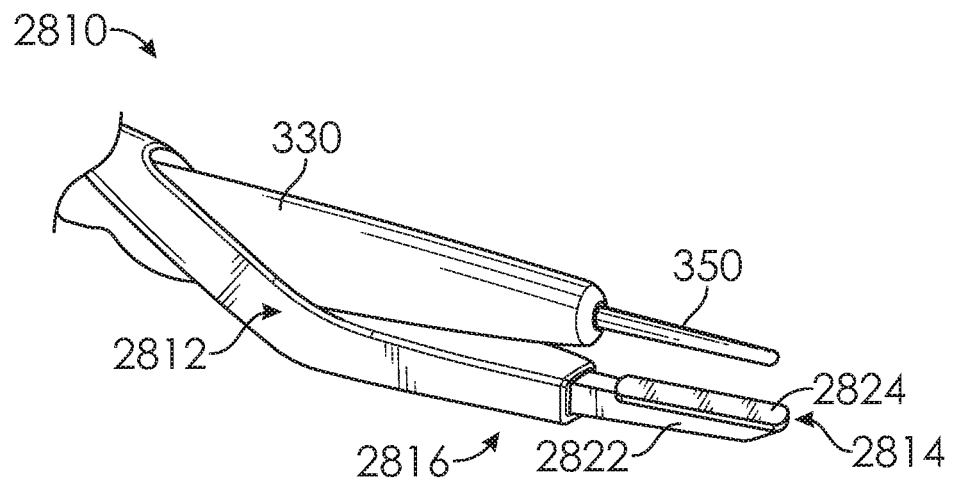
Figure 90B:
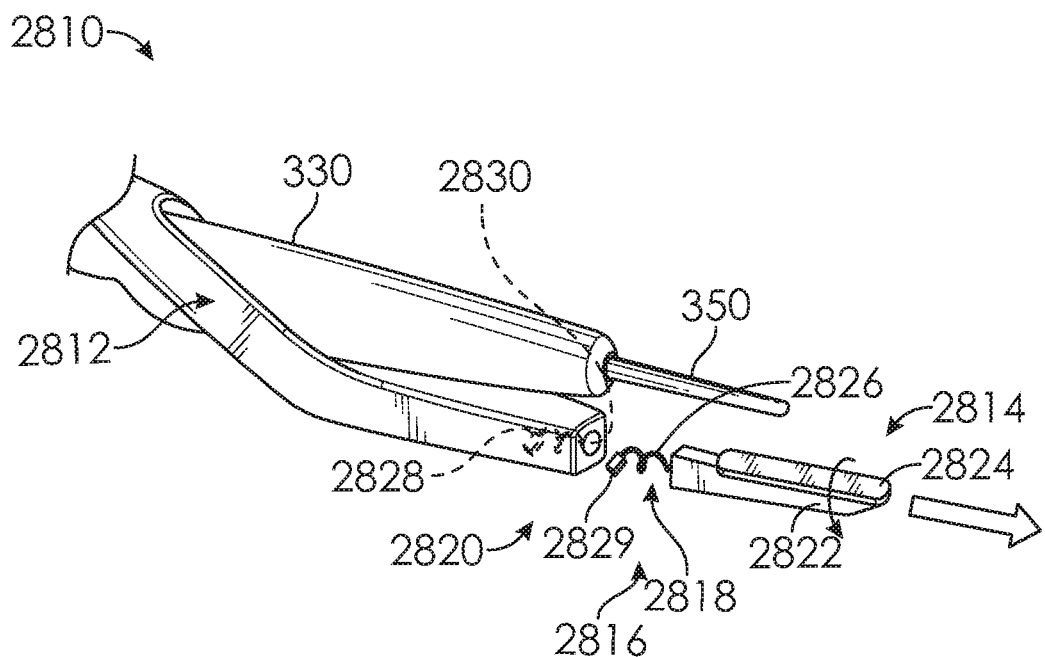
Figure 92:
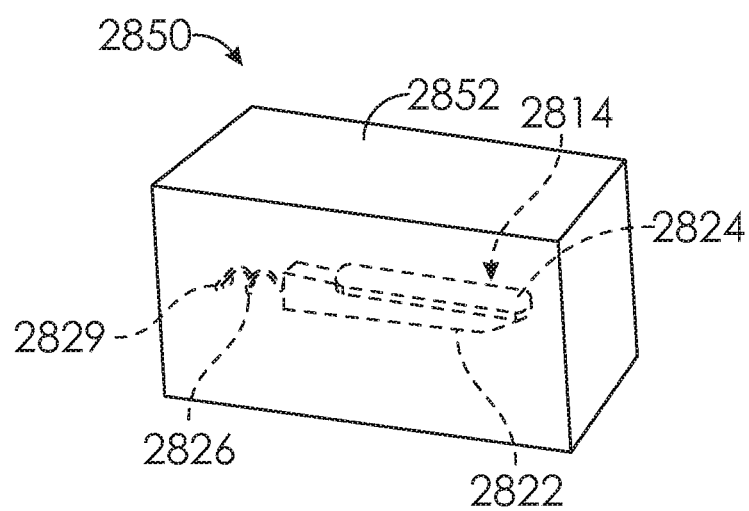
Figure 93:
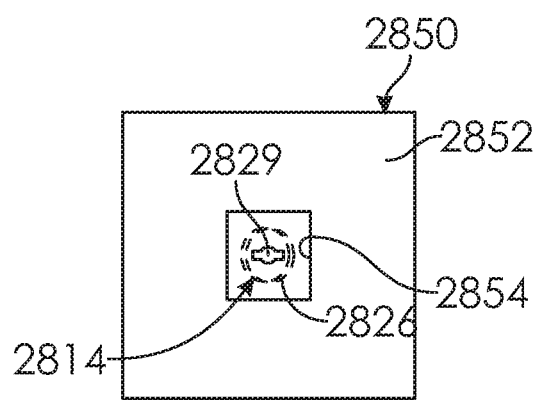
Figure 94A:
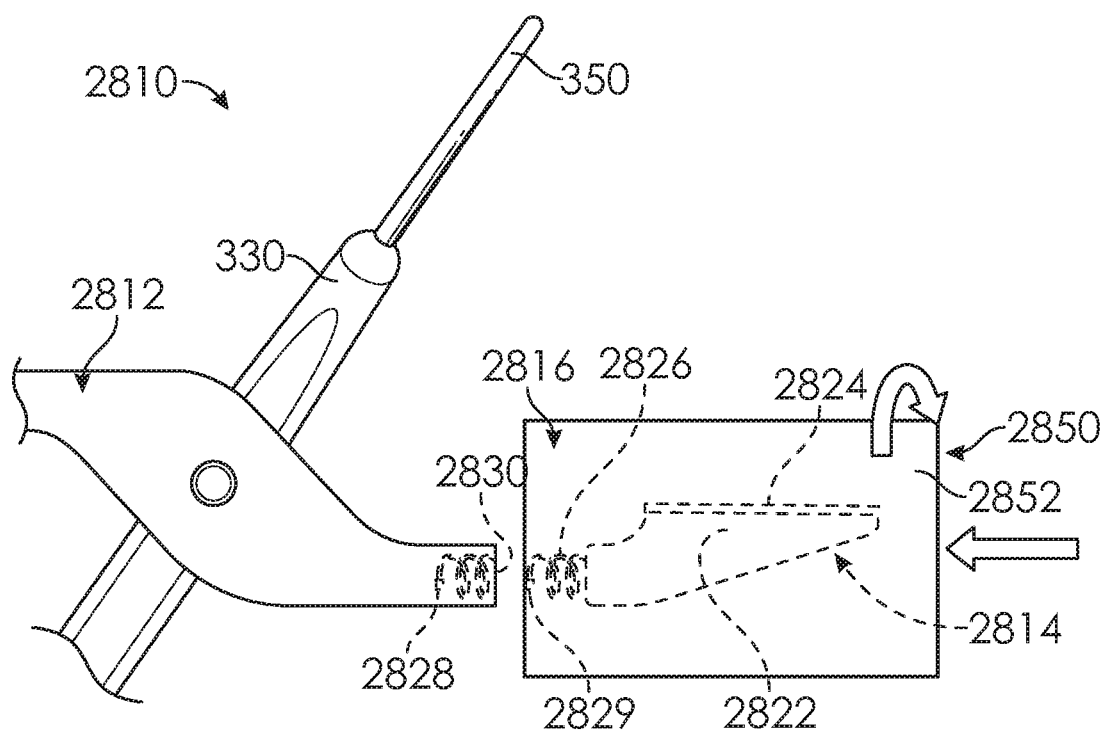
Figure 94B:
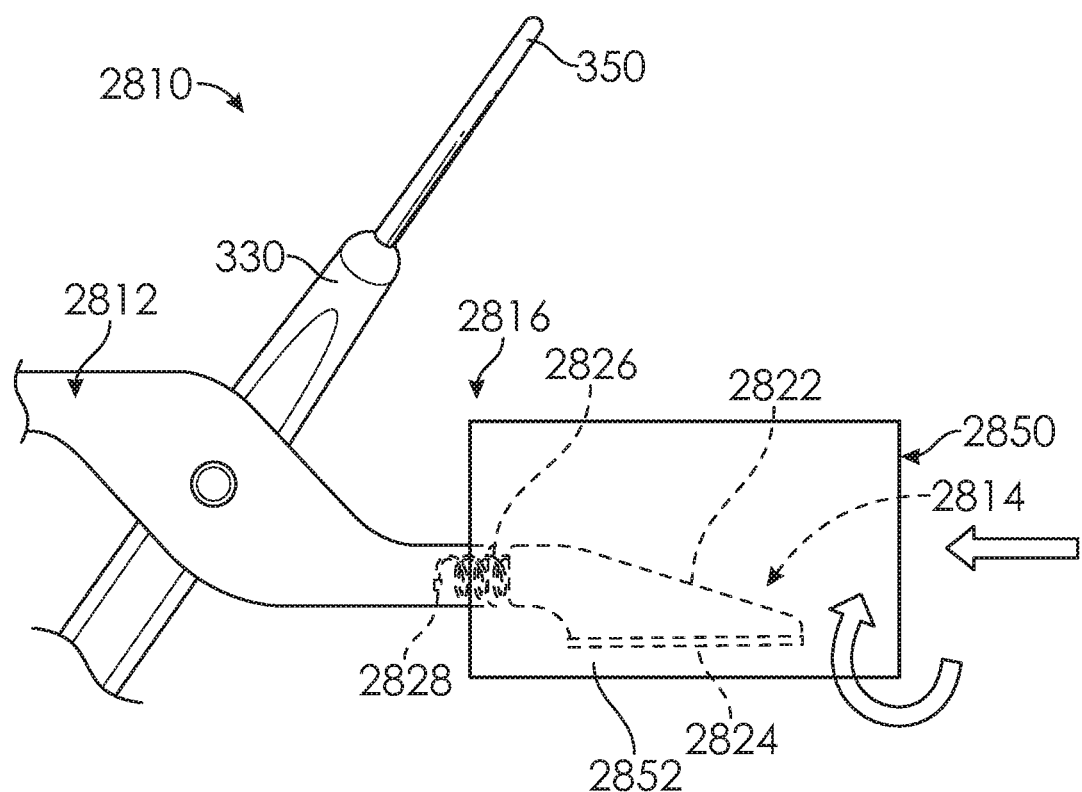
Figure 94C:
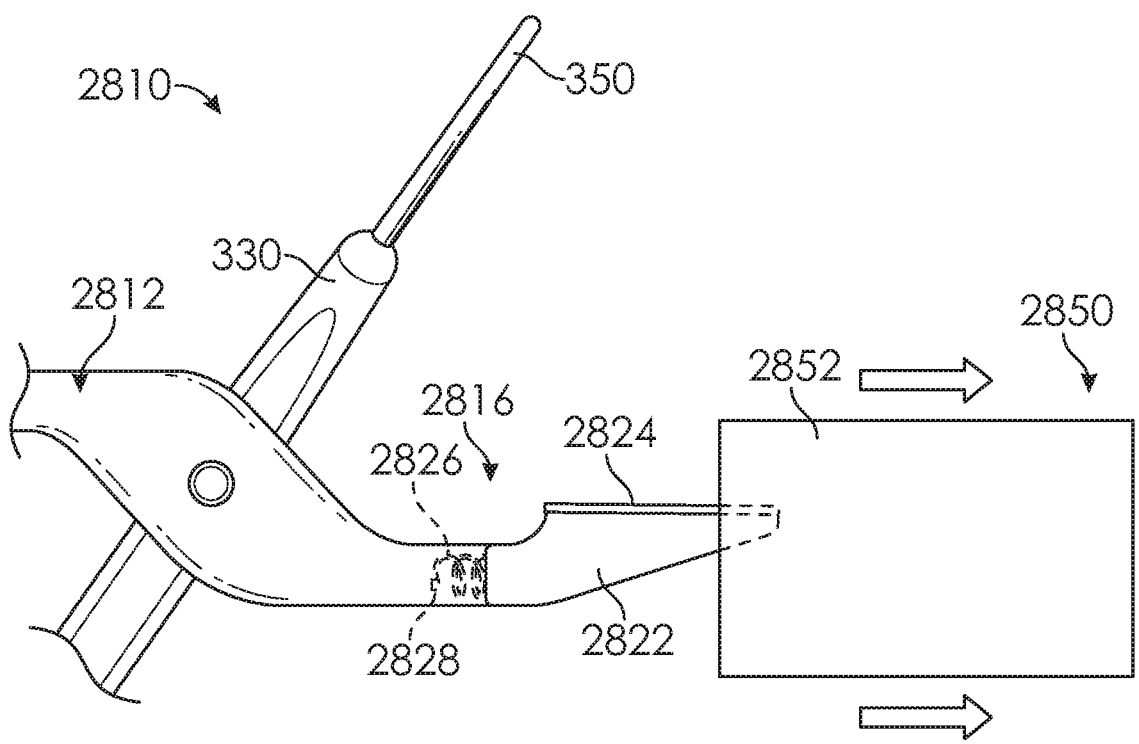
Figure 95:
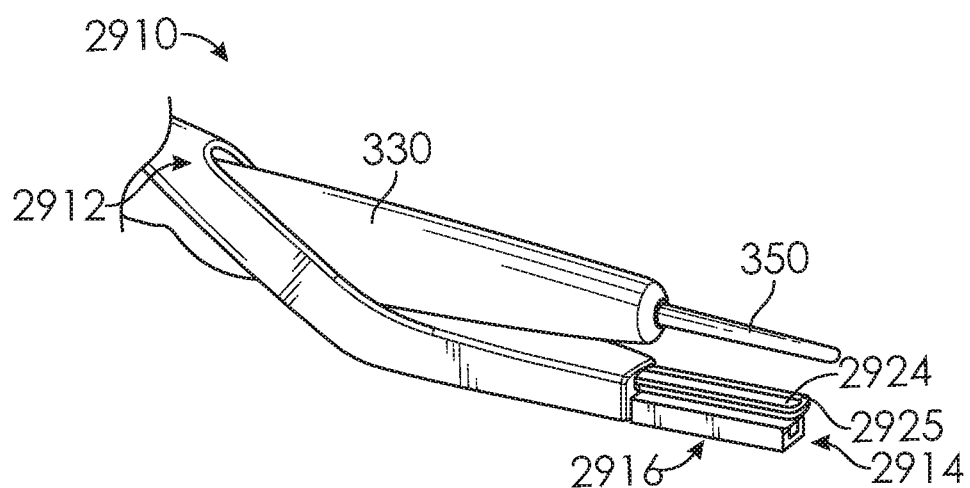
Figure 96:
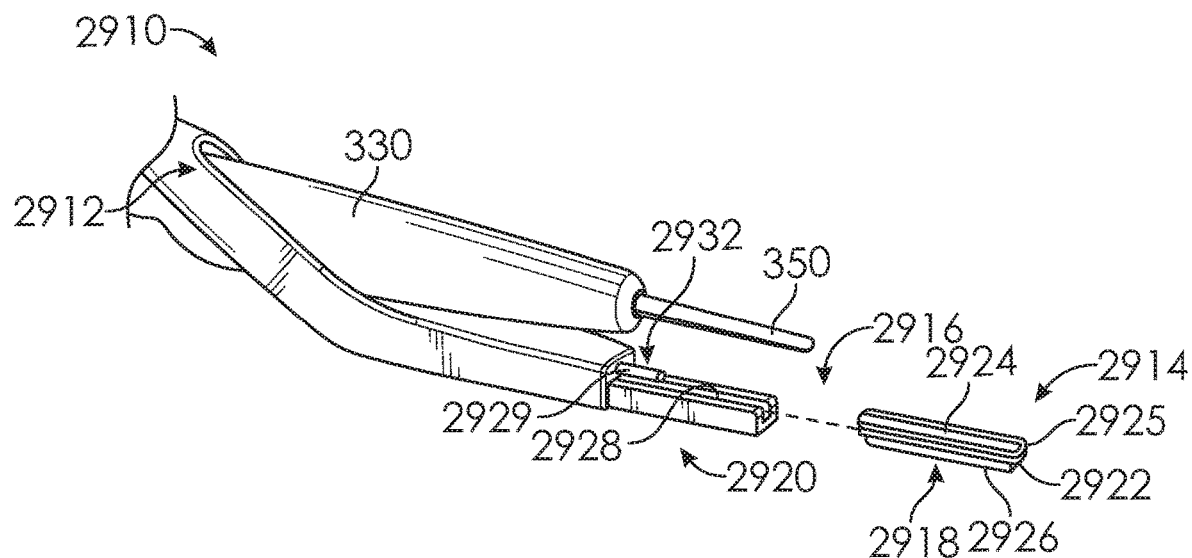
Figure 97:
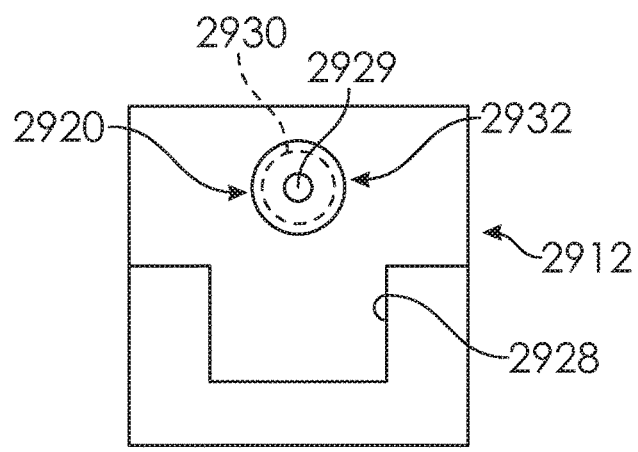
Figure 98:
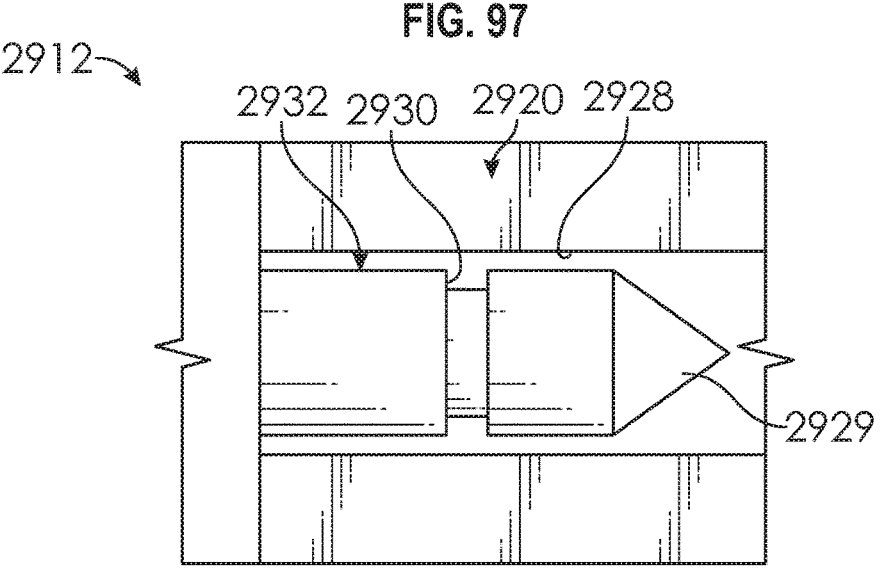
Figure 99:
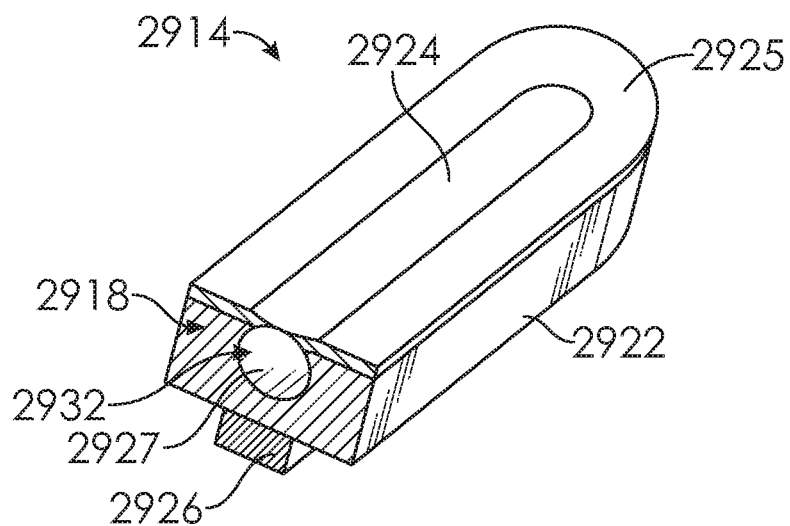
Figure 100:
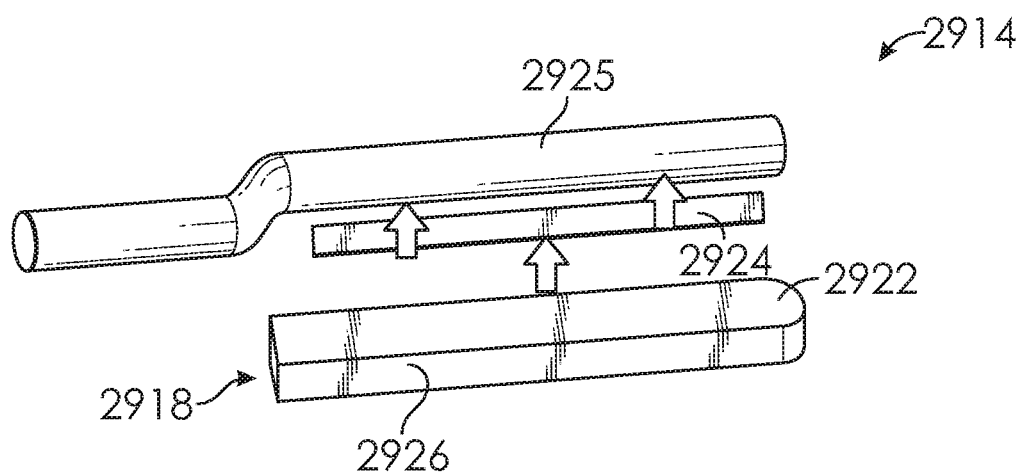
Figure 101:
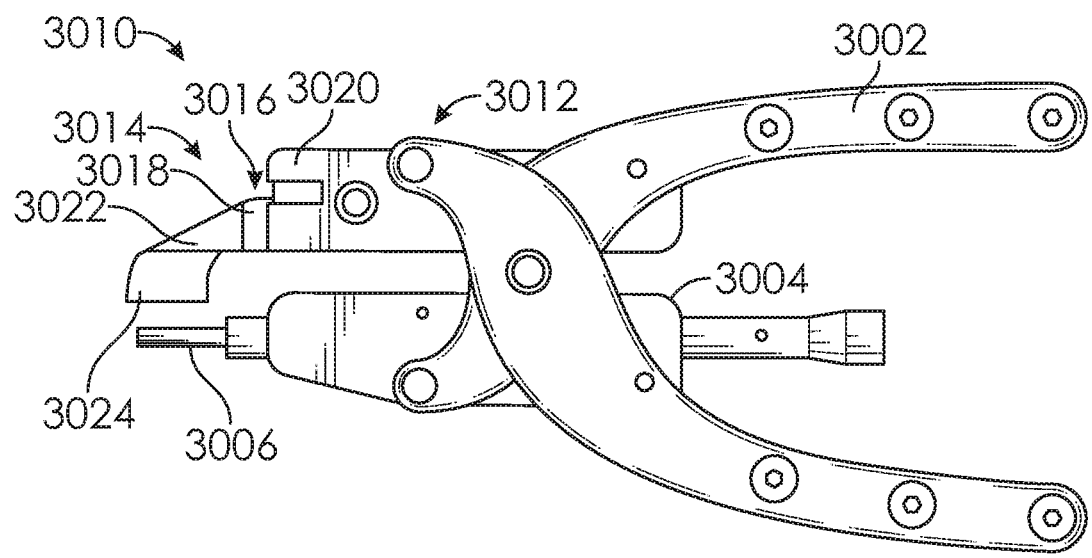
Figure 102:
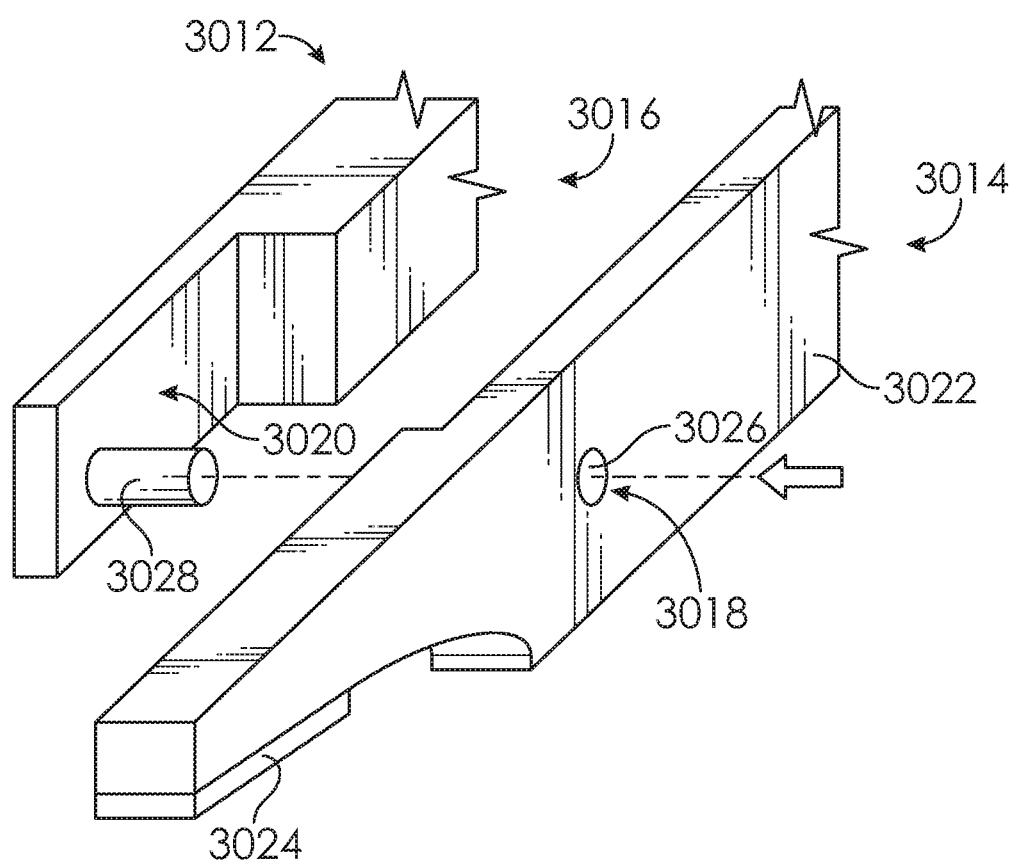
Figure 103:
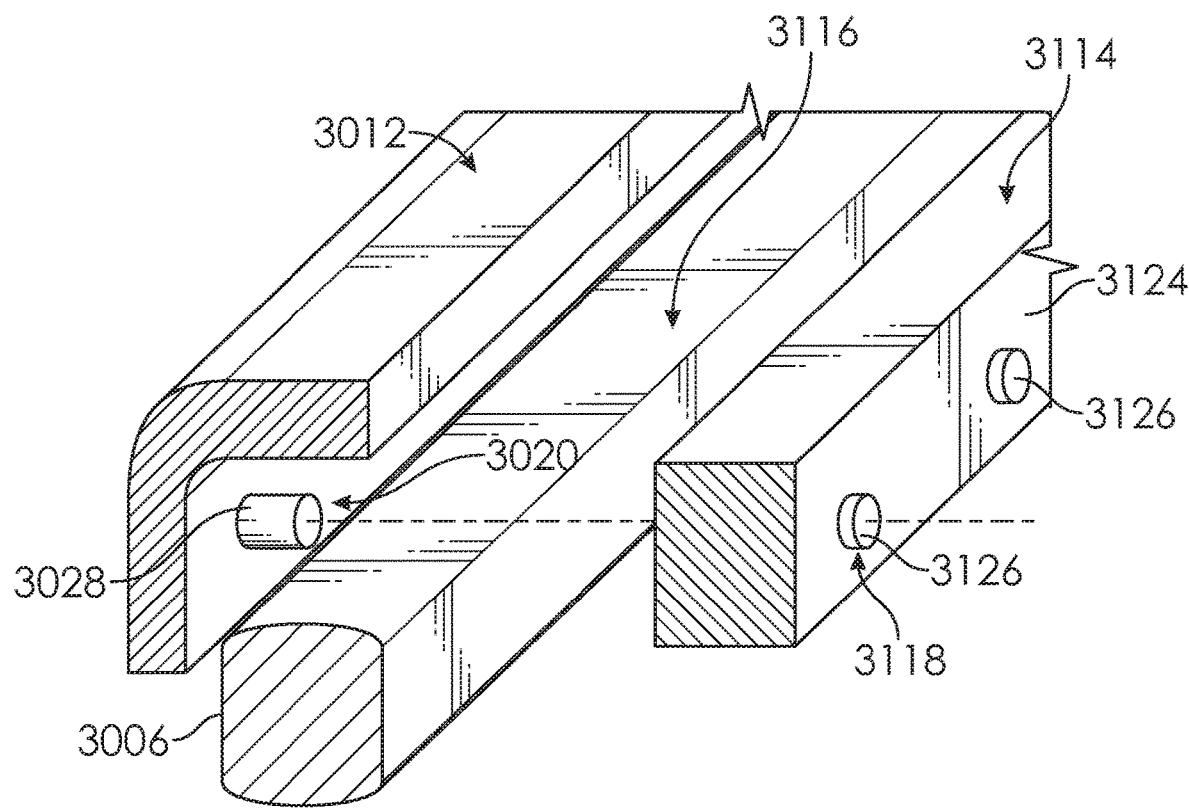
Figure 104:
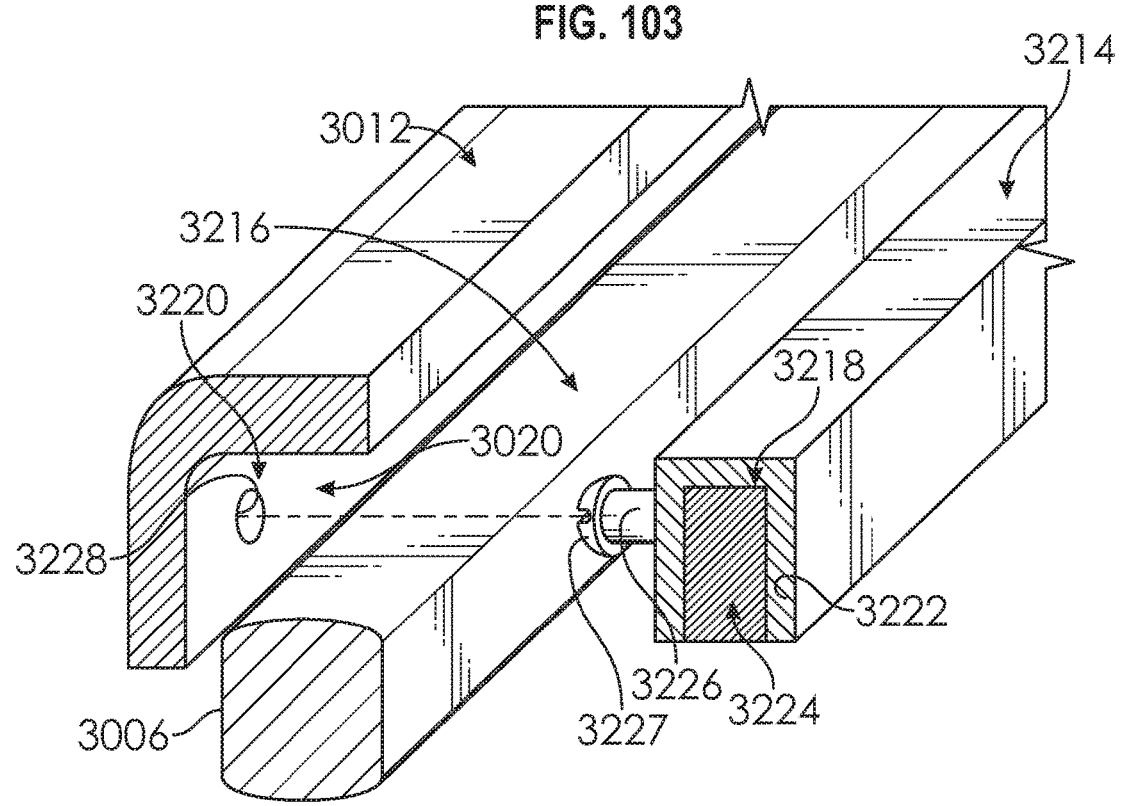
Figure 105:
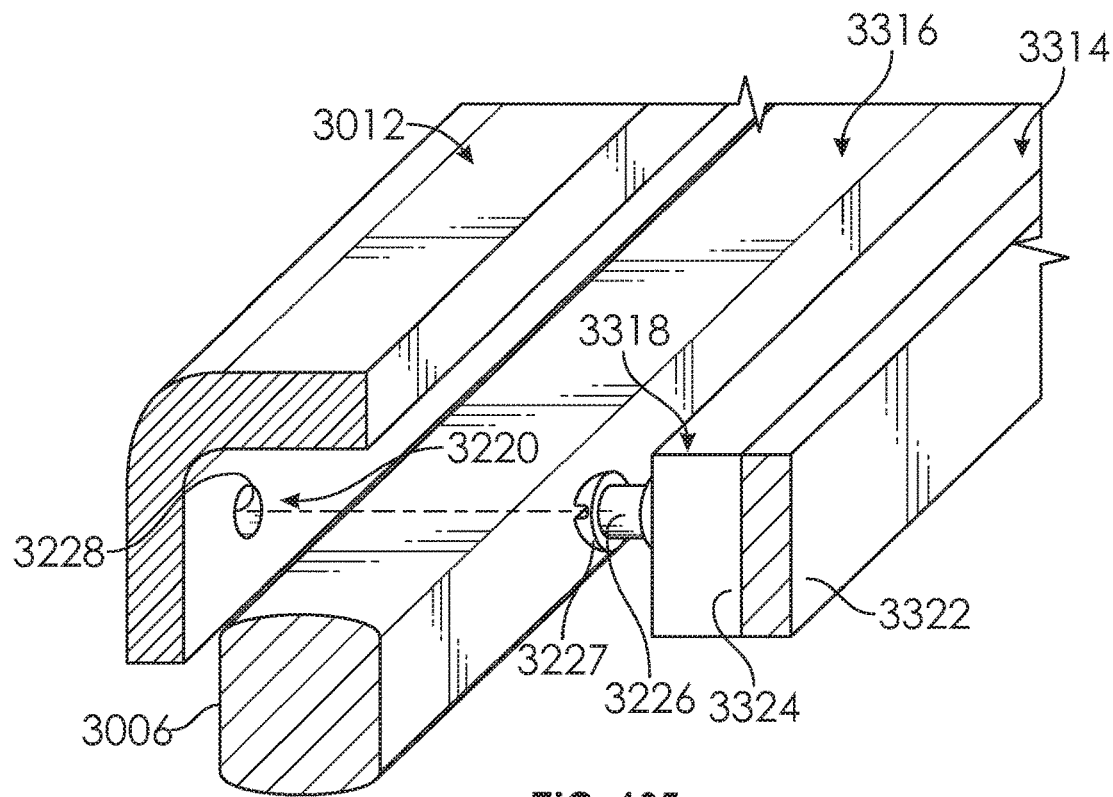
Figure 106:
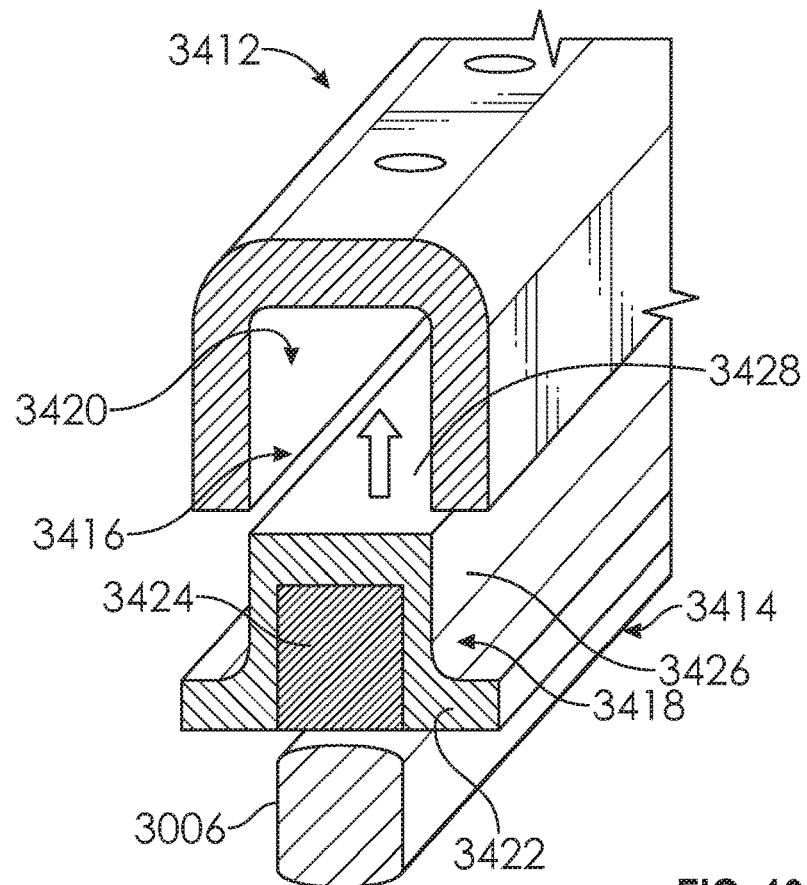
Figure 107:
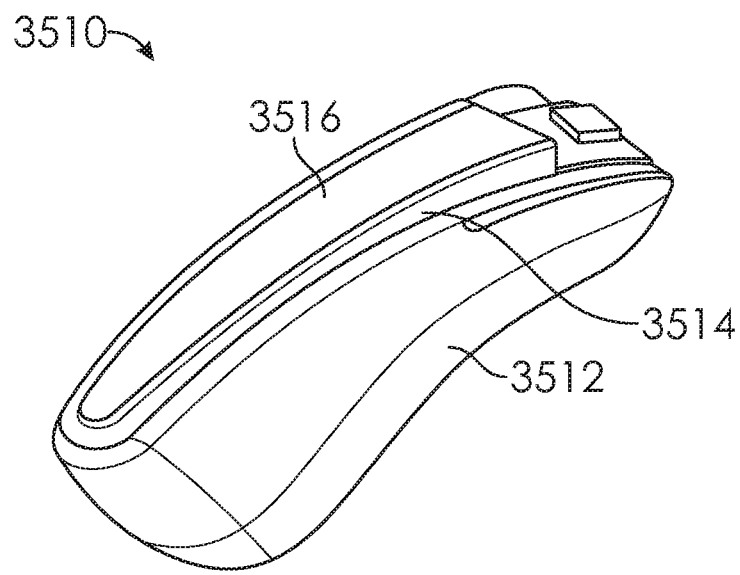
Figure 108:
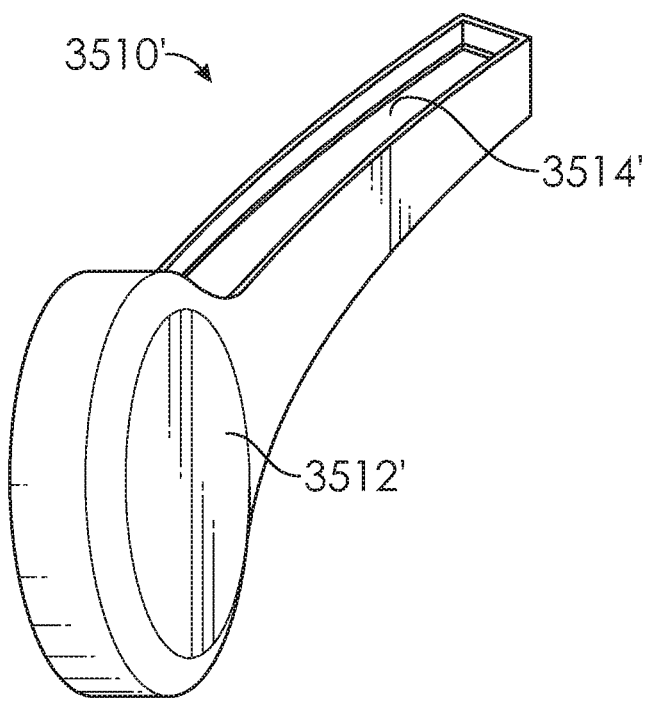
Figure 109:
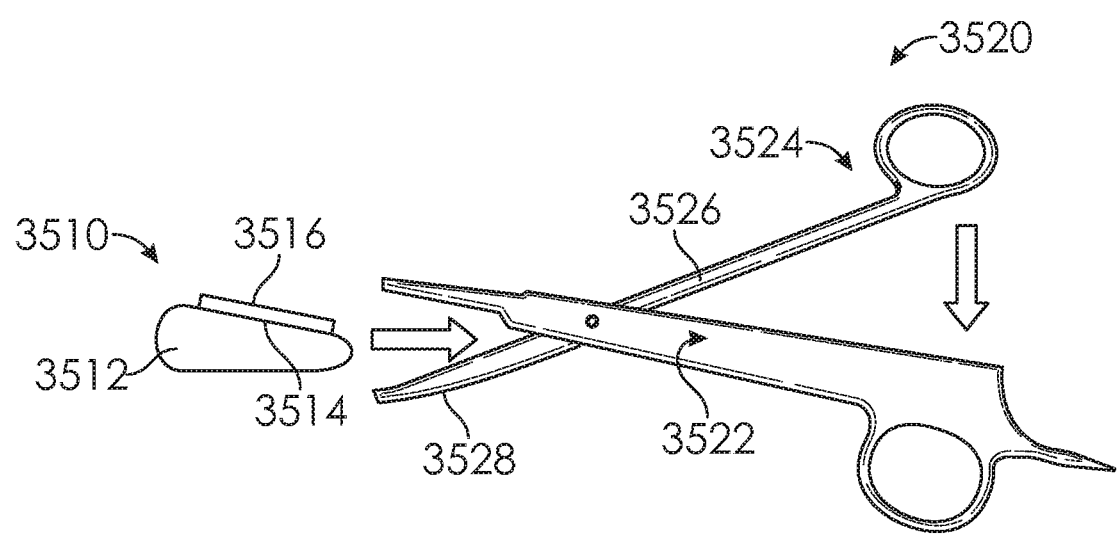
Figure 110:
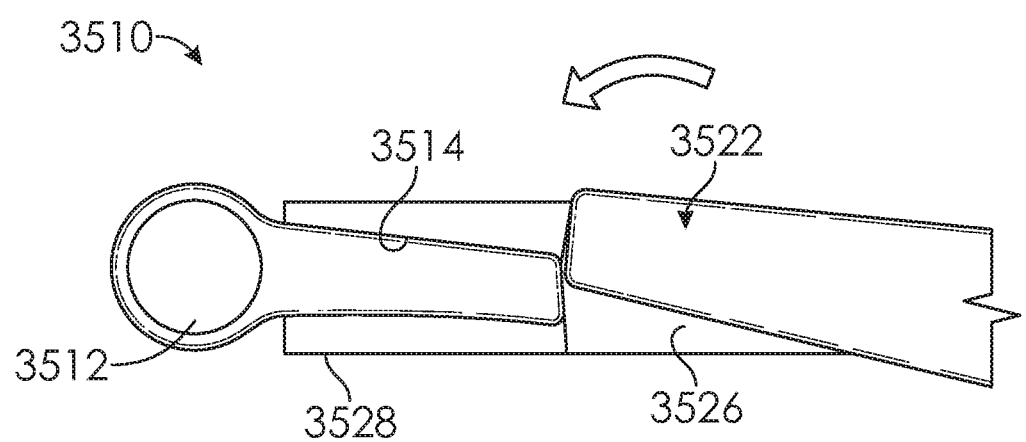
Figure 111A:
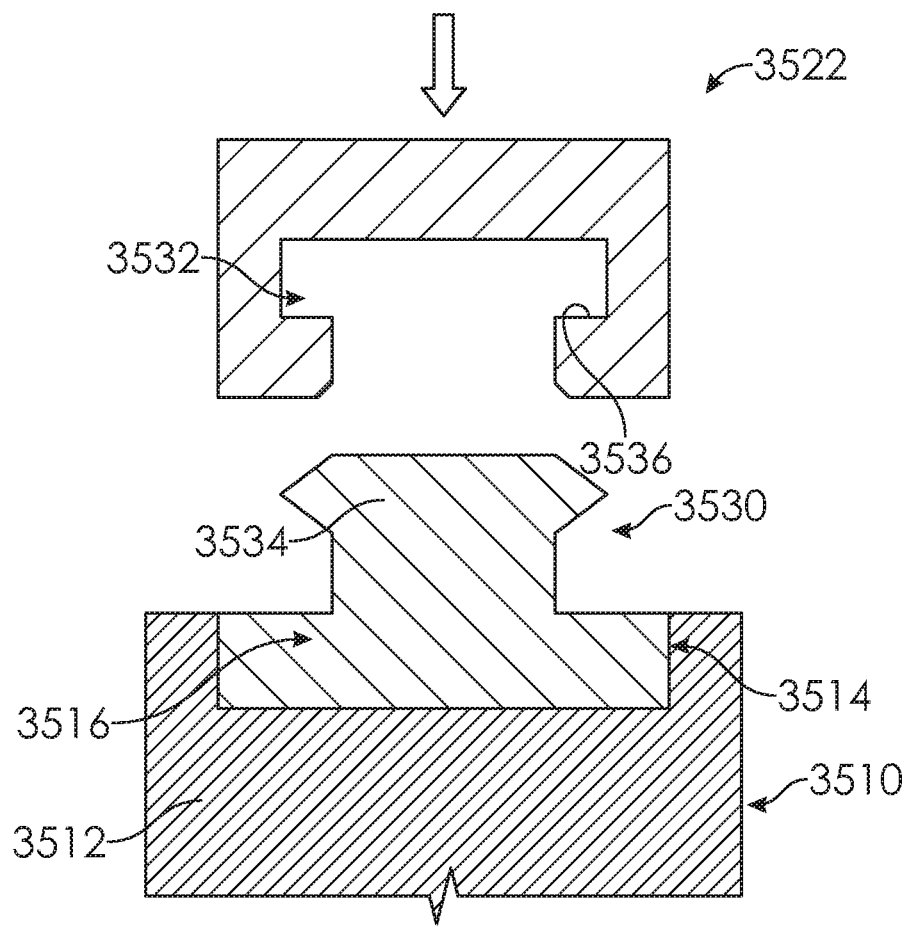
Figure 111B:
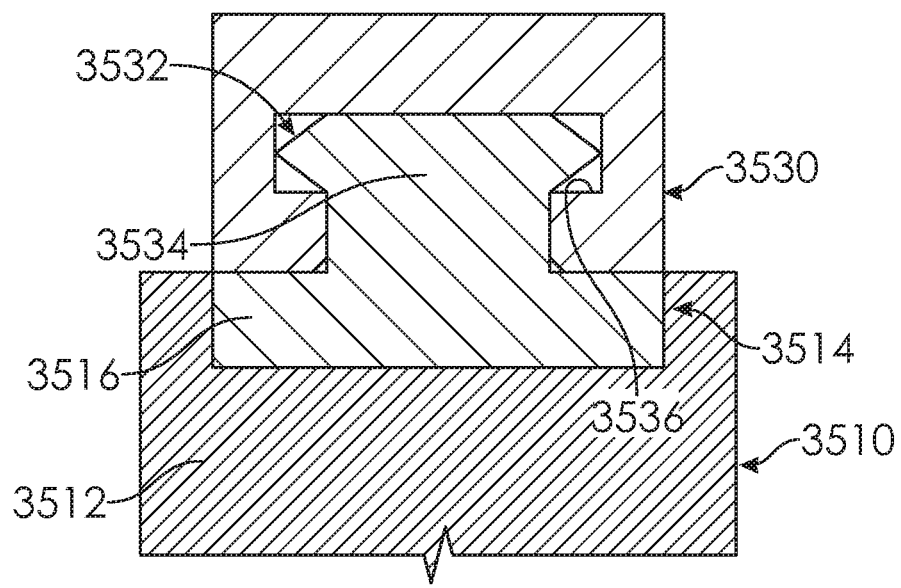
Figure 112:
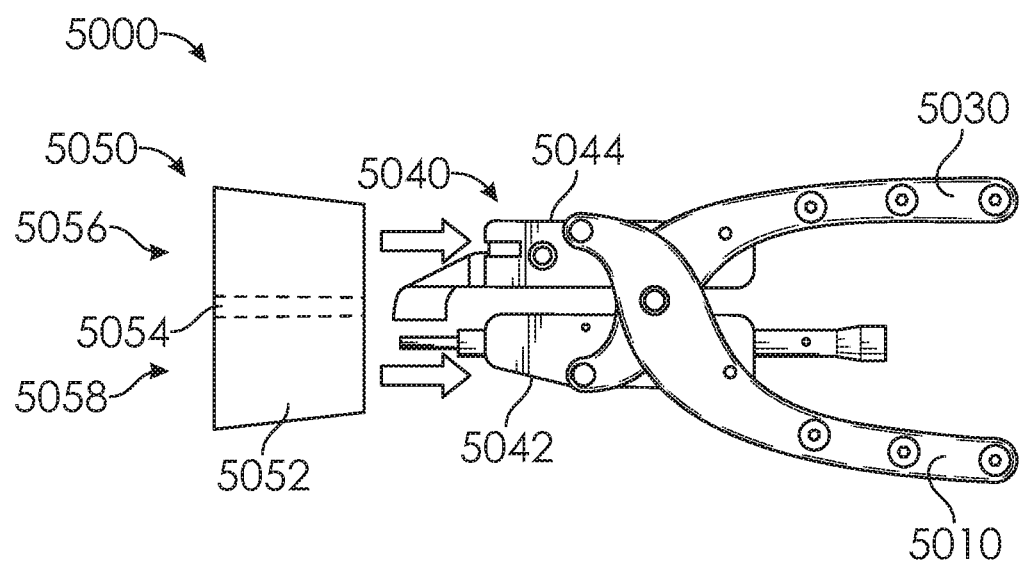
Figure 113:
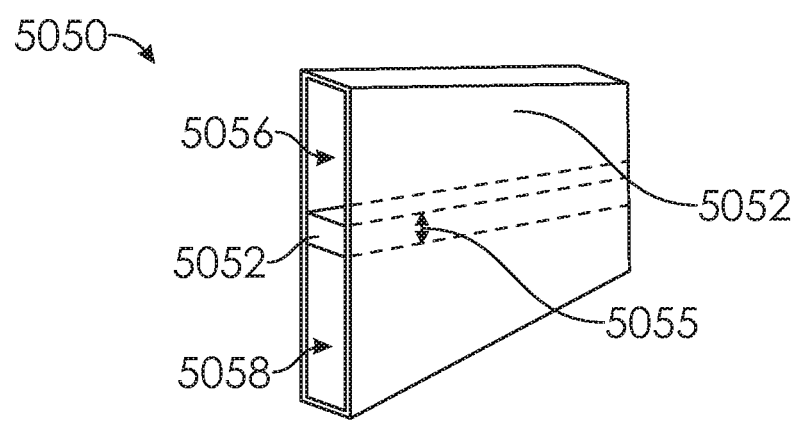
Figure 114A:
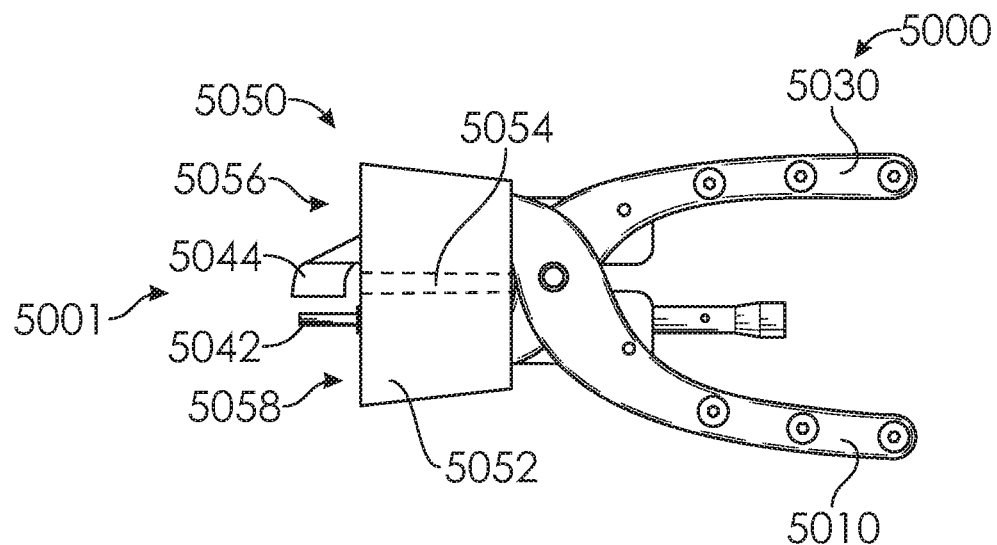
Figure 114B:
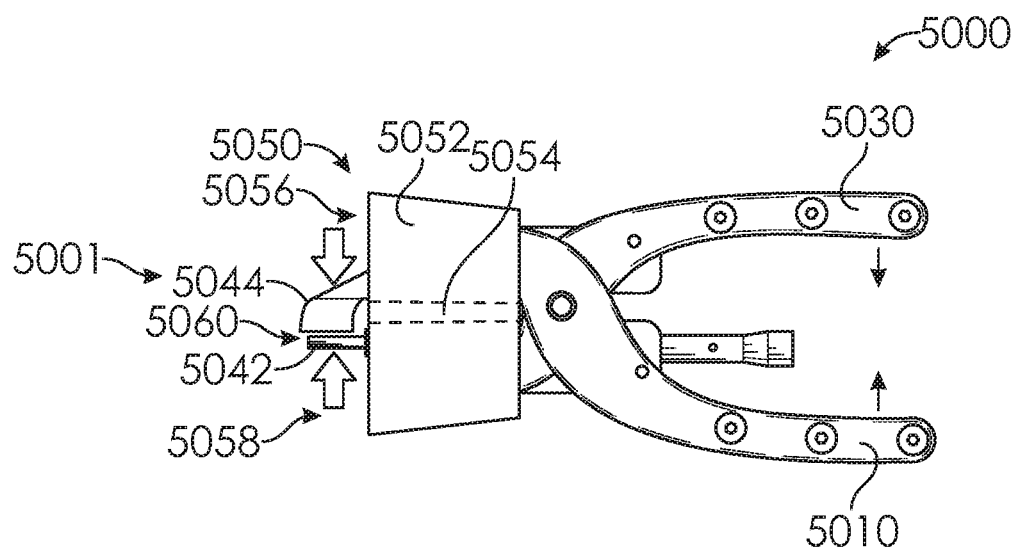
Figure 115:
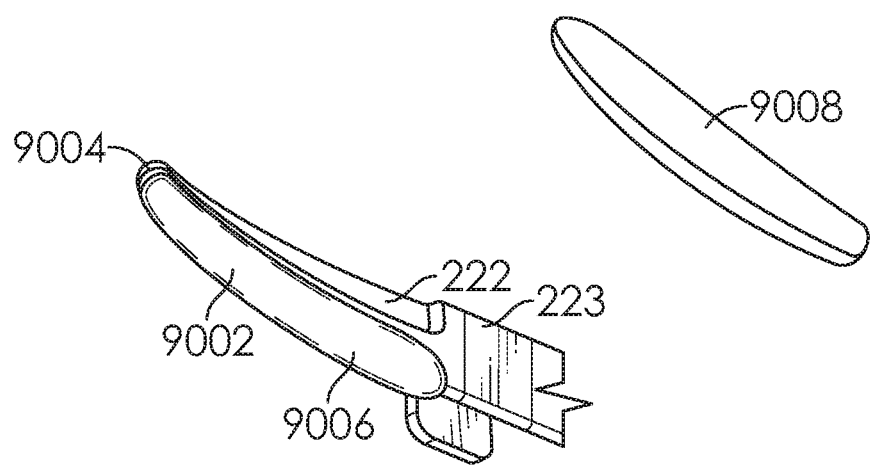
Figure 116:
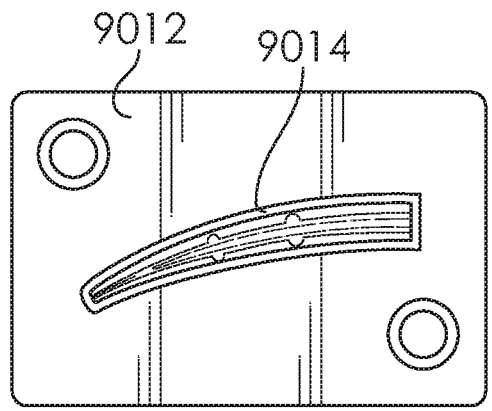
Figure 117:
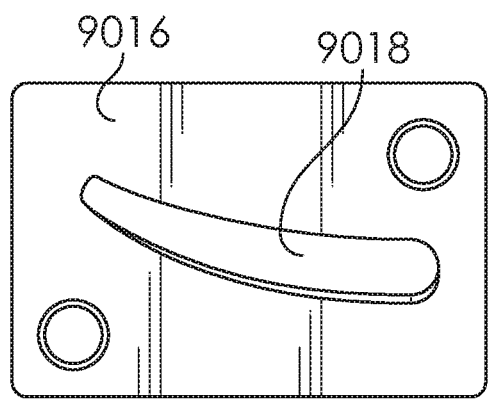
Figure 118:
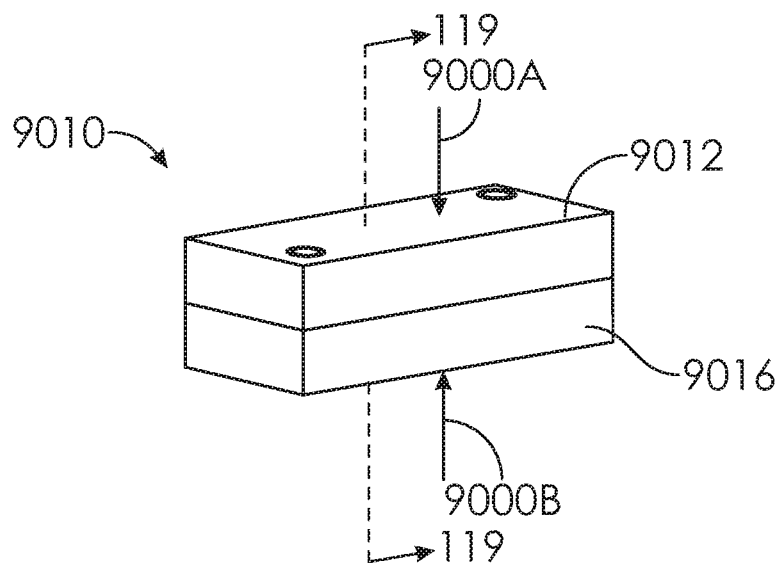
Figure 119:
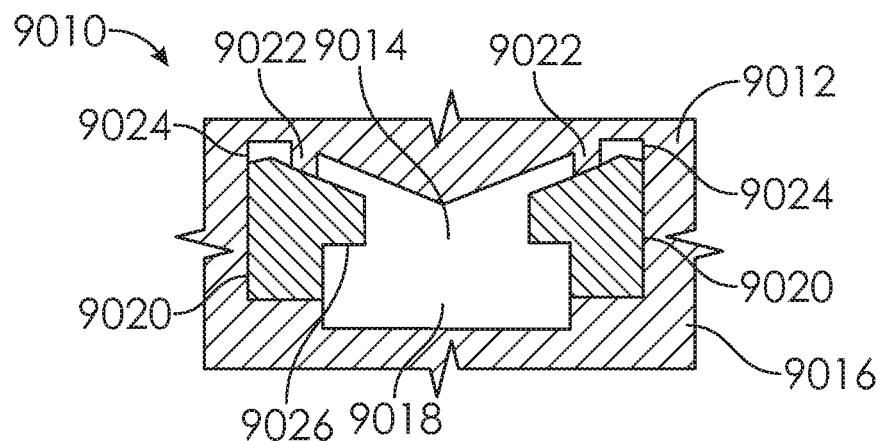
Figure 120:
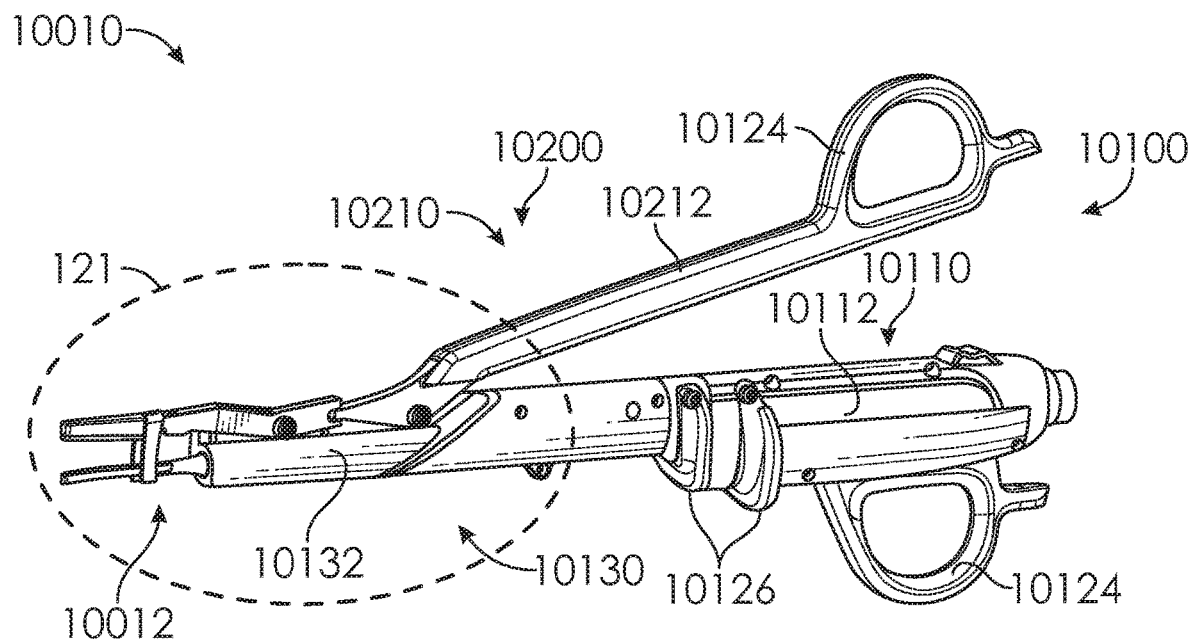
Figure 121:
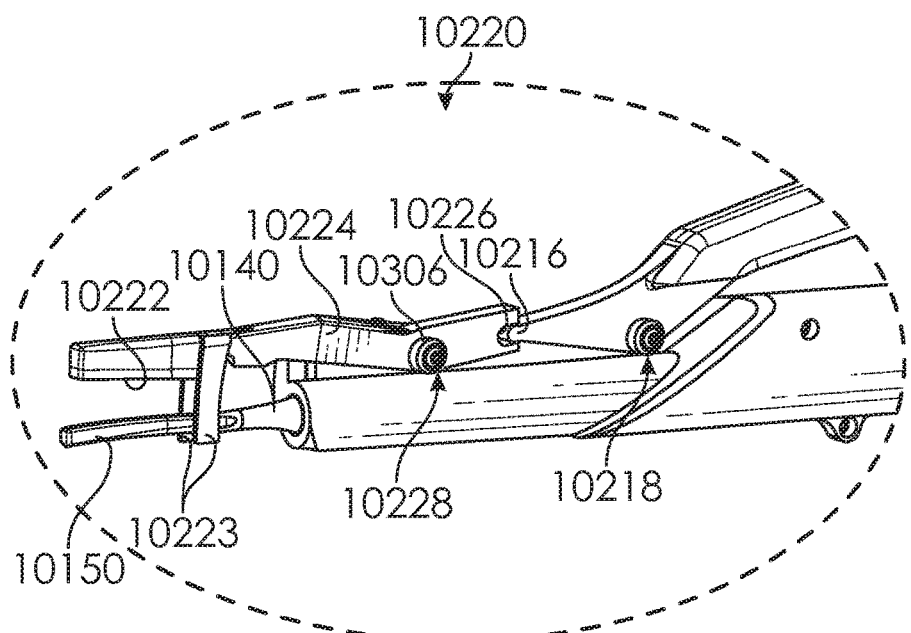
Figure 122:
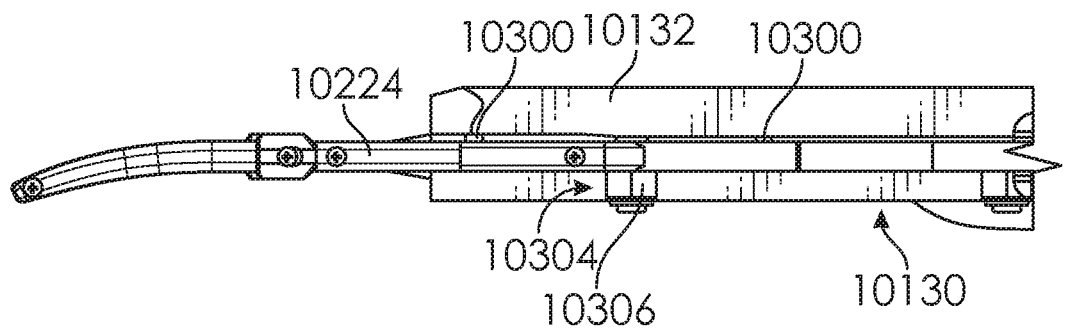
Figure 123:
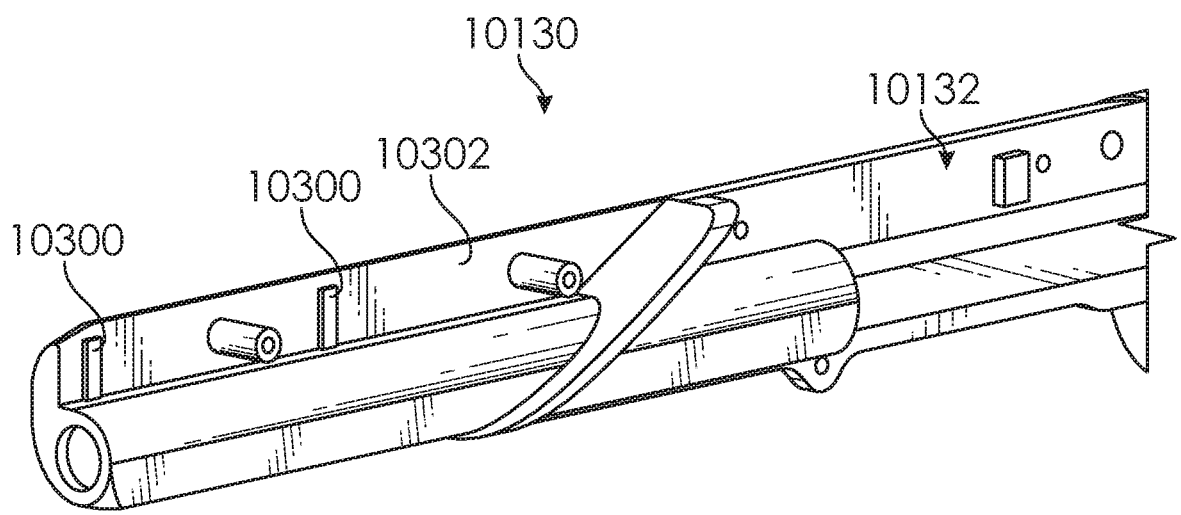

FIG. 92 depicts a fourth modular connection tool containing a replacement clamp arm assembly for replacing the clamp arm assembly of FIG. 90B;

FIG. 93 depicts a proximal end view of the modular connection tool with the replacement clamp arm assembly of FIG. 92;

FIG. 94A depicts an enlarged side view of the surgical instrument of 90A with the clamp arm actuator in an open configuration for connecting the replacement clamp arm assembly thereto with the modular connection tool of FIG. 92;

FIG. 94B depicts the enlarged side view of the surgical instrument and the modular connection tool of FIG. 94A, but showing the modular connection tool with the replacement clamp arm assembly therein being rotatably connected to the clamp arm actuator;

FIG. 94C depicts the enlarged side view of the surgical instrument and the modular connection tool of FIG. 94B, but showing the modular connection tool being removed after connection of the replacement clamp arm assembly to the clamp arm actuator;

FIG. 95 depicts an enlarged perspective view of a twenty-sixth exemplary surgical instrument having a modular body insert coupling associated with a clamp arm assembly;

FIG. 96 depicts an enlarged partially exploded perspective view of the surgical instrument of FIG. 95 showing the clamp arm assembly and a clamp arm actuator;

FIG. 97 depicts distal end view of the clamp arm actuator of FIG. 96;

FIG. 98 depicts a top view of the clamp arm actuator of FIG. 96 having an electromechanical connection;

FIG. 99 depicts a perspective view of the clamp arm assembly of FIG. 96;

FIG. 100 depicts an overmolding process for forming at least a portion of the clamp arm assembly of FIG. 95;

FIG. 101 depicts a side view of a twenty-seventh surgical instrument having a planar compression mechanism with an alternative handle assembly and an alternative clamp arm actuator;

FIG. 102 depicts an enlarged, partially exploded perspective view of a clamp arm assembly of the surgical instrument of FIG. 101 with a first modular side load coupling;

FIG. 103 depicts an enlarged, partially exploded, sectional perspective view of a clamp arm assembly of the surgical instrument of FIG. 101 with a second modular side load coupling;

FIG. 104 depicts an enlarged, partially exploded, sectional perspective view of a clamp arm assembly of the surgical instrument of FIG. 101 with a third modular side load coupling;

FIG. 105 depicts an enlarged, partially exploded, sectional perspective view of a clamp arm assembly of the surgical instrument of FIG. 101 with a fourth modular side load coupling;

FIG. 106 depicts an enlarged, partially exploded, sectional perspective view of a clamp arm assembly of the surgical instrument of FIG. 101 with a modular transverse load coupling;

FIG. 107 depicts a perspective view of a modular connection tool;

FIG. 108 depicts a perspective view of another modular connection tool similar to the modular connection tool of FIG. 107;

FIG. 109 depicts a side view of the modular connection tool of FIG. 107 being received by a twenty-eighth exemplary surgical instrument having a clamp arm assembly and an ultrasonic blade;

FIG. 110 depicts an enlarged side view of the modular connection tool similar to FIG. 109, but showing the modular connection tool compressed between the clamp arm assembly and the ultrasonic blade for connecting a modular clamp pad;

FIG. 111A depicts an enlarged sectional view of a clamp body of the clamp arm assembly of FIG. 110 receiving the clamp pad;

FIG. 111B depicts the enlarged section view of the clamp body similar to FIG. 111A, but showing the modular clamp pad connected to the clamp body;

FIG. 112 depicts a perspective view of an exemplary cover spacer, in a disengaged position with a surgical instrument;

FIG. 113 depicts a perspective view of the cover spacer of FIG. 112;

FIG. 114A depicts a side elevational view of the cover spacer of FIG. 112, in an engaged position with the surgical instrument, the surgical instrument including an end effector in an open position;

FIG. 114B depicts a side elevational view of the cover spacer of FIG. 112, in an engaged position with the surgical instrument and the end effector in an intermediate position;

FIG. 115 depicts a perspective view of an exemplary clamp pad assembly, similar to the clamp pad assembly of FIG. 1A, with an exemplary pad liner disposed thereon and an exemplary blank for use with the clamp pad;

FIG. 116 depicts a top plan view of an exemplary top portion of an exemplary form for coupling the blank to the clamp pad assembly of FIG. 115;

FIG. 117 depicts a top plan view of an exemplary bottom portion of the form for coupling the blank to the clamp pad assembly of FIG. 115;

FIG. 118 depicts a perspective view of an exemplary form using the top portion of FIG. 116 and bottom portion of FIG. 117;

FIG. 119 depicts a cross-sectional view taken along line 119-119 of FIG. 118;

FIG. 120 depicts a perspective view of a twenty-ninth surgical instrument having a three point alignment feature;

FIG. 121 depicts an enlarged partial perspective view of a distal portion of the surgical instrument of FIG. 120;

FIG. 122 depicts a partial top view of the a distal portion of the surgical instrument of FIG. 120; and FIG. 123 depicts a partial perspective view of a distal portion of a handle assembly of the surgical instrument of FIG. 120, with certain portions removed to reveal internal features.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," and "top" are relative terms to provide additional clarity to the figure descriptions provided below. The terms "upper," "lower," "lateral," "transverse," "bottom," and "top" are thus not intended to unnecessarily limit the invention described herein.

I. First Exemplary Ultrasonic Surgical Instrument for Open Surgical Procedures FIGS. 1A-2 and FIGS. 13A-13C illustrate a first exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940; U.S. Pat. Nos. 8,623,027; 9,023,071; 8,461,744; 9,381,058; U.S. Pub. No. 2012/0116265, now abandoned; U.S. Pat. Nos. 9,393,037; 9,095,367; U.S. patent application Ser. No. 61/410,603; and/or U.S. Pub. No. 2015/0080924, issued as U.S. Pat. No. 10,172,636 on Jan. 8, 2019. The disclosures of each of the foregoing patents, publications, and applications are incorporated by reference herein. In addition, or in the alternative, at least part of instrument (10) may be constructed and operable in accordance with at least some of the teachings of U.S. Pub. No. 2017/0105755, entitled "Surgical Instrument with Dual Mode End Effector and Compound Lever with Detents," published Apr. 20, 2017, issued as U.S. Pat. No. 11,020,200 on Jun. 1, 2021, the disclosure of which is incorporated by reference herein; and/or U.S. patent application Ser. No. 62/363,411, entitled "Surgical Instrument with Dual Mode End Effector," filed Jul. 18, 2016, the disclosure of which is incorporated by reference herein.

As described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

Figure 1B:
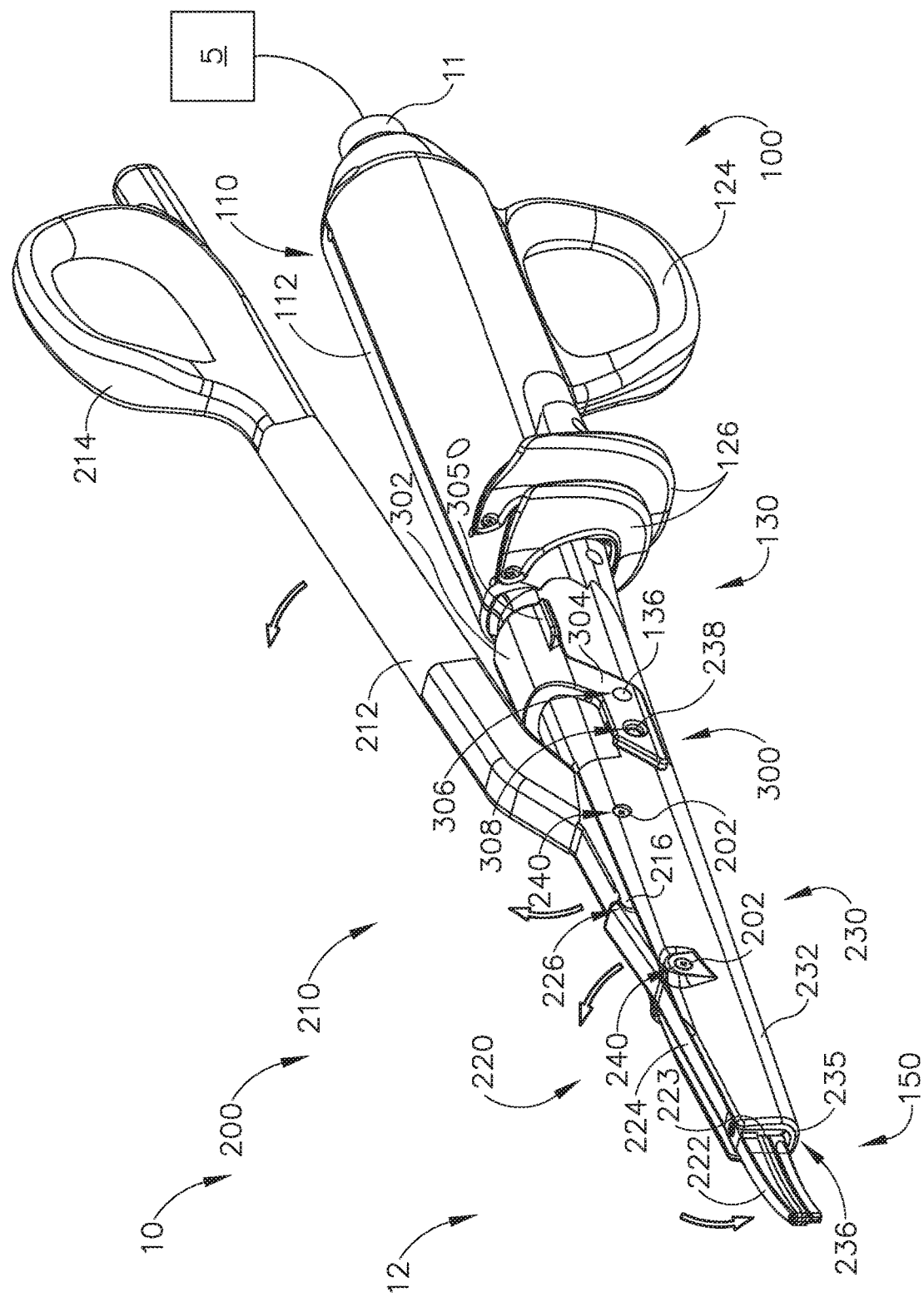
FIG. 1B depicts a perspective view of the instrument of FIG. 1A, with the end effector in a closed configuration.
Figure 2:
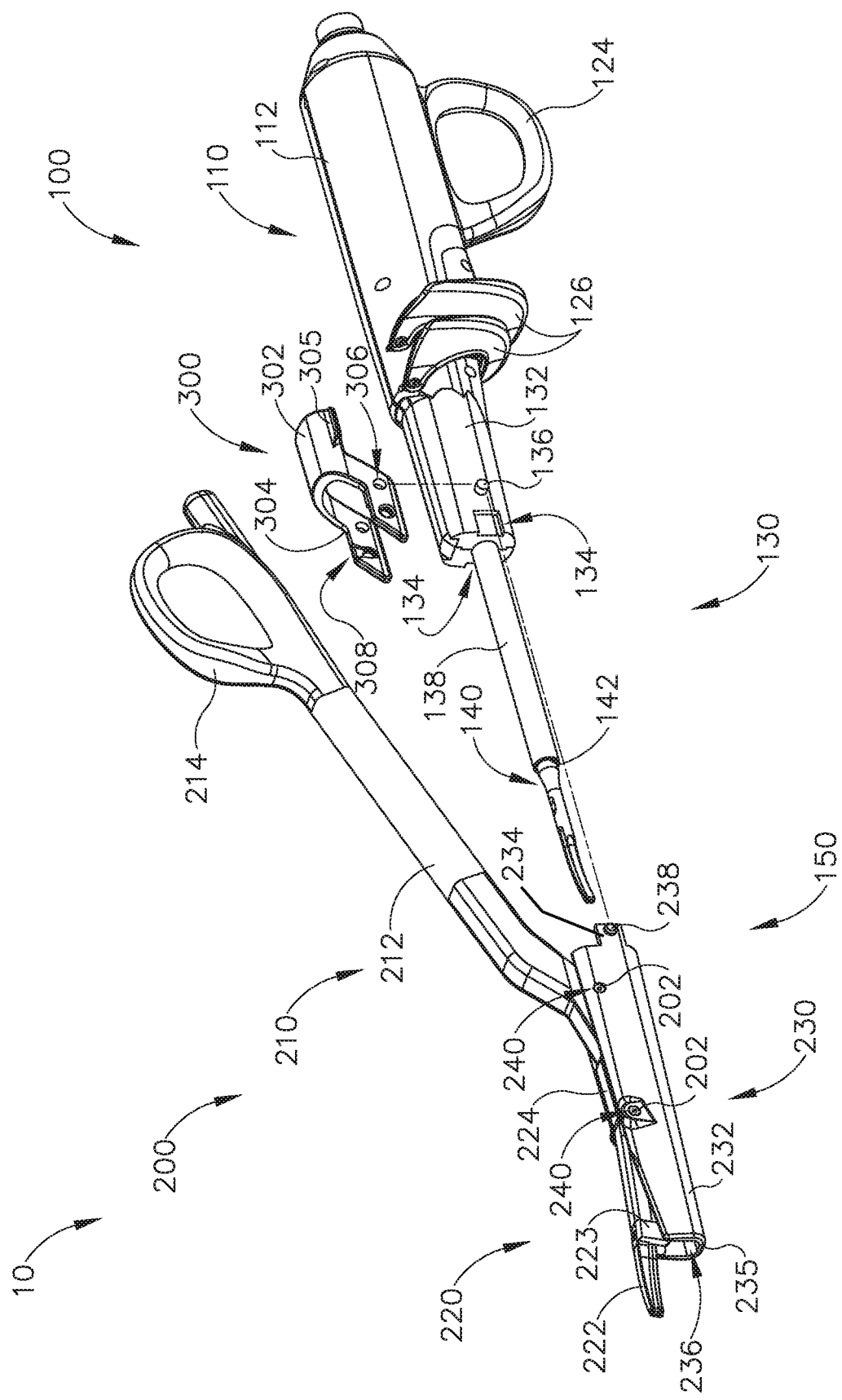
FIG. 2 depicts an exploded perspective view of the instrument of FIG. 1A.
Figure 3:
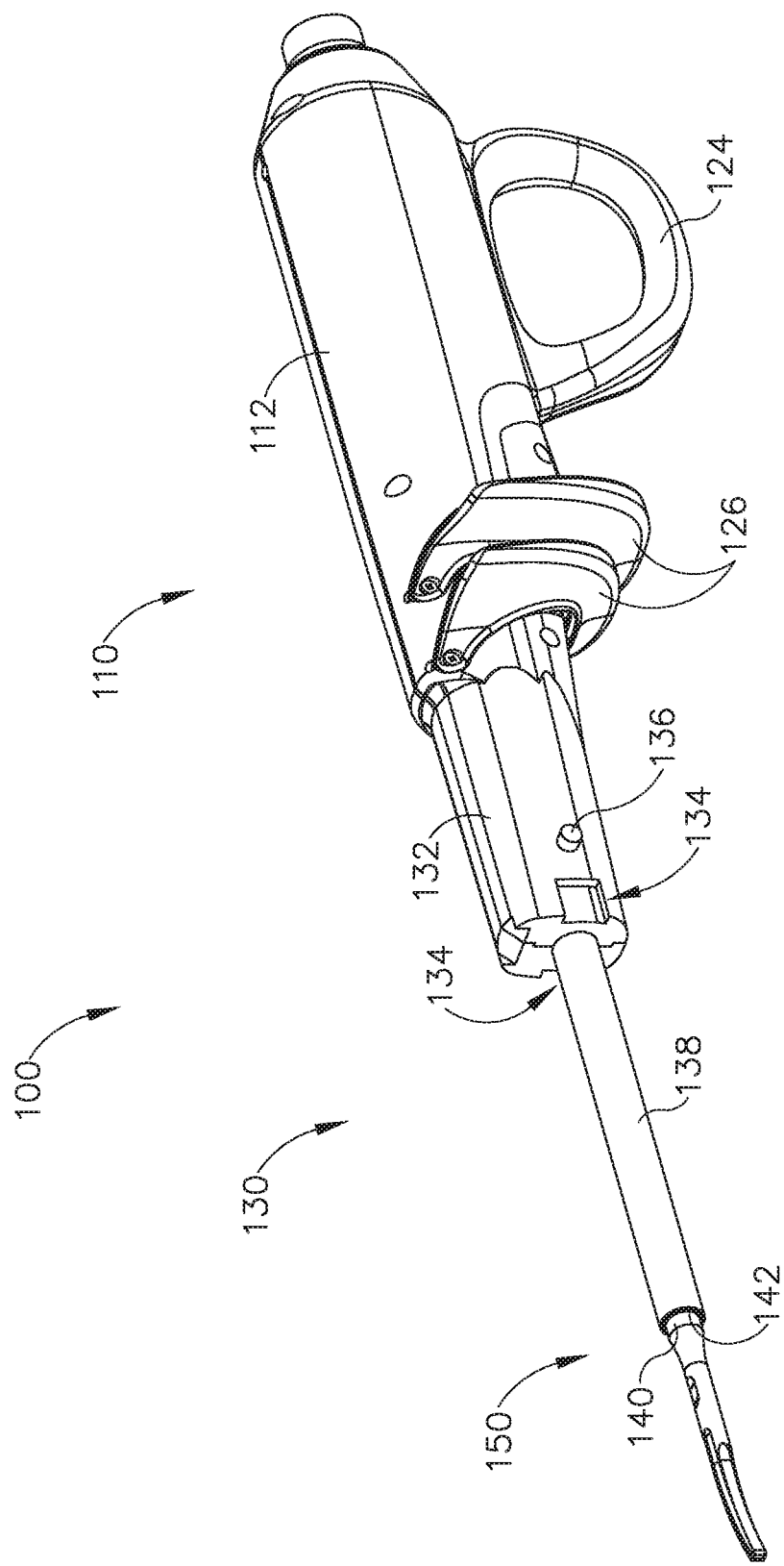
FIG. 3 depicts a perspective view of a first modular assembly of the instrument of FIG. 1A.

Instrument (10) in the present example includes a first modular assembly (100), a second modular assembly (200), and a coupling member (300). As will be described in greater detail below, coupling member (300) may selectively attach first modular assembly (100) with second modular assembly (200) in order to form instrument (10) with an end effector (12). As best seen in FIGS. 1A-1B, end effector (12) comprises an ultrasonic blade (150) and a clamp pad (222) of a clamp pad assembly (220).

Figure 16A:
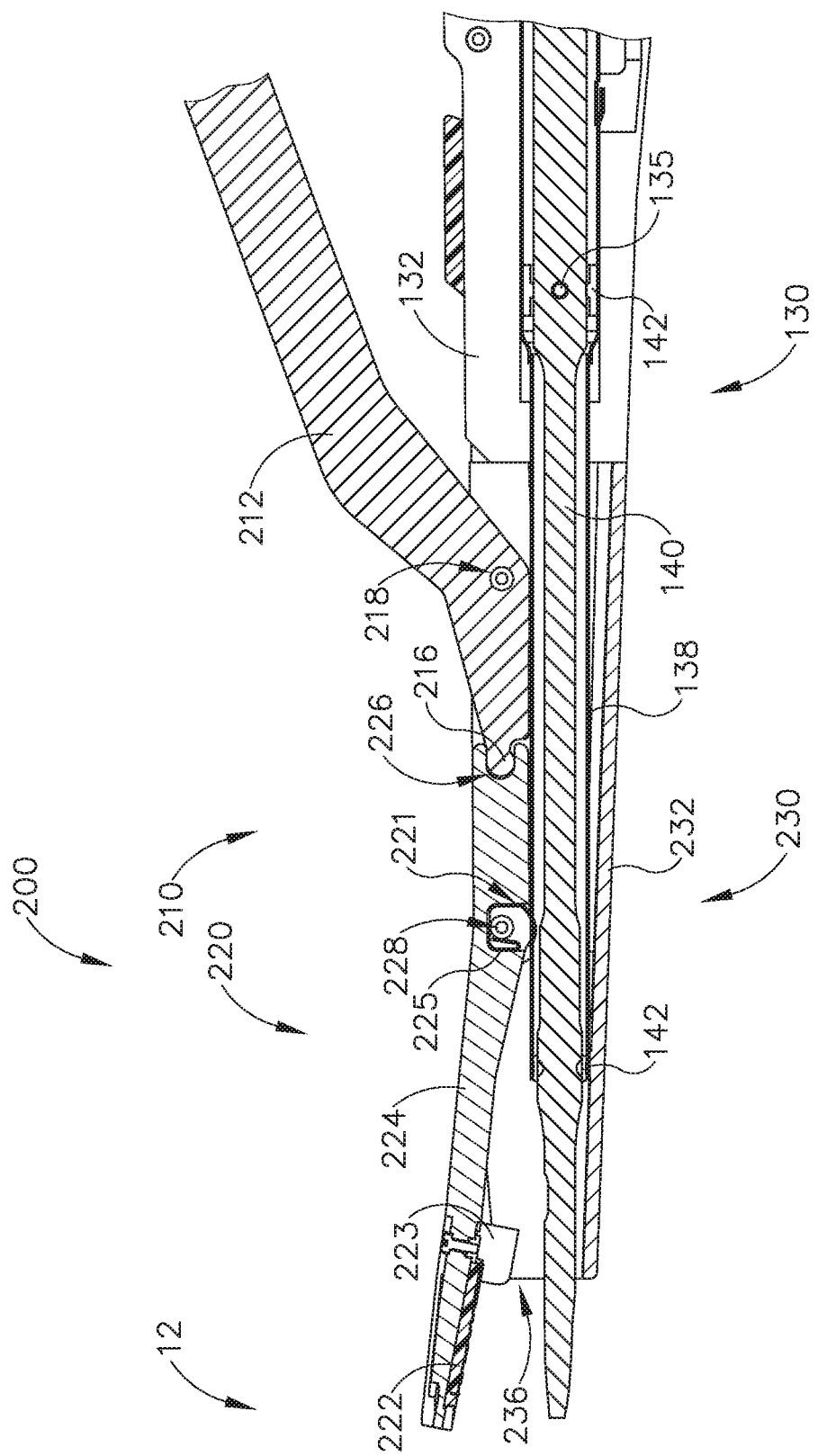
FIG. 16A depicts a cross-sectional side view of the second modular assembly of FIG. 8 coupled with the shaft assembly of FIG. 5, where the end effector is in an open configuration.
Figure 16B:
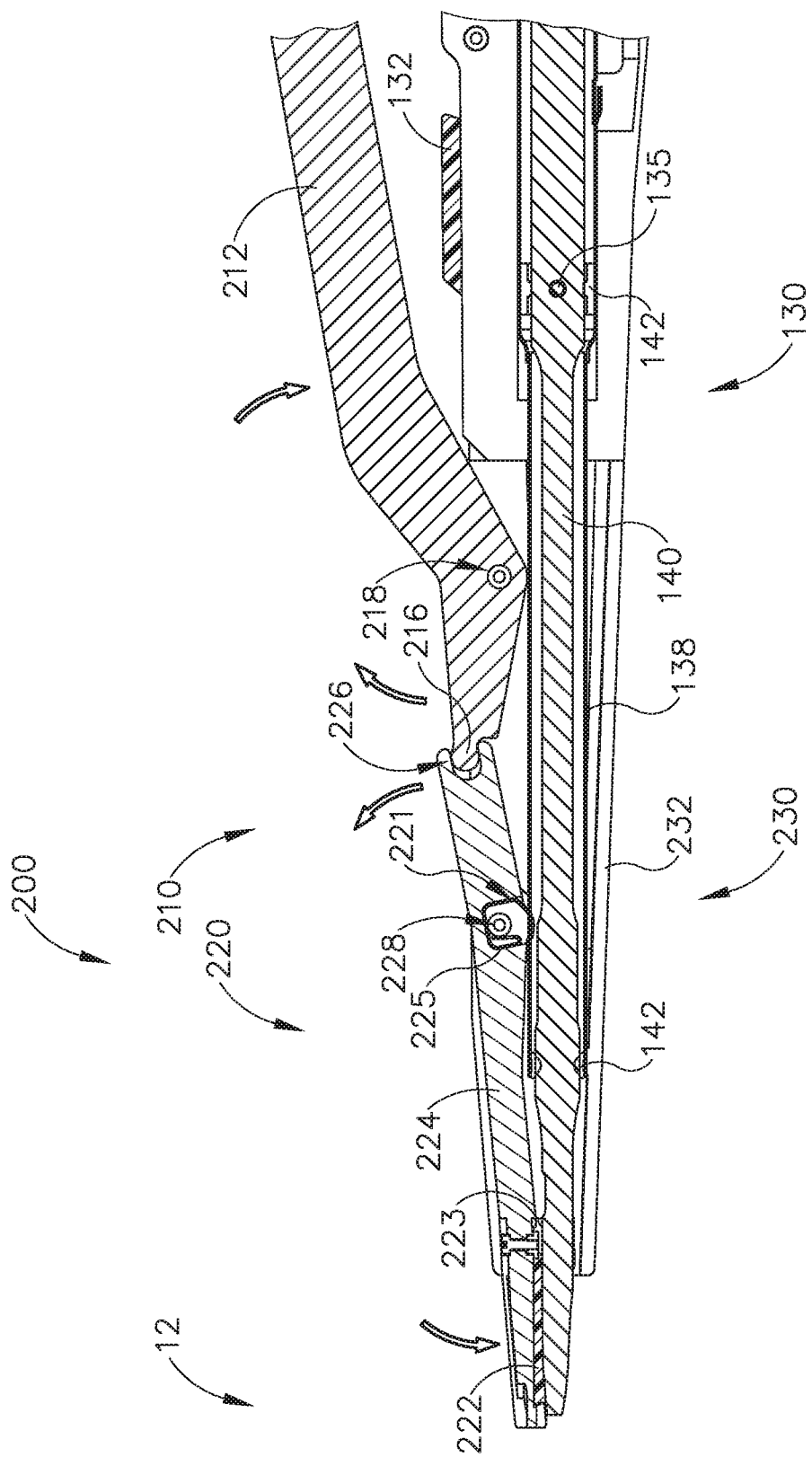
FIG. 16B depicts a cross-sectional side view of the second modular assembly of FIG. 8 coupled with the shaft assembly of FIG. 5, where the end effector is in a closed configuration.

Additionally, as will be described in greater detail below, selected portions of second modular assembly (200) may actuate relative to first modular assembly (100), when properly attached with each other, in order to actuate end effector (12) from an open configuration (FIGS. 1A and 16A), to a closed configuration (FIGS. 1B and 16B). The ability to selectively attach and detach second modular assembly (200) with first modular assembly (100) may provide additional benefits of reusability of either modular assembly (100, 200). For instance, different kinds of first modular assemblies (100) may be used with second modular assembly (200) to provide different kinds of surgical instruments. Similarly, different kinds of second modular assemblies (200) may be used with first modular assembly (100) to provide different kinds of surgical instruments. Additionally, moving components of second modular assembly (200) may be housed within static components of second modular assembly (200), which may provide additional advantages, some of which are described below while others will be apparent to one having ordinary skill in the art in view of the teachings herein.

First modular assembly (100) includes a handle assembly (110), a shaft assembly (130) extending distally from handle assembly (110), and an ultrasonic blade (150) extending distally from shaft assembly (130). Handle assembly (110) includes a body (112), a finger grip ring (124), a pair of buttons (126) distal to finger grip ring (124), and an ultrasonic transducer assembly (30) housed within body (112).

Shaft assembly (130) includes a proximal outer sheath (132) extending distally from body (112), a tube (138) extending distally from proximal outer sheath (132), and a waveguide (140) extending within and through both proximal outer sheath (132) and tube (138). Proximal outer sheath (132) includes a pair of protrusions (136). Additionally, proximal outer sheath (132) defines a pair of recesses (134). As will be described in greater detail below, recesses (134) are dimensioned to mate with a portion of distal outer sheath (230) while protrusions (136) are configured to pivotally couple proximal outer sheath (132) with coupling member (300). Both recesses (134) and protrusions (136) may help couple first modular assembly (100) with coupling member (300).

Proximal outer sheath (132) may be fixed relative to body (112), while tube (138) may be fixed relative to proximal outer sheath (132). As will be described in greater detail below, waveguide (140) may attach to transducer assembly (30) and be supported by portions proximal outer sheath (132) and tube (138). Ultrasonic blade (150) may be unitarily connected to waveguide (140), and also extend distally from waveguide (140). As will be described in greater detail below, waveguide (140) is operable to connect to ultrasonic transducer assembly (30) in order to provide acoustic communication between ultrasonic blade (150) and transducer assembly (30).

Figure 4:
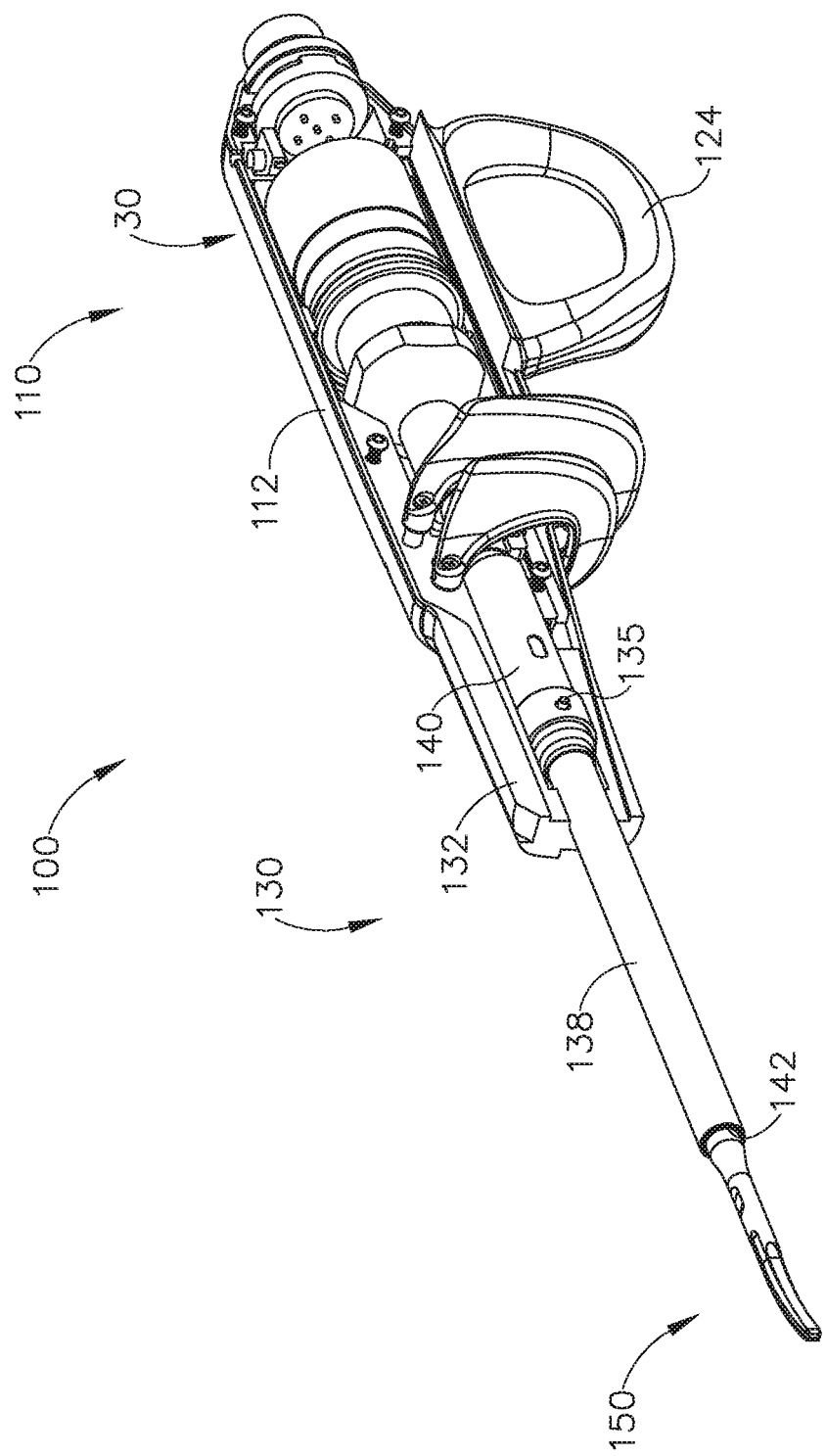
FIG. 4 depicts a perspective view of the first modular assembly of FIG. 3, with selected portions purposefully omitted for clarity.
Figure 5:
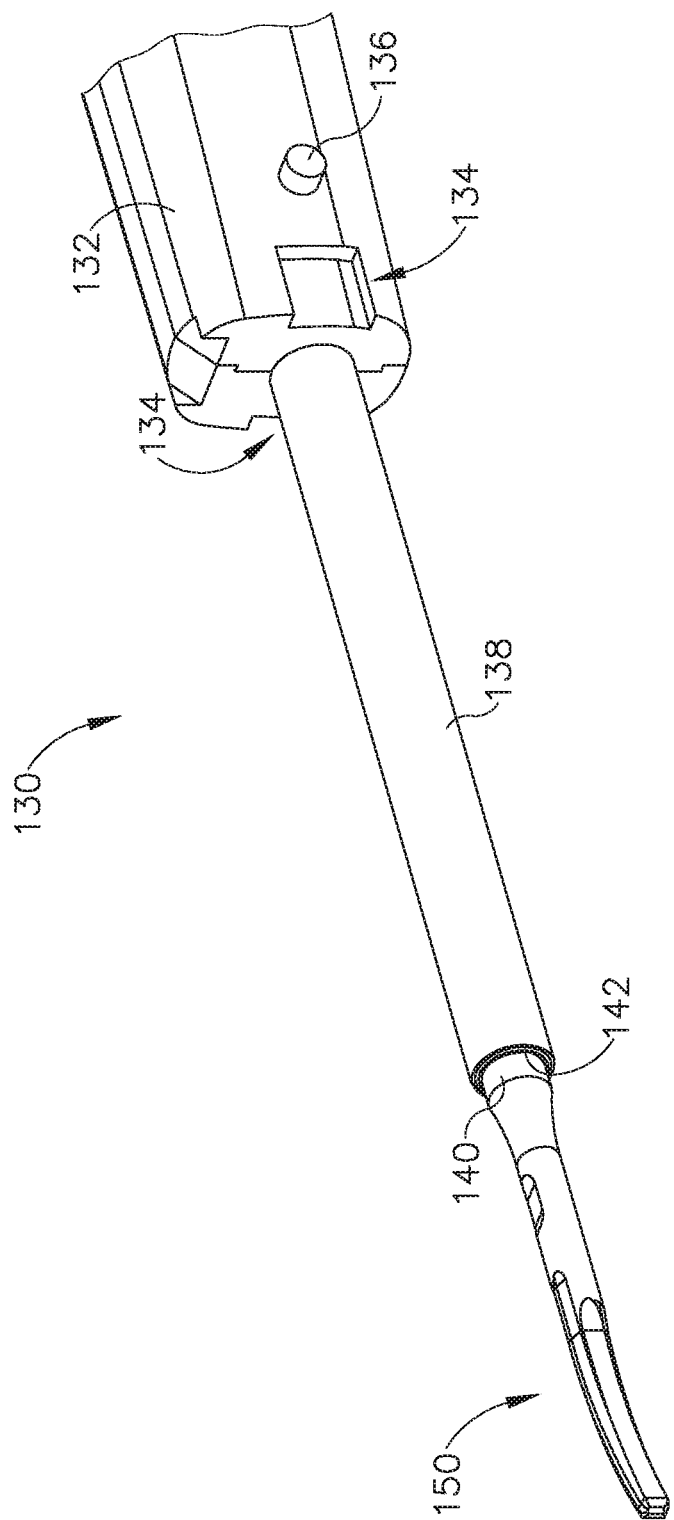
FIG. 5 depicts a perspective view of a shaft assembly and a blade assembly of the first modular assembly of FIG. 3.
Figure 6:
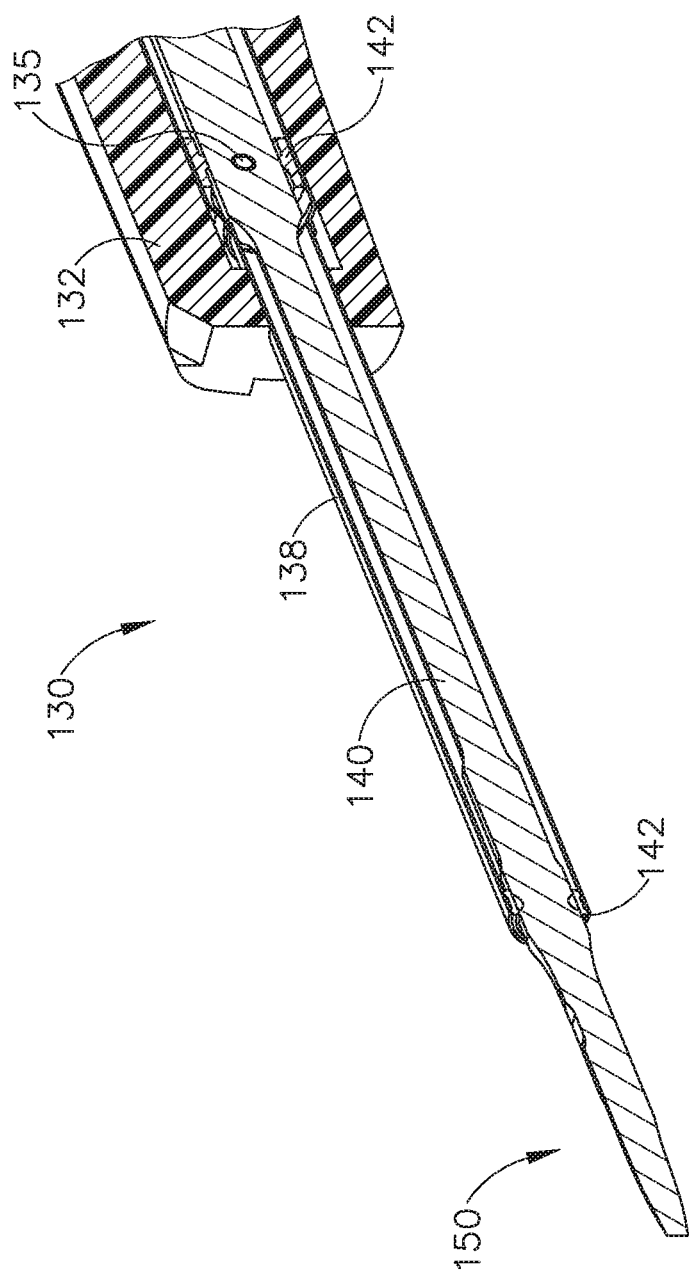
FIG. 6 depicts a cross-sectional perspective view of the shaft assembly and blade assembly of FIG. 5.

Referring to FIG. 4, ultrasonic transducer assembly (30) is housed within body (112) of handle assembly (110). As seen in FIGS. 1A-1B, transducer assembly (30) is coupled with a generator (5) via a plug (11). Transducer assembly (30) receives electrical power from generator (5) and converts that power into ultrasonic vibrations through piezoelectric principles. Generator (5) may include a power source and control module that is configured to provide a power profile to transducer assembly (30) that is particularly suited for the generation of ultrasonic vibrations through transducer assembly (30). Generator (5) may also be configured to provide a power profile that enables end effector (12) to apply RF electrosurgical energy to tissue.

By way of example only, generator (5) may comprise a GEN 300 sold by Ethicon Endo-Surgery, Inc. of Cincinnati, Ohio. In addition or in the alternative, generator (not shown) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (5) may be integrated into handle assembly (110), and that handle assembly (110) may even include a battery or other on-board power source such that plug (11) is omitted. Still other suitable forms that generator (5) may take, as well as various features and operabilities that generator (5) may provide, will be apparent to those of ordinary skill in the art in view of the teachings herein.

Ultrasonic vibrations that are generated by transducer assembly (30) are communicated along acoustic waveguide (140) when properly coupled. Waveguide (140) is mechanically and acoustically coupled with transducer assembly (30). Waveguide (140) extends through shaft assembly (130) to reach ultrasonic blade (150). Waveguide (140) may be secured to proximal outer sheath (132) and/or body (112) via a pin (135) extending through waveguide (140) and proximal outer sheath (132). Pin (135) may help ensure waveguide (140) remains longitudinally and rotationally fixed relative to the rest of shaft assembly (130) when waveguide (140) is in a deactivated state (i.e. not vibrating ultrasonically).

Additionally, waveguide (140) may be supported by tube (138) via seals (142) located between an interior of tube (138) and an exterior of waveguide (140). Seals (142) may also prevent unwanted matter and fluid from entering portions of tube (138) housing waveguide (140). Pin (135) and seals (142) are located at positions along the length of waveguide (140) corresponding to nodes associated with resonant ultrasonic vibrations communicated through waveguide (140). Therefore, contact between waveguide (140) and pin (135), as well as contact between waveguide (140) and seals (142) may not affect ultrasonic vibrations communicated through waveguide (154).

When ultrasonic blade (150) is in an activated state (i.e., vibrating ultrasonically), ultrasonic blade (150) is operable to effectively cut through and seal tissue, particularly when the tissue is being clamped between clamp pad (222) and ultrasonic blade (150). It should be understood that waveguide (140) may be configured to amplify mechanical vibrations transmitted through waveguide (140). Furthermore, waveguide (140) may include features operable to control the gain of the longitudinal vibrations along waveguide (140) and/or features to tune waveguide (140) to the resonant frequency of the system.

In the present example, the distal end of ultrasonic blade (150) is located at a position corresponding to an anti-node associated with resonant ultrasonic vibrations communicated through waveguide (140), in order to tune the acoustic assembly to a preferred resonant frequency $f_o$ when the acoustic assembly is not loaded by tissue. When transducer assembly (30) is energized, the distal end of ultrasonic blade (150) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through the waveguide to (140) reach ultrasonic blade (150), thereby providing oscillation of ultrasonic blade (150) at the resonant ultrasonic frequency. Thus, when tissue is secured between ultrasonic blade (150) and clamp pad (222), the ultrasonic oscillation of ultrasonic blade (150) may simultaneously sever the tissue and denature the proteins in adjacent tissue cells, thereby providing a coagulative effect with relatively little thermal spread.

In some versions, an electrical current may also be provided through ultrasonic blade (150) and/or clamp pad (222) to also seal the tissue. It should therefore be understood that instrument (10) may also be configured to provide radiofrequency (RF) energy to a surgical site via end effector (12). By way of example only, an operator may rely mainly on the use of ultrasonic energy from blade (150) to sever tissue that is captured between ultrasonic blade (150) and clamp pad (222). The operator may further rely on the use of RF energy from end effector (12) to seal the severed tissue. Of course, it will be understood that the ultrasonic energy from blade (150) may seal tissue to some degree, such that the RF energy from end effector (12) may supplement the sealing that would already be provided from the ultrasonic energy. It will also be understood that there may be instances where the operator may wish to simply use end effector (12) to only apply RF energy to tissue, without also applying ultrasonic energy to tissue. As will be appreciated from the description herein, some versions of instrument (10) are capable of providing all of the above noted kinds of functionality. Various ways in which instrument (10) may be configured and operable to provide both ultrasonic and RF electrosurgical modes of operation are described in various references cited herein; while other ways in which instrument (10) may be configured and operable to provide both ultrasonic and RF electrosurgical modes of operation will be apparent to those of ordinary skill in the art in view of the teachings herein.

An operator may activate buttons (126) to selectively activate transducer assembly (30) to thereby activate ultrasonic blade (150). In the present example, two buttons (126) are provided. In some versions, one button (126) is provided for activating ultrasonic blade (150) at a first power profile (e.g., a first frequency and/or first amplitude) and another button (126) is provided for activating ultrasonic blade (150) at a second power profile (e.g., a second frequency and/or second amplitude). In some other versions, one button (126) is provided for activating ultrasonic blade (150) with ultrasonic energy, and the other button (126) is provided for activating end effector (12) with RF energy. In some other versions, one button (126) is operable to activate ultrasonic blade (150) with ultrasonic energy while simultaneously activating end effector (12) with RF energy; while the other button (126) is only operable to activate ultrasonic blade (150) with ultrasonic energy. In some other versions, at least one button (126) is operable to initially activate ultrasonic blade (150) with ultrasonic energy, then based on one or more other conditions (e.g., time, measured impedance, etc.)

while button (126) remains activated, eventually activating end effector (12) with RF energy while still activating ultrasonic blade (150) with ultrasonic energy. In some other versions, at least one button (126) is operable to initially activate ultrasonic blade (150) with ultrasonic energy, then based on one or more other conditions (e.g., time, measured impedance, etc.) while button (126) remains activated, eventually activating end effector (12) with RF energy while ceasing activation of ultrasonic blade (150) with ultrasonic energy. In some other versions, at least one button (126) is operable to initially activate end effector (12) with RF energy, then based on one or more other conditions (e.g., time, measured impedance, etc.) while button (126) remains activated, eventually activating ultrasonic blade (150) with ultrasonic energy while ceasing activation of end effector (12) with RF energy.

It should be understood that any other suitable number of buttons and/or otherwise selectable power levels and/or power modalities may be provided. For instance, a foot pedal may be provided to selectively activate transducer assembly (30).

Buttons (126) of the present example are positioned such that an operator may readily fully operate instrument (10) with a single hand. For instance, when first and second modular assemblies (100, 200) are coupled, the operator may position their thumb in thumb grip ring (214), position their ring finger in finger grip ring (124), position their middle finger about body (112), and manipulate buttons (126) using their index finger. Of course, any other suitable techniques may be used to grip and operate instrument (10); and buttons (126) may be located at any other suitable positions.

Figure 7:
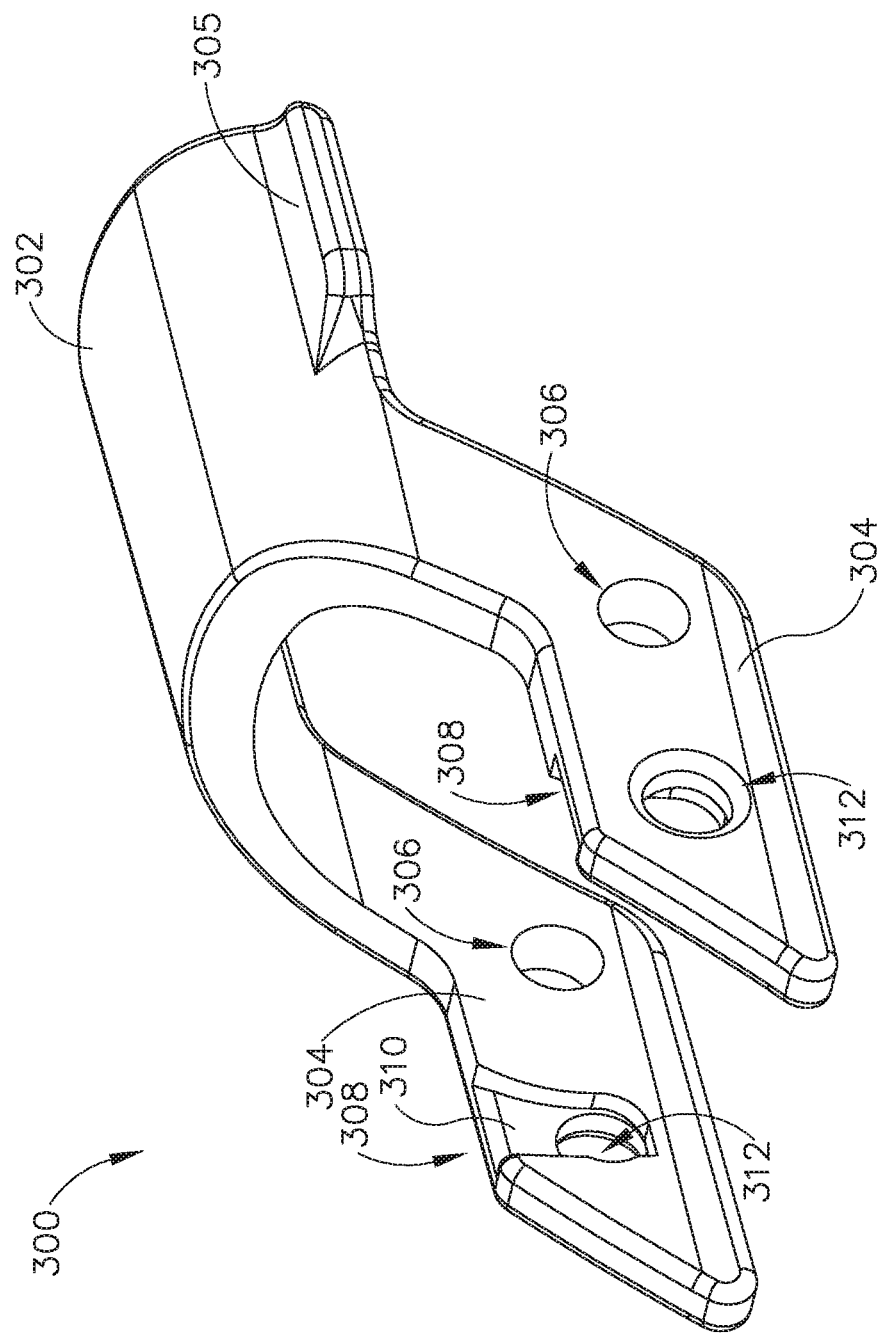
FIG. 7 depicts a perspective view of a coupling member of the instrument of FIG. 1A.
Figure 8:
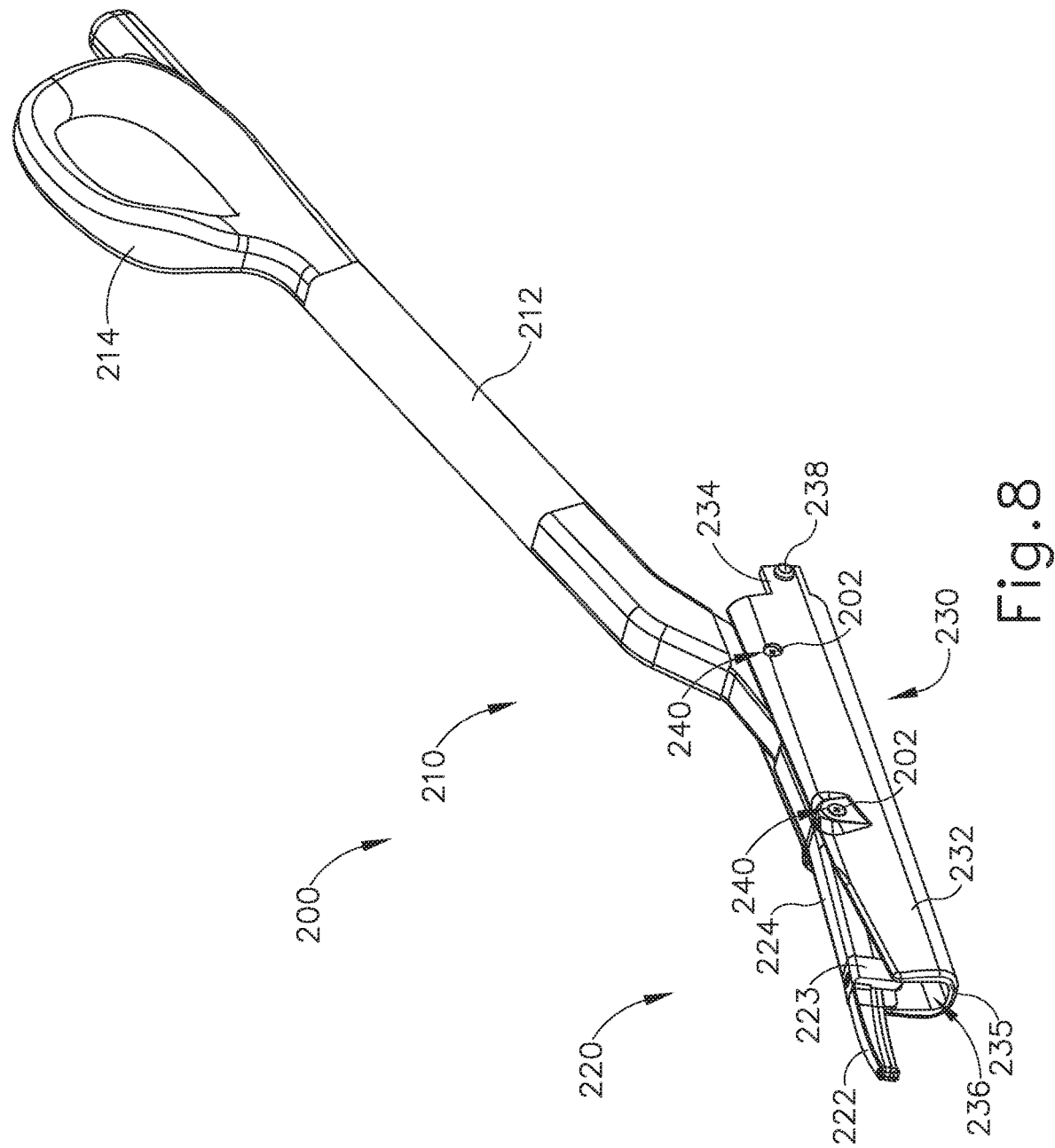
FIG. 8 depicts a perspective view of a second modular assembly of the instrument of FIG. 1A.
Figure 9:
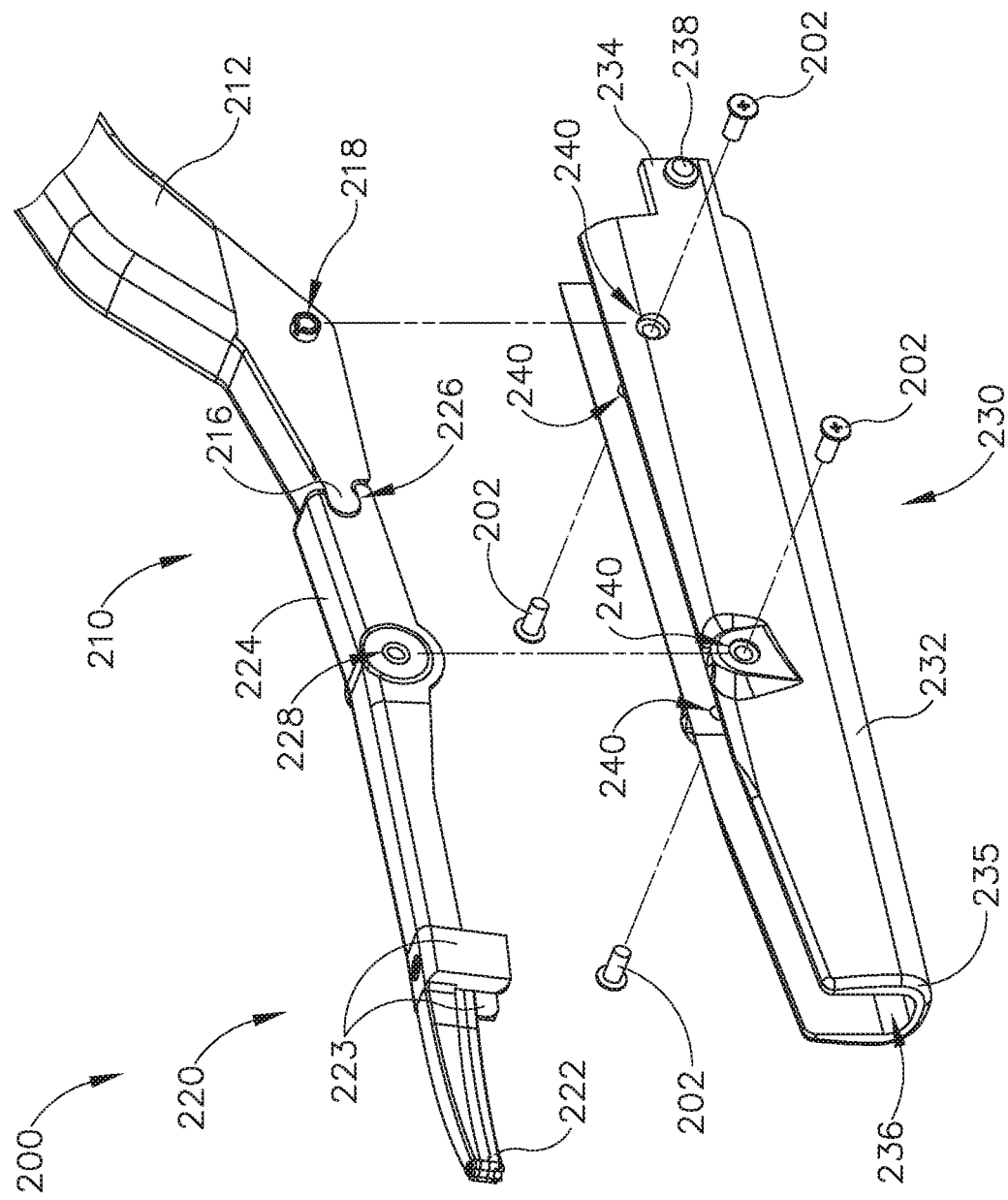
FIG. 9 depicts an exploded perspective view of the second modular assembly of FIG. 8.
Figure 10:
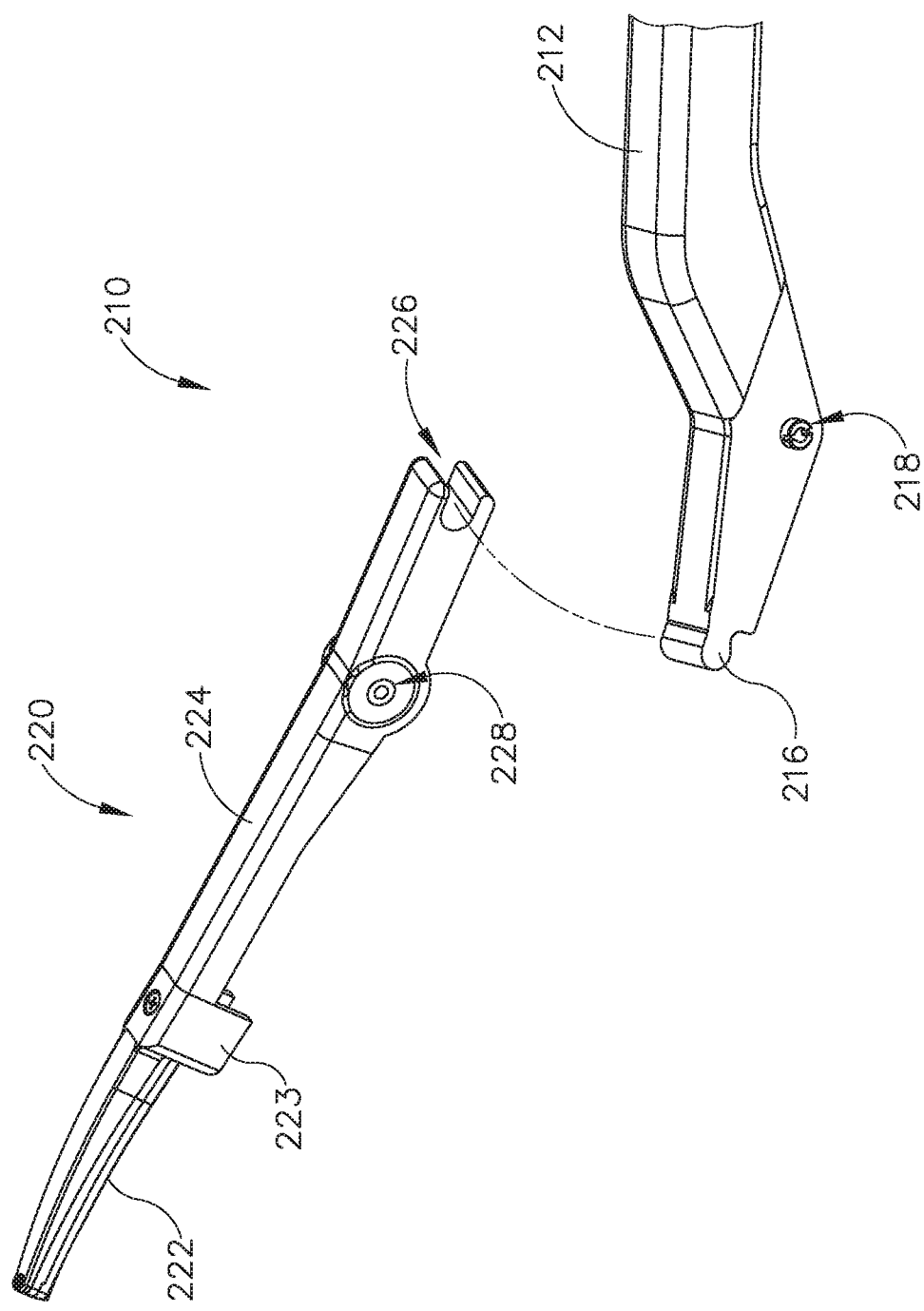
FIG. 10 depicts an exploded perspective view of a clamp arm assembly and a clamp pad assembly of the second modular assembly of FIG. 8.
Figure 11:
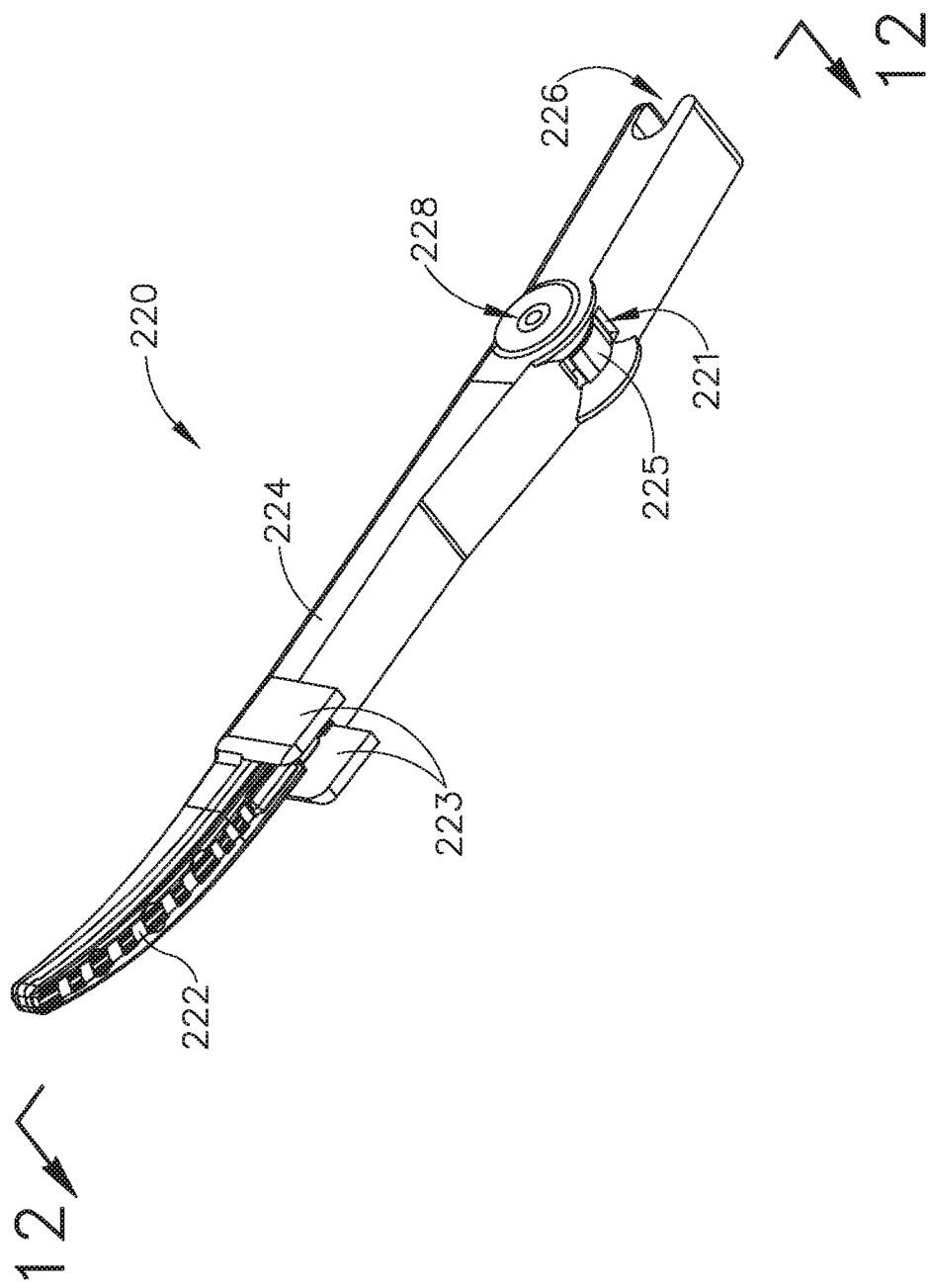
FIG. 11 depicts a perspective view of the clamp arm assembly of FIG. 10.
Figure 12:
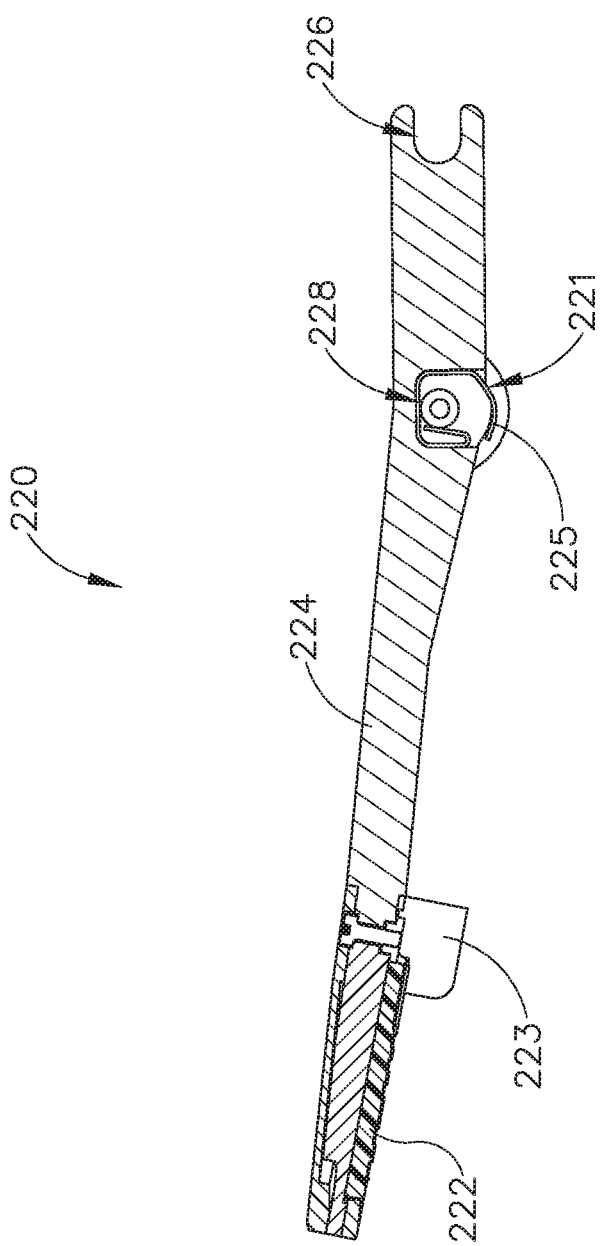
FIG. 12 depicts a cross-sectional side view of the clamp arm assembly of FIG. 10, taken along line 12-12 of FIG. 11.

As mentioned above, and as will be described below, coupling member (300) is configured to selectively couple first modular assembly (100) with second modular assembly (200). As best seen in FIG. 7, coupling member (300) comprises a body (302), a pair of resilient arms (304) extending from body (302), and a pair of grips (305) extending from body (302). Resilient arms (304) each define a respective pivot bore (306) and locking assembly (308). Resilient arms (304) are spaced apart from each other in order to receive proximal outer sheath (132) and to snap-fit pivot bores (306) with respective protrusions (136). Therefore, as shown between FIGS. 13B-13C and 14B-14C, coupling member (300) is configured to pivotally connect with proximal outer sheath (132) via pivot bores (306) and protrusions (136). While in the current example, coupling member (300) and proximal outer sheath (132) are pivotally coupled via snap-fitting, any other type of suitable connection may be used as would be apparent to one having ordinary skill in the art in view of the teachings herein. For example, protrusions (136) may be extendable relative to proximal outer sheath (132) in order to pivotally couple with pivot bore (306) of coupling member (300). Grips (305) may be positioned on body (302) such that an operator may easily rotate coupling member (300) relative to outer sheath (132) via grips (305).

Each locking assembly (308) includes an interior contact wall (310) facing toward each other and a coupling recess (312). As will be described in greater detail below, locking assembly (308) is configured to rotate about pivot bore (306) and protrusions (136) in order to selectively couple with portions of second modular assembly (200).

While coupling member (300) in the current example is used to connect first modular assembly (100) with second modular assembly (200), it should be understood that coupling member (300) may be incorporated into any suitable type of modular assembly that would be apparent to one having ordinary skill in the art in view of the teachings herein. For example, coupling assembly (300) may be modified to couple different modular clamp arm assemblies with first modular assembly (100) where the different modular clamp arm assemblies include clamp arm assemblies such as those taught in U.S. Pub. No. 2017/0105788, entitled "Surgical Instrument with Dual Mode End Effector and Modular Clamp Arm Assembly," published Apr. 20, 2017, issued as U.S. Pat. No. 10,893,914 on Jan. 19, 2021, the disclosure of which is incorporated by reference herein. Thus, one modular clamp arm assembly that may be coupled with first modular assembly (100) may provide pivotal motion of a clamp arm at one side of ultrasonic blade (150) while the other modular clamp arm assembly that may be coupled with first modular assembly (100) may provide pivotal motion of a clamp arm at the other side of ultrasonic blade (150). Other suitable kinds of clamp arm assemblies that may be used to provide different kinds of second modular assemblies (200) will be apparent to those of ordinary skill in the art in view of the teachings herein.

Second modular assembly (200) includes a clamp arm assembly (210), a clamp pad assembly (220), and a distal outer sheath (230). As will be described in greater detail below, distal outer sheath (230) is configured to couple with both coupling member (300) and proximal outer sheath (132) in order to selectively couple first modular assembly (100) with second modular assembly (200). It other words, when properly coupled, proximal outer sheath (132) and distal outer sheath (230) may be fixed relative to one another. As will also be described in greater detail below, clamp arm assembly (210) and clamp pad assembly (220) are both pivotally coupled with distal outer sheath (230). Additionally, clamp arm assembly (210) and clamp pad assembly (220) are dimensioned to mesh with each other such that rotation of one assembly (210, 220) relative to distal outer sheath (230) causes rotation of the other assembly (210, 220) relative to distal outer sheath (230). In other words, clamp arm assembly (210) and clamp pad assembly (220) are capable of rotating each other relative to distal outer sheath (230).

Distal outer sheath (230) includes a U-shaped body (232) extending from a distal face (235) and terminating in a pair of proximally presented projections (234). Proximally presented projections (234) each include a lateral protrusion (238) extending away from U-shaped body (232). U-shaped body (232) defines a longitudinal pathway (236) and a plurality of bores (240). U-shaped body (232) and longitudinal pathway (236) are dimensioned to receive tube (138) and to rotationally house a portion of clamp arm assembly (210) and clamp pad assembly (220). In particular, as best shown between FIGS. 13A-13B, U-shaped body (232) may be inserted over ultrasonic blade (150) and tube (138) such that tube (138) will rest under clamp arm assembly (210) and clamp pad assembly (220). Tube (138) may protect waveguide (140) such that clamp arm assembly (210) and clamp pad assembly (220) do not contact adjacent portions of waveguide (140).

Figure 13A:
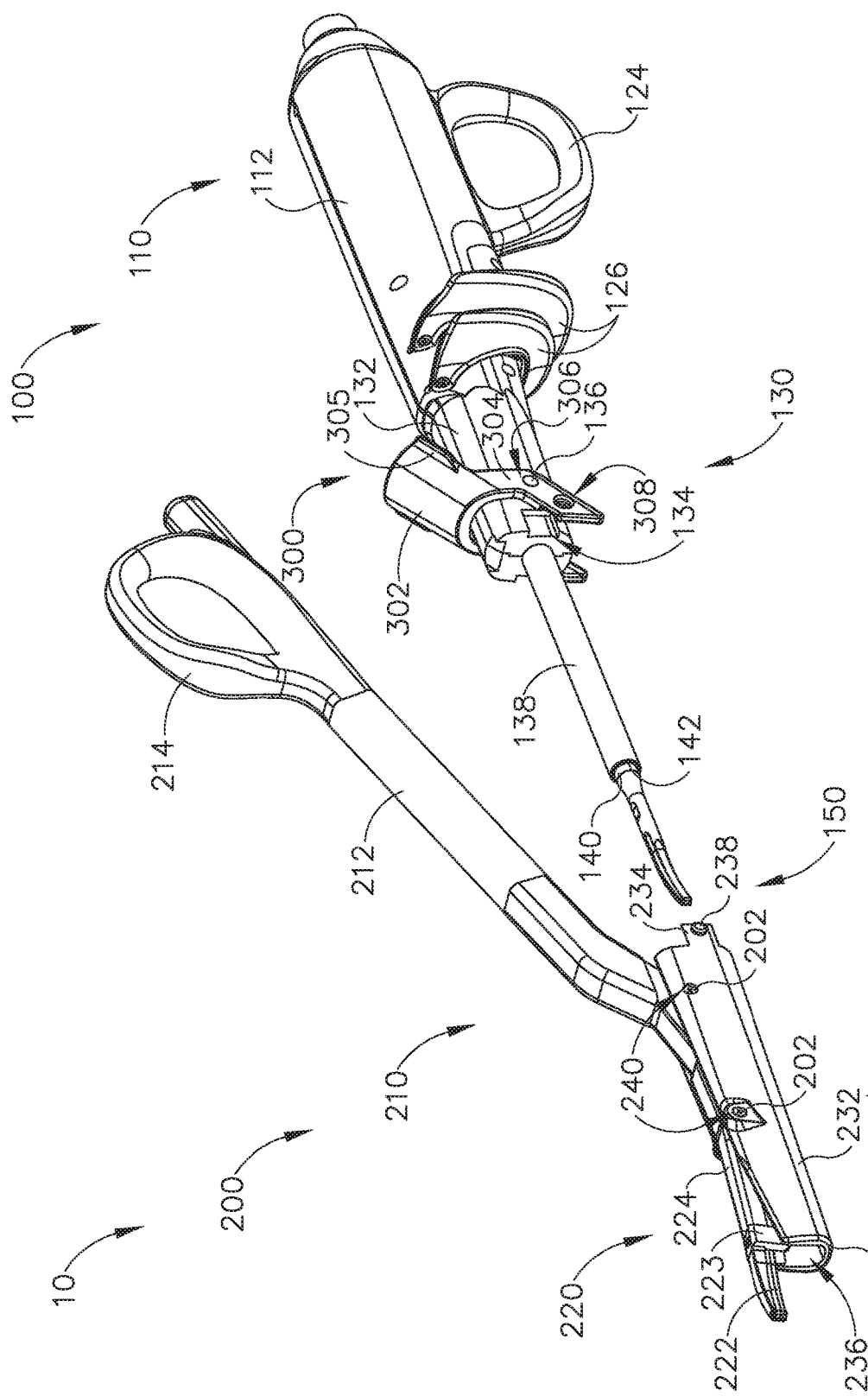
FIG. 13A depicts a perspective view of the second modular assembly of FIG. 8 aligned with the shaft assembly of FIG. 5 in order to couple the modular assemblies together.
Figure 13B:
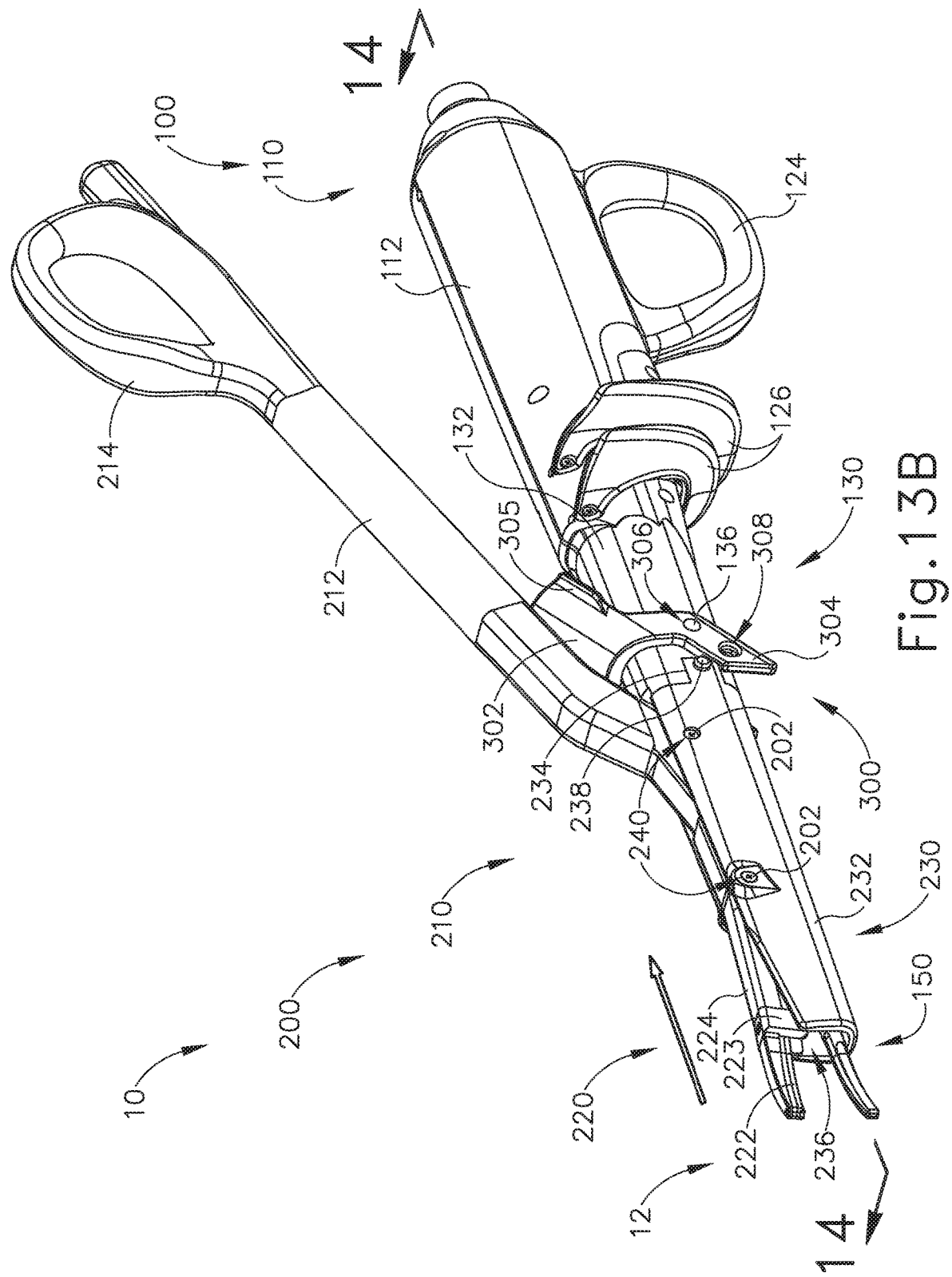
FIG. 13B depicts a perspective view of the second modular assembly of FIG. 8 inserted over the shaft assembly of FIG. 5.
Figure 14A:
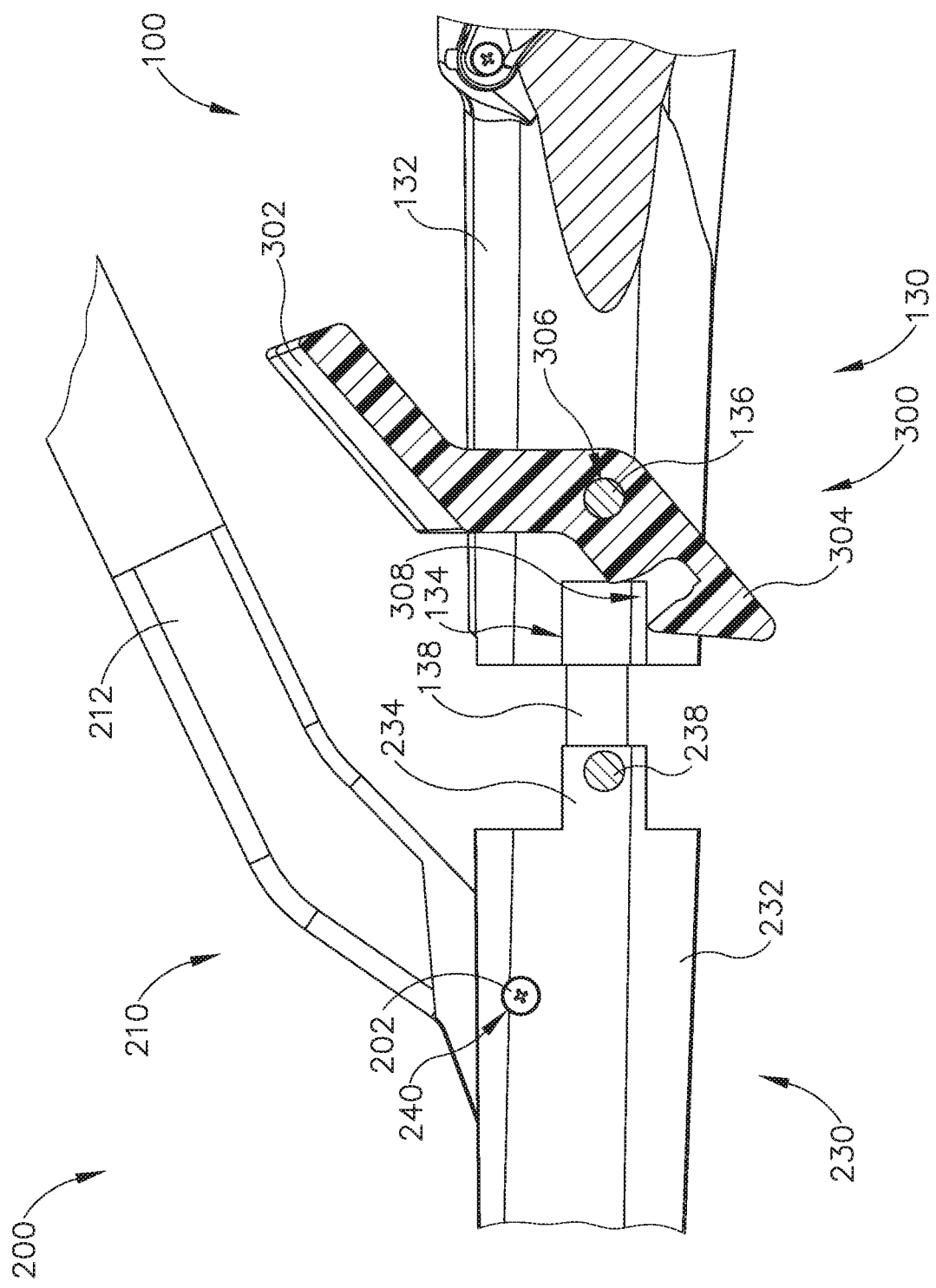
FIG. 14A depicts a cross-sectional side view of the second modular assembly of FIG. 8 partially inserted over the shaft assembly of FIG. 5, taken along line 14-14 of FIG. 13B.

As shown between FIGS. 13A-13B and between FIGS. 14A-14B, proximally presented projections (234) are configured to be inserted into recesses (134) defined by proximal outer sheath (132). When proximally presented projections (234) are inserted into recesses (134), distal outer sheath (230) may not rotate relative to proximal outer sheath (132) about a longitudinal axis defined by tube (138). Therefore, proximally presented projections (234) may mate with recesses (134) in order to rotationally fix distal outer sheath (230) relative to proximal outer sheath (132).

Figure 13C:
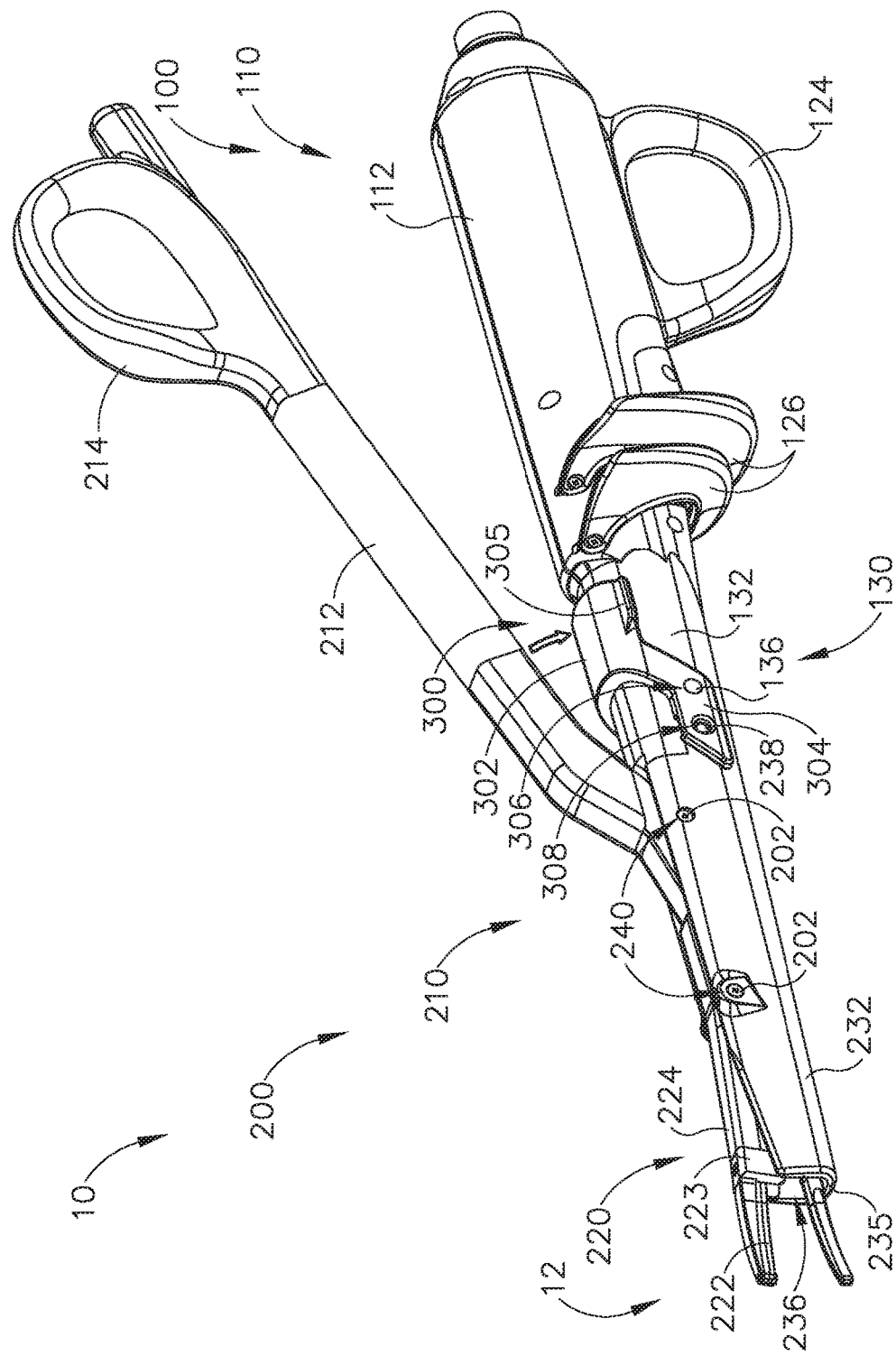
FIG. 13C depicts a perspective view of the second modular assembly of FIG. 8 coupled with the shaft assembly of FIG. 5 via the coupling member of FIG. 7.
Figure 14C:
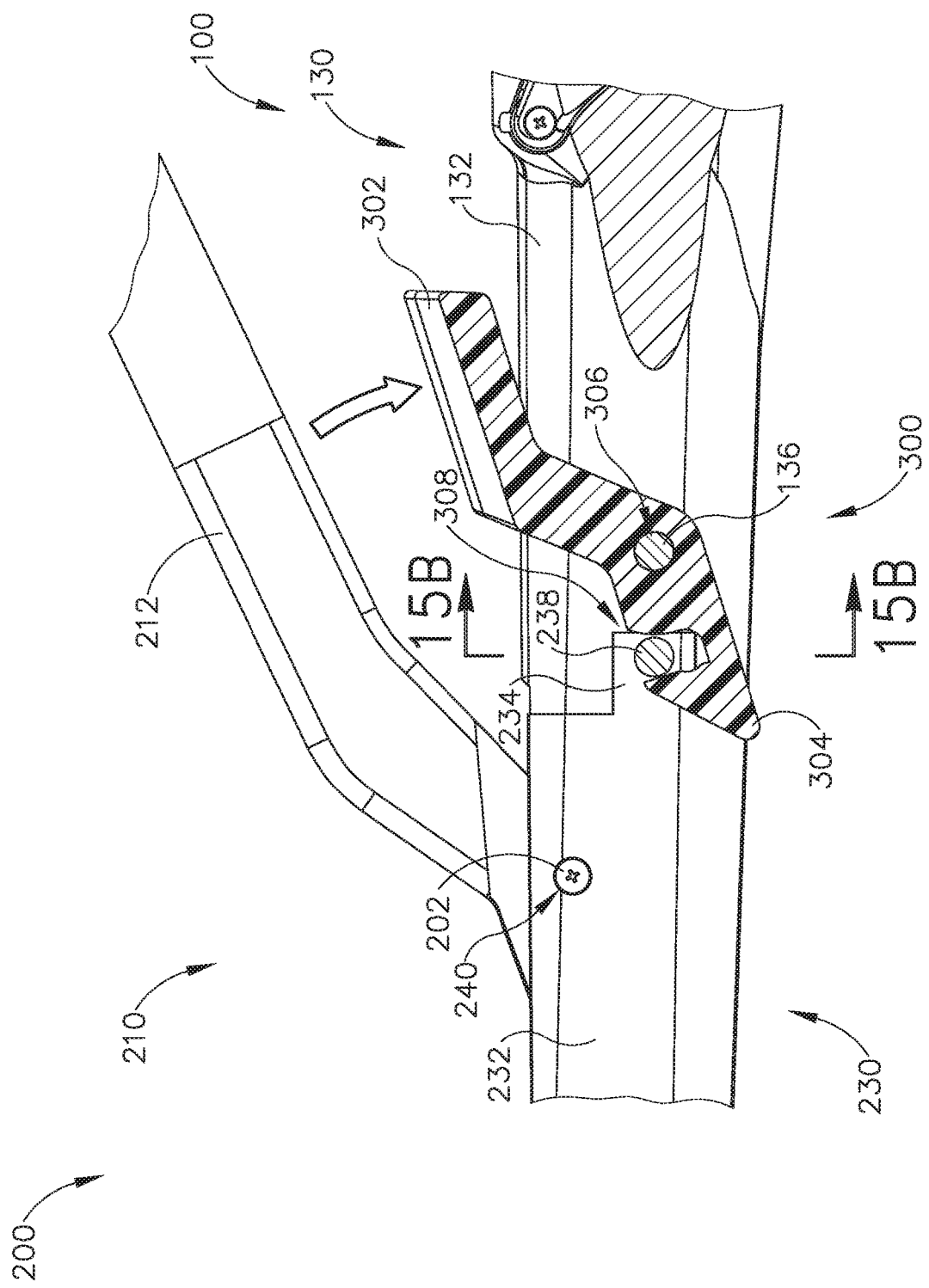
FIG. 14C depicts a cross-sectional side view of the second modular assembly of FIG. 8 inserted over the shaft assembly of FIG. 5 while the coupling member of FIG. 7 is rotated toward a configuration to couple the shaft assembly with the second modular assembly, taken along line 14-14 of FIG. 13B.
Figure 15B:
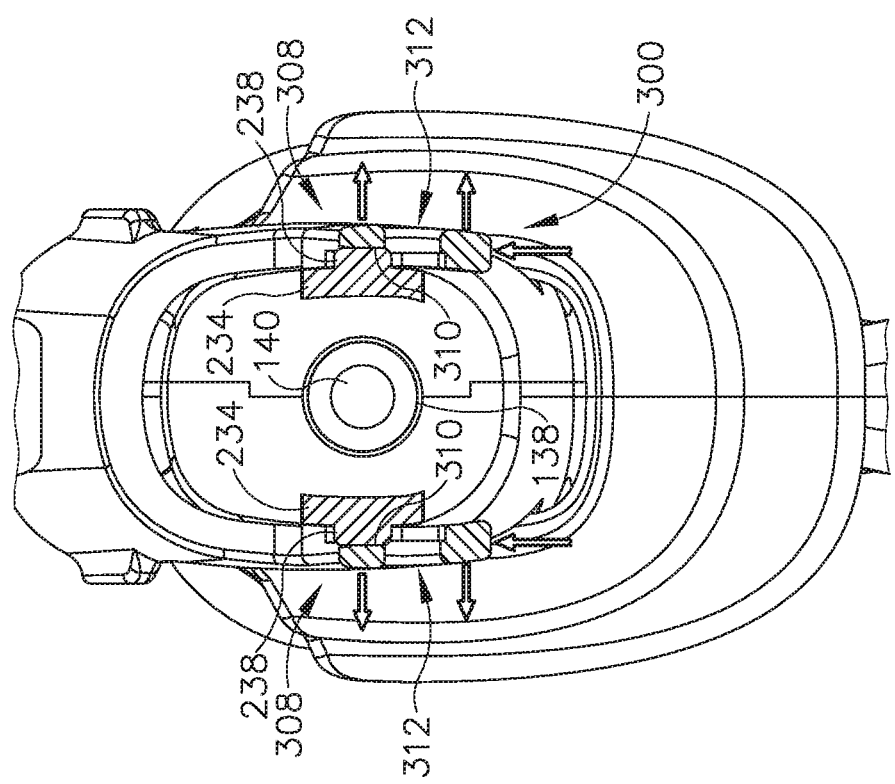
FIG. 15B depicts a cross-sectional front view of the second modular assembly of FIG. 8 inserted over the shaft assembly of FIG. 5 while the coupling member of FIG. 7 is rotated toward a configuration to couple the shaft assembly with the second modular assembly, taken along line 15B-15B of FIG. 14C.

As shown between FIGS. 13B-13C, between FIGS. 14B-14D, and between FIGS. 15A-15C, once distal outer sheath (230) is rotationally fixed relative to proximal outer sheath (132), an operator may rotate coupling member (300) such that locking assembly (308) snap-fits with lateral protrusions (238). In particular, an operator may rotate coupling member (300) about protrusion (136) such that lateral protrusions (238) cam against contact walls (310) of resilient arms (304). As a result, as best seen in FIG. 15B, contact between contact walls (310) and lateral protrusions (238) flex resilient arms (304) outwardly away from proximally presented projections (234). An operator may further rotate coupling member (300) about protrusions (136) such that lateral protrusions (238) no longer abut against contact wall (310), as shown in FIGS. 13C, 14C, and 15C. The resilient nature of resilient arms (304) allows resilient arms (304) to return to a relaxed position such that lateral protrusions (238) rest within coupling recess (312) of locking assembly (308). With locking assembly (308) of coupling member (300) fully attached, and shown in FIGS. 13C, 14D, and 15C, distal outer sheath (230) is longitudinally fixed relative to proximal outer sheath (132), thereby coupling first modular assembly (100) with second modular assembly (200).

If an operator wishes to decouple first modular assembly (100) with second modular assembly (200), an operator may grasp grips (305) to rotate coupling member (300) in the opposite direction about protrusions (136) in order to flex resilient arms (304) to pop out lateral protrusions (238) from coupling recess (312).

As mentioned above, clamp arm assembly (210) and clamp pad assembly (220) are both pivotally coupled with distal outer sheath (230) such that rotation of one assembly (210, 220) relative to distal outer sheath (230) causes rotation of the other assembly (210, 220) relative to distal outer sheath (230).

Clamp arm assembly (210) includes an elongated arm (212), a thumb grip ring (214), a camming protrusion (216), and a pivot coupling (218). Thumb grip ring (214) and elongated arm (212) together provide a scissor grip type configuration in combination with body (112) and finger grip ring (124). Pivot coupling (218) pivotally couples clamp arm assembly (210) with distal outer sheath (230) via pins (202). As will be described in greater detail below, camming protrusion (216) interacts with clamp pad assembly (220) in order to rotate clamp pad assembly (220) in response to rotation of clamp arm assembly (210).

Clamp pad assembly (220) includes a clamp pad (222) facing ultrasonic blade (150), a pair of tissue stops (223) located adjacent to ultrasonic blade (150) and proximal to clamp pad (222), an arm (224) defining both a camming recess (226) and a spring recess (221), a pivot coupling (228), and a leaf spring (225) housed within spring recess (221). In some versions, clamp pad assembly (220) further includes one or more electrodes that is/are operable to apply RF electrosurgical energy to tissue. Various references herein provide examples of how a clamp pad assembly may incorporate one or more electrodes that is/are operable to apply RF electrosurgical energy to tissue, while other examples of how clamp pad assembly (220) may incorporate one or more electrodes that is/are operable to apply RF electrosurgical energy to tissue will be apparent to those of ordinary skill in the art in view of the teachings herein.

In the current example, tissue stops (223) longitudinally align with distal face (235) when end effector (12) is in the closed position. Tissue stops (223) and distal face (235) may cooperate to consistently and simply prevent tissue from inadvertently reaching a proximal position within end effector (12) where ultrasonic energy from blade (150) may not adequately sever or seal the tissue. In providing such prevention, tissue stop (223) may eliminate the need for an operator to visualize proximal region of end effector (12) in order to determine whether the tissue has reached an undesirably proximal position within end effector (12).

Camming protrusion (216) is dimensioned to rotate within camming recess (226) while also contacting camming recess (226). Camming protrusion (216) and camming recess (226) are positioned within distal outer sheath (230) such that both are located between pivot couplings (218, 228) while clamp arm assembly (210) and clamp pad assembly (220) are pivotally coupled to distal outer sheath (230). Therefore, as shown between FIGS. 1A-1B and 16A-16B, when an operator rotates elongated arm (212) about pivot coupling (218) toward distal outer sheath (230), camming protrusion (216) rotates away from distal outer sheath (230) about pivot coupling (218). Because camming protrusion (216) is housed within camming recess (226), upward movement of camming protrusion (216) about pivot coupling (218) causes upward movement of camming recess (226) about pivot coupling (228). Upward movement of camming recess (226) about pivot coupling (228) rotates arm (224) such that clamp pad (222) rotates toward ultrasonic blade (150). Therefore, closure of elongated arm (212) of clamp arm assembly (210) toward handle assembly (110) leads to closure of clamp pad (222) toward ultrasonic blade (150). It should therefore be understood that when first modular assembly (100) and second modular assembly (200) are connected, an operator may squeeze thumb grip ring (214) toward body (112) to thereby clamp tissue between clamp pad assembly (220) and ultrasonic blade (150) to compress tissue against ultrasonic blade (150). When ultrasonic blade (150) is activated during such compression, clamp pad assembly (220) and ultrasonic blade (150) cooperate to transect and/or seal the compressed tissue.

As mentioned above, leaf spring (225) is housed within spring recess (221). As best seen in FIGS. 16A-16B, leaf spring (225) is dimensioned such that a portion of leaf spring (225) extends out of spring recess (221) to make contact against tube (138) in order to provide electrical continuity between the one or more RF electrodes of end effector (12) and the source of electrical power. It should be understood that leaf spring (225) maintains this electrical continuity throughout the range of motion of clamp pad assembly (220). It should also be understood that any other suitable kinds of features may be used to provide electrical continuity between the one or more RF electrodes of end effector (12) and the source of electrical power.

In some versions, one or more resilient members are used to bias clamp pad assembly (220) toward the open position shown in FIGS. 1A and 16A. Of course, any other suitable kind of resilient member may be used as would be apparent to one having ordinary skill in the art in view of the teachings herein, such as a torsion spring. Alternatively, clamp pad assembly (220) need not necessarily be biased toward the open position.

Pivot couplings (218, 228) of clamp arm assembly (210) and clamp pad assembly (220) being located within longitudinal pathway (236) of distal outer sheath (230) may provide certain desirable advantages as compared to clamp arm assembly (210) and clamp pad assembly (220) pivotally coupling with an exterior of distal outer sheath (230). For instance, there may be a reduced chance of inadvertently pinching tissue due to rotation of clamp arm assembly (210) and clamp pad assembly (220) with pivot couplings (218, 228) being housed within U-shaped body (232). In other words, U-shaped body (232) may protect tissue from being inadvertently pinched by rotation of clamp arm assembly (210) and clamp pad assembly (220) relative to distal outer sheath (230). Additionally, the width of second modular assembly (200) may be reduced due to pivot couplings (218, 228) being housed within longitudinal pathway (236) of distal outer sheath (230). It may also be easier to fabricate desired components due to the simplified shapes of clamp arm assembly (210) and clamp pad assembly (220). A reduction of tolerance stack may also be an advantage to storing pivot couplings (218, 228) within the interior of distal outer sheath (230).

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783, 524; U.S. Pub. No. 2006/0079874, now abandoned; U.S. Pub. No. 2007/0191713, now abandoned; U.S. Pub. No. 2007/0282333, now abandoned; U.S. Pub. No. 2008/ 0200940, now abandoned; U.S. Pat. Nos. 9,023,071; 8,461, 744; 9,381,058; U.S. Pub. No. 2012/0116265, now abandoned; U.S. Pat. Nos. 9,393,037; 9,095,367; and/or U.S. Pub. No. 2015/0080925, entitled "Alignment Features for Ultrasonic Surgical Instrument," published Mar. 19, 2015, now abandoned, the disclosure of which is incorporated by reference herein.

Figure 17:
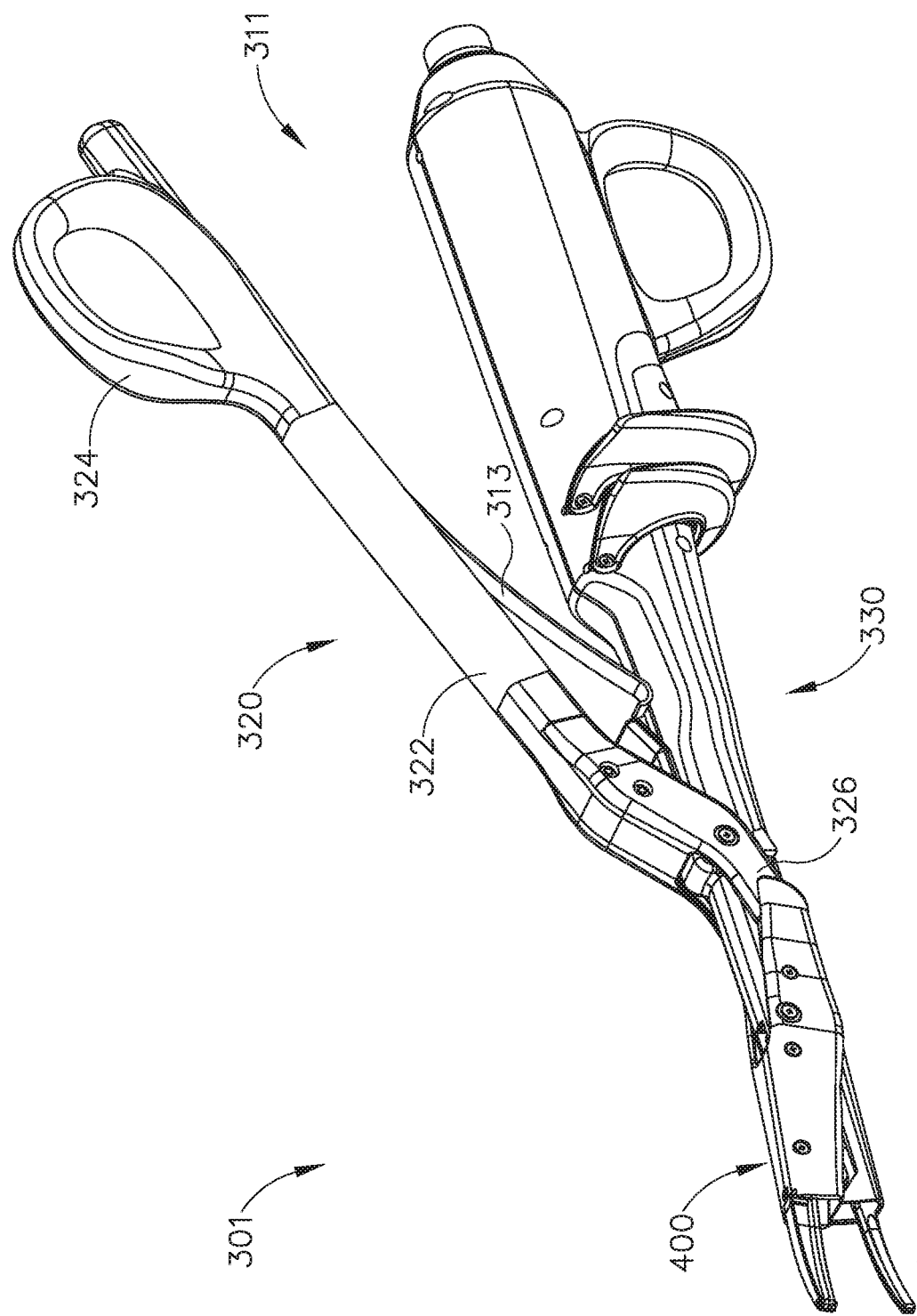
FIG. 17 depicts a perspective view of a second exemplary surgical instrument, with an end effector of the instrument in an open configuration.
Figure 18:
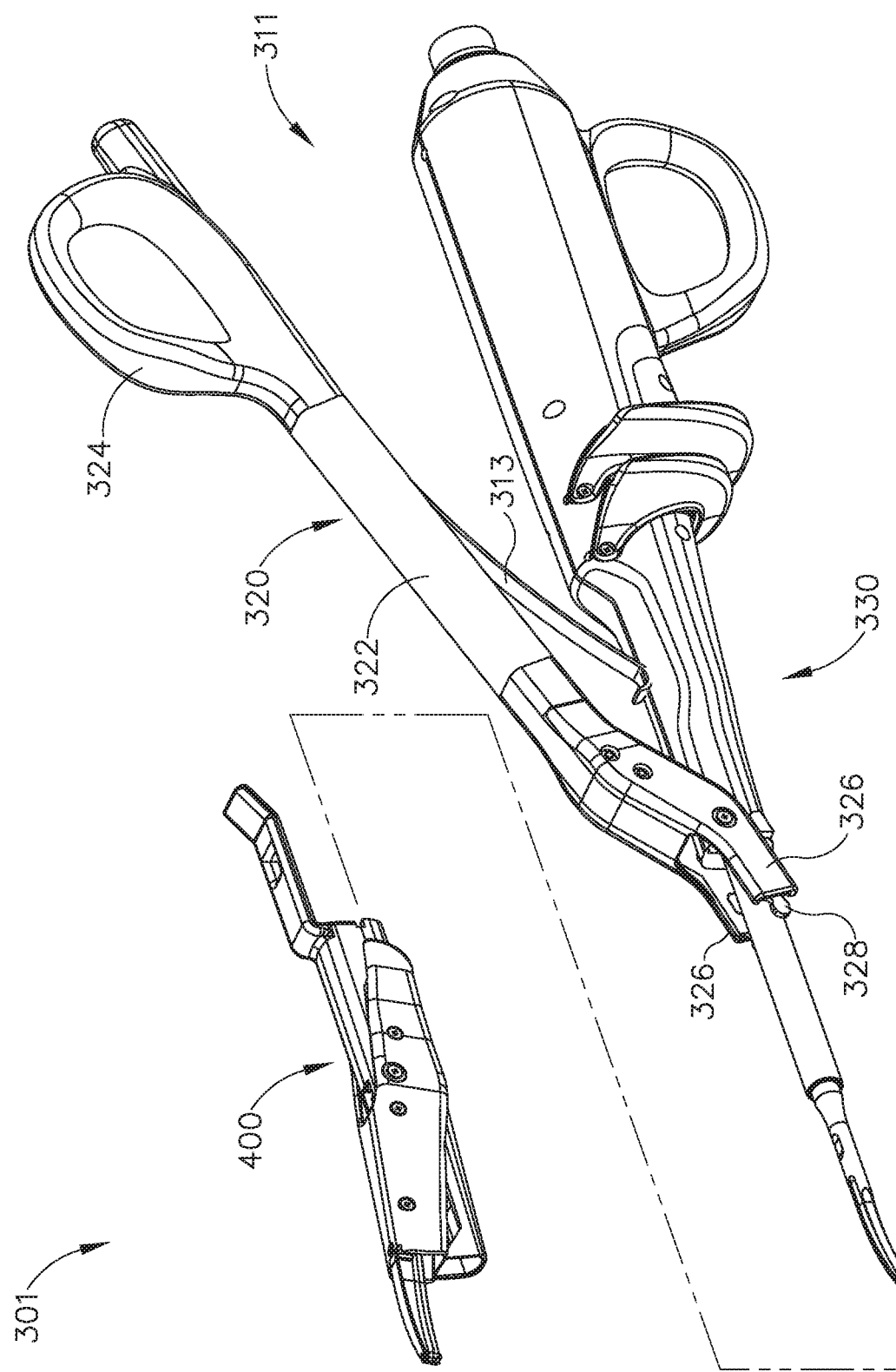
FIG. 18 depicts a partially exploded perspective view of the instrument of FIG. 17.

II. Second Exemplary Ultrasonic Surgical Instrument for Open Surgical Procedures FIGS. 17-18 show a second exemplary ultrasonic surgical instrument (301). Except as otherwise described below, instrument (301) of this example may be constructed and operable just like instrument (10) described above. Certain details of instrument (301) will therefore be omitted from the following description, it being understood that such details are already provided above in the description of instrument (10).

Instrument (301) of the present example comprises a handle assembly (311), a clamp arm actuator (320), a shaft assembly (330), and a clamp arm assembly (400). Handle assembly (311) of this example is configured and operable just like handle assembly (110) described above, such that details of handle assembly (311) will not be reiterated here.

Figure 19:
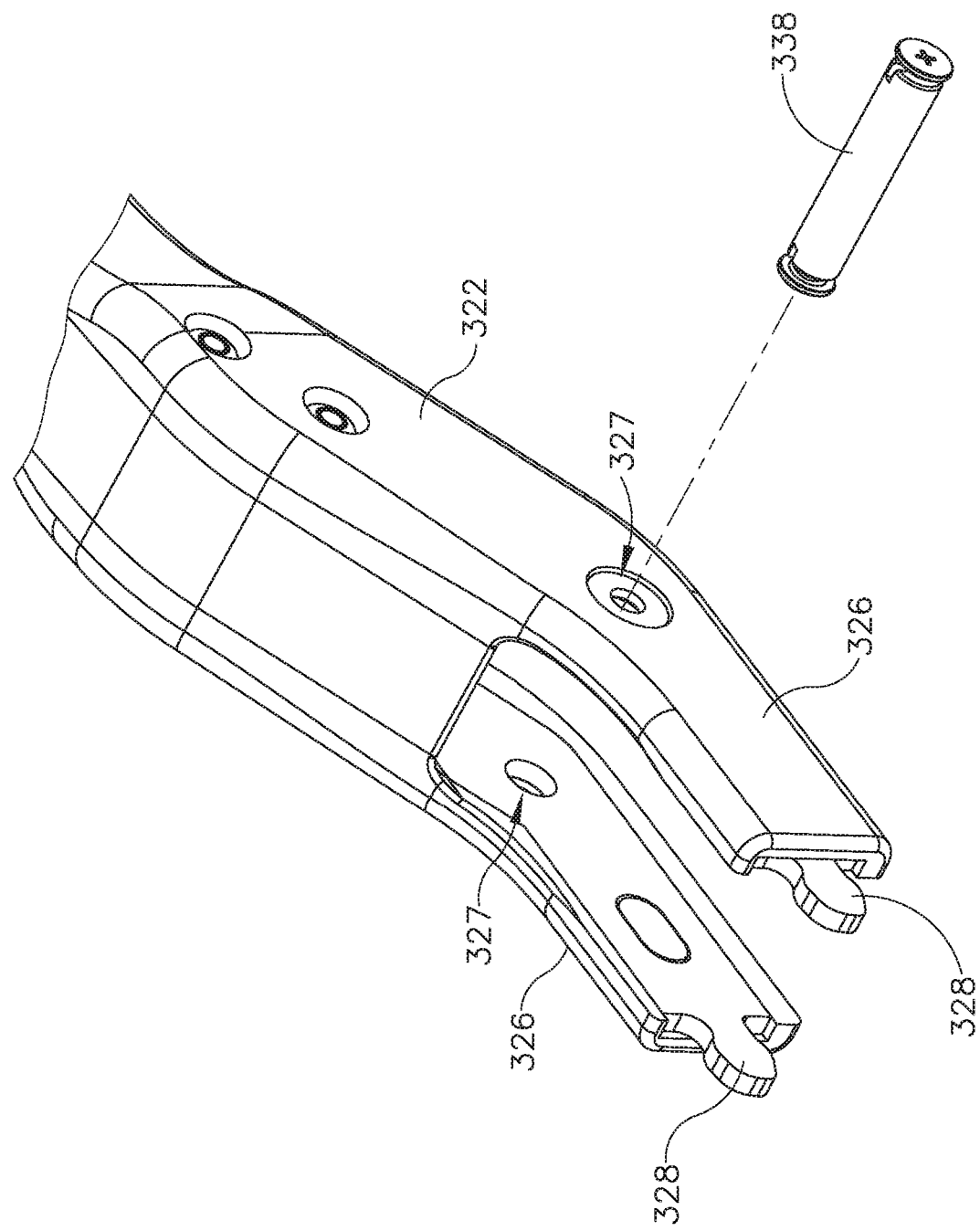
FIG. 19 depicts a partial perspective view of the distal end of a clamp arm actuator of the instrument of FIG. 17.

Clamp arm actuator (320) is pivotably coupled with shaft assembly (330). In the present example, clamp arm actuator (320) is not removable from shaft assembly (330). Clamp arm actuator (320) of the present example comprises a shaft (322). A thumb ring (324) is positioned at the proximal end of shaft (322). As best seen in FIGS. 18-19, pair of projections (326) extend distally from shaft (322). Projections (326) are laterally spaced apart from each other and extend parallel to each other. As best seen in FIG. 19, the distal end of each projection (326) includes a camming protrusion (328). Camming protrusions (328) are configured to cooperate with clamp arm assembly (400), in a manner similar to camming protrusions (216), as will be described below. As also best seen in FIG. 19, projections (326) also define a pair of pin openings (327), which are configured to receive pin (338). Pin (338) provides a pivotable coupling between clamp arm actuator (320) and shaft assembly (330).

Figure 20:
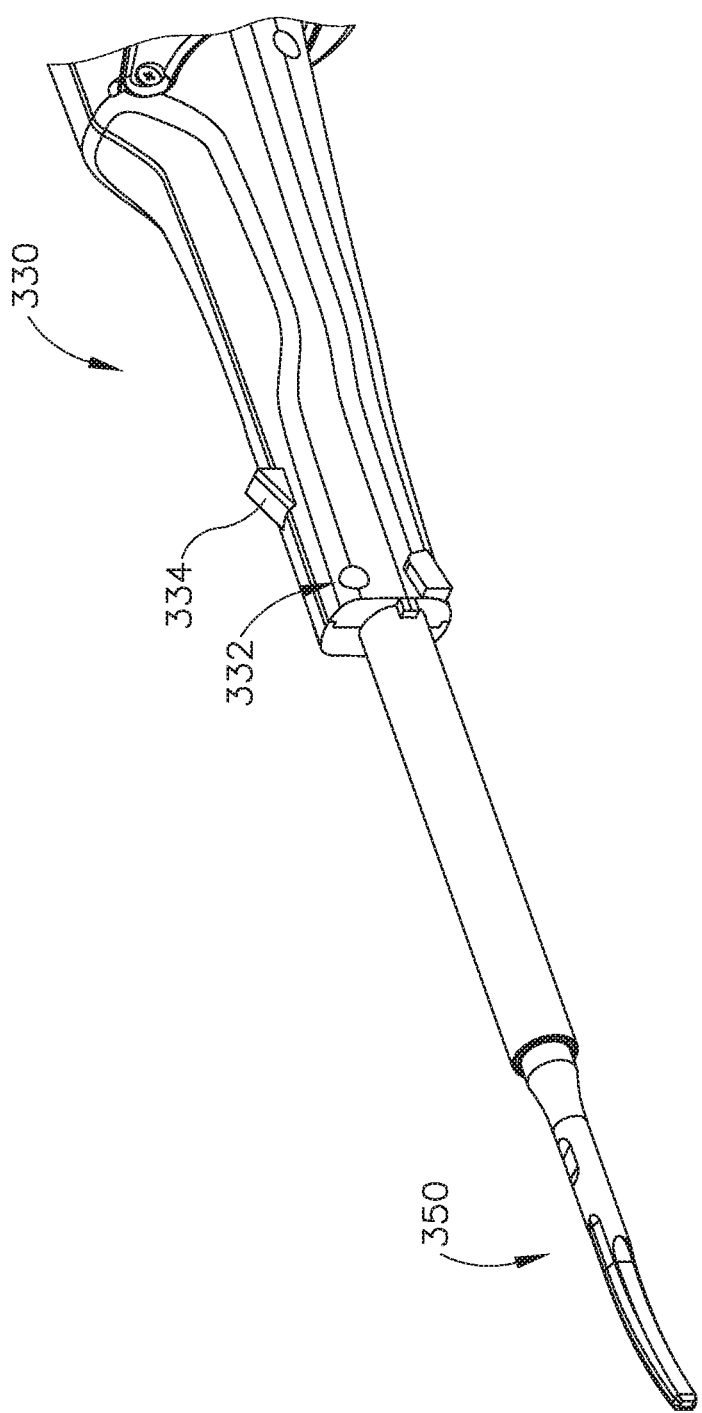
FIG. 20 depicts a perspective view of a shaft assembly and ultrasonic blade of the instrument of FIG. 17.

Shaft assembly (330) extends distally from handle assembly (311) and is substantially identical to shaft assembly (130) described above except for the differences described below. An ultrasonic blade (350), which is identical to ultrasonic blade (150) described above, is positioned at the distal end of shaft assembly (130). As best seen in FIG. 20, shaft assembly (330) defines an opening (332) that is configured to receive pin (338) to thereby provide a pivotable coupling between clamp arm actuator (320) and shaft assembly (330). As also shown in FIG. 20, shaft assembly (330) includes a ramped latch protrusion (334), which is configured to engage clamp arm assembly (400) as will be described in greater detail below.

Figure 21:
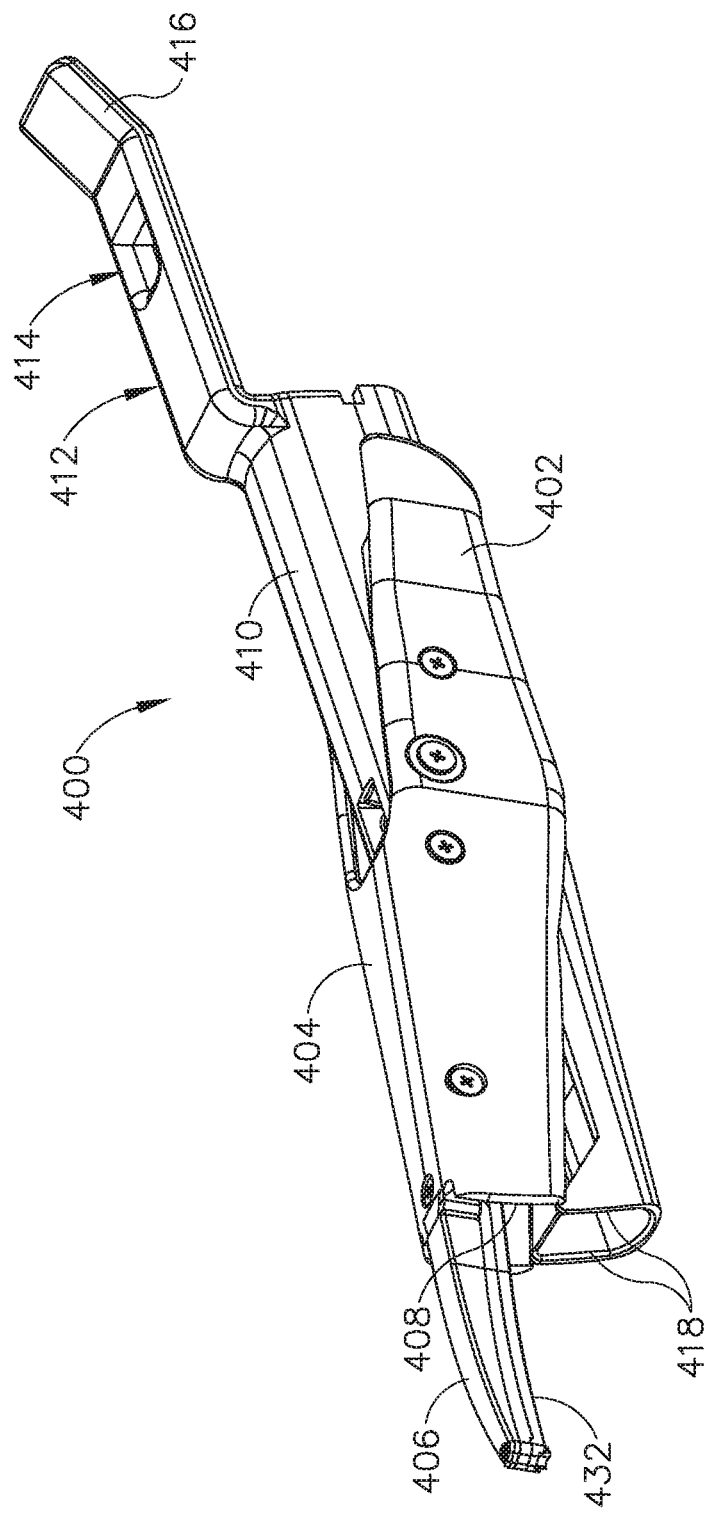
FIG. 21 depicts a perspective view of a removable clamp arm assembly of the instrument of FIG. 17.
Figure 22:
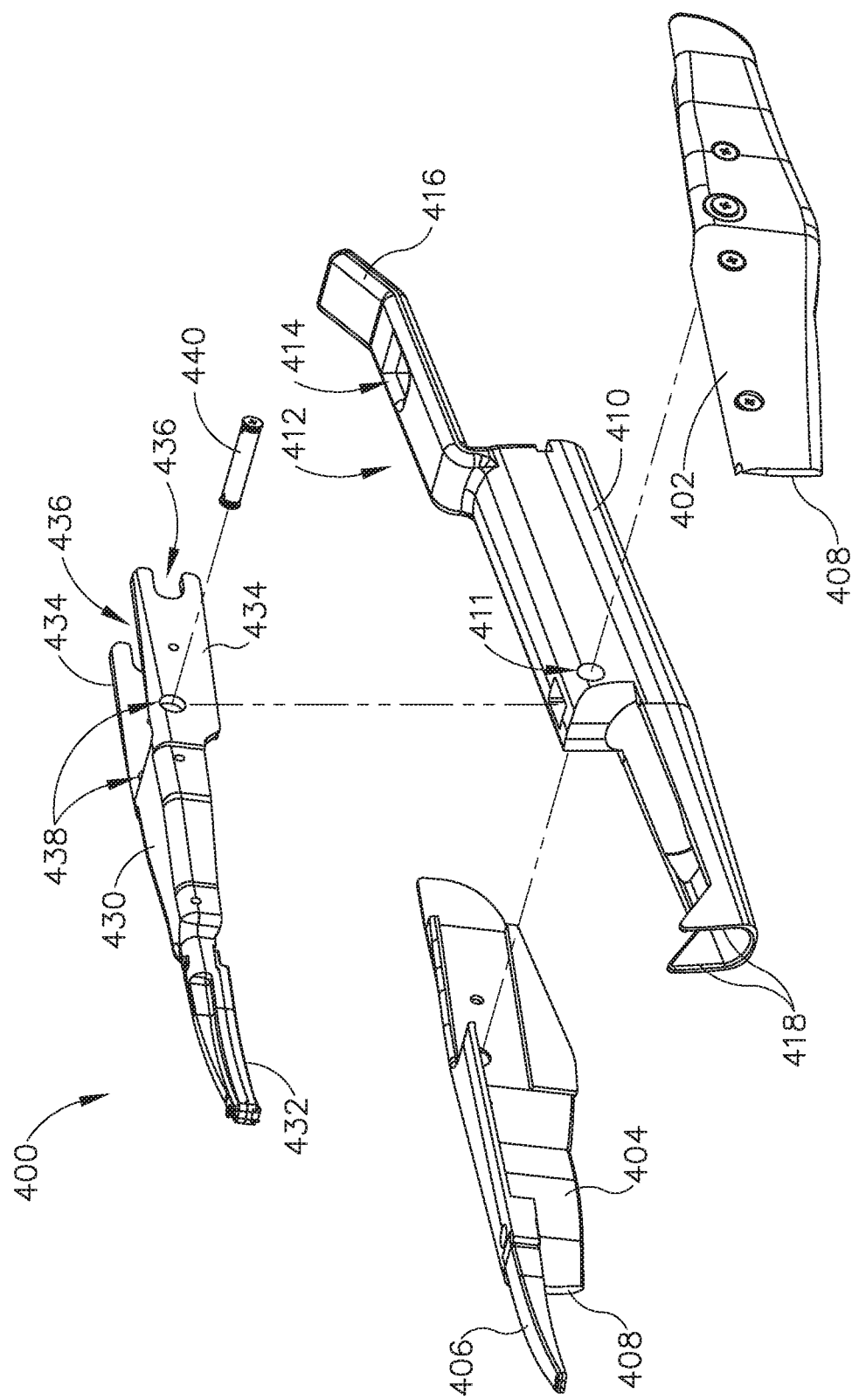
FIG. 22 depicts an exploded perspective view of the clamp arm assembly of FIG. 21.

As shown in FIGS. 21-22, clamp arm assembly (400) of the present example comprises a pair of shrouds (402, 404) partially encompassing a clamp arm body (430), which is pivotally coupled with a stationary body (410). Each shroud includes a distally presented tissue stop edge (408). Stationary body (410) also includes a pair of distally presented tissue stop edges (418). Edges (408, 418) are configured to cooperate to consistently and restrict proximal positioning of tissue like tissue stops (223) and distal face (235) described above. Shroud (404) of the present example also includes a distally projecting shield member (406).

Stationary body (410) of the present example further includes a pin opening (411) and a proximally projecting latch member (412). Latch member (412) defines a latch opening (414) and a ramp (416). Latch member (412) is configured to cooperate with latch protrusion (334) of shaft assembly (330) to selectively secure clamp arm assembly (400) to shaft assembly (330). In particular, when clamp arm assembly (400) is initially provided separately from shaft assembly (330), an operator may align clamp arm assembly (400) with shaft assembly (330) along a common axis, and then insert blade (350) and the remaining distal portion of shaft assembly (330) into clamp arm assembly (400). Ramp (416) will eventually engage latch protrusion (334), which will provide a camming action that causes latch member (412) to deflect away from the longitudinal axis. As the operator continues to insert shaft assembly (330) through clamp arm assembly (400), latch protrusion (334) eventually reaches latch opening (414), at which point latch member (412) resiliently returns to a straight, non-deflected state. At this stage, latch protrusion (334) is disposed in latch opening (414) and thereby secures clamp arm assembly (400) to shaft assembly (330). When the operator wishes to remove clamp arm assembly (400) from shaft assembly (330), the operator may simply engage ramp (416) and thereby urge latch member (412) to a deflected state where latch member (412) can clear latch protrusion (334); then pull clamp arm assembly (400) away from shaft assembly (330). Other suitable structures and techniques that may be used to secure clamp arm assembly (400) to shaft assembly (330), and to remove clamp arm assembly (400) from shaft assembly (330), will be apparent to those of ordinary skill in the art in view of the teachings herein.

Clamp arm body (430) of the present example comprises a clamp pad (432) and a pair of proximal projections (434). Clamp pad (432) is positioned and configured to compress tissue against ultrasonic blade (350) when clamp arm assembly (400) is secured to shaft assembly (330). Shield member (406) of shroud (404) is configured to extend over the exterior of the distal end of clamp arm body (430), without covering clamp pad (432). Shield member (406) thus enables clamp pad (432) to contact tissue directly. Projections (438) each comprise a respective proximally presented recess (436) and a pair of pin openings (438). A pin (440) is positioned in pin openings (411, 438) to thereby pivotally couple clamp arm body (430) with stationary body (410). Shrouds (402, 404) are fixedly secured to clamp arm body (430) such that shrouds (402, 404) pivot with clamp arm body (430) relative to stationary body (410).

Figure 23:
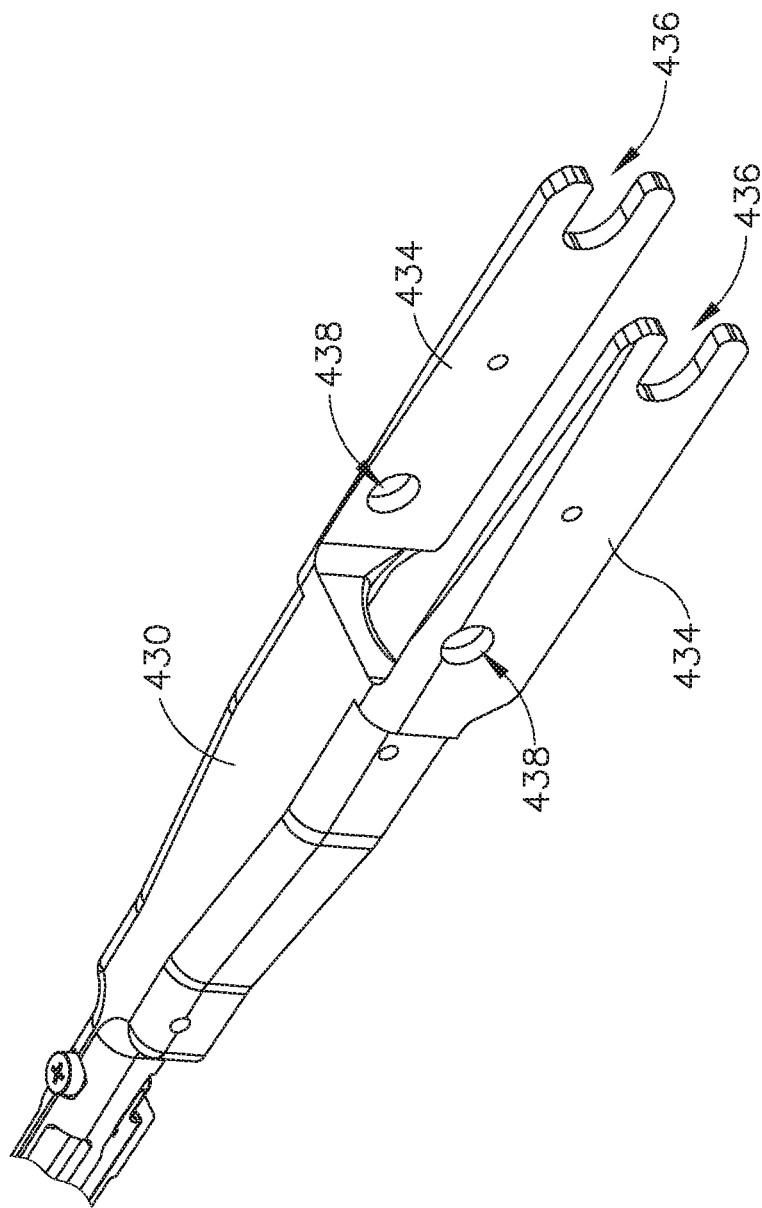
FIG. 23 depicts a partial perspective view of a proximal end of a clamp arm body of the clamp arm assembly of FIG. 22.
Figure 24:
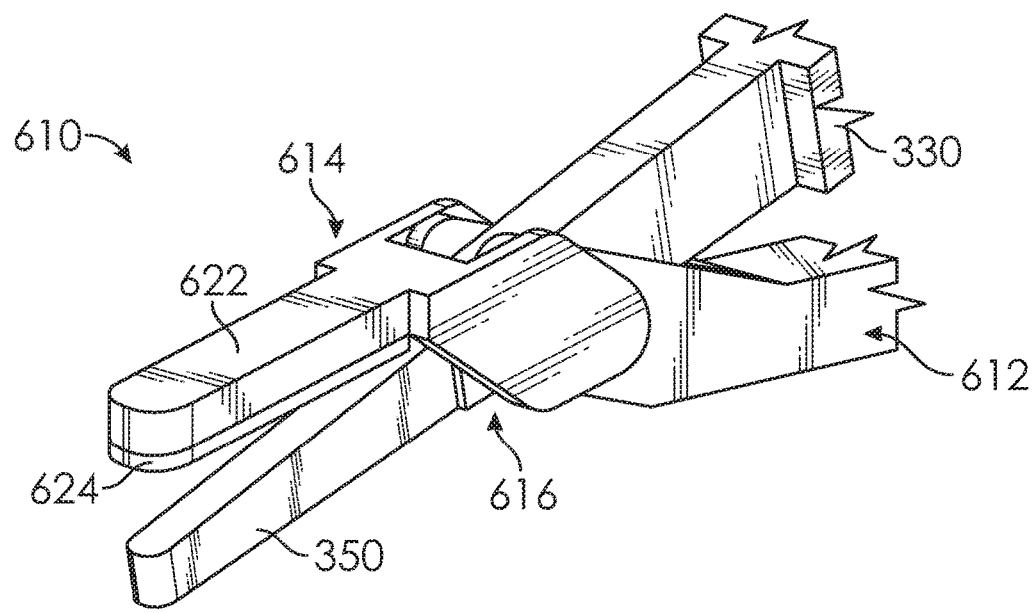
FIG. 24 depicts an enlarged perspective view of a third exemplary surgical instrument having a first modular alignment release coupling associated with an end effector, the end effector being in an open configuration.

As shown in FIG. 23, recesses (436) have a generally U-shaped configuration. Recesses (436) are configured to receive camming protrusions (328) of clamp arm actuator (320). In other words, when shaft assembly (330) is inserted into clamp arm assembly (400) as described above, camming protrusions (328) will enter recesses (436) when latch member (412) reaches the point at which latch member (412) secures clamp arm assembly (400) to shaft assembly (330). When the operator removes clamp arm assembly (400) from shaft assembly (330), camming protrusions (328) may freely exit recesses (436), as clamp arm actuator (320) remains secured to shaft assembly (330). As best seen in FIG. 17, shrouds (402, 404) are configured to cover the interfaces between recesses (436) and camming protrusions (328). It should be understood that the relationship between recesses (436) and camming protrusions (328) is substantially identical to the relationship between camming protrusion (216) and camming recess (226) described above. Thus, recesses (436) and camming protrusions (328) provide a pivoting coupling between clamp arm body (430) and clamp arm actuator (320).

As noted above, clamp arm actuator (320) is pivotally coupled with shaft assembly (330) via pin (338); and clamp arm body (430) is pivotally coupled with stationary body (410) via pin (440); while stationary body (410) is fixedly secured to shaft assembly (330). The pivoting interface between recesses (436) and camming protrusions (328) is longitudinally positioned between the longitudinal positions of pins (338, 440). It should therefore be understood that clamp arm actuator (320) and clamp arm body (430) cooperate to provide a compound lever assembly. When an operator pivots thumb ring (324) toward handle assembly (311), the compound lever action provides corresponding pivotal movement of clamp pad (432) toward ultrasonic blade (350).

In the present example, a resilient beam (313) is secured to clamp arm actuator (320) and slidably bears against shaft assembly (330), such that resilient beam (313) resiliently urges clamp arm actuator (320) away from handle assembly (311). Thus, when an operator relaxes their grip on thumb ring (324), resilient beam (313) will urge thumb ring (324) away from handle assembly (311), thereby urging clamp pad (432) away from ultrasonic blade (350). Of course, any other suitable components and arrangements may be used to provide a resilient bias to clamp arm actuator (320). Alternatively, such resilient bias may simply be omitted.

III. Alternative Exemplary Ultrasonic Surgical Instruments and Various Replaceable End Effector Features Surgical instruments (10, 301) described above have a variety of coupling mechanisms including associated connections for respective modular assemblies and other removably connected features. While such coupling mechanisms may be useful in many circumstances before, during, or after a surgical procedure, in one example, removing a replaceable portion of surgical instrument from a remainder of surgical instrument (10, 301) allows for replacement of the replaceable portion and reuse of the remainder of surgical instrument (10, 301). One such replaceable portion is clamp pad (222, 432), which tends to wear with use, and may be replaced by the operator as desired. However, additional replacement portions for end effector (12) include, but are not limited to, clamp arm assemblies (210, 400), and electrode assemblies, such as electrodes (not shown) discussed briefly above.

The operator disconnects removable portions of end effector (12) for replacement by manipulating modular couplings (616, 716, 816, 916, 1016, 1116, 1316, 1416, 1516, 1616, 1716, 1816, 1916, 2016, 2116, 2216, 2316, 2416, 2516, 2616, 2716, 2816, 2916, 3016, 3116, 3216, 3316, 3416, 3533, 9516), directly or indirectly, as described below in greater detail. While the following modular couplings (616, 716, 816, 916, 1016, 1116, 1316, 1416, 1516, 1616, 1716, 1816, 1916, 2016, 2116, 2216, 2316, 2416, 2516, 2616, 2716, 2816, 2916, 3016, 3116, 3216, 3316, 3416, 3533, 9516) are shown in distinct positions between reusable and replaceable features for removable connection, for any of the following modular couplings (616, 716, 816, 916, 1016, 1116, 1316, 1416, 1516, 1616, 1716, 1816, 1916, 2016, 2116, 2216, 2316, 2416, 2516, 2616, 2716, 2816, 2916, 3016, 3116, 3216, 3316, 3416, 3533, 9516), it will be appreciated that modular couplings (616, 716, 816, 916, 1016, 1116, 1316, 1416, 1516, 1616, 1716, 1816, 1916, 2016, 2116, 2216, 2316, 2416, 2516, 2616, 2716, 2816, 2916, 3016, 3116, 3216, 3316, 3416, 3533, 9516) may be incorporated into any surgical instrument described herein, exchanged, or moved so as to make one or more portions of a surgical instrument removable from a remainder of the surgical instrument. To this end, other suitable kinds of clamp arm assemblies that may be used to provide different kinds of modular assemblies will be apparent to those of ordinary skill in the art in view of the teachings herein.

Like reference numerals described above indicate like features below. In addition, the following will provide descriptions of removal for modular couplings (616, 716, 816, 916, 1016, 1116, 1316, 1416, 1516, 1616, 1716, 1816, 1916, 2016, 2116, 2216, 2316, 2416, 2516, 2616, 2716, 2816, 2916, 3016, 3116, 3216, 3316, 3416, 3533, 9516), but, unless otherwise noted, replacement of a replaceable portion, such as a replacement clamp arm assembly, is performed in reverse movement and steps for reassembly thereof. The following thus applied to both removal and replacement of various replaceable end effector features and is not intended to be limited to only removal thereof.

A. Third Exemplary Ultrasonic Surgical Instrument with a First Modular Alignment Release Coupling FIGS. 24-28D illustrate a third exemplary surgical instrument (610) having handle assembly (311), shaft assembly (330), a clamp arm actuator (612), a clamp arm assembly (614), and a fourth modular alignment release coupling (616). With respect to FIGS. 24 and 25, clamp arm assembly (614) is removably connected to clamp arm actuator (612) with modular alignment release coupling (616), which includes a clamp body connection (618) extending from clamp arm assembly (614) and a clamp actuator connection (620) extending from clamp arm actuator (612). Clamp arm assembly (614) includes a clamp body (622) and a clamp pad (624). Clamp pad (624) is connected to clamp body (622) such that clamp pad (624) faces ultrasonic blade (350) for receiving and clamping tissue therebetween. Selective movement of clamp arm actuator (612) relative to handle assembly (311) from an opened configuration to a closed configuration respectively moves clamp arm assembly (614) from an opened position configured to receive tissue to a closed position configured to clamp the tissue. In the present example, selective movement of clamp arm actuator (612) to a release configuration aligns clamp actuator connection (620) relative to the clamp body connection (618) to disconnect clamp arm assembly (614) from clamp arm actuator (612) for removal and replacement of clamp arm assembly (614). While not shown with respect to surgical instrument (610), clamp arm assembly (614) may further include one or more electrodes configured to deliver RF energy to tissue for affecting the tissue, such as coagulating vessels in use.

Figure 25:
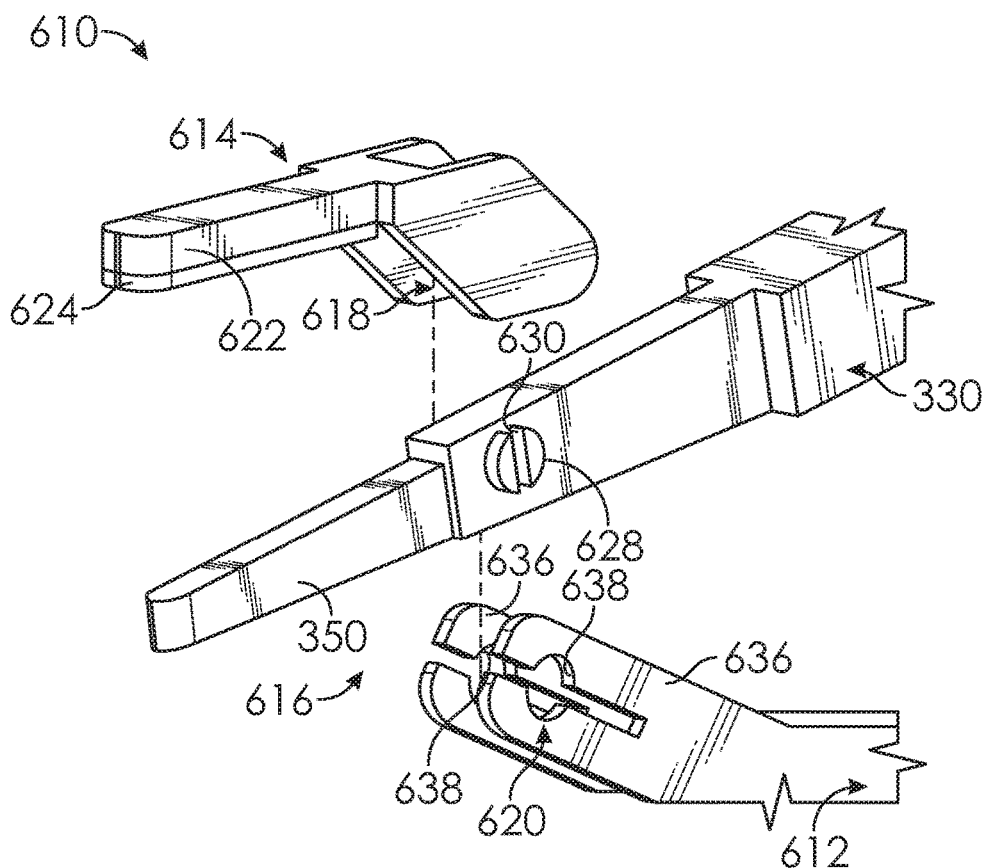
FIG. 25 depicts an enlarged exploded perspective view of the surgical instrument and modular alignment release coupling of FIG. 24.
Figure 26:
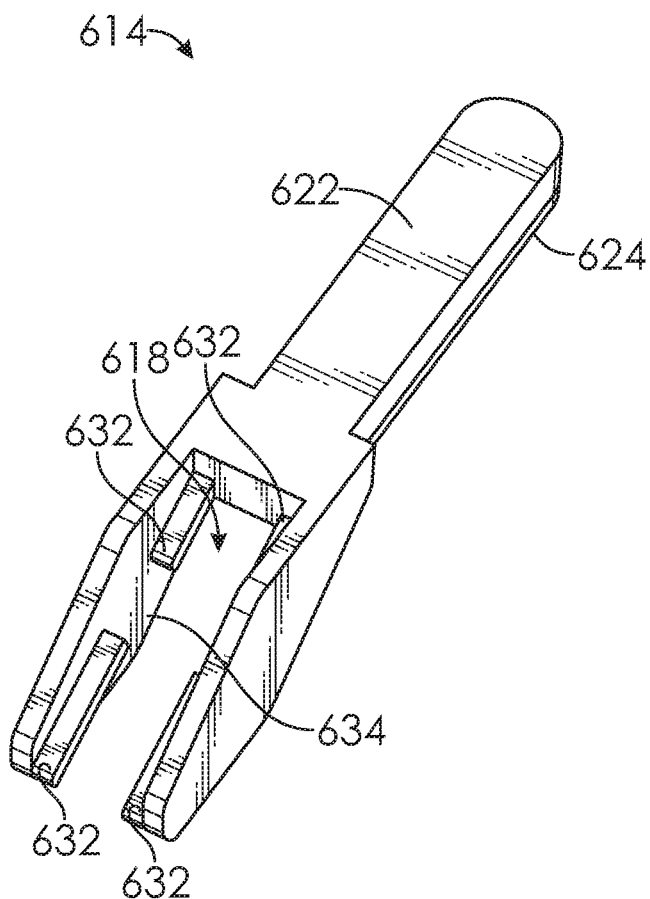
FIG. 26 depicts a perspective view of a clamp arm assembly of the surgical instrument of FIG. 24.
Figure 27:
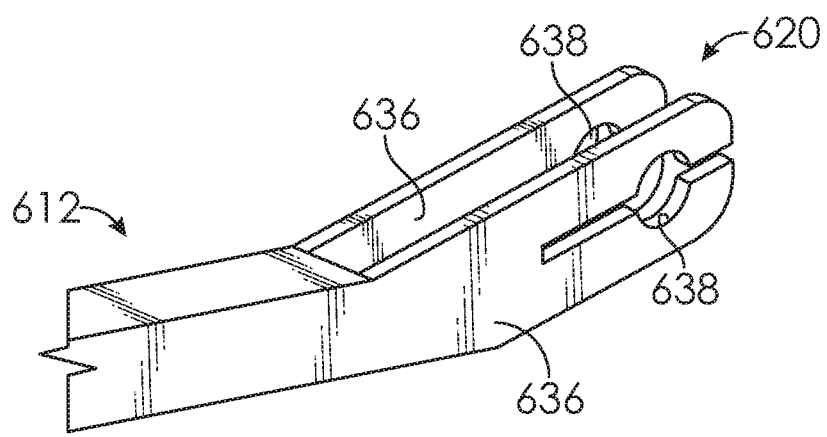
FIG. 27 depicts an enlarged perspective view of a clamp arm actuator of the surgical instrument of FIG. 24.
Figure 28A:
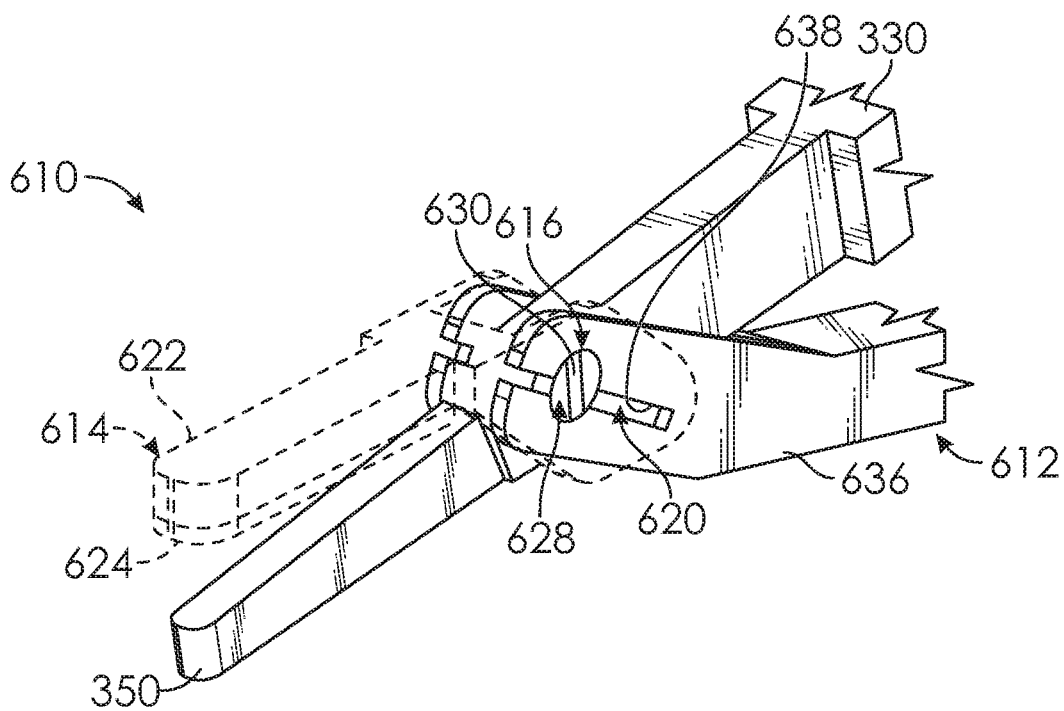
FIG. 28A depicts the enlarged perspective view of the surgical instrument and modular alignment release coupling in the open configuration similar to FIG. 24, but having various components hidden for clarity.
Figure 28B:
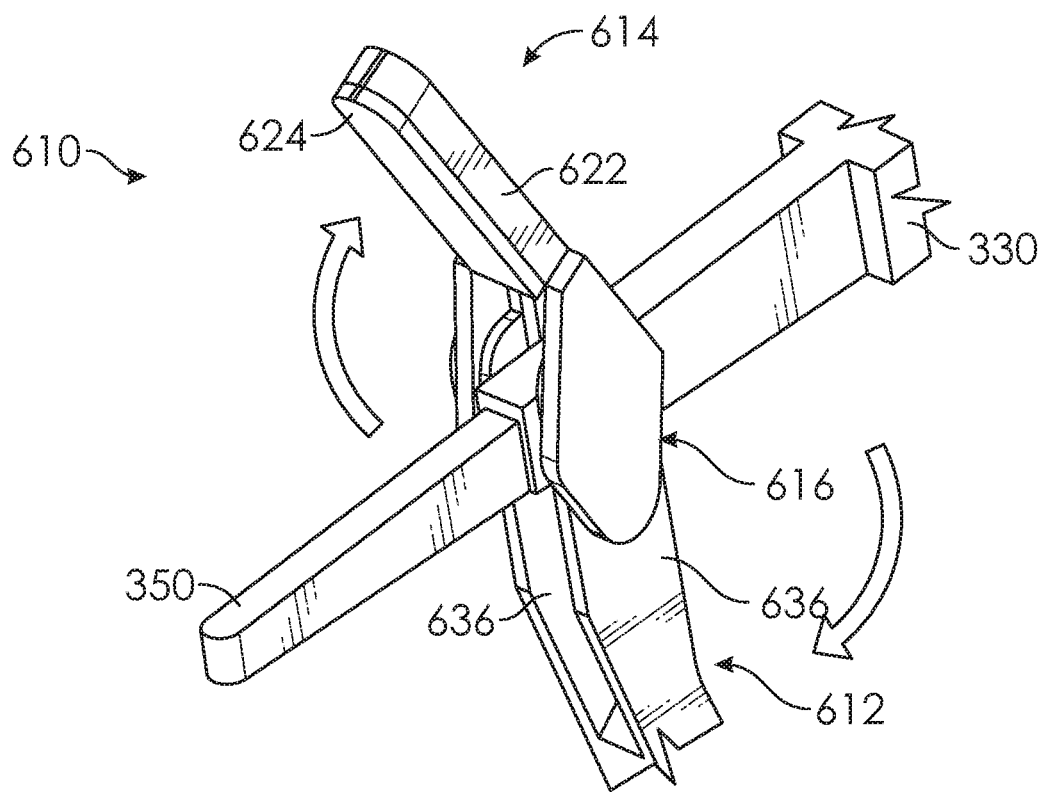
FIG. 28B depicts the enlarged perspective view of the surgical instrument and modular alignment release coupling similar to FIG. 28A, but with the surgical instrument in a release configuration.
Figure 28C:
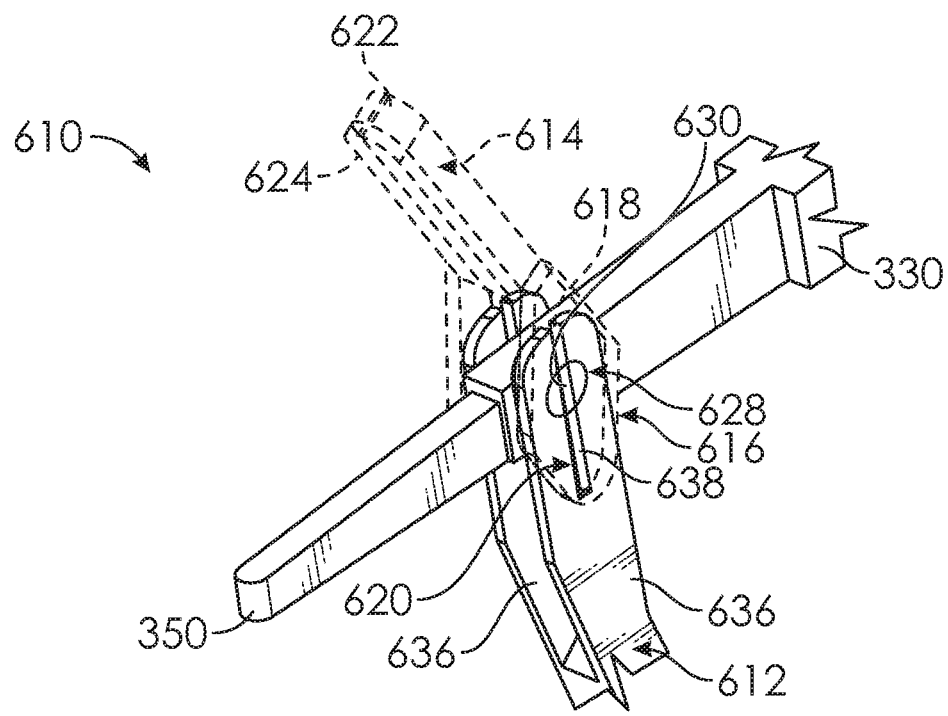
FIG. 28C depicts the enlarged perspective view of the surgical instrument and modular alignment release coupling similar to FIG. 28B, but having various components hidden for clarity.

FIG. 25 illustrates shaft assembly (330) configured to receive each of clamp arm actuator (612) and clamp arm assembly (614) for use. Shaft assembly (311) has a pair of opposing cylindrical pins (628) of modular alignment release coupling (616) extending laterally from opposing sides thereof. Each cylindrical pin (628) has a transverse slot (630) linearly extending through a face thereof. The outer radial surfaces of cylindrical pins (628) are configured to removably receive a distal portion of clamp arm actuator (612), whereas transverse slots (630) of cylindrical pins (628) are configured to receive a proximal portion of clamp arm assembly (614) shown in FIGS. 26 and 27 in more detail. To this end, proximal portion of clamp arm assembly (614) has clamp inner shoulders (632) of clamp body connection (618) defining a pair of opposing gaps (634), whereas the distal portion of clamp arm actuator (612) has a pair of elongate flanges with respective mounting holes (638) of clamp actuator connection (620). As shown in FIG. 28A, mounting holes (638) rotatably receive cylindrical pins (628) while inner shoulders (632) straddle cylindrical pins (628) within an elongate portion of mounting holes (638). Thus, clamp arm assembly (614) is removably connected to clamp arm actuator (612) via cylindrical pins (628) of modular alignment release coupling (616). However, aligning inner shoulders (632), transverse slot (630), and elongate portions of mounting holes (638) to the release configuration releases clamp arm assembly (6140 for removal. In the present example, movement of clamp arm actuator (612) about pins (628) is below longitudinal axis, but movement of clamp arm assembly (614) is above the longitudinal axis, because pins (628) laterally intersect the longitudinal axis.

Figure 28D:
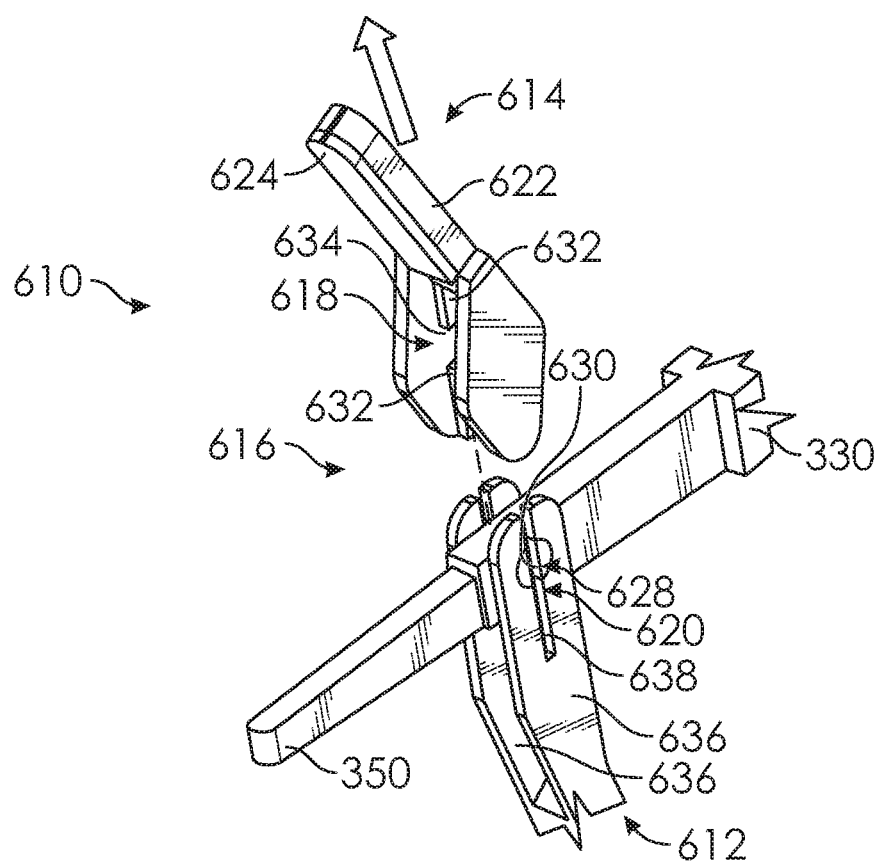
FIG. 28D depicts the enlarged perspective view of the surgical instrument and modular alignment release coupling similar to FIG. 28C, but having the clamp arm assembly removed from a handle assembly of the surgical instrument.
Figure 29:
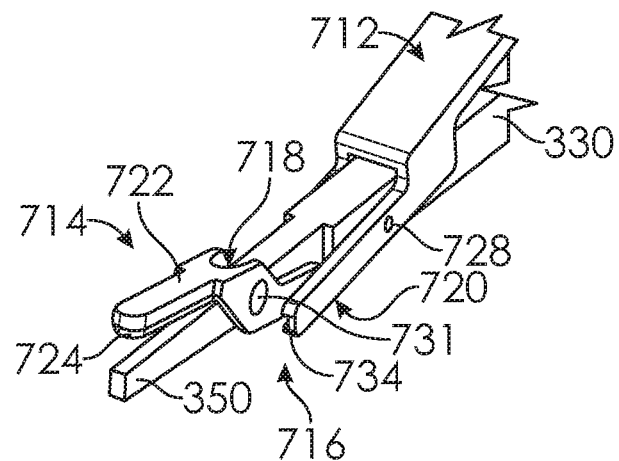
FIG. 29 depicts an enlarged perspective view of a fourth exemplary surgical instrument having a second modular alignment release coupling associated with an end effector, the end effector being in an open configuration.

In use, FIGS. 28A-28D illustrate clamp arm actuator (612) and clamp arm assembly (614) collectively in closed and released configurations. With respect to FIG. 28C, the operator aligns inner shoulders (632), transverse slot (630), and elongate portions of mounting holes (638) to the release configuration shown in FIG. 28C. The operator then translates clamp arm assembly (614) away from clamp arm actuator (612) until removed therefrom as shown in FIG. 28D. Furthermore, clamp arm actuator (612) is removable from pins (628) by manipulating flanges (636) laterally outward away from shaft assembly (330).

B. Fourth Exemplary Ultrasonic Surgical Instrument with a Second Modular Alignment Release Coupling FIGS. 29-33B illustrate a fourth exemplary surgical instrument (710) having handle assembly (311), shaft assembly (330), a clamp arm actuator (712), a clamp arm assembly (714), and a second modular alignment release coupling (716). With respect to FIGS. 29 and 30, clamp arm assembly (714) is removably connected to clamp arm actuator (712) with modular alignment release coupling (716), which includes a clamp body connection (718) extending from clamp arm assembly (714) and a clamp actuator connection (720) extending from clamp arm actuator (712). Clamp arm assembly (714) includes a clamp body (722) and a clamp pad (724). Clamp pad (724) is connected to clamp body (722) such that clamp pad (724) faces ultrasonic blade (350) for receiving and clamping tissue therebetween. Selective movement of clamp arm actuator (712) relative to handle assembly (311) from an opened configuration to a closed configuration respectively moves clamp arm assembly (714) from an opened position configured to receive tissue to a closed position configured to clamp the tissue. In the present example, selective movement of clamp arm actuator (712) to a release configuration aligns clamp actuator connection (720) relative to the clamp body connection (718) to disconnect clamp arm assembly (714) from clamp arm actuator (712) for removal and replacement of clamp arm assembly (714). While not shown with respect to surgical instrument (710), clamp arm assembly (714) may further include one or more electrodes configured to deliver RF energy to tissue for affecting the tissue, such as coagulating vessels in use.

Figure 30:
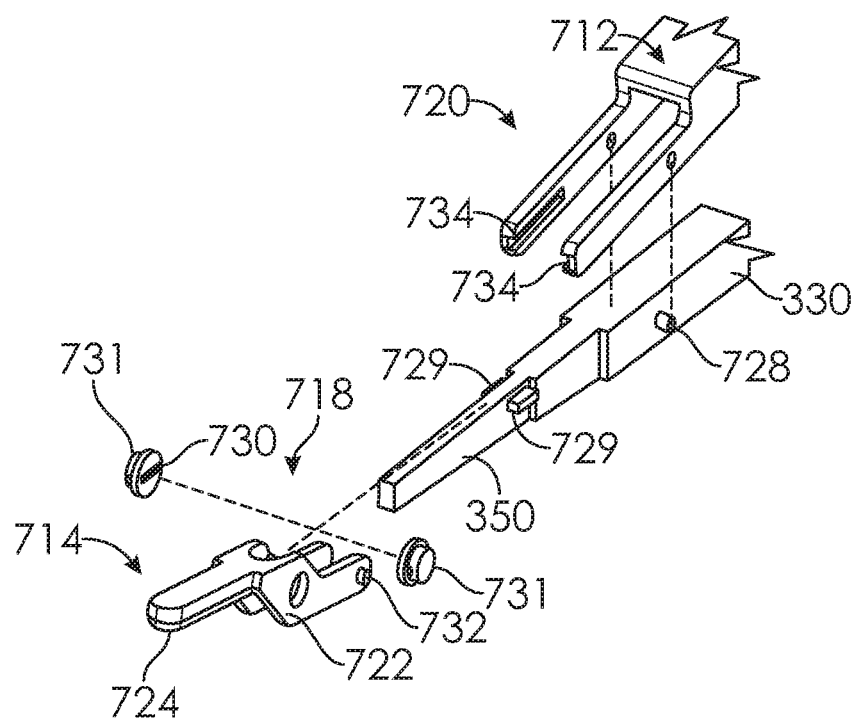
FIG. 30 depicts an enlarged exploded perspective view of the surgical instrument and modular alignment release coupling of FIG. 29.

FIG. 30 illustrates shaft assembly (330) configured to receive each of clamp arm actuator (712) and clamp arm assembly (714) for use. Shaft assembly (311) has a pair of opposing cylindrical pins (728) extending laterally from opposing sides thereof. The cylindrical pins (728) are configured to be received respectively in a pair of holes of a distal portion of clamp arm actuator (712) such that clamp arm actuator (712) is pivotally connected to shaft assembly (330). Similarly, shaft assembly (330) further includes a pair of opposing shoulders (729) laterally extending therefrom and distally positioned from pins (728). The shoulders (729) are configured to be received within transverse slot (730) of cylindrical pins (731) rotatably mounted in clamp arm assembly (714) for pivotally connecting clamp arm assembly (714) to shaft assembly (330). In the present example, movement of clamp arm actuator (712) about pins (728) is generally above the longitudinal axis, but the releasable connection with clamp arm assembly (714) is below the longitudinal axis. However, clamp body (722) straddles the longitudinal axis such that the movement of clamp pad (724) is above the longitudinal axis.

Figure 31A:
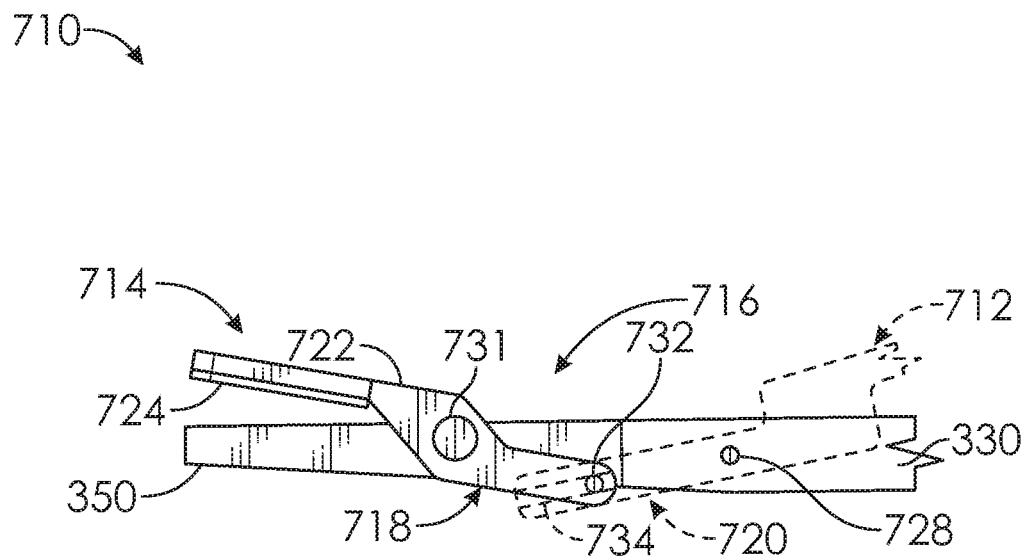
FIG. 31A depicts the enlarged side view of the surgical instrument of FIG. 29 in the open configuration.
Figure 31B:
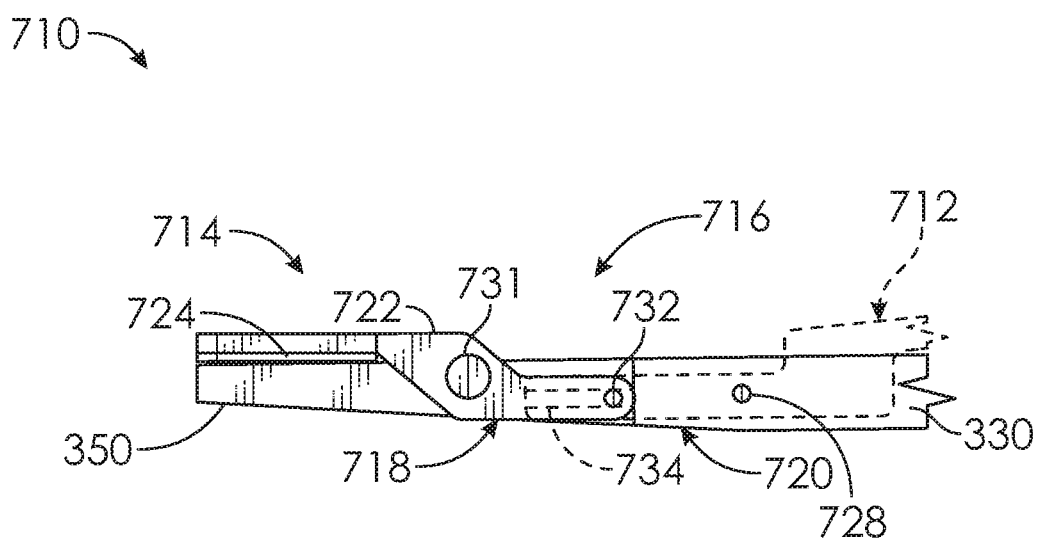
FIG. 31B depicts the enlarged side view of the surgical instrument similar to FIG. 29, but with the surgical instrument in a closed configuration.
Figure 32:
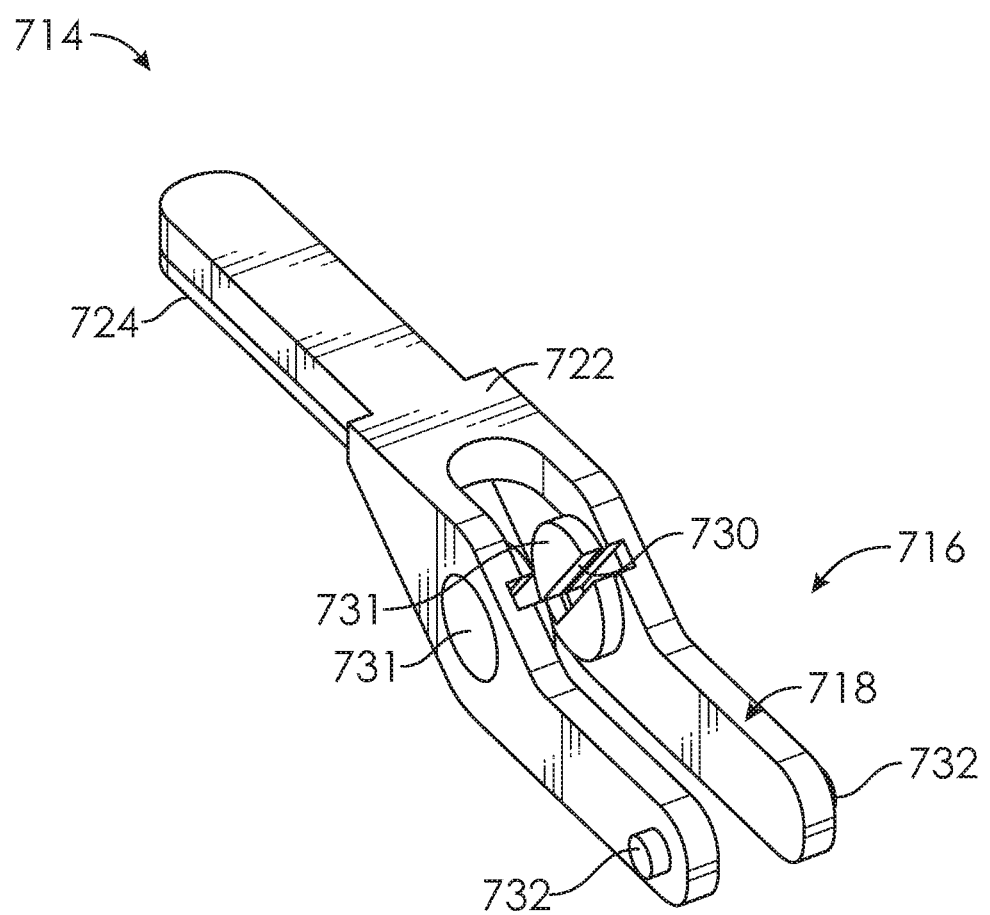
FIG. 32 depicts a perspective view of a clamp arm assembly of the surgical instrument of FIG. 29.

In addition to cylindrical pins (728), slotted cyclical pins (731), and shoulders (729), modular alignment release coupling (716) also has clamp body connection (718), which includes a pair of opposing arm pins (732), and clamp actuator connection (718), which includes a pair of elongate slots (734). Arm pins (732) extend laterally outward from the longitudinal axis, whereas elongate slots (734) face inward toward the longitudinal axis to respectively receive arm pins (732) as shown in FIGS. 31A-32. In the opened configuration of FIG. 31A, each arm pin (732) is relatively distally located in elongate slot (734). However, in the closed configuration of FIG. 31B, each arm pin (732) is relatively proximally located in elongate slot (734). In the present example, movement of clamp arm actuator (712) about pins (728) is below longitudinal axis, but movement of clamp arm assembly (714) is above the longitudinal axis, because pins (728) laterally intersect the longitudinal axis.

Figure 33A:
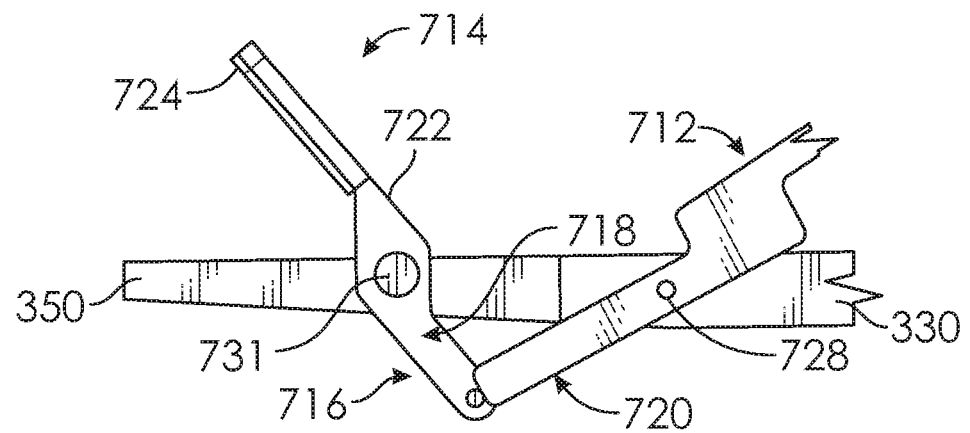
FIG. 33A depicts an enlarged side view of the surgical instrument of FIG. 29 in a release configuration.
Figure 33B:
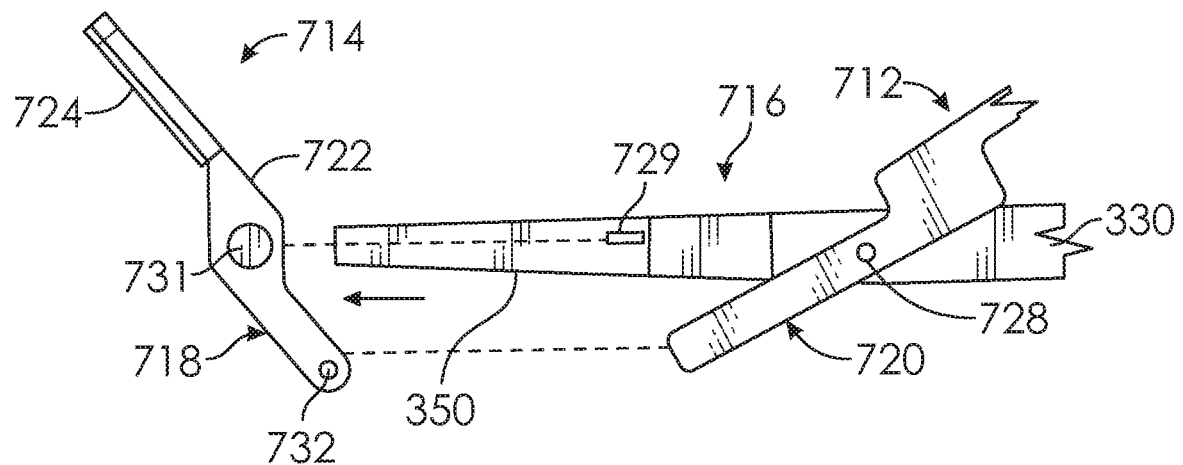
FIG. 33B depicts the enlarged side view of the surgical instrument similar to FIG. 33A, but showing the clamp arm assembly removed from a handle assembly of the surgical instrument.
Figure 34:
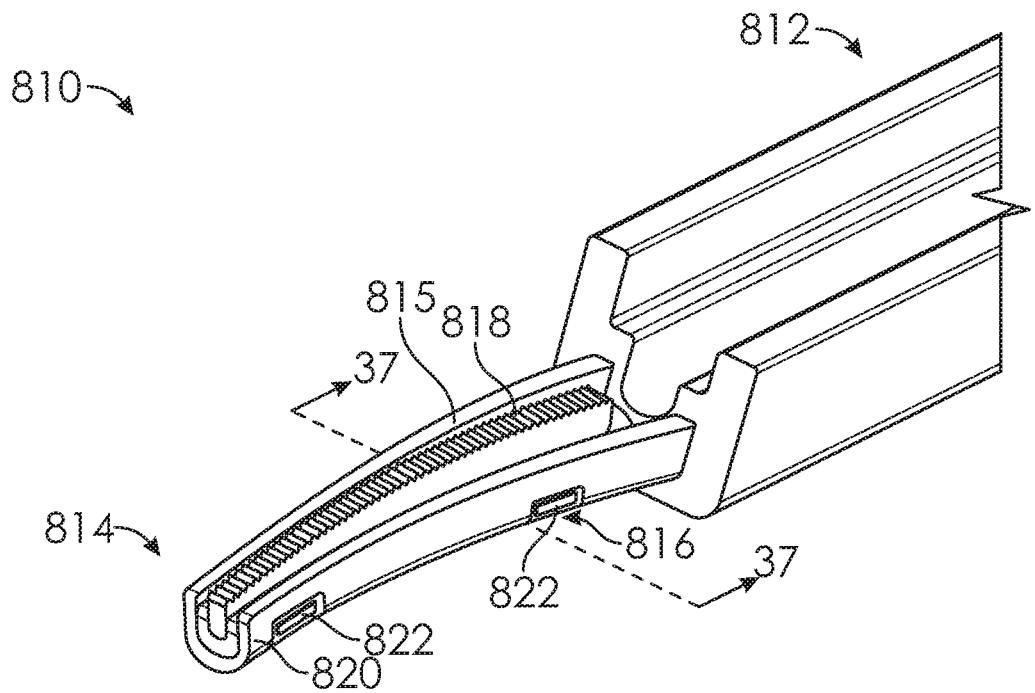
FIG. 34 depicts an enlarged perspective view of a fifth exemplary surgical instrument having a first modular pad coupling with a clamp pad being removable from a remainder of a clamp arm assembly.
Figure 35:
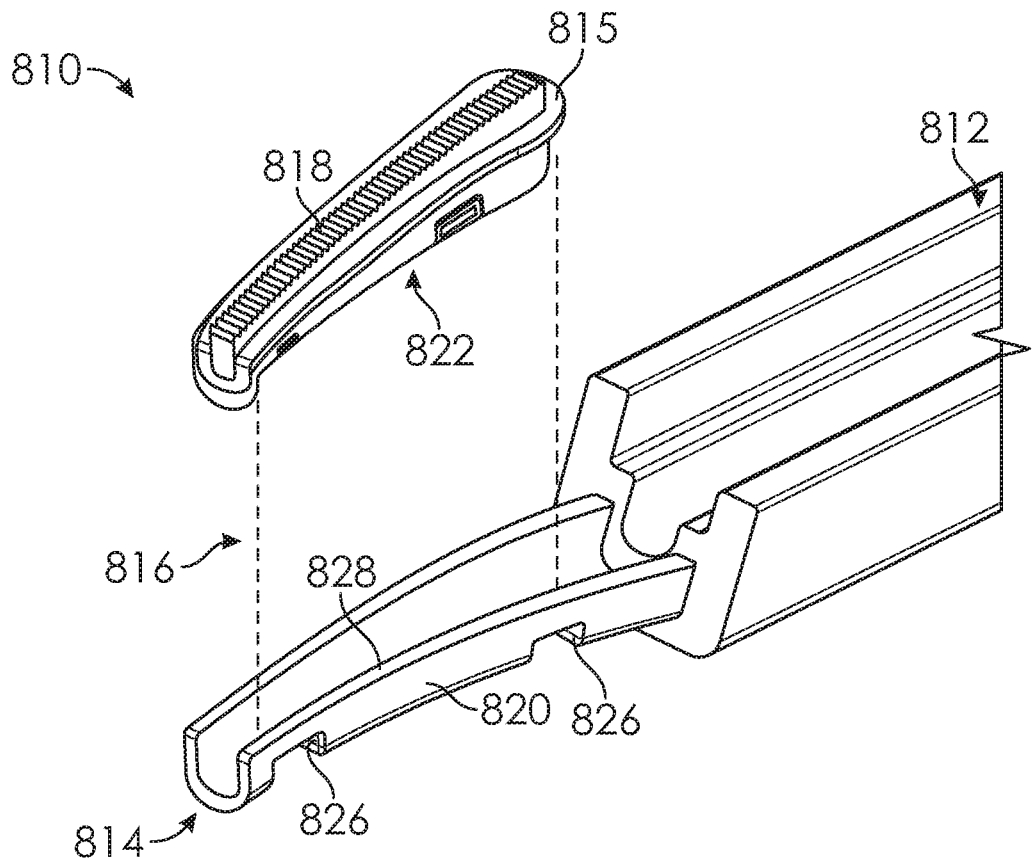
FIG. 35 depicts a partially exploded perspective view of the surgical instrument and modular pad coupling of FIG. 34.
Figure 36:
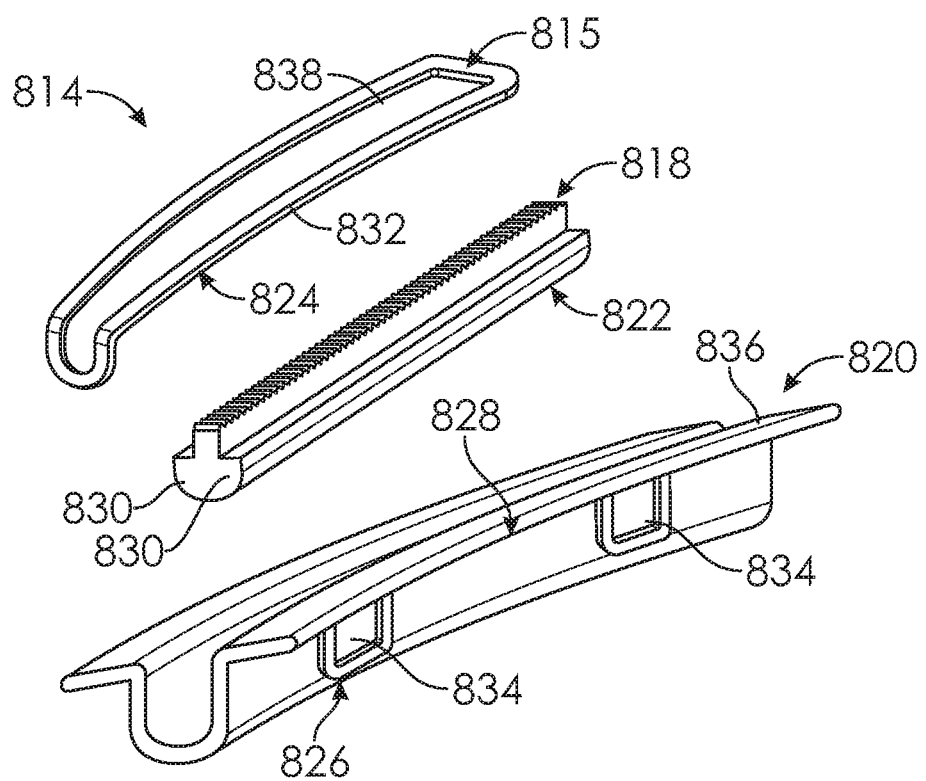
FIG. 36 depicts an exploded view of the modular pad coupling and clamp arm assembly of FIG. 34.
Figure 37:
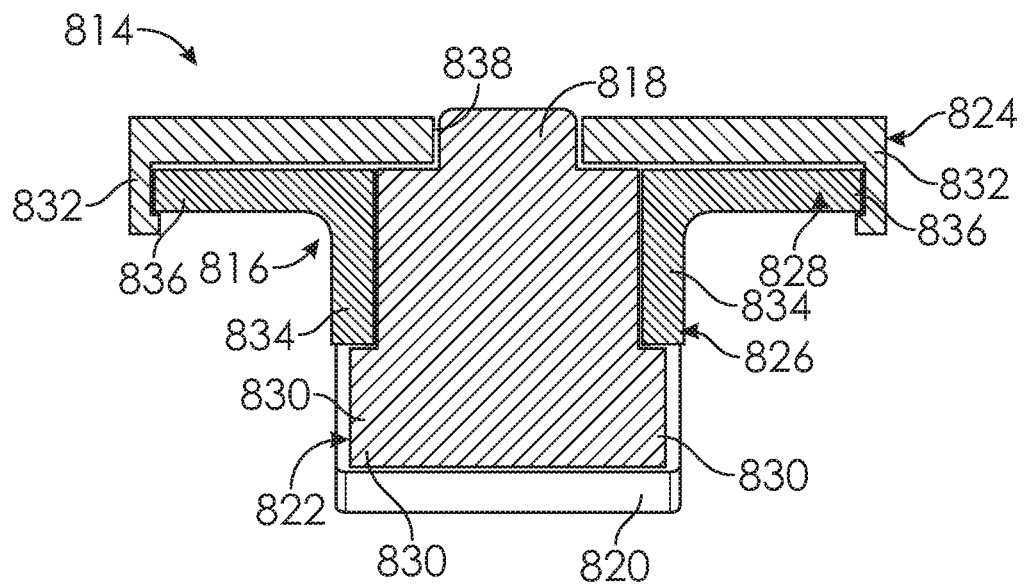
FIG. 37 depicts a cross-sectional view of the surgical instrument of FIG. 34 taken along section line 37-37 of FIG. 34.

In use, FIG. 33A illustrate clamp arm actuator (712) and clamp arm assembly (714) collectively in the released configuration, which is pivoted beyond the opened configuration (see FIG. 31A). In the released configuration, arm pins (732) distally slide relative to elongate slot (734) until exiting from each elongate slot (734). Once arm pins (732) are free from elongate slots (734), the operator removes clamp arm assembly (714) from shoulders (729) with distal translation thereof.

C. Fifth Exemplary Ultrasonic Surgical Instrument with a First Modular Pad Coupling FIGS. 34-37 illustrate a fifth exemplary surgical instrument (810) having a clamp arm actuator (812), a clamp arm assembly (814) with a clamp pad cap (815), and a first modular pad coupling (816). With respect to FIGS. 34-36, clamp arm assembly (814) further includes a clamp pad (818) and a clamp body (820), which is configured to removably receive clamp pad cap (815) and clamp pad (818). To this end, clamp body (820) of the present example extends rigidly from clamp arm actuator (812) with modular pad coupling (816) between clamp pad cap (815) and clamp body (812) for removably connecting clamp pad (818) into clamp body (820).

Modular pad coupling (816) includes a clamp pad connection (822), a cap connection (824) and a pair of clamp body connections (826, 828). As shown in greater detail in FIGS. 36 and 37, clamp pad connection (822) includes a pair of elongate pad shoulders (830), while cap connection (824) includes a resilient outer lip (832). One of the clamp body connections (826) has a plurality of resilient clips (834), whereas the other of the clamp body connections (828) has a rigid outer lip (836). Each resilient clip (834) engages an upper surface of elongate pad shoulders (830) for removably securing clamp pad (818) into clamp body (820). In addition, resilient outer lip (832) on clamp pad cap (815) engages rigid outer lip (836) to removably secure clamp pad cap (815) to clamp body (820) thereby capturing clamp pad (818) therebetween. In the present example, a portion of clamp pad (818) extends through an elongate hole (838) in clamp pad cap (815). This portion may include reduced friction coating, such as polytetrafluoroethylene, for inhibiting tissue adhesion during use. Clamp pad cap (815) is also electrically connected upon connection with clamp body (820) to an RF energy source such that clamp pad cap (815) is also an RF electrode, although clamp pad cap (815) may not be an RF electrode in alternative examples.

In use, the operator pries clamp pad cap (815) from clamp body (820) by overcoming the engagement force between resilient outer lip (832) and rigid outer lip (836). The operator then pries clamp pad (818) from clamp body (820) by similarly overcoming the engagement force between elongate pad shoulders (830) and clips (834) and may discard the used clamp pad (818). A replacement clamp pad (818) snaps into clamp body (820) followed by snapping the clamp pad cap (815) to the clamp body (820) in order to capture the replacement clamp pad (818) for use.

Figure 38:
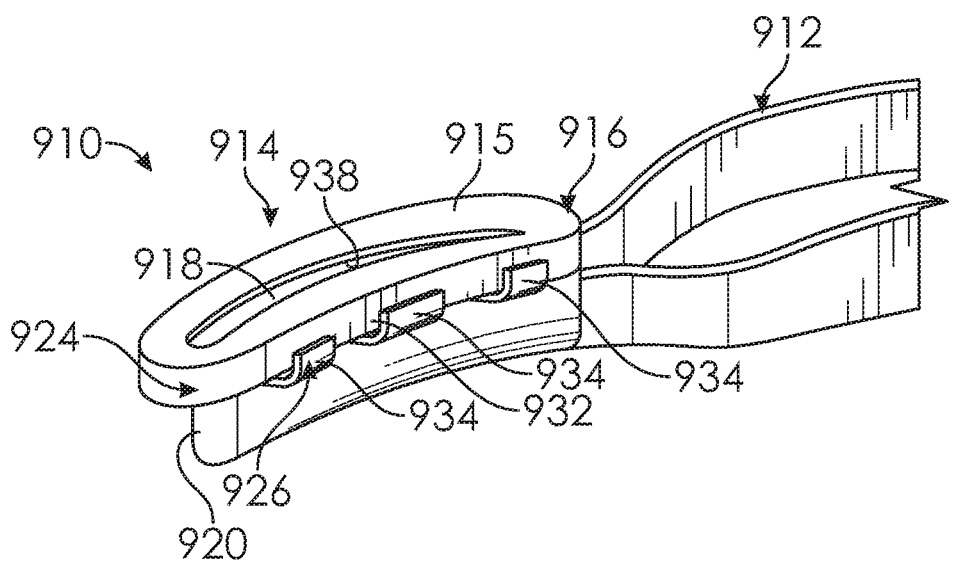
FIG. 38 depicts an enlarged perspective view of a sixth exemplary surgical instrument having a second modular pad coupling with a clamp pad being removable from a remainder of a clamp arm assembly.
Figure 39:
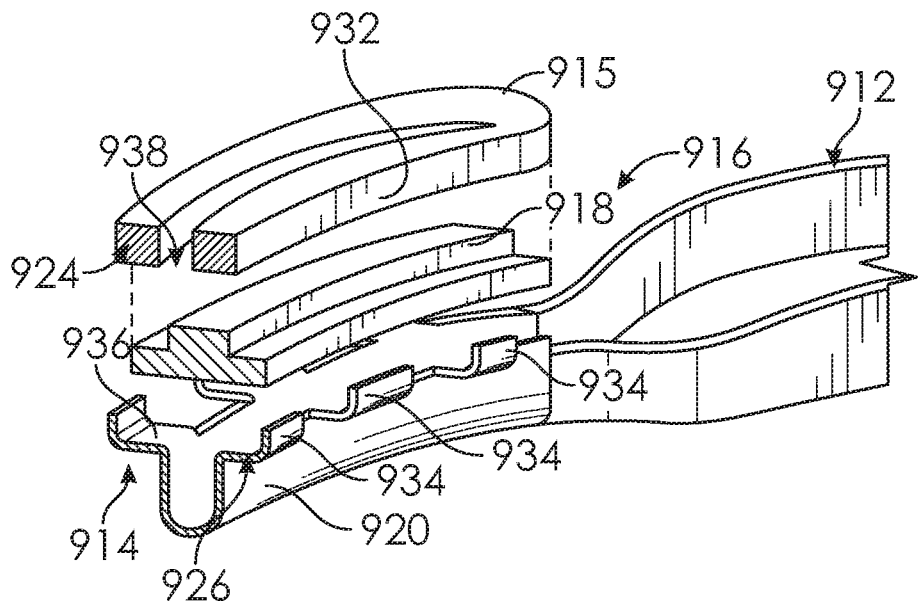
FIG. 39 depicts a partially exploded, sectional perspective view of the surgical instrument and modular pad coupling of FIG. 38.
Figure 40:
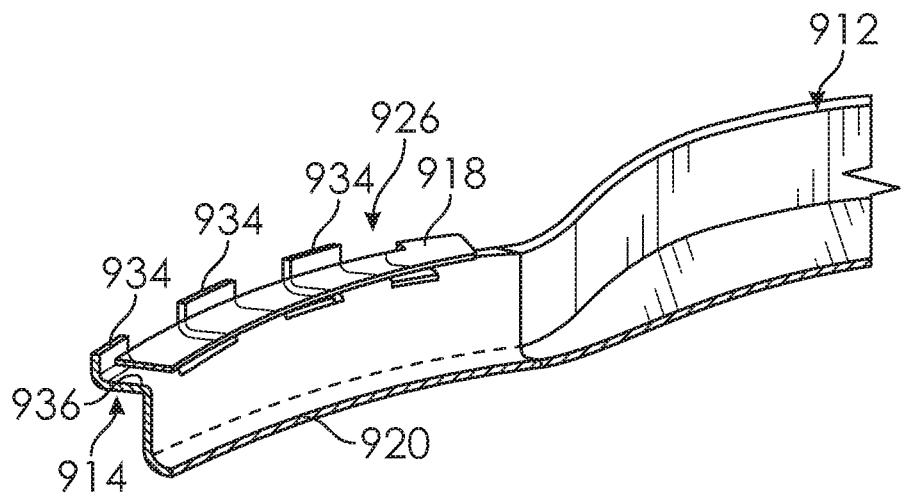
FIG. 40 depicts a sectional perspective view of the surgical instrument of FIG. 38 taken generally along a centerline thereof.

D. Sixth Exemplary Ultrasonic Surgical Instrument with a Second Modular Pad Coupling FIGS. 38-40 illustrate a sixth exemplary surgical instrument (910) having a clamp arm actuator (912), a clamp arm assembly (914) with a clamp pad cap (915), and a second modular pad coupling (916). Clamp arm assembly (914) further includes a clamp pad (918) and a clamp body (920), which is configured to removably receive clamp pad cap (915) and (918). To this end, clamp body (920) of the present example extends rigidly from clamp arm actuator (912) with modular pad coupling (916) between clamp pad cap (915) and clamp body (912) for removably connecting clamp pad (918) into clamp body (920).

Modular pad coupling (916) includes a cap connection (924) and a clamp body connection (926). Cap connection (924) includes a resilient outer lip (932), whereas clamp body connection (926) has a plurality of resilient clips (934). Each resilient clip (934) extending upward from clamp body (920) engages resilient outer lip (932) on clamp pad cap (915) for removably securing clamp pad cap (915) to clamp body (920). Thereby, clamp pad cap (915) compresses and removably captures clamp pad (918) against a support surface (936) of clamp body (920). In the present example, a portion of clamp pad (918) extends through an elongate hole (938) in clamp pad cap (915). Clamp pad cap (915) is also electrically connected upon connection with clamp body (920) to an RF energy source such that clamp pad cap (915) is also an RF electrode, although clamp pad cap (915) may not be an RF electrode in alternative examples.

In use, the operator pries clamp pad cap (915) from clamp body (920) by overcoming the engagement force between resilient outer lip (932) and the plurality of resilient clips (934). The operator then simply removes and may discard clamp pad (918) from clamp body (920). A replacement clamp pad (918) is positioned on support surface (936) and clamp pad cap (915) snaps into clamp body (920) in order to capture the replacement clamp pad (918) for use.

Figure 41:
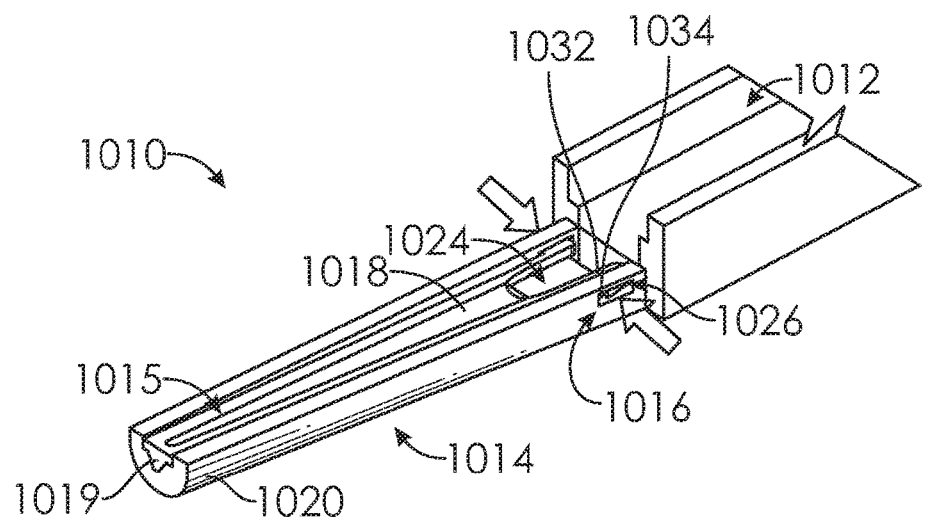
FIG. 41 depicts an enlarged perspective view of a seventh exemplary surgical instrument having a third modular pad coupling with a clamp pad being removable from a remainder of a clamp arm assembly.
Figure 42:
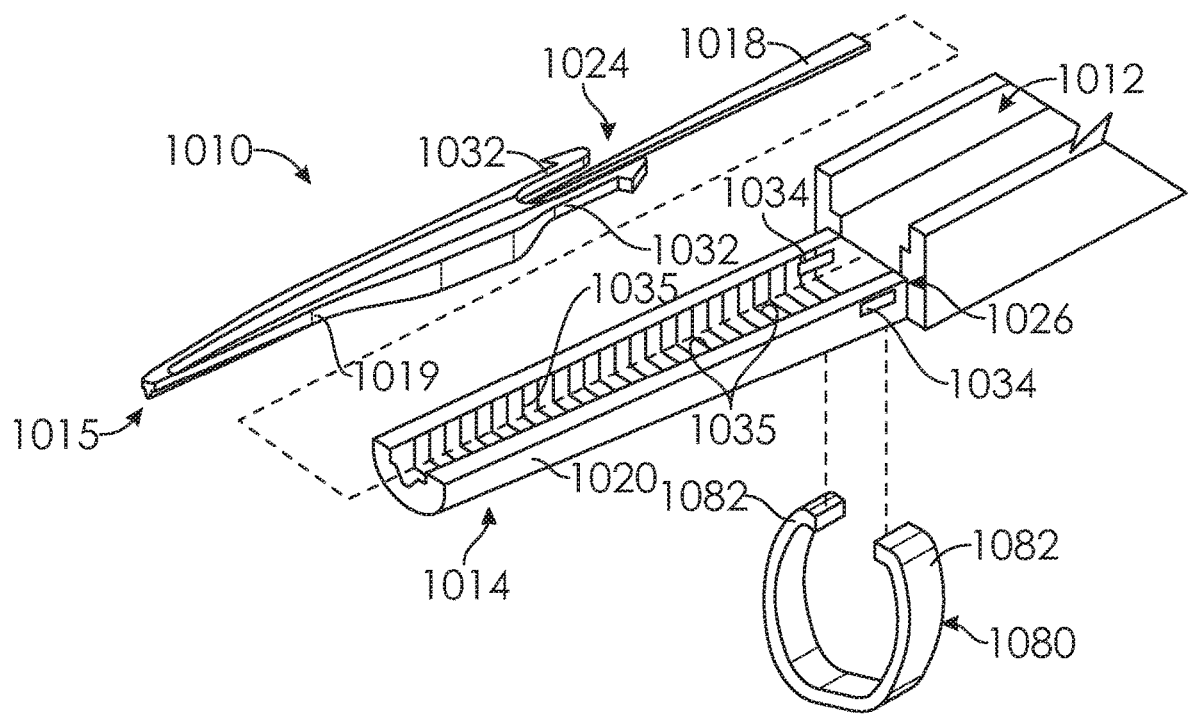
FIG. 42 depicts a partially exploded perspective view of the surgical instrument and modular pad coupling of FIG. 41 as well as a first modular connection tool.
Figure 43:
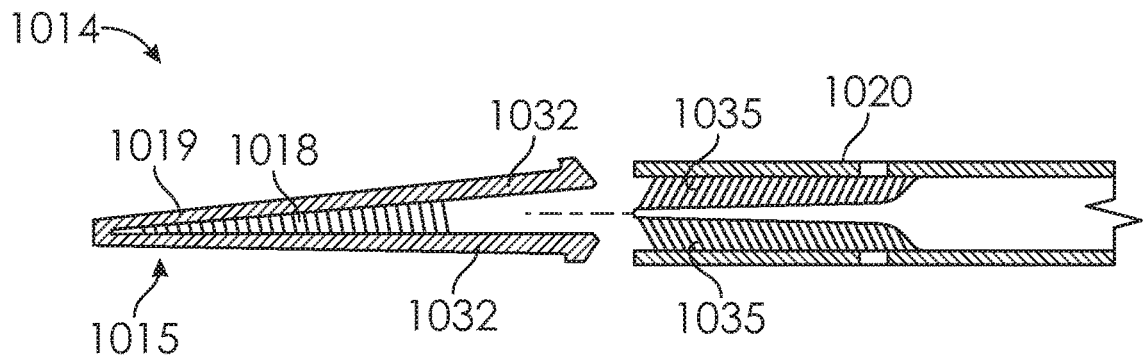
FIG. 43 depicts a partially exploded top view of the surgical instrument and modular pad coupling of FIG. 41.

E. Seventh Exemplary Ultrasonic Surgical Instrument with a Third Modular Pad Coupling FIGS. 41-43 illustrate a seventh exemplary surgical instrument (1010) having a clamp arm actuator (1012), a clamp arm assembly (1014) with a separable clamp pad assembly (1015), and a third modular pad coupling (1016). Clamp arm assembly (1014) further includes clamp pad assembly (1015) with a clamp pad (1018) and a pad housing (1019) as well as a clamp body (1020), which is configured to removably receive clamp pad assembly (1015). To this end, clamp body (1020) of the present example extends rigidly from clamp arm actuator (1012) with modular pad coupling (1016) between clamp pad assembly (1040) and clamp body (1012) for removably connecting pad housing (1019) into clamp body (1020).

Modular pad coupling (1016) includes a clamp pad connection (1024) and a clamp body connection (1026). Clamp pad connection (1024) includes a pair of resilient clips (1032) proximally extending from pad housing (1019), whereas clamp body connection (1026) includes a pair of lateral apertures (1034) extending through a proximal portion of clamp body (1020). Lateral apertures (1034) are configured to respectively receive resilient clips (1032) to removably securing pad housing (1019) into clamp body (1020). Clamp arm assembly (1014) further includes a plurality of resilient strand members (1035) projecting distally within clamp body (1020) and configured to further secure pad housing (1019) in clamp body (1020) as shown in FIGS. 42 and 43. While not shown with respect to surgical instrument (1010), clamp arm assembly (1014) may further include one or more electrodes configured to deliver RF energy to tissue for affecting the tissue, such as coagulating vessels in use.

In use, the operator urges resilient clips (1032) laterally inward toward the longitudinal axis and out from lateral apertures (1034). In one example, a modular connection tool (1080) is provided to aid with disconnecting clamp pad assembly (1015) from clamp body (1020). Modular connection tool (1080) is U-shaped having keyed projections (1082) on respective ends that are configured to be inserted into lateral aperture (1034) for urging resilient clips (1032) laterally inward. Once disconnected, the operator pries clamp pad assembly (1015) past resilient strand members (1035) for removal. A replacement clamp pad (1018) with a replacement clamp pad assembly (1015) is positioned into clamp body (1020) and snapped therein, in order to capture the replacement clamp pad (1018) for use.

Figure 44:
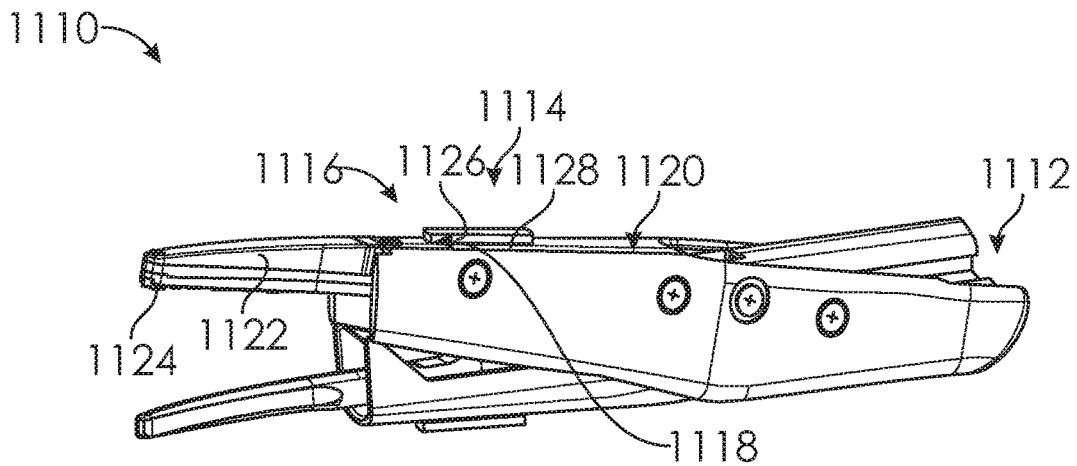
FIG. 44 depicts an enlarged perspective view of an eighth exemplary surgical instrument having a first modular snap coupling.
Figure 45:
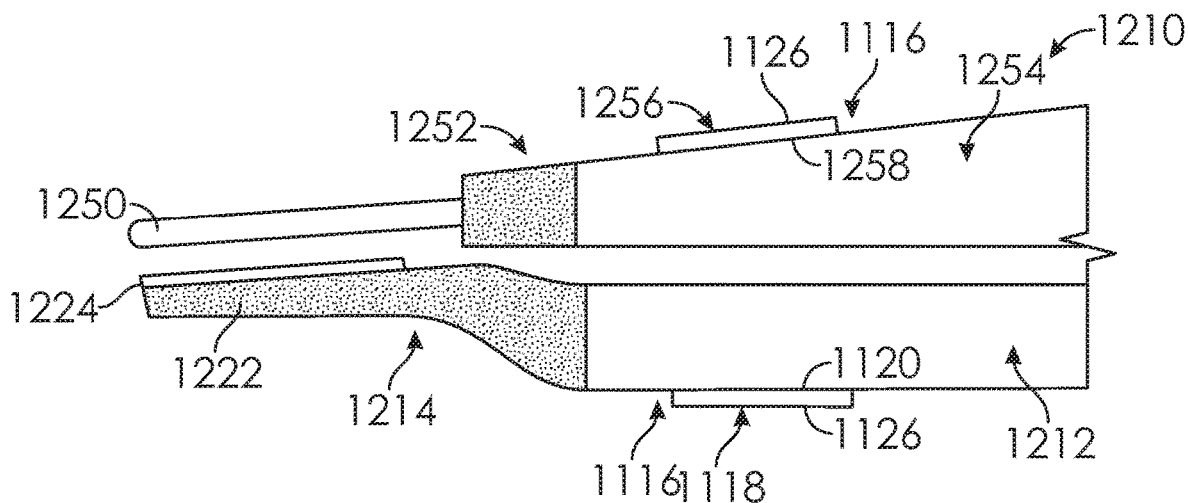
FIG. 45 depicts an enlarged side view of a ninth exemplary surgical instrument having the modular snap coupling of FIG. 44 associated with each of a clamp arm assembly and an electrode assembly.

F. Eighth Exemplary Ultrasonic Surgical Instrument with a First Modular Snap Coupling FIG. 44 illustrates a ninth exemplary surgical instrument (1110) having a shaft assembly (330), a clamp arm actuator (1112), a clamp arm assembly (1114), and a first modular snap coupling (1116). Clamp arm assembly (1114) is removably connected to clamp arm actuator (1112) with modular snap coupling (1116), which includes a clamp body connection (1118) on clamp arm assembly (1114) and a clamp actuator connection (1120) on clamp arm actuator (1112). Clamp arm assembly (1114) includes a clamp body (1122) and a clamp pad (1124). Clamp pad (1124) is connected to clamp body (1122) such that clamp pad (1124) faces ultrasonic blade (350) for receiving and clamping tissue therebetween. Selective movement of clamp arm actuator (1112) relative to shaft assembly (330) from an opened configuration to a closed configuration respectively moves clamp arm assembly (1114) from an opened position configured to receive tissue to a closed position configured to clamp the tissue. While not shown with respect to surgical instrument (1110), clamp arm assembly (1114) may further include one or more electrodes configured to deliver RF energy to tissue for affecting the tissue, such as coagulating vessels in use.

While surgical instrument (1110) has ultrasonic blade (350) as shown and described above with respect to FIG. 44, an alternative example, such as a tenth exemplary surgical instrument (1210) (see FIGS. 45-48), has an electrode assembly (1252) positioned opposite clamp arm assembly (1114). To this end, modular snap coupling (1116) will be described in conjunction with electrode assembly (1252) (see FIGS. 45-48) of surgical instrument (1210) (see FIGS. 45-48). Additional description with respect to modular snap coupling (1116) provided below similarly applies to surgical instrument (1110) above.

G. Ninth Exemplary Ultrasonic Surgical Instrument with the First Modular Snap Coupling FIGS. 45-48 illustrate ninth exemplary surgical instrument (1210) having a clamp arm actuator (1212), a clamp arm assembly (1214), and a pair of modular snap couplings (1116) discussed briefly above. Clamp arm assembly (1214) is removably connected to clamp arm actuator (1212) with modular snap coupling (1116), which includes clamp body connection (1118) on clamp arm assembly (1214) and clamp actuator connection (1120) on clamp arm actuator (1212). Clamp arm assembly (1214) includes a clamp body (1222) and a clamp pad (1224). Clamp pad (1224) is connected to clamp body (1222) such that clamp pad (1224) faces an electrode (1250) of an electrode assembly (1252) for receiving and clamping tissue therebetween. Modular snap coupling (1116) is also incorporated into electrode assembly (1252) for removably connecting electrode (1250) to an electrode actuator (1254). Selective movement of clamp arm actuator (1212) relative to electrode actuator (1254) from an opened configuration to a closed configuration respectively moves clamp arm assembly (1214) from an opened position configured to receive tissue to a closed position configured to clamp the tissue. Electrode (1250) of the present example is an RF electrode operative connected to an RF energy source and configured to deliver the RF energy to the tissue.

While surgical instrument (1110) has ultrasonic blade (350) as shown and described above with respect to FIG. 44, an alternative example, such as a ninth exemplary surgical instrument (1210) (see FIGS. 45-48), has an electrode assembly (1250) positioned opposite clamp arm assembly (1114). To this end, modular snap coupling (1116) will be described in conjunction with electrode assembly (1252) (see FIGS. 45-48) of surgical instrument (1210) (see FIGS. 45-48). Additional description with respect to modular snap coupling (1116) provided below similarly applies to surgical instrument (1110) above.

Figure 46:
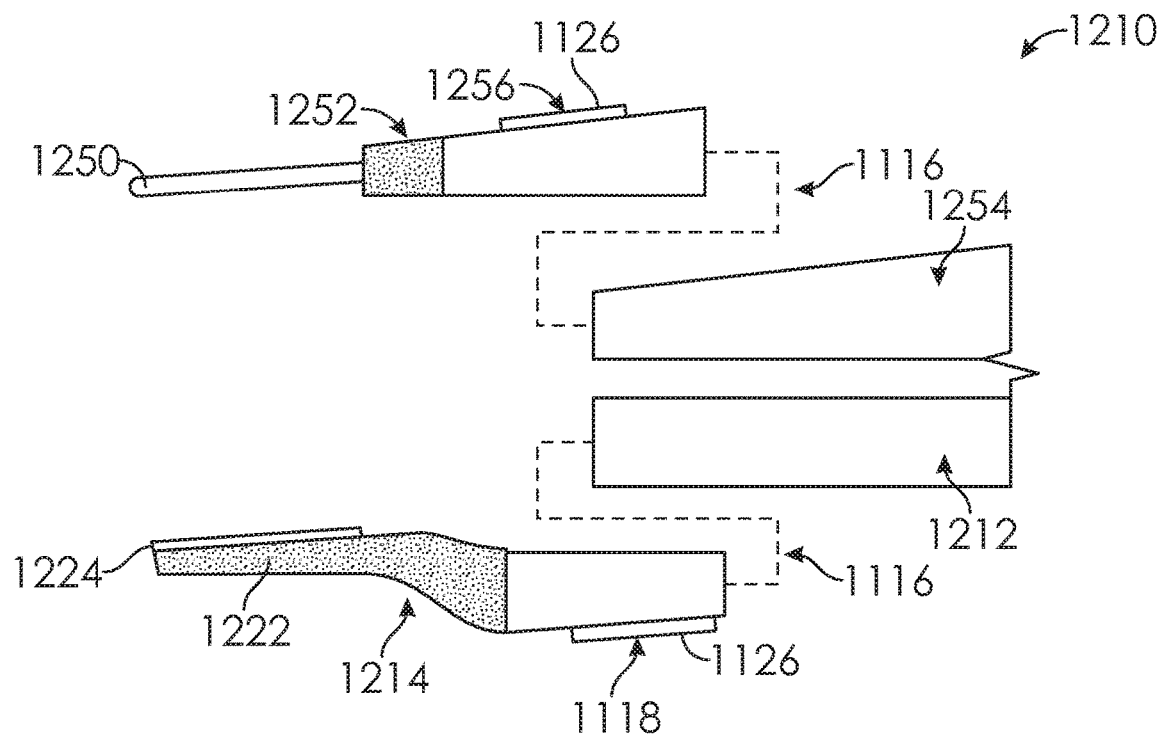
FIG. 46 depicts an enlarged partially exploded view of the surgical instrument with the modular snap couplings of FIG. 45.

With respect to FIG. 46, modular snap coupling (1116) has clamp body connection (1118) with a biased projection tab (1126) proximally extending from a proximal portion of clamp arm assembly (1214). Modular snap coupling (1116) also has clamp actuator connection (1120) with a lower aperture (1128) extending transversely through a lower surface of clamp arm actuator (1212). Lower aperture (1128) receives biased projection tab (1126) and releasably captures biased projection tab (1126) to thereby removably connect clamp arm assembly (1214) to clamp arm actuator (1212).

Figure 47A:
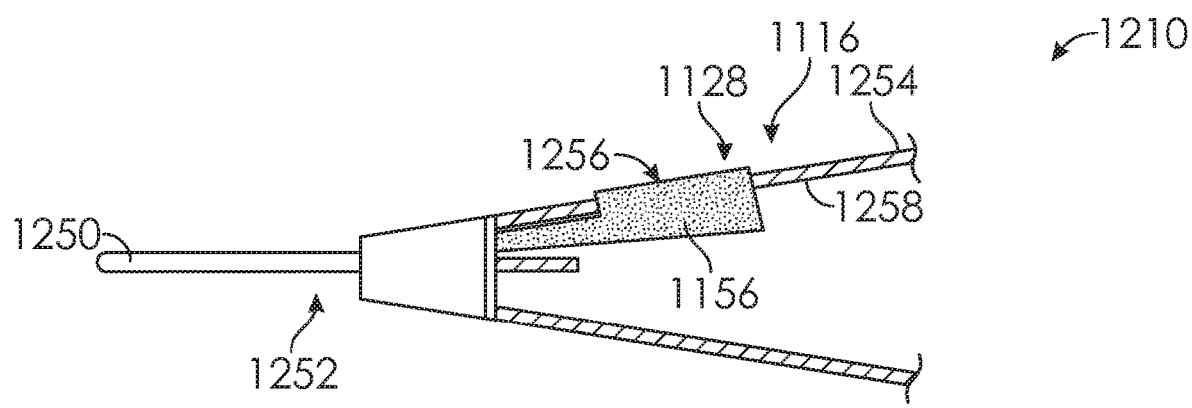
FIG. 47A depicts an enlarged side sectional view of the electrode assembly of FIG. 45.
Figure 47B:
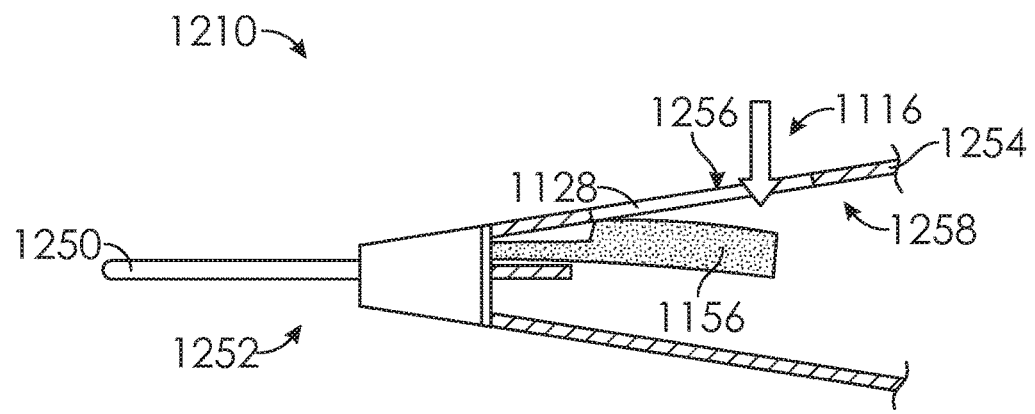
FIG. 47B depicts the enlarged side sectional view of the electrode assembly similar to FIG. 47A, but showing a biased projection tab being depressed for removal of the electrode assembly from a remainder of an end effector.
Figure 47C:
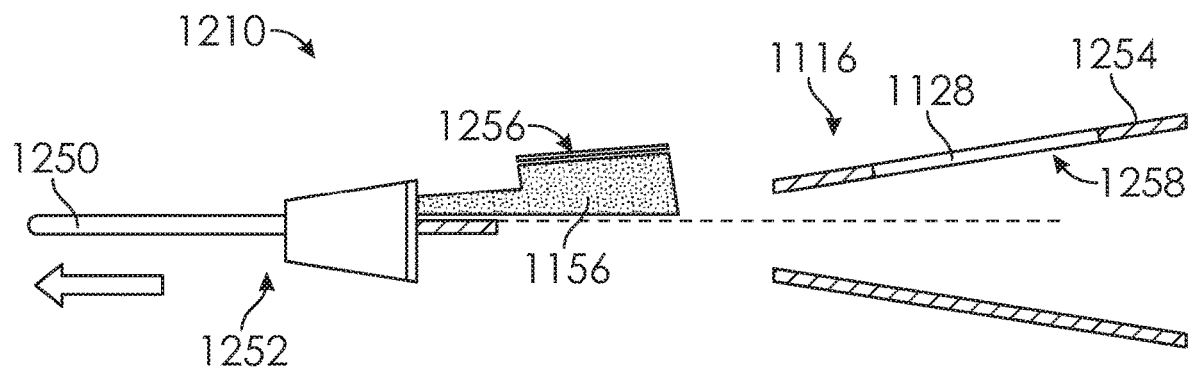
FIG. 47C depicts the enlarged side sectional view of the electrode assembly similar to FIG. 47B, but showing the electrode assembly being removed from the remainder of the end effector.

In addition, FIGS. 46-47A illustrate modular snap coupling (1116) having an electrode assembly connection (1256) with biased projection tab (1126) proximally extending from a proximal portion of electrode assembly (1252). Modular snap coupling (1116) also has electrode actuator connection (1258) with an upper aperture (1128) extending transversely through an upper surface of electrode actuator (1254). Upper aperture (1128) receives biased projection tab (1126) and releasably captures biased projection tab (1126) to thereby removably connect electrode assembly (1252) to electrode actuator (1254).

Figure 48:
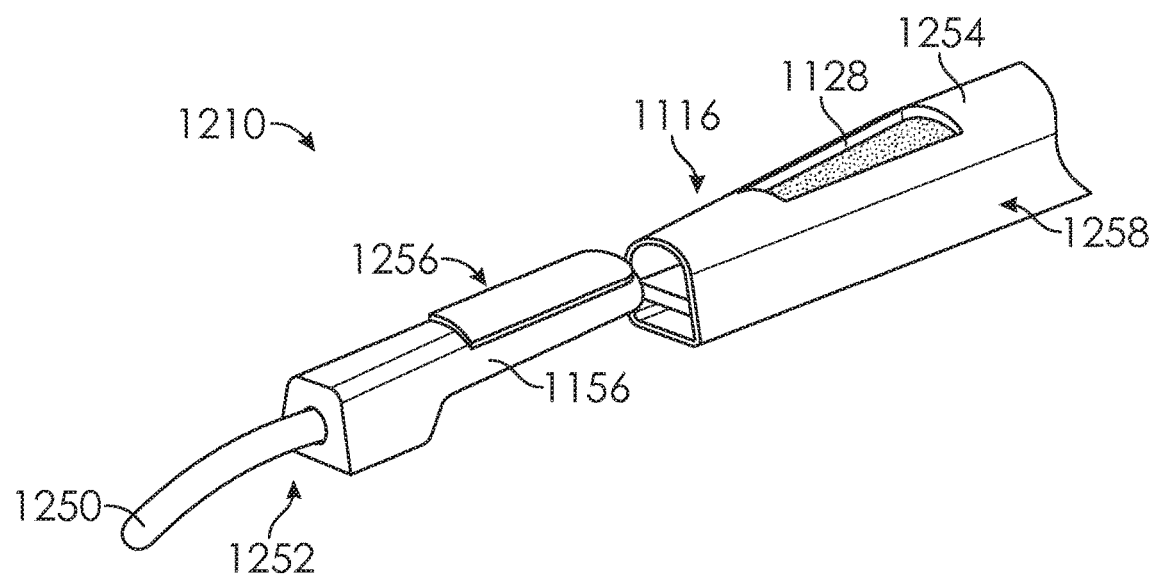
FIG. 48 depicts an enlarged perspective view of the electrode assembly removed from the remainder of the end effector of the surgical instrument of FIG. 45.

In use, with respect to FIGS. 47A-48, the operator transversely depresses biased projection tab (1126) until longitudinally clear of upper aperture (1128) in electrode actuator (1254). Once clear, the operator distally translates electrode assembly (1252) relative to electrode actuator (1254). A replacement electrode assembly (1252) is positioned into electrode actuator (1254) and snapped therein, in order to capture the replacement electrode assembly (1252) for use. A replacement clamp arm assembly (1214) may also be removed and replaced via modular snap coupling (1116) as discussed with respect to electrode assembly (1252).

Figure 49A:
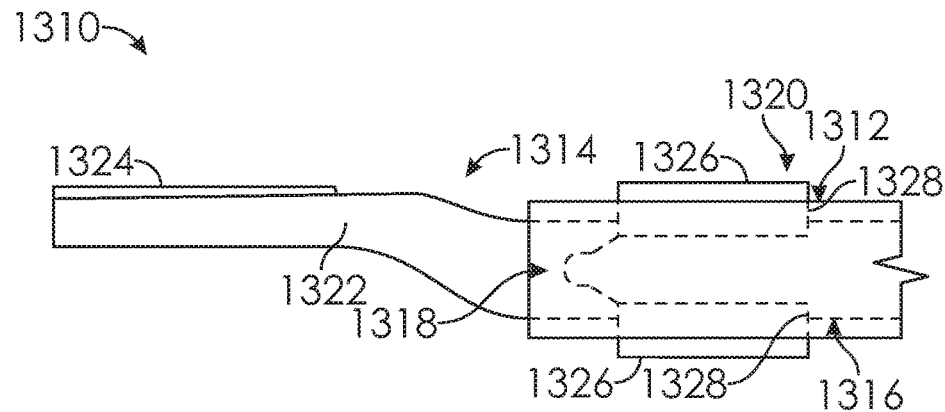
FIG. 49A depicts an enlarged side view of a clamp arm assembly of a tenth exemplary surgical instrument having a second modular snap coupling.
Figure 49B:
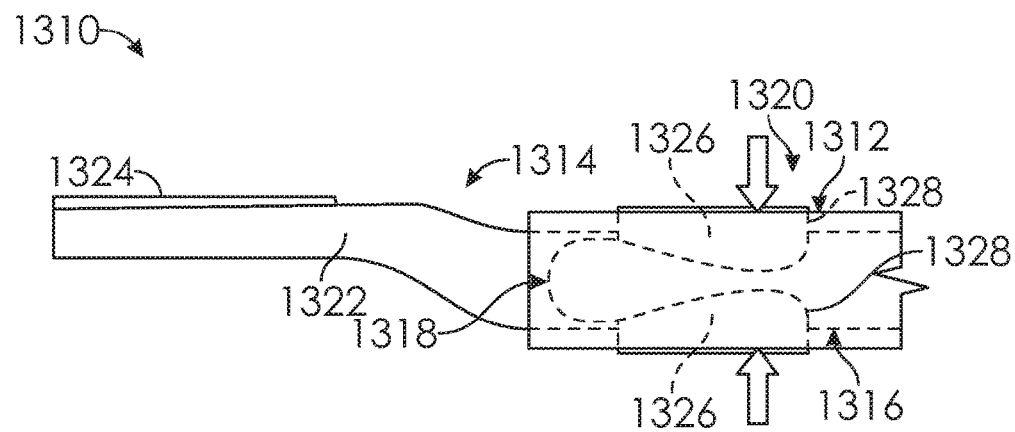
FIG. 49B depicts the enlarged side view of the clamp arm assembly similar to FIG. 49A, but showing a pair of biased projection tabs being depressed for removal of the clamp arm assembly.
Figure 49C:
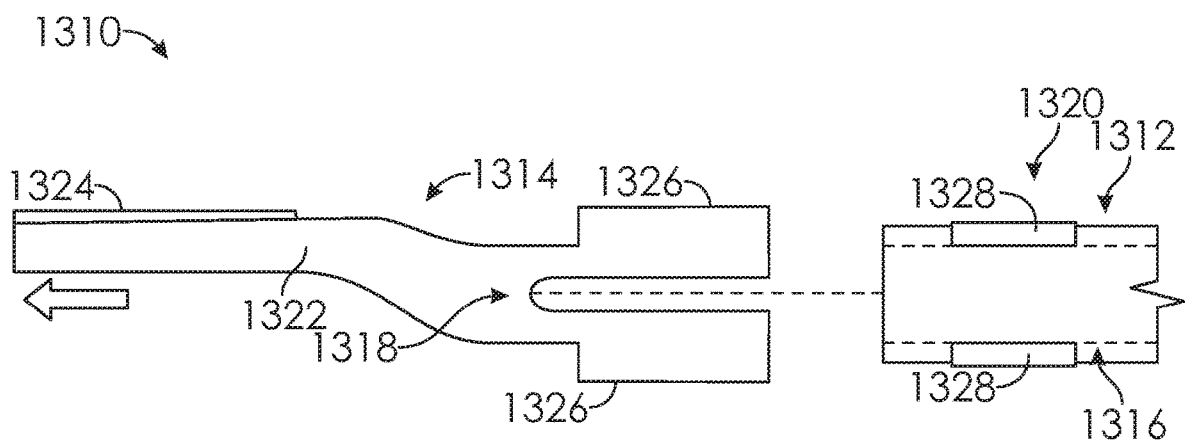
FIG. 49C depicts the enlarged side view of the clamp arm assembly similar to FIG. 49B, but showing the clamp arm assembly removed from a clamp arm actuator.

H. Tenth Exemplary Ultrasonic Surgical Instrument with a Second Modular Snap Coupling FIGS. 49A-49C illustrate eleventh tenth exemplary surgical instrument (1310) having a clamp arm actuator (1312), a clamp arm assembly (1314), and a second modular snap coupling (1316). Clamp arm assembly (1314) is removably connected to clamp arm actuator (1312) with modular snap coupling (1316), which includes a clamp body connection (1318) on clamp arm assembly (1314) and a clamp actuator connection (1320) on clamp arm actuator (1312). Clamp arm assembly (1314) includes a clamp body (1322) and a clamp pad (1324). Clamp pad (1324) is connected to clamp body (1322) such that clamp pad (1324) faces ultrasonic blade (not shown) for receiving and clamping tissue therebetween. Selective movement of clamp arm actuator (1312) relative to shaft assembly (not shown) from an opened configuration to a closed configuration respectively moves clamp arm assembly (1314) from an opened position configured to receive tissue to a closed position configured to clamp the tissue. While not shown with respect to surgical instrument (1310), clamp arm assembly (1314) may further include one or more electrodes configured to deliver RF energy to tissue for affecting the tissue, such as coagulating vessels in use.

Clamp body connection (1318) includes a pair of upper and lower biased projection tabs (1326) extending proximally from the proximal portion of clamp arm assembly (1314), whereas clamp actuator connection (1320) includes a pair of upper and lower apertures (1328) extending transversely through upper and lower surfaces of clamp arm actuator (1312). Upper and lower apertures (1328) respectively receive upper and lower biased projection tabs (1326) and capture biased projection tabs (1326) to thereby removably connect clamp arm assembly (1314) to clamp arm actuator (1312). In addition, upper and lower biased projection tabs (1326) are relatively oversized and project transversely beyond upper and lower surfaces of clamp arm actuator (1312) for more direct access by the operator in use.

In use, the operator transversely and simultaneously depresses upper and lower biased projection tabs (1326)

until longitudinally clear of upper and lower apertures (1328) in clamp arm actuator (1312). Once clear, the operator distally translates clamp arm assembly (1314) relative to clamp arm actuator (1312). A replacement clamp arm assembly (1314) is positioned into clamp arm actuator (1312) and snapped therein in order to capture replacement clamp arm assembly (1314) for use.

Figure 50A:
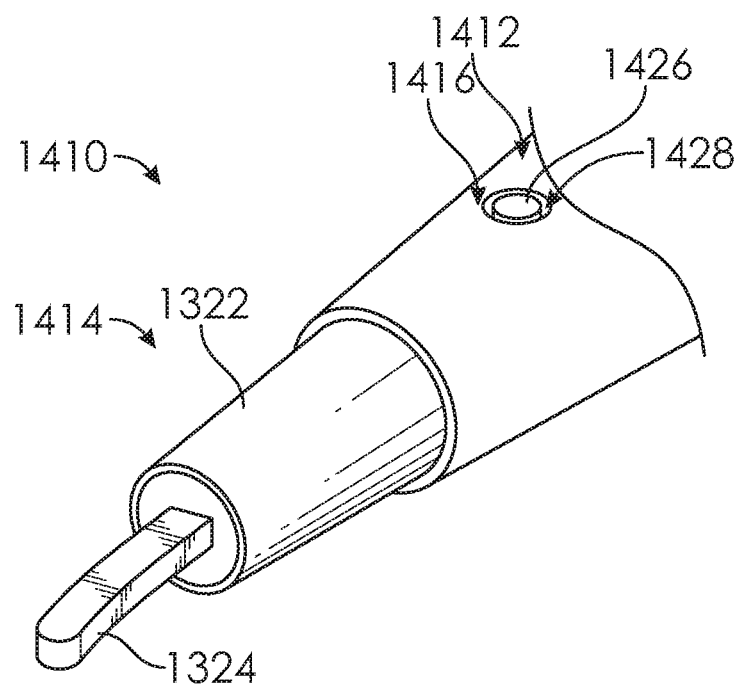
FIG. 50A depicts an enlarged perspective view of an electrode pad assembly of an eleventh exemplary surgical instrument having a third modular snap coupling.
Figure 50B:
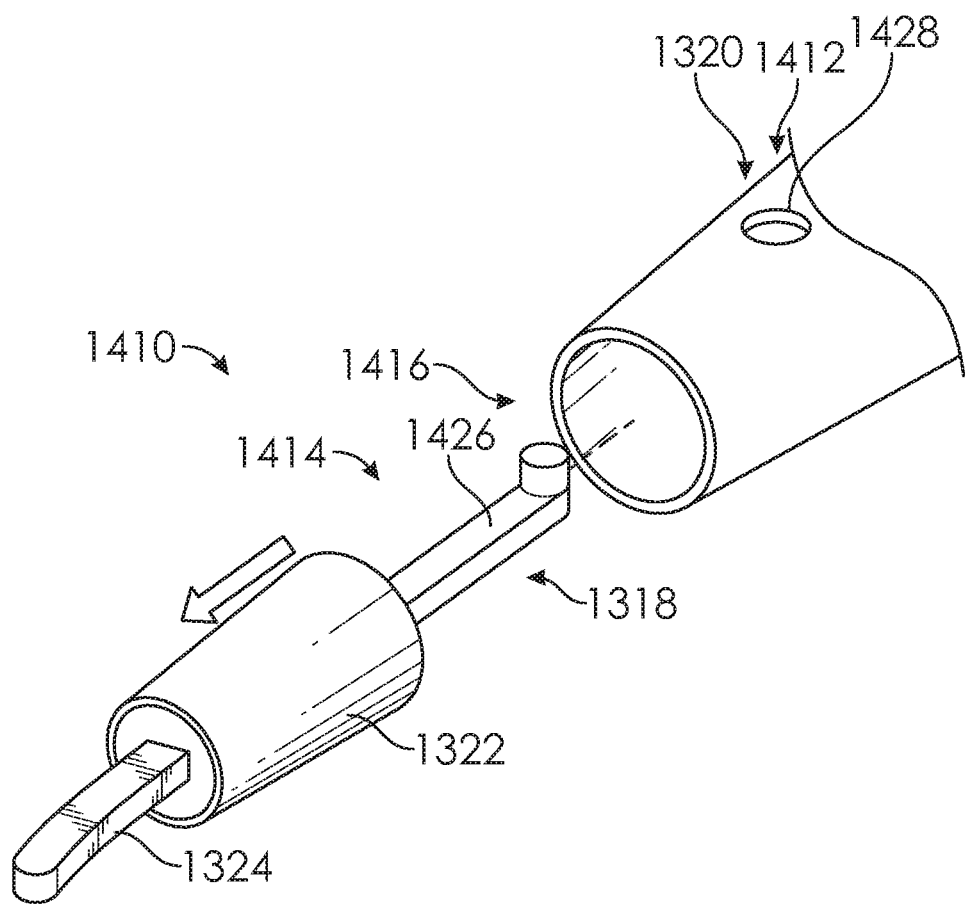
FIG. 50B depicts the enlarged perspective view of the electrode pad assembly similar to FIG. 50A, but showing the electrode pad assembly removed from the remainder of the end effector.

I. Eleventh Exemplary Ultrasonic Surgical Instrument with a Third Modular Snap Coupling FIGS. 50A and 50B illustrate an eleventh exemplary surgical instrument (1410) having a clamp arm actuator (1412), a clamp arm assembly (1414), and a third modular snap coupling (1416). To this end, clamp arm actuator (1412) and clamp arm assembly (1414) with modular snap coupling (1416) operate similar to modular snap coupling (1316) discussed above with biased projection tab and aperture (1328) (see FIGS. 49A-49C). However, a single biased projection tab (1426) cooperates with aperture (1428) of the present example such that tab (1426) is relatively undersized and flush with upper surface of clamp arm actuator (1412) for inhibiting the operator from inadvertently manipulating biased projection tab (1426) and removing clamp arm assembly (1414) from clamp arm actuator (1412) in use.

Figure 51:
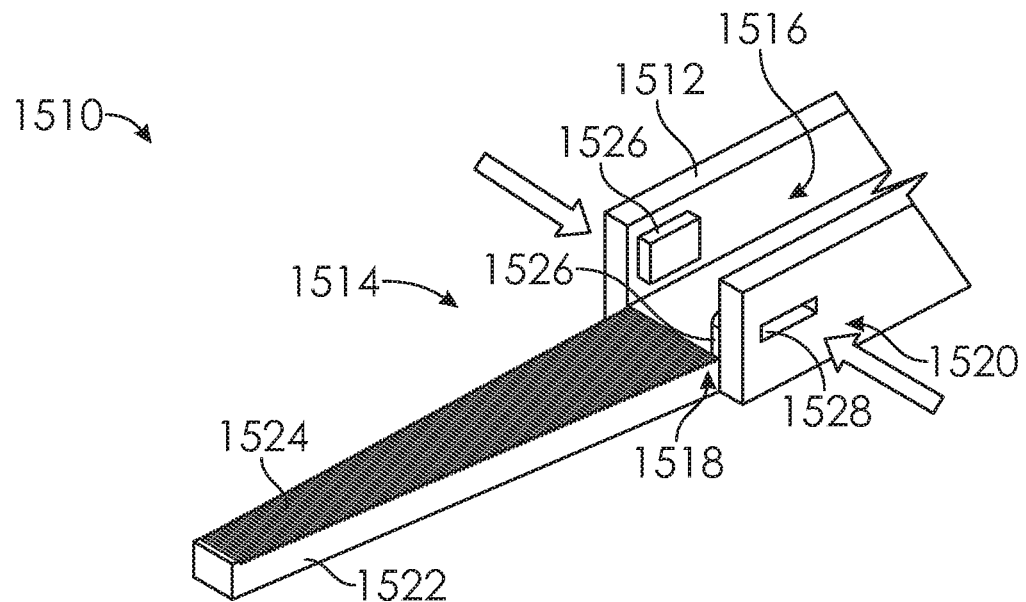
FIG. 51 depicts an enlarged perspective view of a twelfth exemplary surgical instrument having a fourth modular snap coupling associated with a clamp arm assembly.
Figure 52:
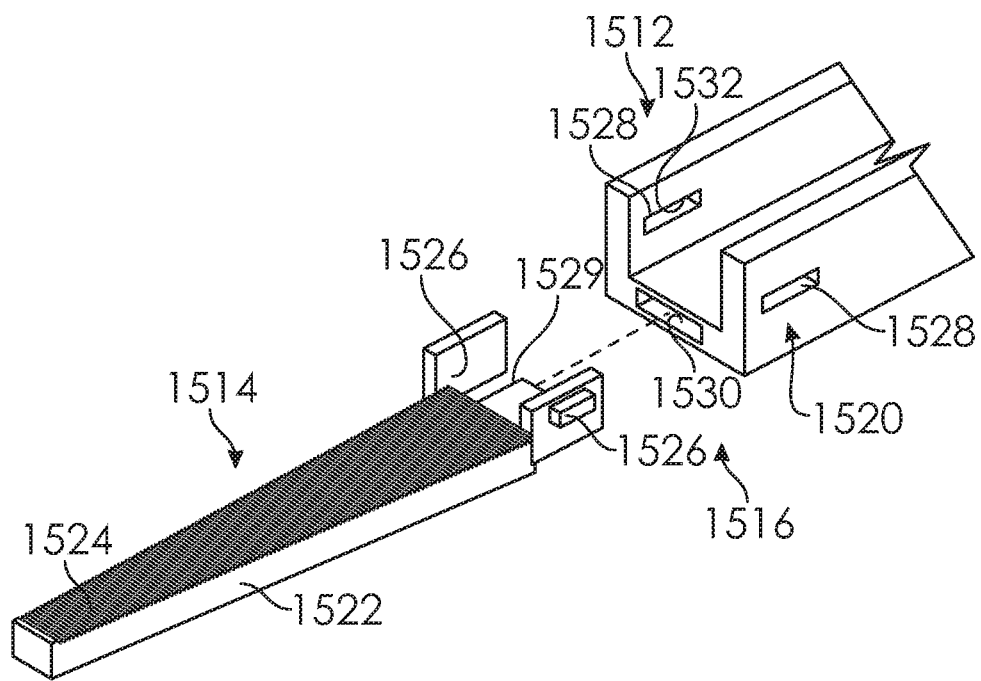
FIG. 52 depicts an enlarged partially exploded perspective view of the clamp arm assembly and modular snap coupling of FIG. 51.
Figure 53:
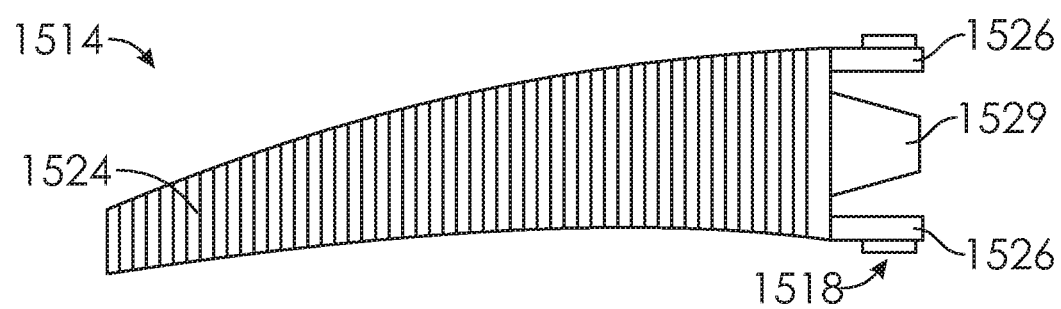
FIG. 53 depicts a top view of the clamp arm assembly of FIG. 51.

J. Twelfth Exemplary Ultrasonic Surgical Instrument with a Fourth Modular Snap Coupling FIGS. 51-53 illustrate a twelfth exemplary surgical instrument (1510) having a clamp arm actuator (1512), a clamp arm assembly (1514), and a fourth modular snap coupling (1516). Clamp arm assembly (1514) is removably connected to clamp arm actuator (1512) with modular snap coupling (1516), which includes a clamp body connection (1518) on clamp arm assembly (1514) and a clamp actuator connection (1520) on clamp arm actuator (1512). Clamp arm assembly (1514) includes a clamp body (1522) and a clamp pad (1524). Clamp pad (1524) is connected to clamp body (1522) such that clamp pad (1524) faces ultrasonic blade (not shown) for receiving and clamping tissue therebetween. Selective movement of clamp arm actuator (1512) relative to shaft assembly (not shown) from an opened configuration to a closed configuration respectively moves clamp arm assembly (1514) from an opened position configured to receive tissue to a closed position configured to clamp the tissue. While not shown with respect to surgical instrument (1510), clamp arm assembly (1514) may further include one or more electrodes configured to deliver RF energy to tissue for affecting the tissue, such as coagulating vessels in use.

Clamp body connection (1518) includes a pair of opposing lateral biased projection tabs (1526) extending proximally and laterally from the proximal portion of clamp arm assembly (1514), whereas clamp actuator connection (1520) includes a pair of lateral apertures (1528) extending laterally through sidewalls of clamp arm actuator (1512). Lateral apertures (1528) respectively receive lateral biased projection tabs (1526) and capture lateral biased projection tabs (1526) to thereby removably connect clamp arm assembly (1514) to clamp arm actuator (1512).

In addition, clamp body connection (1518) further includes a brace (1529) extending proximally from the proximal portion of clamp arm assembly (1514) toward a support bore (1530), which extends proximally through a distal end of clamp arm actuator (1512). Support bore (1530) is configured to receive brace (1529) with lateral biased projection tabs (1526) snapped into lateral apertures (1528). Brace (1529) and clamp arm actuator (1512) are thereby configured to provide additional structural support while clamping tissue in use to inhibit bending or breakage. A connection switch (1532) is further included with the present example and positioned in at least one of the lateral apertures (1528). Connection switch (1532) is configured to sense the presence of lateral biased projection tabs (1526) in apertures (1528) and communicate this connected state to a controller (not shown) for indicating that clamp arm assembly (1514) is connected to clamp arm actuator (1512) for use in the surgical procedure.

In use, the operator laterally and simultaneously depresses lateral biased projection tabs (1626) until longitudinally clear of lateral apertures (1528) in clamp arm actuator (1512). Once clear, the operator distally translates clamp arm assembly (1514) relative to clamp arm actuator (1512). Connection switch (1532) further communicates to the operator via controller (not shown) that clamp arm assembly (1514) is removed from clamp arm actuator (1512). A replacement clamp arm assembly (1514) is positioned into clamp arm actuator (1512) and snapped therein in order to capture replacement clamp arm assembly (1514) for use and indicate such connection to the operator via connection switch (1532).

Figure 54:
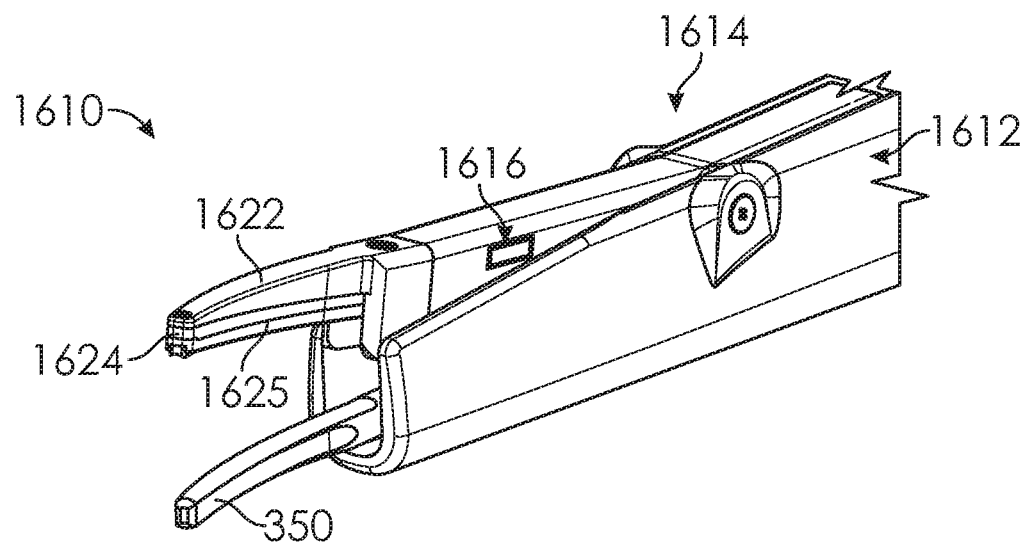
FIG. 54 depicts an enlarged perspective view of a thirteenth exemplary surgical instrument having a fifth modular snap coupling associated with a clamp arm assembly.
Figure 55A:
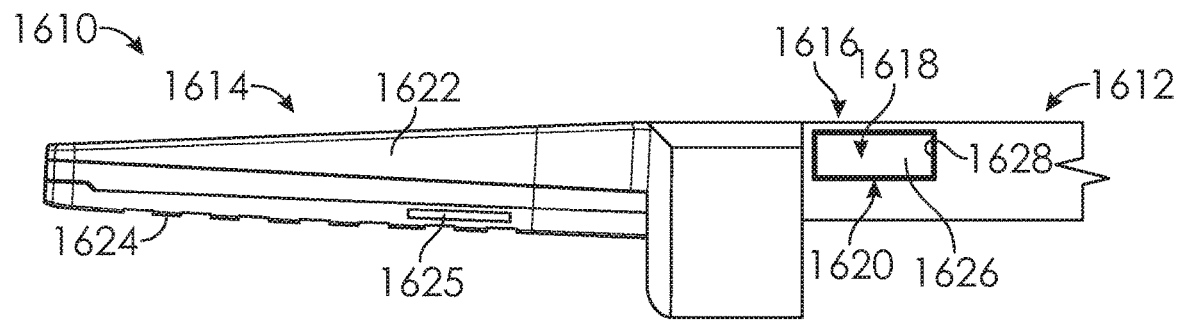
FIG. 55A depicts an enlarged side view of the clamp arm assembly and modular snap coupling of FIG. 54.
Figure 55B:
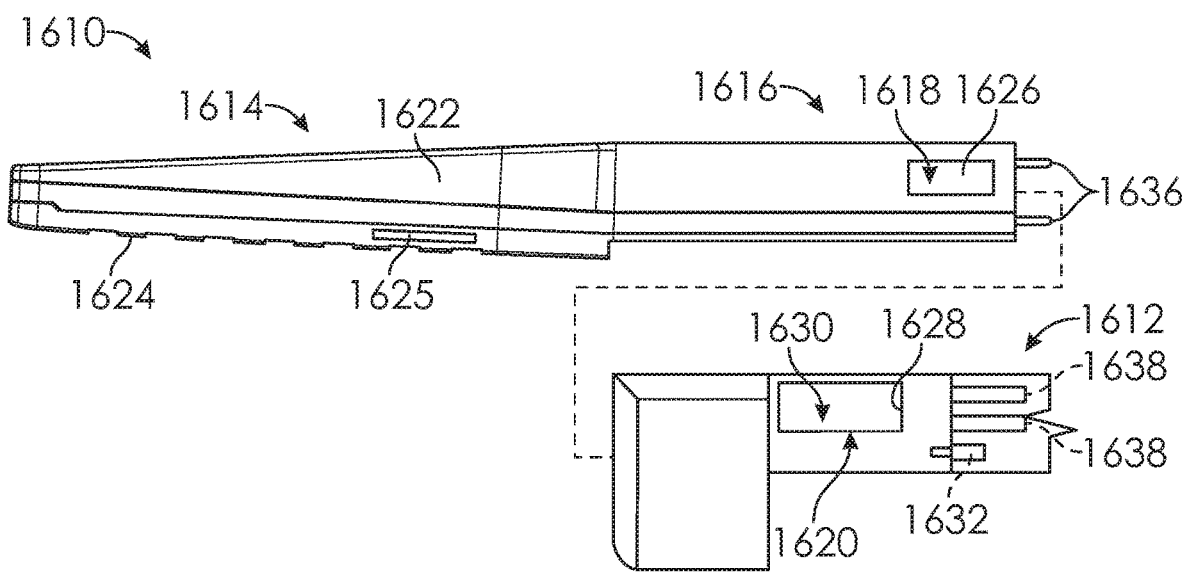
FIG. 55B depicts the enlarged side view of the clamp arm assembly and modular snap coupling similar to FIG. 54, but showing the clamp arm assembly removed from a clamp arm actuator.

K. Thirteenth Exemplary Ultrasonic Surgical Instrument with a Fifth Modular Snap Coupling FIGS. 54-55B illustrate a thirteenth exemplary surgical instrument (1610) having a clamp arm actuator (1612), a clamp arm assembly (1614), and a fifth modular snap coupling (1616). Clamp arm assembly (1614) is removably connected to clamp arm actuator (1612) with modular snap coupling (1616), which includes a clamp body connection (1618) on clamp arm assembly (1614) and a clamp actuator connection (1620) on clamp arm actuator (1612). Clamp arm assembly (1614) includes a clamp body (1622) and a clamp pad (1624). Clamp pad (1624) is connected to clamp body (1622) such that clamp pad (1624) faces ultrasonic blade (not shown) for receiving and clamping tissue therebetween. Selective movement of clamp arm actuator (1612) relative to shaft assembly (not shown) from an opened configuration to a closed configuration respectively moves clamp arm assembly (1614) from an opened position configured to receive tissue to a closed position configured to clamp the tissue. Clamp arm assembly of the present example further includes at least one RF electrode (1625) operatively connected to an RF energy source and configured to deliver RF energy to tissue for affecting the tissue, such as coagulating vessels in use.

Clamp body connection (1618) includes a pair of opposing lateral biased projection tabs (1626) extending proximally and laterally on a body brace (1629) of clamp arm assembly (1614) discussed below in more detail. Clamp actuator connection (1620) includes a pair of lateral apertures (1628) extending laterally through sidewalls of clamp arm actuator (1612). Lateral apertures (1628) respectively receive lateral biased projection tabs (1626) and capture lateral biased projection tabs (1626) to thereby removably connect clamp arm assembly (1614) to clamp arm actuator (1612).

In addition, clamp body connection (1618) further includes body brace (1629) extending proximally from the proximal portion of clamp arm assembly (1614) toward a support bore (1630), which extends proximally through a distal end of clamp arm actuator (1612). Support bore (1630) is configured to receive body brace (1629) with lateral biased projection tabs (1626) snapped into lateral apertures (1628). Body brace (1629) and clamp arm actuator (1612) are thereby configured to provide structural support while clamping tissue in use to inhibit bending or breakage. A connection switch (1632) is further included with the present example and positioned in a proximal portion of support bore (1630). Connection switch (1632) is configured to sense the presence of body brace (1629) functionally connected into support bore (1630) and communicate this connected state to a controller (not shown) for indicating that clamp arm assembly (1614) is connected to clamp arm actuator (1612) for use in the surgical procedure.

Modular snap coupling (1616) further includes an electrical connection (1634), which includes a male electrical coupling (1636) and a female electrical coupling (1638). Male and female electrical couplings (1636, 1638) are configured to removably connect together to communicate electrical signals and RF energy to RF electrode (1625), but allow for removal and replacement of clamp arm assembly (1614).

In use, the operator laterally and simultaneously depresses lateral biased projection tabs (1626) until longitudinally clear of lateral apertures (1628) in clamp arm actuator (1612). Once clear, the operator distally translates clamp arm assembly (1614) relative to clamp arm actuator (1612) and disconnects male and female electrical couplings (1636, 1638). Connection switch (1632) further communicates to the operator via controller (not shown) that clamp arm assembly (1614) is removed from clamp arm actuator (1612). A replacement clamp arm assembly (1614) is positioned into clamp arm actuator (1612) and snapped therein in order to capture replacement clamp arm assembly (1614) for use and indicate such connection to the operator via connection switch (1632).

Figure 56A:
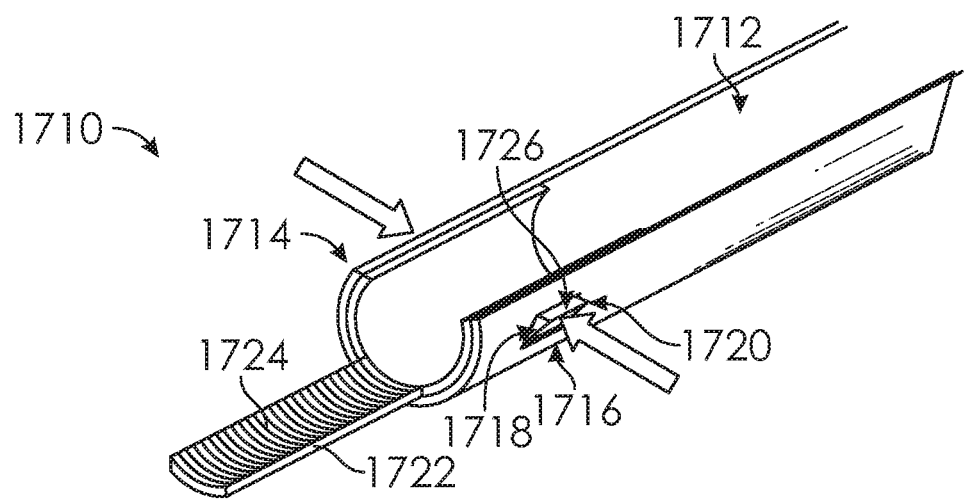
FIG. 56A depicts an enlarged perspective view of a fourteenth exemplary surgical instrument having a sixth modular snap coupling associated with a clamp arm assembly.
Figure 56B:
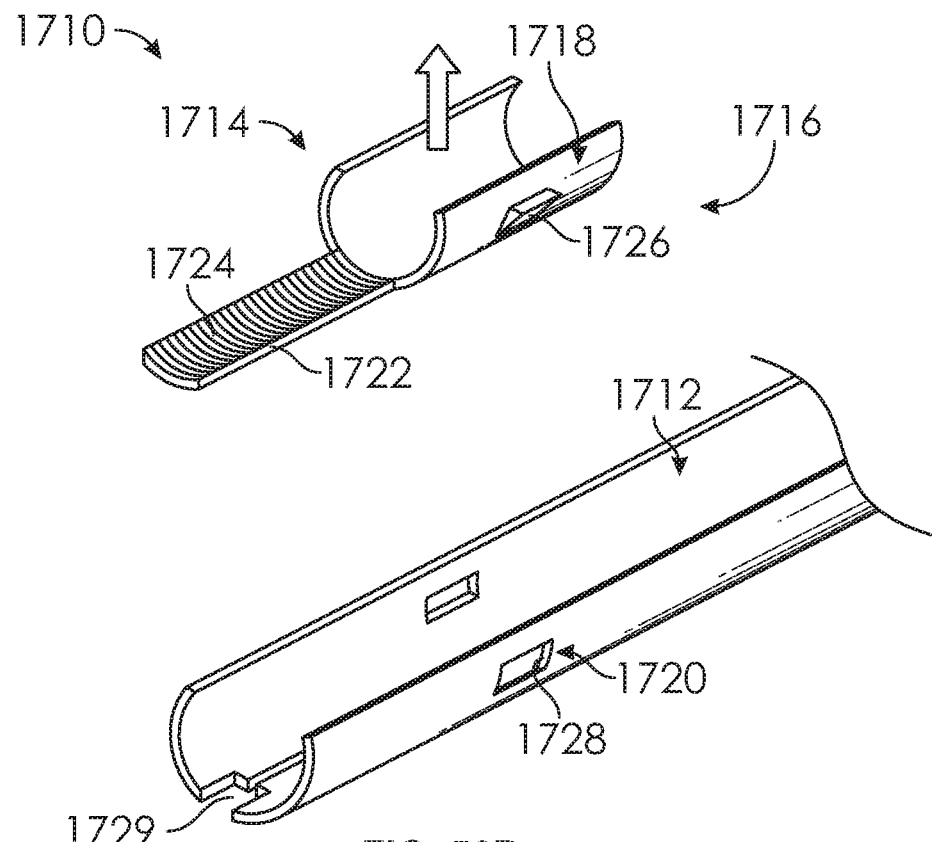
FIG. 56B depicts the enlarged perspective view of the surgical instrument and modular snap coupling similar to FIG. 56A, but showing the clamp arm assembly removed from a clamp arm actuator.
Figure 57:
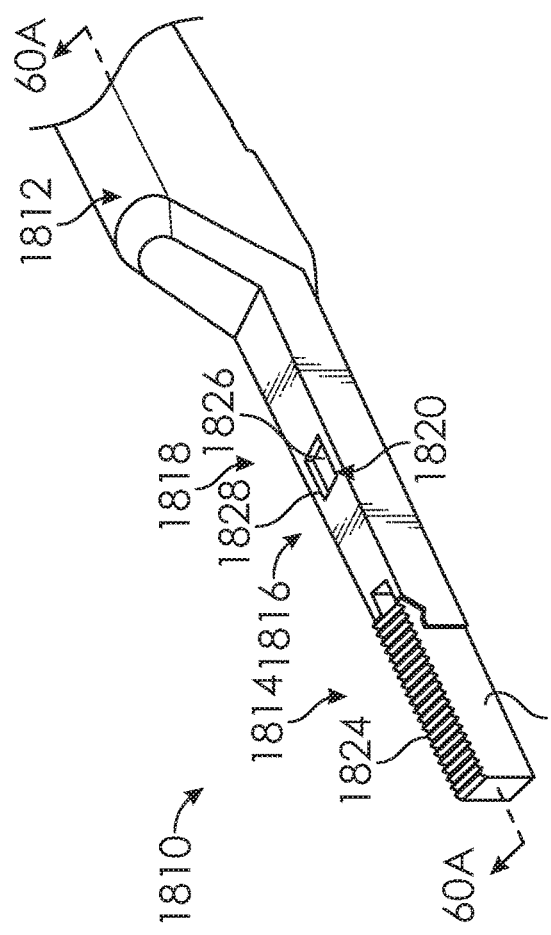
FIG. 57 depicts an enlarged perspective view of a fifteenth exemplary surgical instrument having a seventh modular snap coupling associated with a clamp arm assembly.
Figure 58:
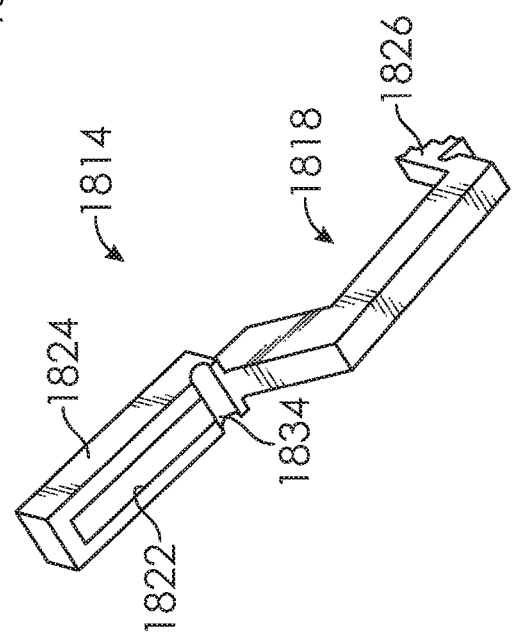
FIG. 58 depicts a perspective view of the clamp arm assembly of FIG. 57.
Figure 59:
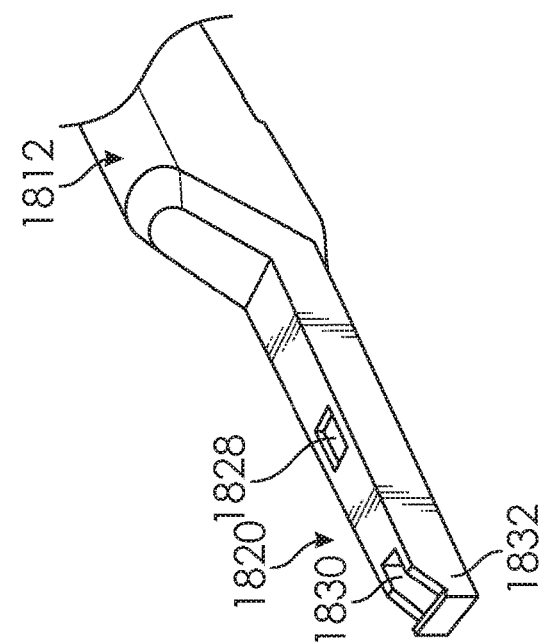
FIG. 59 depicts an enlarged perspective view of a clamp arm actuator of the surgical instrument of FIG. 57.

L. Fourteenth Exemplary Ultrasonic Surgical Instrument with a Sixth Modular Snap Coupling FIGS. 56A and 56B illustrate a fourteenth exemplary surgical instrument (1710) having a clamp arm actuator (1712), a clamp arm assembly (1714), and a sixth modular snap coupling (1716). Clamp arm assembly (1714) is removably connected to clamp arm actuator (1712) with modular snap coupling (1716), which includes a clamp body connection (1718) on clamp arm assembly (1714) and a clamp actuator connection (1720) on clamp arm actuator (1712). Clamp arm assembly (1714) includes a clamp body (1722) and a clamp pad (1724). Clamp pad (1724) is connected to clamp body (1722) such that clamp pad (1724) faces ultrasonic blade (not shown) for receiving and clamping tissue therebetween. Selective movement of clamp arm actuator (1712) relative to shaft assembly (not shown) from an opened configuration to a closed configuration respectively moves clamp arm assembly (1714) from an opened position configured to receive tissue to a closed position configured to clamp the tissue. While not shown with respect to surgical instrument (1710), clamp arm assembly (1714) may further include one or more electrodes configured to deliver RF energy to tissue for affecting the tissue, such as coagulating vessels in use.

Clamp body connection (1718) includes a pair of opposing lateral biased projection tabs (1726) extending laterally from a proximal portion of clamp arm assembly (1714), whereas clamp actuator connection (1720) includes a pair of lateral apertures (1728) extending laterally through sidewalls of clamp arm actuator (1712). Lateral apertures (1728) respectively receive lateral biased projection tabs (1726) and capture lateral biased projection tabs (1726) to thereby removably connect clamp arm assembly (1714) to clamp arm actuator (1712).

Clamp arm assembly (1714) of the present example is received transversely into clamp arm actuator (1712) such that a distal portion of clamp arm actuator (1712) supports clamp body (1722) thereon. Clamp arm actuator (1712) and clamp body (1722) are thereby configured to provide additional structural support while clamping tissue in use to inhibit bending or breakage. The distal portion of clamp arm actuator (1712) also includes an end slot (1729) configured to receive portion of clamp arm assembly (1714) such that clamp pad (1724) is approximately flush with a lower surface of clamp arm actuator (1712).

In use, the operator laterally and simultaneously depresses lateral biased projection tabs (1726) until longitudinally clear of lateral apertures (1728) in clamp arm actuator (1712). Once clear, the operator distally translates clamp arm assembly (1714) relative to clamp arm actuator (1712). A replacement clamp arm assembly (1714) is positioned into and supported on clamp arm actuator (1712) and snapped therein in order to capture replacement clamp arm assembly (1714) for use.

M. Fifteenth Exemplary Ultrasonic Surgical Instrument with a Seventh Modular Snap Coupling FIGS. 57-60B illustrate a fifteenth exemplary surgical instrument (1810) having a clamp arm actuator (1812), a clamp arm assembly (1814), and a seventh modular snap coupling (1816). Clamp arm assembly (1814) is removably connected to clamp arm actuator (1812) with modular snap coupling (1816), which includes a clamp body connection (1818) on clamp arm assembly (1814) and a clamp actuator connection (1820) on clamp arm actuator (1812). Clamp arm assembly (1814) includes a clamp body (1822) and a clamp pad (1824). Clamp pad (1824) is connected to clamp body (1822) such that clamp pad (1824) faces ultrasonic blade (not shown) for receiving and clamping tissue therebetween. Selective movement of clamp arm actuator (1812) relative to shaft assembly (not shown) from an opened configuration to a closed configuration respectively moves clamp arm assembly (1814) from an opened position configured to receive tissue to a closed position configured to clamp the tissue. While not shown with respect to surgical instrument (1810), clamp arm assembly (1814) may further include one or more electrodes configured to deliver RF energy to tissue for affecting the tissue, such as coagulating vessels in use.

Clamp body connection (1818) includes a transverse biased projection tab (1826) extending transversely from the proximal portion of clamp arm assembly (1814), whereas clamp actuator connection (1820) includes a transverse aperture (1828) extending transversely through clamp arm actuator (1812). Transverse aperture (1828) receives transverse biased projection tab (1826) and captures biased projection tab (1826) to thereby removably connect clamp arm assembly (1814) to clamp arm actuator (1812).

Modular snap coupling (1816) further cooperates with a proximal portion of clamp body (1822) for further connecting clamp arm assembly (1814) to clamp arm actuator (1812). To this end, with respect to FIGS. 58 and 59, clamp arm actuator has a distal transverse hole (1830) extending therethrough and distally positioned relative to transverse aperture (1828). Distal transverse hole (1830) is configured to receive the proximal portion of clamp body (1822) therethrough in a transverse direction and pivoted to the longitudinal direction for alignment with clamp arm actuator (1812). Clamp arm actuator (1812) further includes a distal nose (1832) configured to be received within a nose channel (1834) on a lower surface of clamp body (1822). Clamp body (1822) is thereby configured to be pivoted about distal nose (1832) and further supported by distal nose (1832) for use.

Figure 60A:
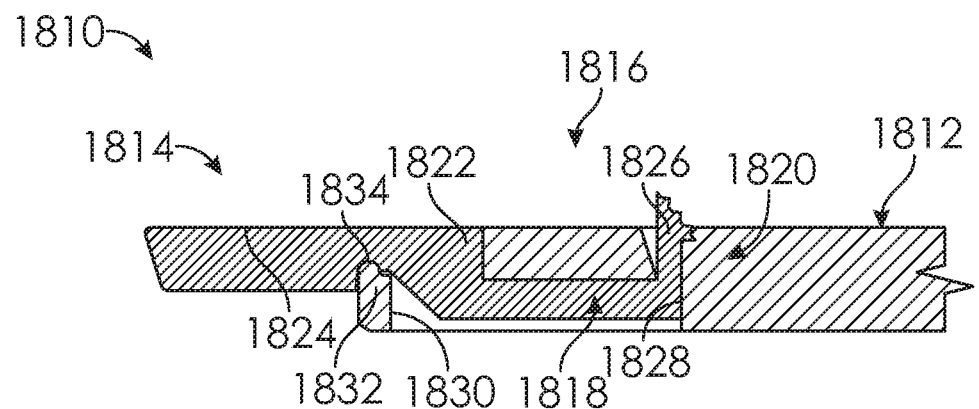
FIG. 60A depicts an enlarged cross-sectional view of the surgical instrument of FIG. 57 taken along section line 60A-60A of FIG. 57.
Figure 60B:
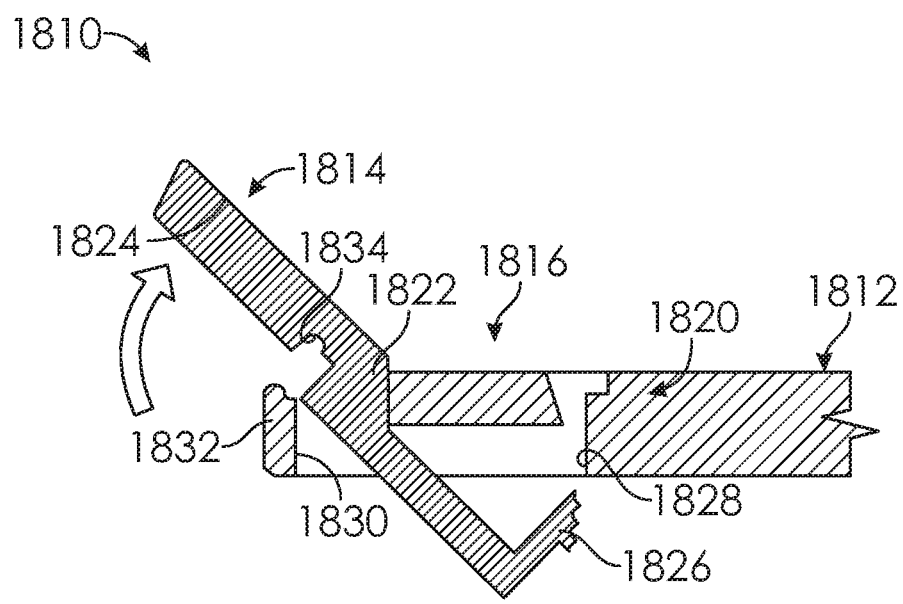
FIG. 60B depicts the enlarged cross-sectional view of the surgical instrument similar to FIG. 60A, but showing the clamp arm assembly being removed from the clamp arm actuator.

In use, with respect to FIGS. 60A and 60B, the operator transversely and longitudinally depresses biased projection tab (1826) until transversely clear of aperture (1828) in clamp arm actuator (1812). Once clear, the operator pivots clamp arm assembly (1814) relative to clamp arm actuator (1812) about distal nose (1832) and transversely removes clamp body (1822) from distal transverse hole (1830). A replacement clamp arm assembly (1814) is positioned into clamp arm actuator (1812) and snapped therein in order to capture replacement clamp arm assembly (1814) for use.

N. An Eighth Exemplary Modular Snap Coupling

Figure 61A:
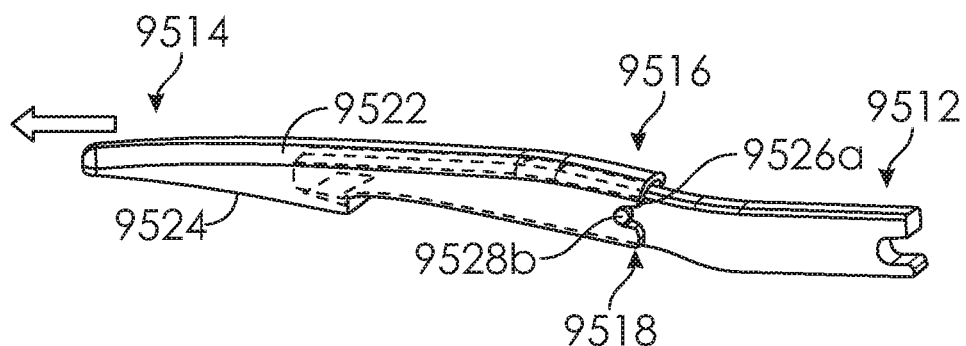
FIG. 61A depicts a perspective view of a clamp arm assembly and a clamp arm actuator with an eighth modular snap coupling for removable connection therebetween.
Figure 61B:
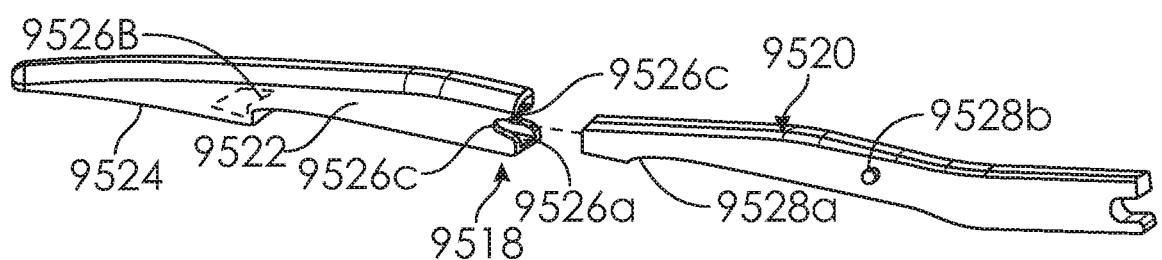
FIG. 61B depicts the perspective view of the clamp arm assembly, the clamp arm actuator, and the modular snap coupling similar to FIG. 61A, but showing the clamp arm assembly removed from the clamp arm actuator.

FIGS. 61A and 61B illustrate an eighth modular snap coupling (9516) for a clamp arm actuator (9512) and a clamp arm assembly (9514). Clamp arm assembly (9514) is removably connected to clamp arm actuator (9512) with modular snap coupling (9516), which includes a clamp body connection (9518) on clamp arm assembly (9514) and a clamp actuator connection (9520) on clamp arm actuator (9512). Clamp arm assembly (9514) includes a clamp body (9522) and a clamp pad (9524). Clamp pad (9524) is connected to clamp body (9522) such that clamp pad (9524) faces ultrasonic blade (not shown) for receiving and clamping tissue therebetween. Selective movement of clamp arm actuator (9512) relative to shaft assembly (not shown) from an opened configuration to a closed configuration respectively moves clamp arm assembly (9514) from an opened position configured to receive tissue to a closed position configured to clamp the tissue. While not shown, clamp arm assembly (9514) may further include one or more electrodes configured to deliver RF energy to tissue for affecting the tissue, such as coagulating vessels and/or otherwise sealing the tissue.

Clamp body connection (9518) includes an inner hole (9526a) extending distally from the proximal portion of clamp arm assembly (9514) and configured to receive a distal portion of clamp arm actuator (9512). Clamp body connection (9518) further includes an inner shoulder (9526b) and a pair of lateral slots (9526c) extending through respectively lateral sidewalls of clamp body (9522) to inner hole (9526a). In the present example, inner shoulder (9526b) is distally positioned relative to lateral slots (9526c), which proximally extend to a proximal face of clamp body (9522). Clamp actuator connection (9520) includes a distally extending hook (9528a) and a pair of opposing, laterally extending tabs (9528b). Inner hole (9526) is configured to receive hook (9528a) such that hook (9528a) releasably engages inner shoulder (9526b) and lateral tabs (9528b) releasably engage sidewalls within lateral slots (9526c). More particularly, hook (9528a) resiliently cooperates with inner shoulder (9526b) while lateral tabs (9528b) resiliently cooperate within lateral slots (9526c) of sidewalls such that the distal end portion of clamp actuator (9512) resiliently snaps into removable connection with the proximal portion of clamp body (9522).

In use, the operator distally withdraws clamp actuator assembly (9514) relative to clamp actuator (9512) with sufficient force to overcome the resilient engagement between hook (9528a) and inner shoulder (9526b) as well as lateral tabs (9528b) and lateral slots (9526c) of sidewalls. Once the resilient engagement is overcome, the operator further distally withdraws clamp actuator assembly (9514) until clamp actuator (9512) is removed from inner hole (9526a). A replacement clamp arm assembly (9514) is positioned onto clamp arm actuator (9512) and snapped therein in order to capture replacement clamp arm assembly (9514) for use.

Figure 62A:
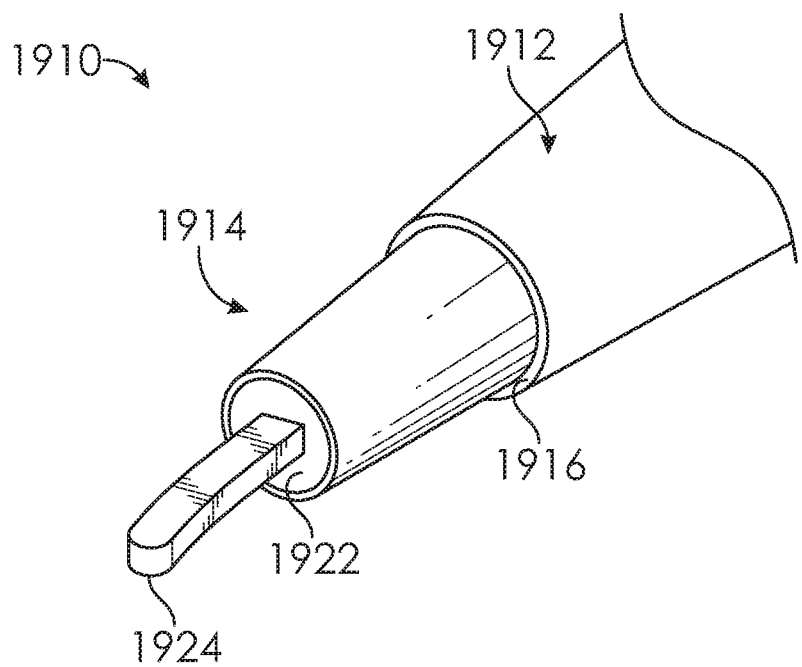
FIG. 62A depicts an enlarged perspective view of a sixteenth exemplary surgical instrument having a modular threaded coupling associated with an electrode assembly.
Figure 62B:
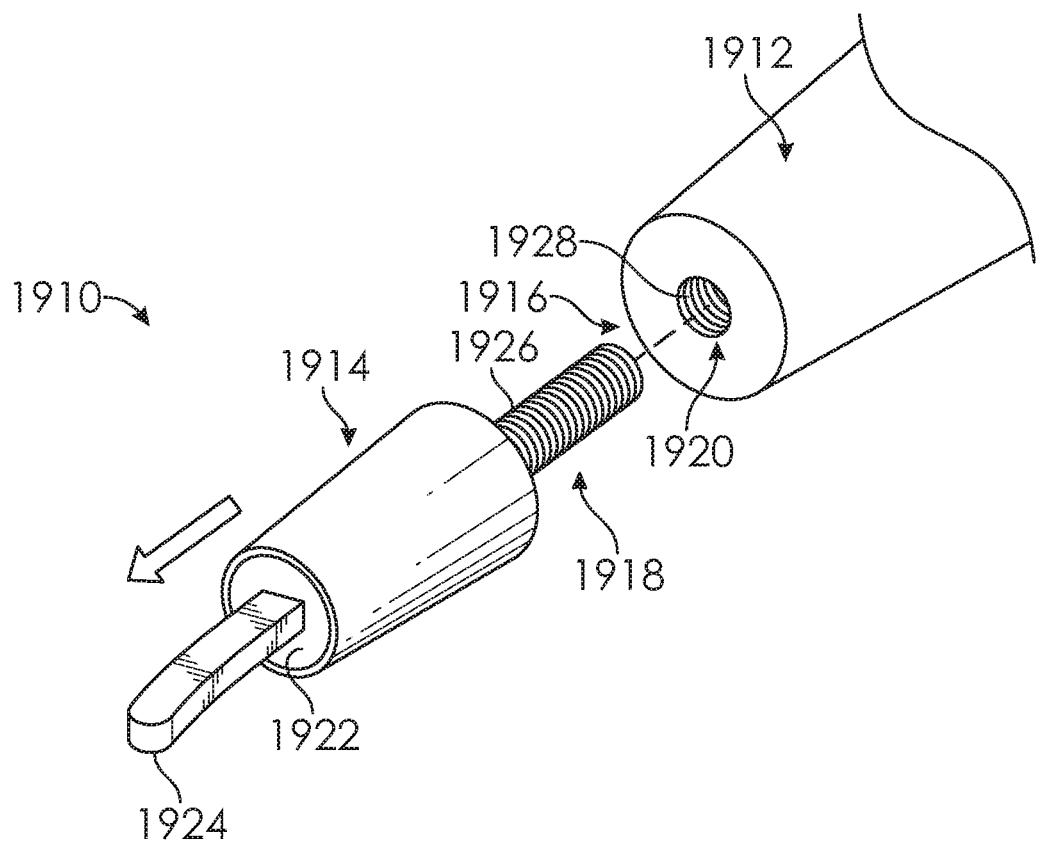
FIG. 62B depicts the enlarged perspective view of the surgical instrument similar to FIG. 62A, but having the electrode assembly removed from a remainder of the surgical instrument.
Figure 63:
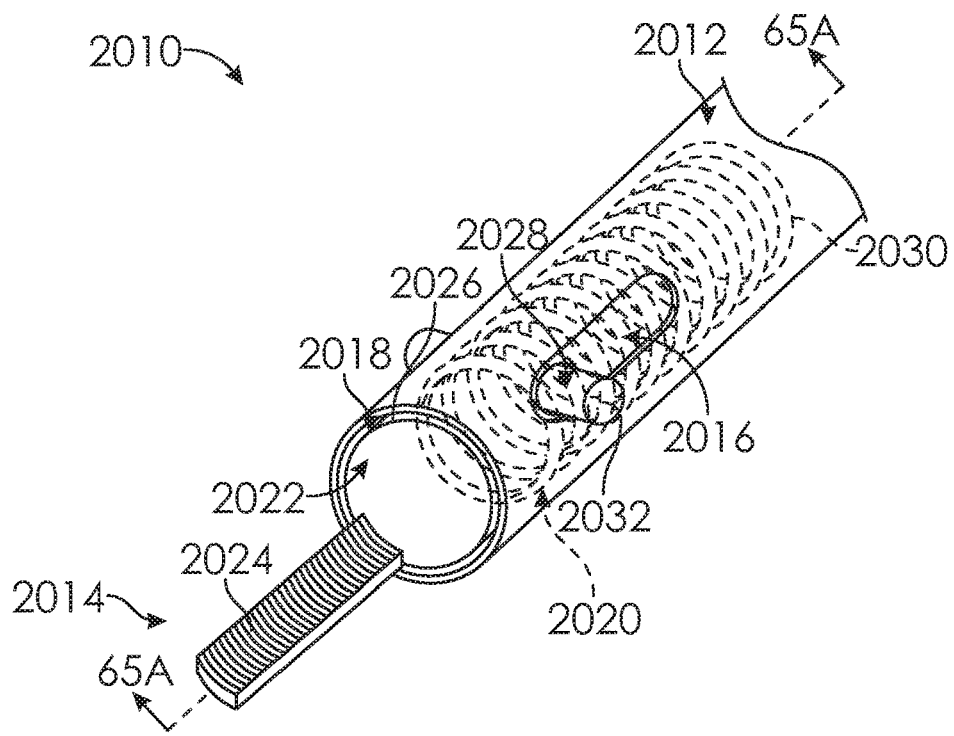
FIG. 63 depicts an enlarged perspective view of a seventeenth exemplary surgical instrument having a modular compression coupling associated with a clamp arm assembly.
Figure 64:
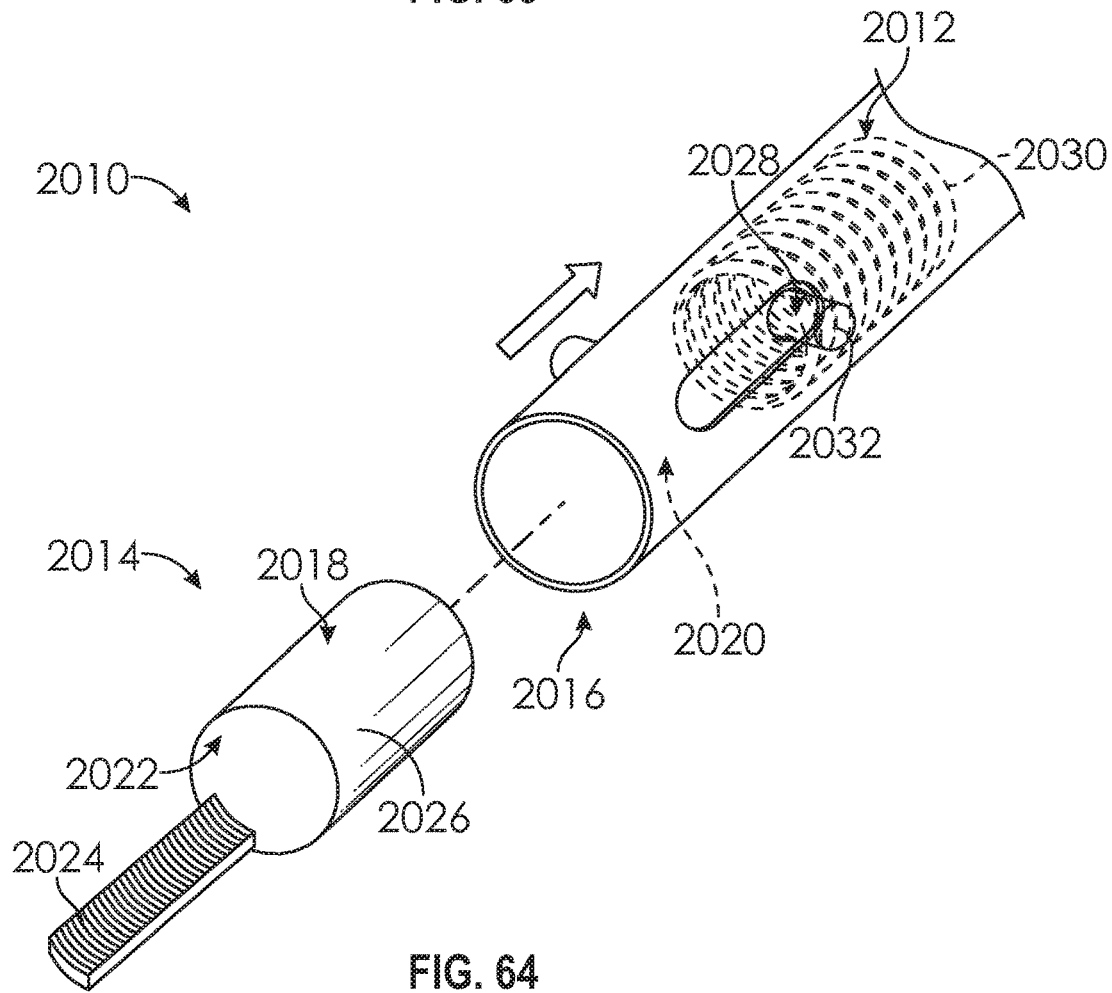
FIG. 64 depicts an enlarged partially exploded perspective view of a clamp arm assembly removed from a radial capture lock of a clamp arm actuator.

O. Sixteenth Exemplary Ultrasonic Surgical Instrument with a Modular Threaded Coupling FIGS. 62A and 62B illustrate a sixteenth exemplary surgical instrument (1910) having a clamp arm actuator (1912), a clamp arm assembly (1914), and a modular threaded coupling (1916). Clamp arm assembly (1914) is removably connected to clamp arm actuator (1912) with modular threaded coupling (1916), which includes a clamp body connection (1918) on clamp arm assembly (1914) and a clamp actuator connection (1920) on clamp arm actuator (1912). Clamp arm assembly (1914) includes a clamp body (1922) and a clamp pad (1924). Clamp pad (1924) is connected to clamp body (1922) such that clamp pad (1924) faces ultrasonic blade (not shown) for receiving and clamping tissue therebetween. Selective movement of clamp arm actuator (1912) relative to shaft assembly (not shown) from an opened configuration to a closed configuration respectively moves clamp arm assembly (1914) from an opened position configured to receive tissue to a closed position configured to clamp the tissue. While not shown with respect to surgical instrument (1910), clamp arm assembly (1914) may further include one or more electrodes configured to deliver RF energy to tissue for affecting the tissue, such as coagulating vessels in use.

Clamp body connection (1918) includes a threaded stud (1926) extending proximally from a proximal portion of clamp arm assembly (1914), whereas clamp actuator connection (1920) includes a threaded aperture (1928) extending proximally through a distal end of clamp arm actuator (1912). Threaded aperture (1928) rotatably receives threaded stud (1926) and tightens therein (1926) to thereby removably connect clamp arm assembly (1914) to clamp arm actuator (1912).

In use, the operator rotatably loosens threaded stud (1926) from threaded aperture (1928) until longitudinally clear of threaded aperture (1928) in clamp arm actuator (1912). Once clear, the operator distally removes clamp arm assembly (1914) relative to clamp arm actuator (1912). A replacement clamp arm assembly (1914) is positioned into clamp arm actuator (1912) and rotatably threaded therein in order to tighten and capture replacement clamp arm assembly (1914) for use.

P. Seventeenth Exemplary Ultrasonic Surgical Instrument with a Modular Compression Coupling FIGS. 63-65C illustrate a seventeenth exemplary surgical instrument (2010) having a clamp arm actuator (2012), a clamp arm assembly (2014), and a modular compressive coupling (2016). With respect to FIGS. 63 and 64, clamp arm assembly (2014) is removably connected to clamp arm actuator (2012) with modular compressive coupling (2016), which includes a clamp body connection (2018) on clamp arm assembly (2014) and a clamp actuator connection (2020) on clamp arm actuator (2012). Clamp arm assembly (2014) includes a clamp body (2022) and a clamp pad (2024). Clamp pad (2024) is connected to clamp body (2022) such that clamp pad (2024) faces ultrasonic blade (not shown) for receiving and clamping tissue therebetween. Selective movement of clamp arm actuator (2012) relative to shaft assembly (not shown) from an opened configuration to a closed configuration respectively moves clamp arm assembly (2014) from an opened position configured to receive tissue to a closed position configured to clamp the tissue. While not shown with respect to surgical instrument (2010), clamp arm assembly (2014) may further include one or more electrodes configured to deliver RF energy to tissue for affecting the tissue, such as coagulating vessels in use.

Clamp body connection (2018) includes an outer surface (2026) of clamp body (2022), whereas clamp actuator connection (2020) includes a radial capture lock (2028) configured to frictionally engage outer surface (2026) of clamp body (2022) for removable connection. In the present example, radial capture lock (2028) includes a biasing member, such as a spring (2030), and a latch (2032) configured to be selectively moved from a locked configuration to an unlocked configuration. Spring (2030) is generally in compression and biased toward the locked configuration such that spring (2030) has a relatively small diameter and radially engages outer surface (2026). In addition, distally pulling on clamp arm assembly (2014) effectively constricts spring (2030) radially inward to further frictionally engage outer surface (2026). However, selectively manipulating latch (2032) in the proximal direction compresses spring (2030) such that spring (2030) has a relatively large diameter and radially disengages outer surface (2026). Radial capture lock (2028) thereby releases clamp arm assembly (2014) for removal in the unlocked configuration.

Figure 65A:
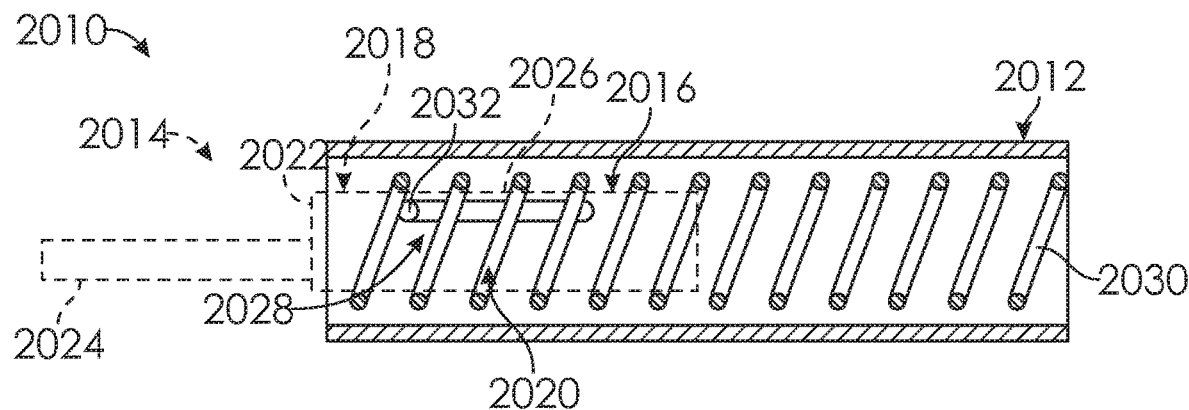
FIG. 65A depicts an enlarged side sectional view of the surgical instrument of FIG. 63 taken along section line 65A-65A of FIG. 63 showing the radial capture lock of the modular compression coupling in a locked position and having various components hidden for clarity.
Figure 65B:
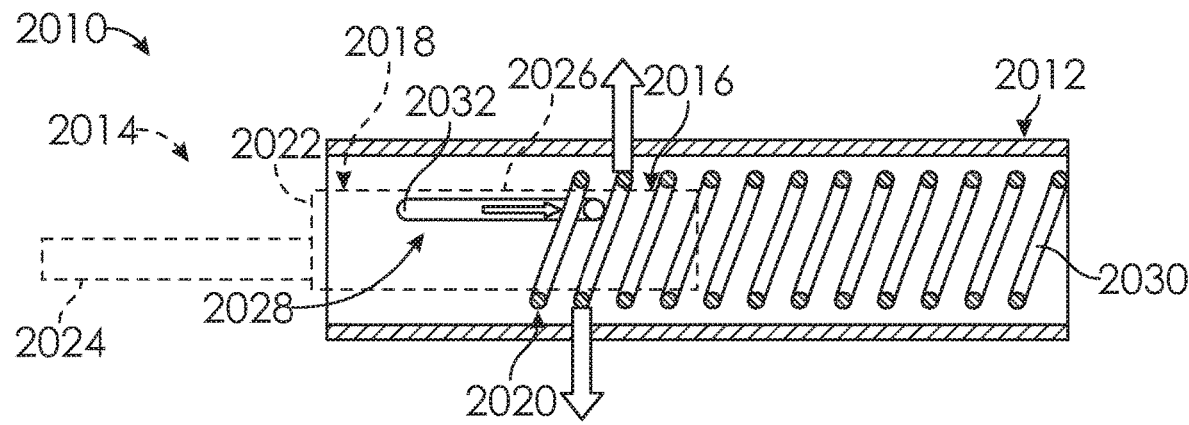
FIG. 65B depicts the enlarged side sectional view of the surgical instrument similar to FIG. 65A, but showing the radial capture lock of the modular compression coupling in an unlocked position.

In use, with respect to FIGS. 65A-65C, the operator proximally urges latch (2032) from the locked configuration to the unlocked configuration such that spring (2030) disengages from outer surface (2026) of clamp arm assembly (2014). The operator then distally translates clamp arm assembly (2014) from with spring (2030) until clear of spring (2030) and removed from clamp arm actuator (2012). A replacement clamp arm assembly (2014) is positioned into clamp arm actuator (2012) and latch (2032) distally returns to the locked configuration in order to capture replacement clamp arm assembly (2014) for use.

Figure 66B:
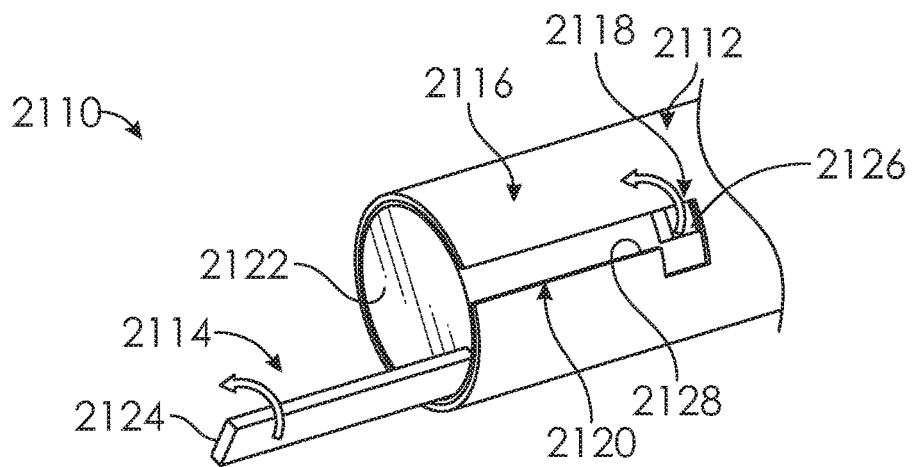
FIG. 66B depicts the enlarged perspective view of the surgical instrument similar to FIG. 66A, but showing the clamp arm assembly being removed from a clamp arm actuator.
Figure 66C:
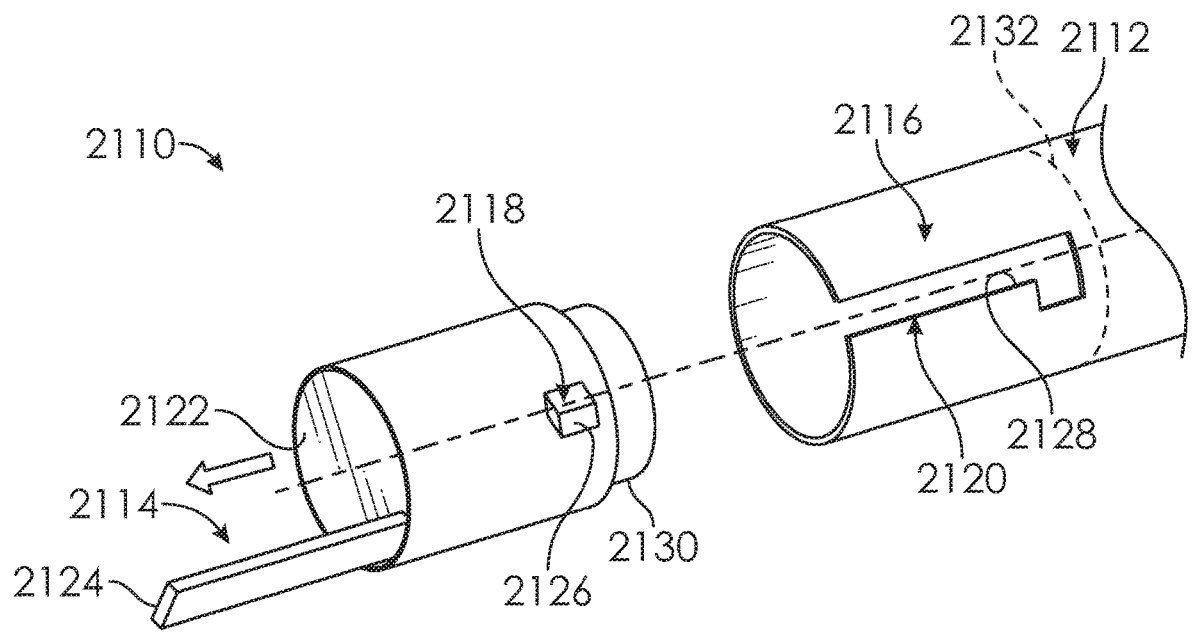
FIG. 66C depicts the enlarged perspective view of the surgical instrument similar to FIG. 66B, but showing the clamp arm assembly removed from the clamp arm actuator.

Q. Eighteenth Exemplary Ultrasonic Surgical Instrument with a Modular Bayonet Coupling FIGS. 66A-66C illustrate an eighteenth exemplary surgical instrument (2110) having a clamp arm actuator (2112), a clamp arm assembly (2114), and a modular bayonet coupling (2116). Clamp arm assembly (2114) is removably connected to clamp arm actuator (2112) with modular bayonet coupling (2116), which includes a clamp body connection (2118) on clamp arm assembly (2114) and a clamp actuator connection (2120) on clamp arm actuator (2112). Clamp arm assembly (2114) includes a clamp body (2122) and a clamp pad (2124). Clamp pad (2124) is connected to clamp body (2122) such that clamp pad (2124) faces ultrasonic blade (not shown) for receiving and clamping tissue therebetween. Selective movement of clamp arm actuator (2112) relative to shaft assembly (not shown) from an opened configuration to a closed configuration respectively moves clamp arm assembly (2114) from an opened position configured to receive tissue to a closed position configured to clamp the tissue. While not shown with respect to surgical instrument (2110), clamp arm assembly (2114) may further include one or more electrodes configured to deliver RF energy to tissue for affecting the tissue, such as coagulating vessels in use.

Clamp body connection (2118) includes a bayonet tab (2126) extending radially outward from a proximal portion thereof, whereas clamp actuator connection (2120) includes a bayonet slot (2128) configured to slidably receive bayonet tab (2126) for removable connection. In the present example, bayonet slot (2128) proximally extends through a distal end sidewall along a longitudinal portion of bayonet slot (2128) and an intersecting transverse portion of bayonet slot (2128). Bayonet tab (2126) generally remains captured in the transverse portion of bayonet slot (2128) during use, but is rotated such that bayonet tab (2126) is in longitudinal portion for proximal removal. In order to aid removal, clamp arm assembly (2114) further includes a proximal, resilient cap (2130) that bottoms out in compression within clamp arm actuator (2112) against a seat (2132). Thus, resilient cap (2130) resiliently extends from compression to urge clamp body (2122) and clamp pad (2124) distally from within clamp arm actuator (2112) for removal.

In use, with respect to FIGS. 66A-66C, the operator rotates bayonet tab (2126) through the transverse portion of bayonet slot (2128) with the remainder of clamp arm assembly (2114) and resilient cap (2130) urges clamp arm assembly (2113) distally. The operator then distally translates bayonet tab (2126) distally through the longitudinal portion of bayonet slot (2128) until clamp arm assembly (2114) is removed from clamp arm actuator (2112). A replacement clamp arm assembly (2114) is positioned into clamp arm actuator (2112) and rotated to in order to capture bayonet tab (2126) in the transverse portion of bayonet slot (2118) for use.

Figure 67A:
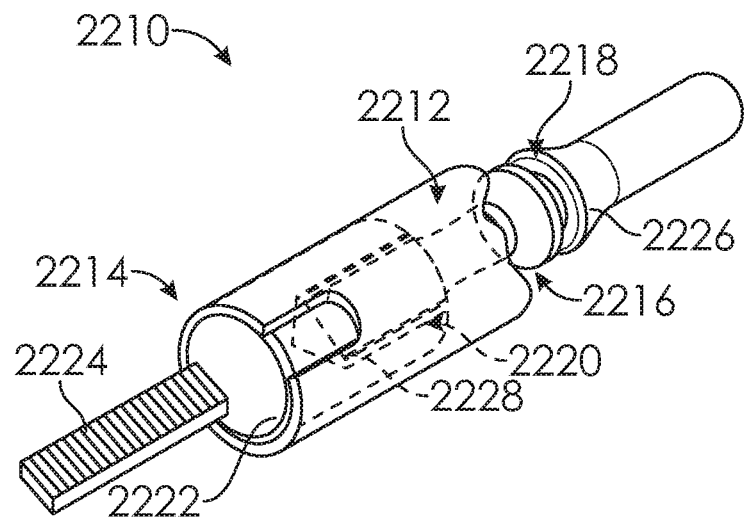
FIG. 67A depicts an enlarged perspective view of a nineteenth exemplary surgical instrument having a modular luer coupling associated with a clamp arm assembly.
Figure 67B:
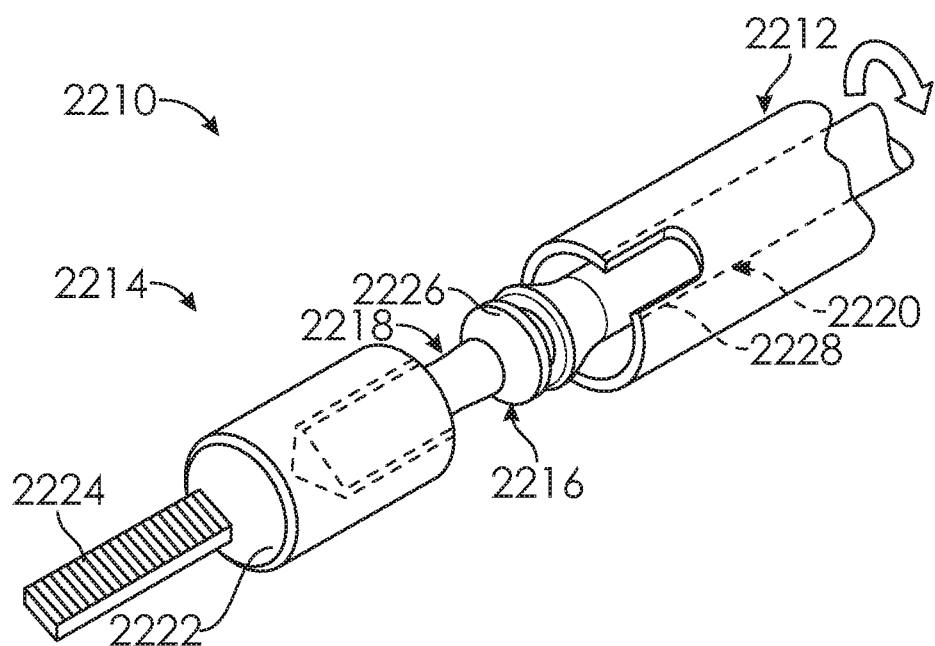
FIG. 67B depicts the enlarged perspective view of the surgical instrument similar to FIG. 67A, but showing the clamp arm assembly removed from a clamp arm actuator.
Figure 68:
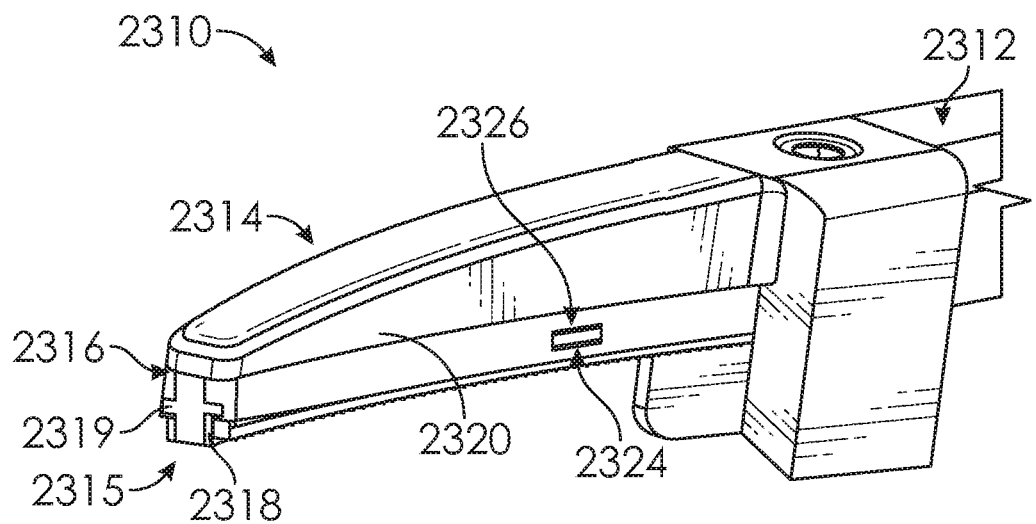
FIG. 68 depicts an enlarged perspective view of a twentieth exemplary surgical instrument having a modular pad insert coupling associated with a clamp arm assembly having a removable pad.
Figure 69:
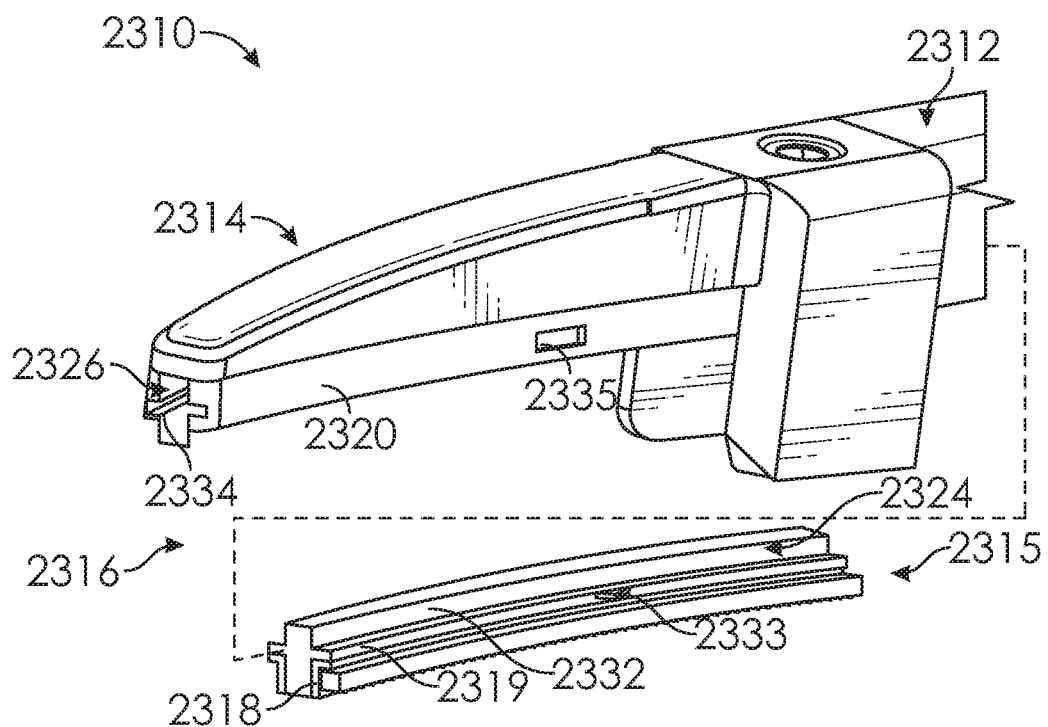
FIG. 69 depicts an enlarged partially exploded view of the surgical instrument of FIG. 68 with the clamp pad removed from a clamp body of the clamp arm assembly.
Figure 70:
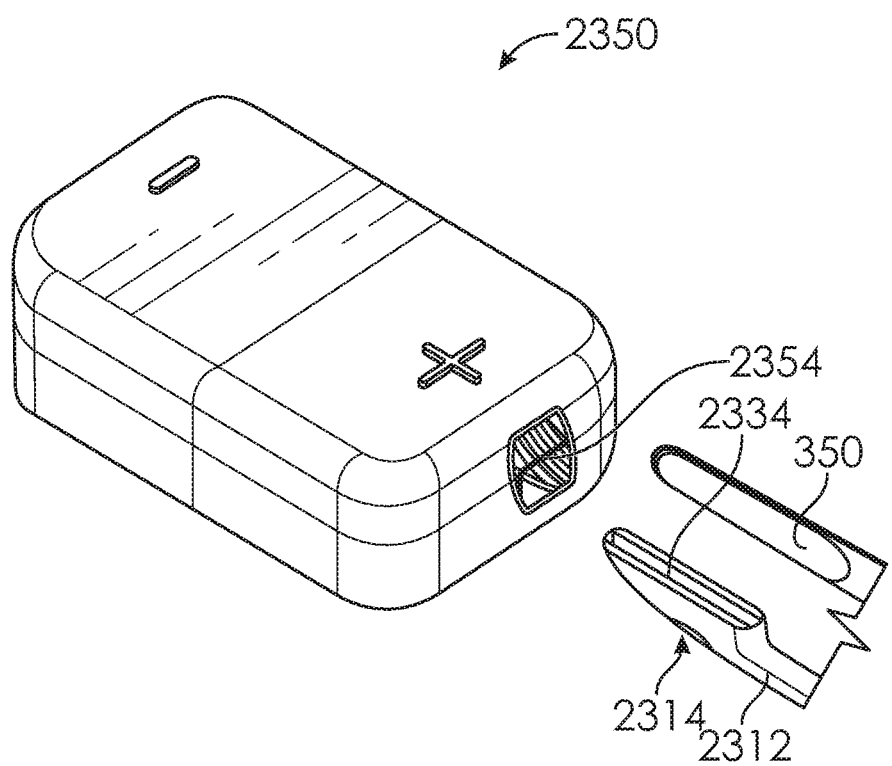
FIG. 70 depicts an enlarged perspective view of a second modular connection tool containing a replacement clamp pad of FIG. 69.
Figure 71:
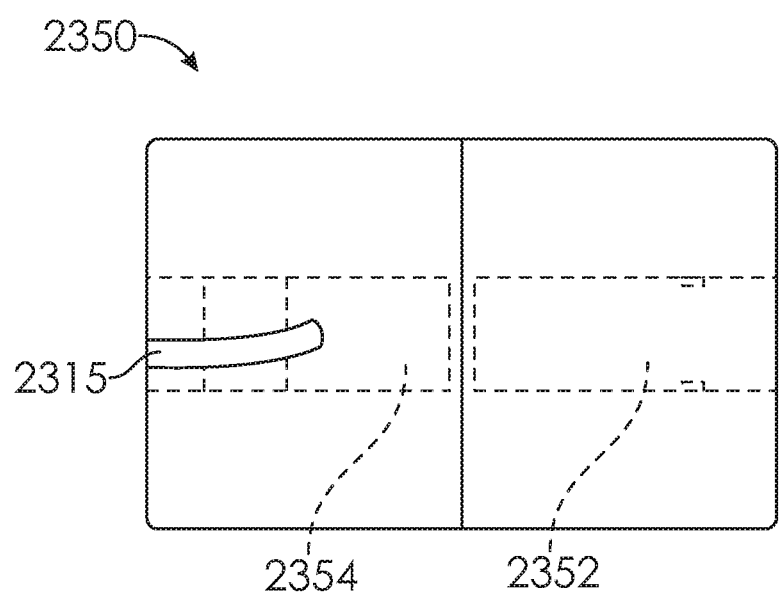
FIG. 71 depicts a top view of the modular connection tool of FIG. 70.
Figure 72:
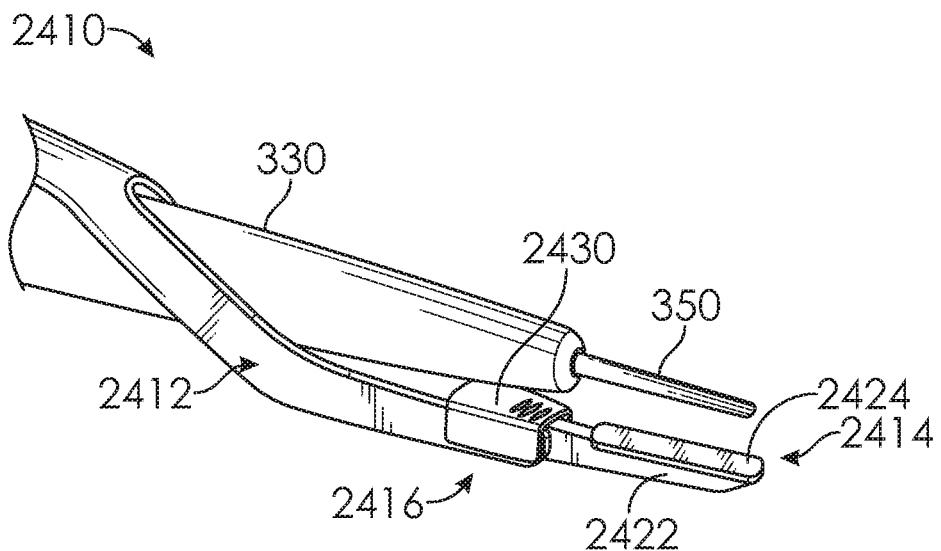
FIG. 72 depicts an enlarged perspective view of a twenty-first exemplary surgical instrument having a modular latch coupling and a latch lock associated with a clamp arm assembly.
Figure 73:
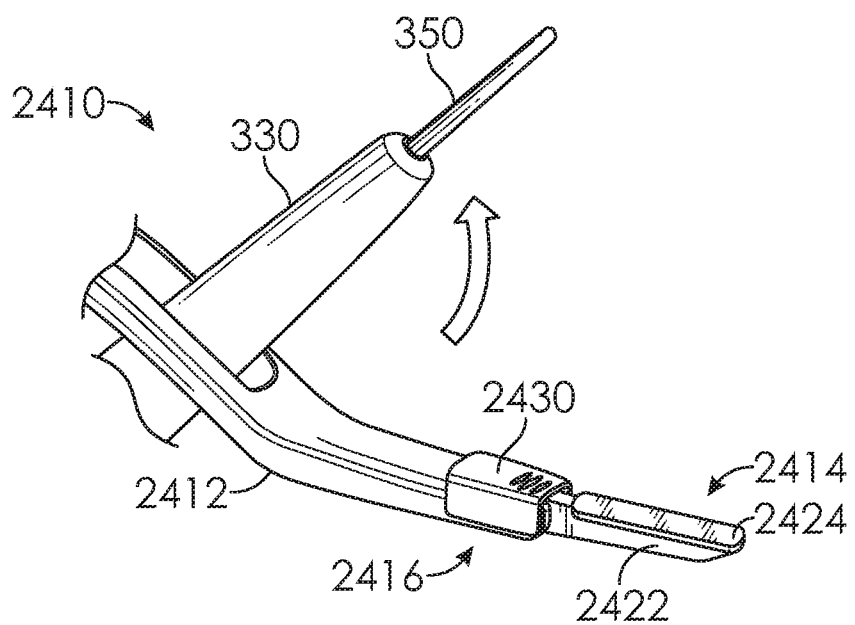
FIG. 73 depicts an enlarged perspective view of the surgical instrument of FIG. 72 with a clamp arm actuator and the clamp arm assembly in an opened configuration and the latch lock in a locked position.

R. Nineteenth Exemplary Ultrasonic Surgical Instrument with a Modular Luer Coupling FIGS. 67A and 67B illustrate a nineteenth exemplary surgical instrument (2210) having a clamp arm actuator (2212), a clamp arm assembly (2214), and a modular luer coupling (2216). Clamp arm assembly (2214) is removably connected to clamp arm actuator (2212) with modular luer coupling (2216), which includes a clamp body connection (2218) on clamp arm assembly (2214) and a clamp actuator connection (2220) on clamp arm actuator (2212). Clamp arm assembly (2214) includes a clamp body (2222) and a clamp pad (2224). Clamp pad (2224) is connected to clamp body (2222) such that clamp pad (2224) faces ultrasonic blade (not shown) for receiving and clamping tissue therebetween. Selective movement of clamp arm actuator (2212) relative to shaft assembly (not shown) from an opened configuration to a closed configuration respectively moves clamp arm assembly (2214) from an opened position configured to receive tissue to a closed position configured to clamp the tissue. While not shown with respect to surgical instrument (2210), clamp arm assembly (2214) may further include one or more electrodes configured to deliver RF energy to tissue for affecting the tissue, such as coagulating vessels in use.

Clamp body connection (2218) includes a male luer lock (2226) proximally extending from a proximal portion (2226) thereof, whereas clamp actuator connection (2220) includes a female luer lock (2228) within a distal portion thereof. Female luer lock (2228) is configured to rotatably receive male luer lock (2226) in order to removably connect clamp arm assembly (2214) to clamp arm actuator (2212).

In use, the operator rotates clamp arm assembly (2214) with male luer lock (226) relative to clamp arm actuator (2212) to release and withdrawal clamp arm assembly (2214) in the distal direction. The operator then distally translates clamp arm assembly (2214) until clamp arm assembly (2214) is removed from clamp arm actuator (2212). A replacement clamp arm assembly (2214) is positioned into clamp arm actuator (2212) and rotated to in order to capture male luer lock (2226) in female luer lock (2218) for use.

S. Twentieth Exemplary Ultrasonic Surgical Instrument with a Modular Pad Insert Coupling FIGS. 68-71 illustrate a twentieth exemplary surgical instrument (2310) having a clamp arm actuator (2312), a clamp arm assembly (2314) with a separable clamp pad assembly (2315), and a modular pad insert coupling (2316). Clamp arm assembly (2314) further includes clamp pad assembly (2315) with a clamp pad (2118) and a pad housing (2319) as well as a clamp body (2320), which is configured to removably receive clamp pad assembly (2315). To this end, clamp body (2320) of the present example extends rigidly from clamp arm actuator (2312) with modular pad insert coupling (2316) between clamp pad assembly (2340) and clamp body (2312) for removably connecting pad housing (2319) into clamp body (2320).

Modular pad insert coupling (2316) includes a clamp pad connection (2324) and a clamp body connection (2326). Clamp pad connection (2324) includes a longitudinal tab (2332) extending along an upper surface of pad housing (2319) and a pair of lateral tabs (2333) extending from respective side of pad housing (2319), whereas clamp body connection (2326) includes a longitudinal slot (2334) extending along a lower surface of clamp body (2320) and a pair of lateral apertures (2335) through respective sides of clamp body (2320). Longitudinal slot (2334) is configured to receive longitudinal tab (2332) to removably secure pad housing (2319) into clamp body (2320). More particularly, in the present example, longitudinal tab (2332) is distally introduced into a proximal end of longitudinal slot (2332) until a distal end of longitudinal tab (2332) is flush with a distal end of longitudinal slot (2334).

In use, the operator urges clamp pad assembly (2315) proximally such that longitudinal tab (2332) moves proximally through longitudinal slot (2334) until removed from longitudinal slot (2334). Such manipulation of clamp pad assembly (2315) is aided with a modular connection tool (2350) shown in FIGS. 70 and 71. Modular connection tool (2350) has an unload cavity (2352), in which to deposit used clamp pad assembly (2314) and a load cavity (2354), from which to retrieve a replacement clamp pad assembly (2314). More particularly, unload cavity (2352) has an inner surface configured to urge lateral tabs (2333) from lateral slots (2335) and clamp pad assembly (2318) from longitudinal slot (2334) for depositing clamp pad assembly (2318) therein. Replacement clamp pad assembly (2318) is suspended in load cavity (2352) such that the operator inserts longitudinal slot (2334) on clamp body (2320) beyond replacement clamp pad assembly (2318) and then withdraws clamp body (2320) from within load cavity (2354). Thereby, longitudinal tab (2332) is pulled through longitudinal slot (2334) until connected for use and modular connection tool (2350) may be discarded.

T. Twenty-First Exemplary Ultrasonic Surgical Instrument with a Modular Latch Coupling FIGS. 72-74C illustrate a twenty-first exemplary surgical instrument (2410) having a clamp arm actuator (2412), a clamp arm assembly (2414), and a modular latch coupling (2416). With respect to FIGS. 72-74A, clamp arm assembly (2414) is removably connected to clamp arm actuator (2412) with modular latch coupling (2416), which includes a clamp body connection (2418) on clamp arm assembly (2414) and a clamp actuator connection (2420) on clamp arm actuator (2412). Clamp arm assembly (2414) includes a clamp body (2422) and a clamp pad (2424). Clamp pad (2424) is connected to clamp body (2422) such that clamp pad (2424) faces ultrasonic blade (350) for receiving and clamping tissue therebetween. Selective movement of clamp arm actuator (2412) relative to shaft assembly (330) from an opened configuration to a closed configuration respectively moves clamp arm assembly (2414) from an opened position configured to receive tissue to a closed position configured to clamp the tissue. While not shown with respect to surgical instrument (2410), clamp arm assembly (2414) may further include one or more electrodes configured to deliver RF energy to tissue for affecting the tissue, such as coagulating vessels in use.

Clamp body connection (2418) includes a catch member, such as a catch bulbous member (2426), proximally extending from clamp body (2422), whereas clamp actuator connection (2420) includes catch groove (2428) in a distal end portion thereof. Catch groove (2428) is configured to support and cradle catch bulbous member (2426). Modular latch coupling (2416) further includes a latch (2430) configured to be selectively moved from a locked configuration to an unlocked configuration. In the locked configuration, latch (2430) covers and captures catch bulbous member (2426) in catch groove (2428) such that clamp arm assembly (2414) is removably connected to clamp arm actuator (2412). However, in the unlocked configuration, latch (2430) uncovers and releases catch bulbous member (2426) such that catch bulbous member (2426) is removable from catch groove (2428). In the present example, catch bulbous member (2426) is oblong and catch groove (2428) is hooked such that catch bulbous member (2426) is generally captured within hooked catch groove (2428) unless pivoted for removal.

Figure 74A:
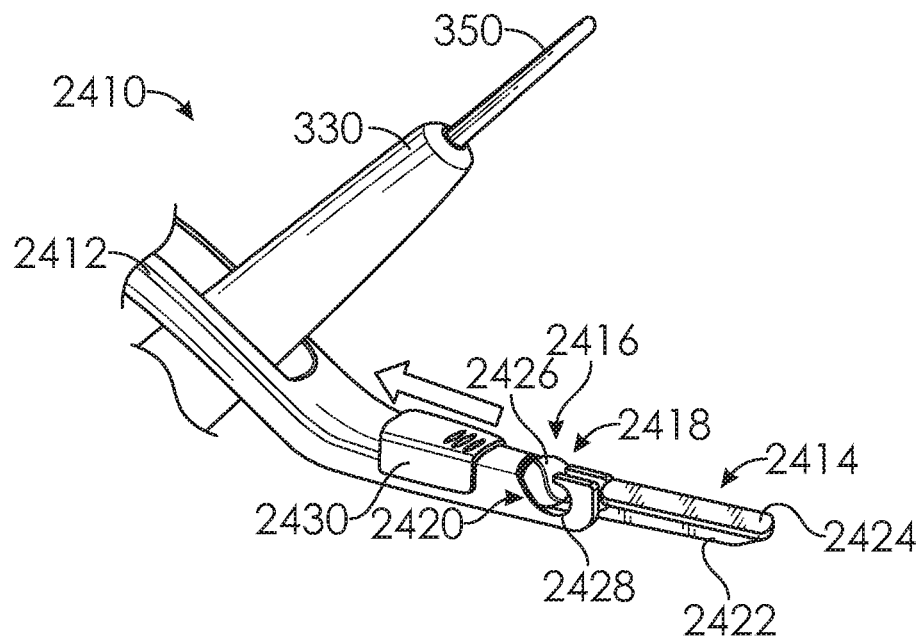
FIG. 74A depicts an enlarged perspective view of the surgical instrument of FIG. 72 with the clamp arm actuator and the clamp arm assembly in the opened configuration and the latch lock in an unlocked position.
Figure 74B:
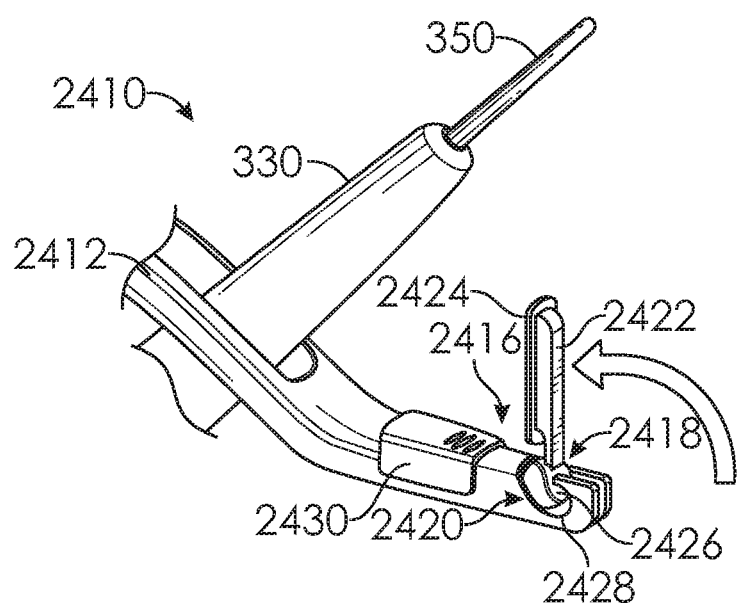
FIG. 74B depicts the enlarged perspective view of the surgical instrument similar to FIG. 74A, but showing the clamp arm assembly being removed from the clamp arm actuator.
Figure 74C:
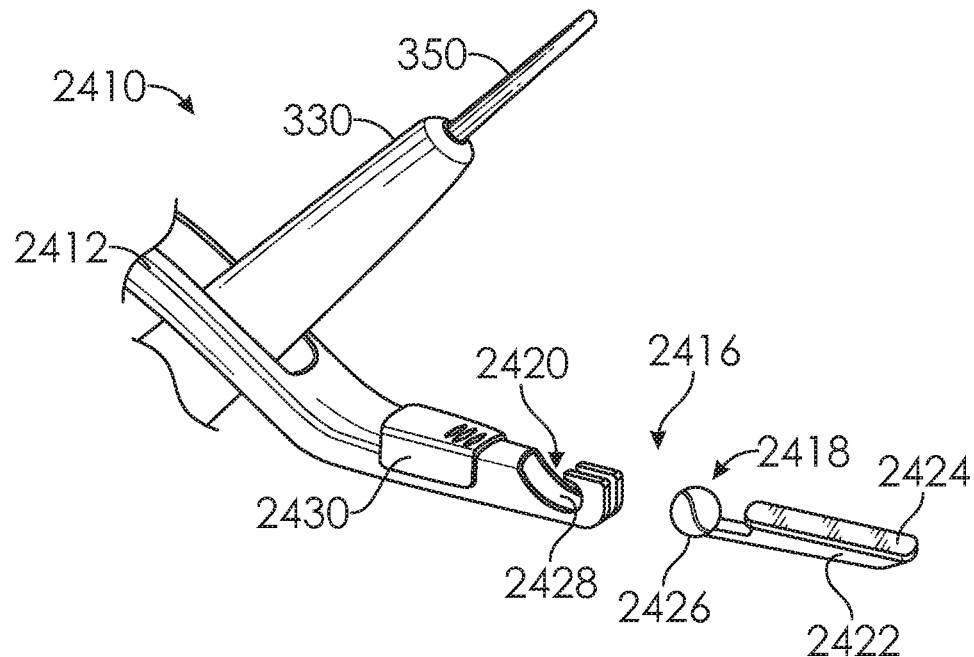
FIG. 74C depicts the enlarged perspective view of the surgical instrument similar to FIG. 74B, but showing the clamp arm assembly removed from the clamp arm actuator.
Figure 75:
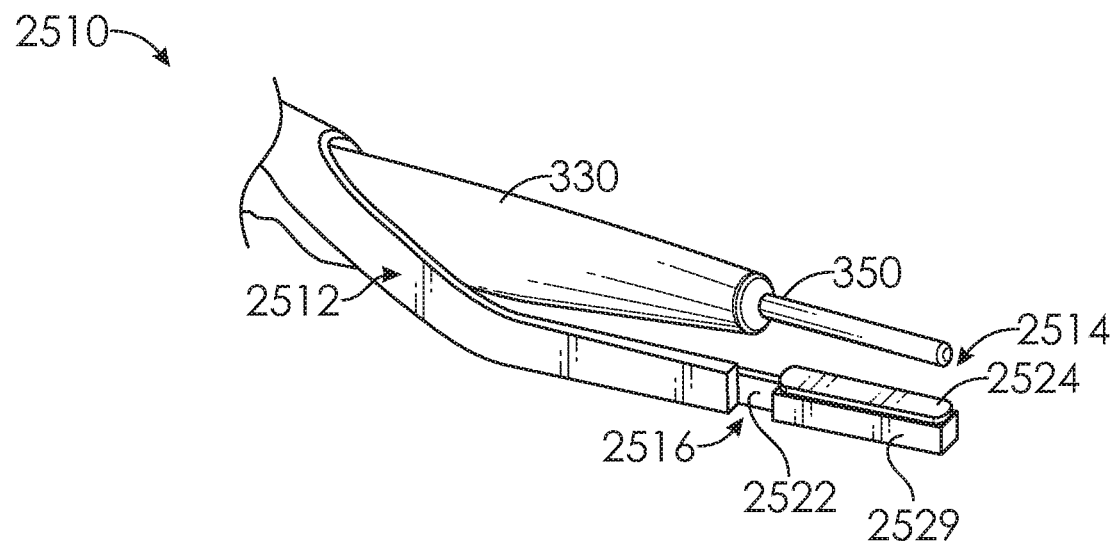
FIG. 75 depicts an enlarged perspective view of a twenty-second exemplary surgical instrument having a first modular multi-position coupling associated with a clamp arm assembly.
Figure 76:
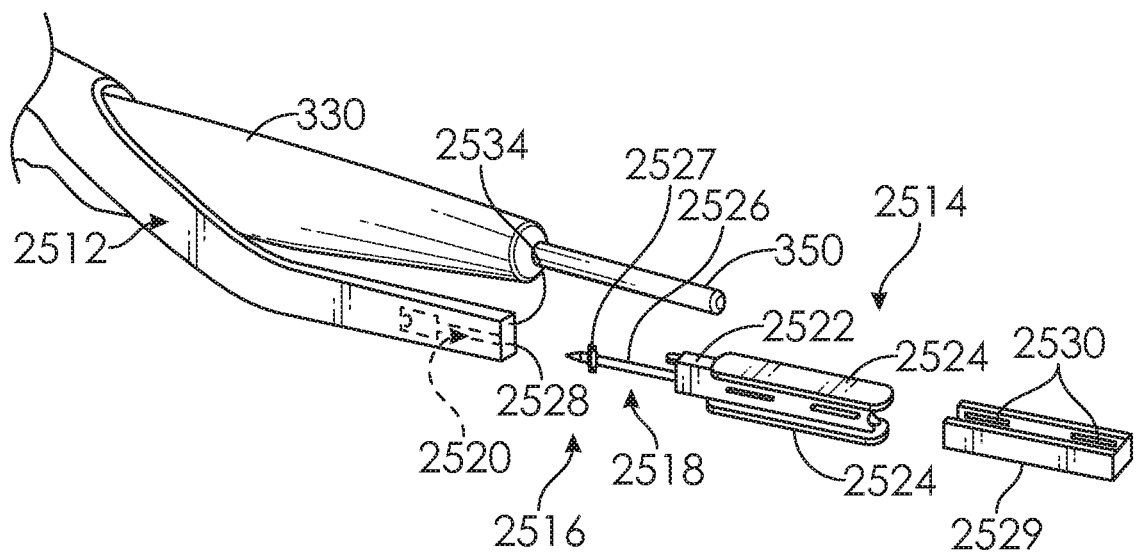
FIG. 76 depicts an enlarged partially exploded perspective view of the surgical instrument of FIG. 75 including a pair of clamp pads on the clamp arm assembly and a pad cover.
Figure 77:
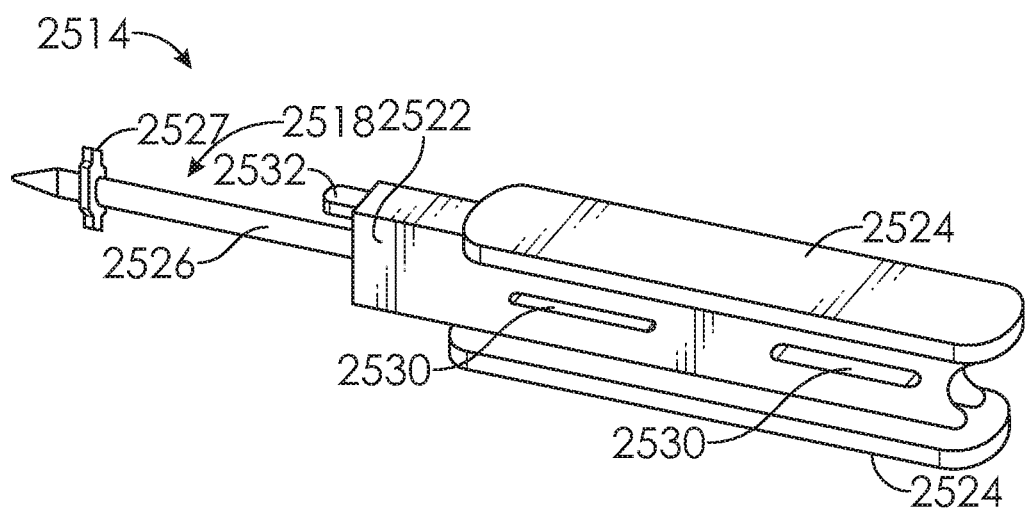
FIG. 77 depicts a perspective view of the clamp arm assembly of FIG. 75 without the pad cover.

In use, with respect to FIGS. 74A-74C, the operator proximally urges latch (2430) from the locked configuration to the unlocked configuration and pivots clamp arm assembly (2414) transversely upward. The operator then transversely translates clamp arm assembly (2414) until clear of hooked catch groove (2428) and removed from clamp arm actuator (2412). A replacement clamp arm assembly (2414) is positioned into clamp arm actuator (2412) and latch (2430) is directed back to the closed configuration in order to capture replacement clamp arm assembly (2414) for use.

U. Twenty-Second Exemplary Ultrasonic Surgical Instrument with a First Modular Multi-Position Coupling FIGS. 75-78C illustrate a twenty-second exemplary surgical instrument (2510) having a clamp arm actuator (2512), a clamp arm assembly (2514), and a first modular multi-position coupling (2516). With respect to FIGS. 75-77, clamp arm assembly (2514) is movably connected to clamp arm actuator (2512) with modular multi-position coupling (2516), which includes a clamp body connection (2518) on clamp arm assembly (2514) and a clamp actuator connection (2520) on clamp arm actuator (2512). Clamp arm assembly (2514) includes a clamp body (2522) and a pair of clamp pads (2524). Clamp pads (2524) are connected to opposing upper and lower surfaces of clamp body (2522) such that each clamp pad (2524) respectively faces ultrasonic blade (350) in a first use position or a second use position for receiving and clamping tissue therebetween. Selective movement of clamp arm actuator (2512) relative to shaft assembly (330) from an opened configuration to a closed configuration respectively moves clamp arm assembly (2514) from an opened position configured to receive tissue to a closed position configured to clamp the tissue. While not shown with respect to surgical instrument (2510), clamp arm assembly (2514) may further include one or more electrodes configured to deliver RF energy to tissue for affecting the tissue, such as coagulating vessels in use.

Clamp body connection (2518) includes longitudinal pin (2526) with a stop (2527) proximally extending from clamp body (2522), whereas clamp actuator connection (2520) includes a pin bore (2528) proximally extending through a distal end portion thereof. Pin bore (2528) is configured to slidably receive longitudinal pin (2526) such that longitudinal pin (2526) selectively slides between a proximal, locked position and a distal, unlocked position. Stop (2527)

engages a distal wall of clamp arm actuator (2512) in the unlocked position to inhibit further distal translation such that clamp arm assembly (2514) remains at least somewhat moveable without being removed from pin bore (2528). In an alternative example, longitudinal pin (2526) may be removable from pin bore (2528) without stop (2527). In the present example, clamp arm assembly (2514) further includes a lower pad cover (2529) configured to cover the remaining clamp pad (2524) facing away from ultrasonic blade (350). Clamp body (2522) and lower pad cover (2529) each have respective ridges (2530) configured to transversely overlap for selective engagement between clamp body (2522) and lower pad cover (2529).

Modular multi-position coupling (2516) further includes a proximally extending tab (2532) configured to be received within one of a pair of tab holes (2534) that respectively correspond to the first use position and the second use position. With tab (2532) in upper tab hole (2534), a first of clamp pads (2524) faces ultrasonic blade (350) for use. With tab (2532) in lower tab hole (2534), a second of clamp pads (2524) faces ultrasonic blade (350) for use. In either case, tab holes (2534) with tab (2532) received there are configured to inhibit rotation of clamp arm assembly (2514).

Figure 78A:
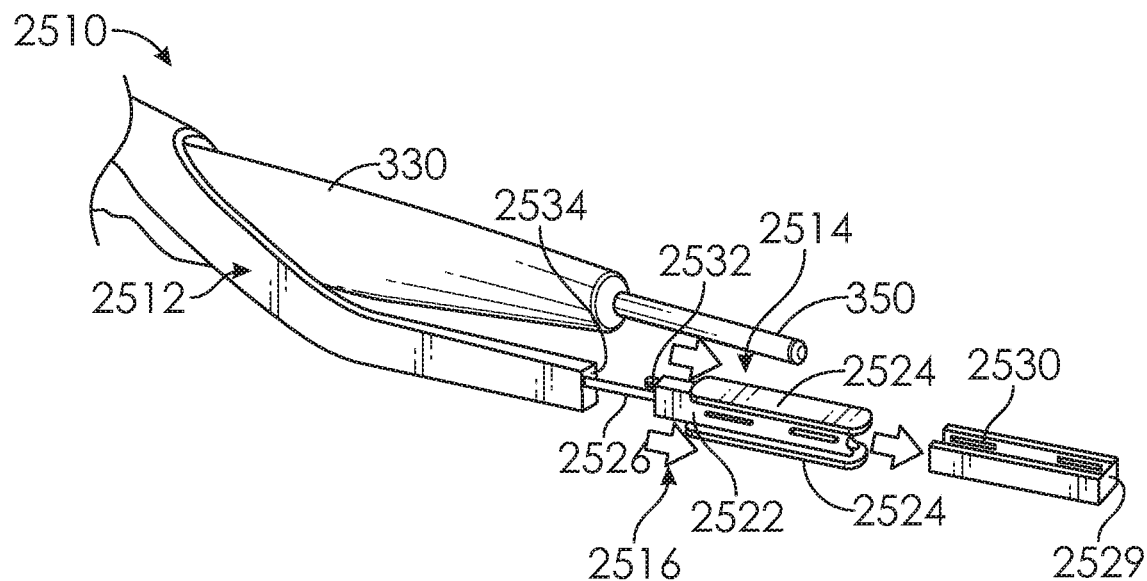
FIG. 78A depicts an enlarged perspective view of the surgical instrument of FIG. 75 with the clamp arm assembly being selectively moved from a locked position to an unlocked position and the pad cover being removed.
Figure 78B:
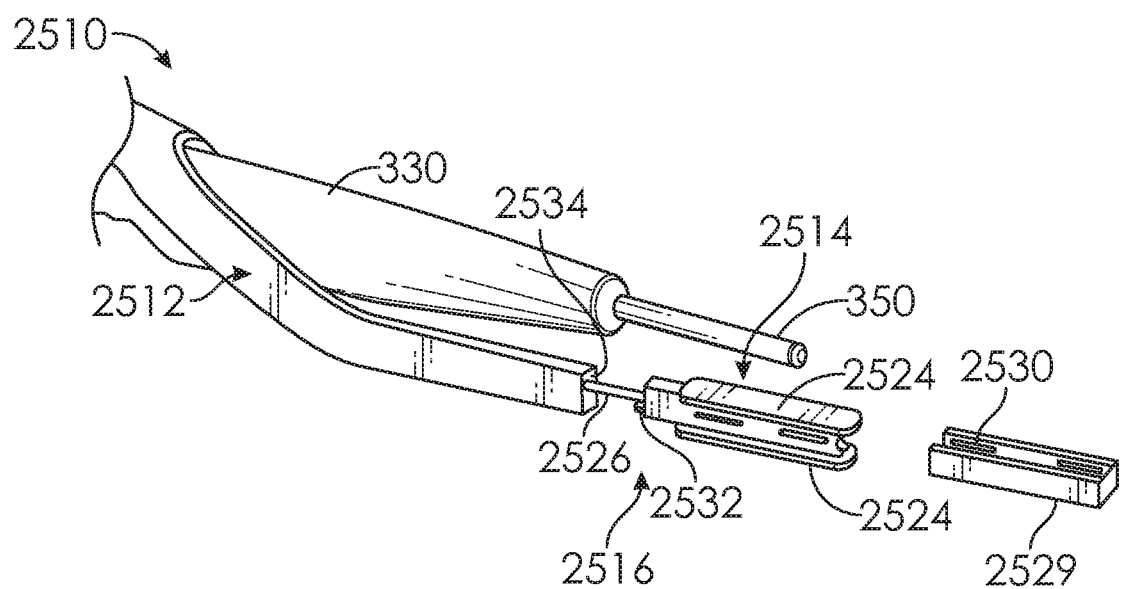
FIG. 78B depicts the enlarged perspective view of the surgical instrument similar to FIG. 78A, but showing the clamp arm assembly without the pad cover being rotated from a first use position to a second use position.
Figure 78C:
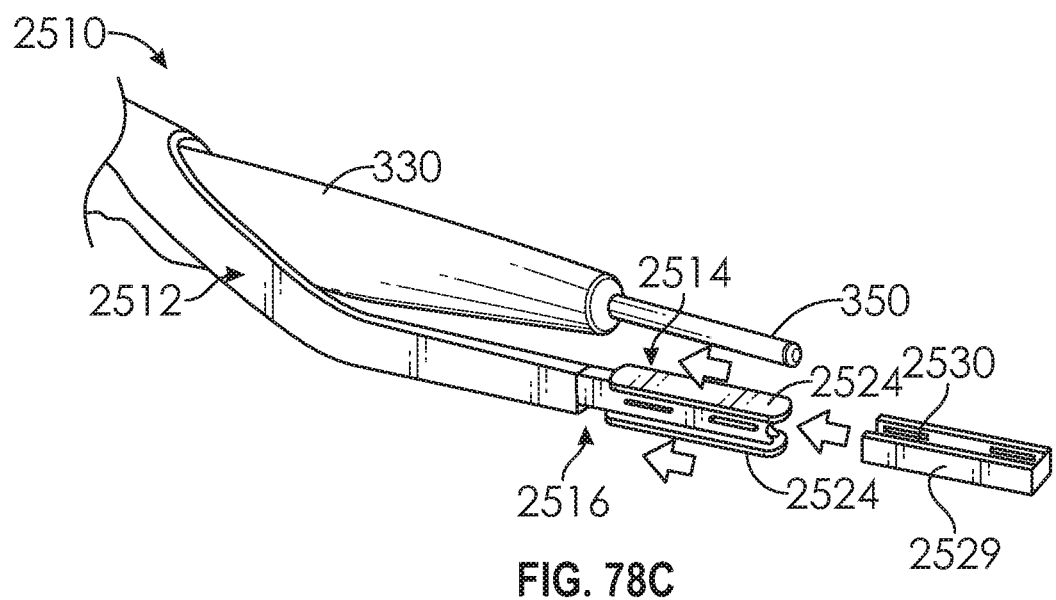
FIG. 78C depicts the enlarged perspective view of the surgical instrument similar to FIG. 78B, but showing the clamp arm assembly being selectively moved from the unlocked position to the locked position in the second use position and reconnection of the pad cover.

In use, with respect to FIGS. 78A-78C, the operator distally removes lower pad cover (2529) from clamp body (2522) and also distally translates clamp body (2522) along a longitudinal axis from the first use position by disengaging tab (2532) from tab hole (2534) such that clamp body (2522) with dual clamp pads (2522) is freely rotatable. The operator then rotates clamp body (2522) about the longitudinal axis with dual clamp pads (2522) from the first use position toward the second use position in order to face the second clamp pad (2524) toward ultrasonic blade (350). Once aligned, the operator translates clamp body (2522) proximally and engages tab (2532) with tab hole (2534) into the second use position and reattaches lower pad cover (2529) for another use.

V. Twenty-Third Exemplary Ultrasonic Surgical Instrument with a Second Modular Multi-Position Coupling FIGS. 79A-81 illustrate a twenty-third exemplary surgical instrument (2610) having a clamp arm actuator (2612), a clamp arm assembly (2614), and a second modular multi-position coupling (2616). With respect to FIGS. 79A and 79B, clamp arm assembly (2614) is movably connected to clamp arm actuator (2612) with modular multi-position coupling (2616), which includes a clamp body connection (2618) on clamp arm assembly (2614) and a clamp actuator connection (2620) on clamp arm actuator (2612). Clamp arm assembly (2614) includes a clamp body (2622) and a pair of clamp pad (2624). Clamp pad (2624) are connected to opposing upper and lower surfaces of opposing distal and proximal end portions of clamp body (2622) such that each clamp pad (2624) respectively faces ultrasonic blade (350) in a first use position or a second use position for receiving and clamping tissue therebetween. Selective movement of clamp arm actuator (2612) relative to shaft assembly (330) from an opened configuration to a closed configuration respectively moves clamp arm assembly (2614) from an opened position configured to receive tissue to a closed position configured to clamp the tissue. In addition, with respect to FIGS. 80 and 81, clamp arm assembly (2614) further includes a plurality of RF electrodes (2625) extending along each clamp pad (2624). Each RF electrode (2625) is operatively connected to an RF energy source and configured to deliver RF energy to tissue for affecting the tissue, such as coagulating vessels in use.

Figure 79A:
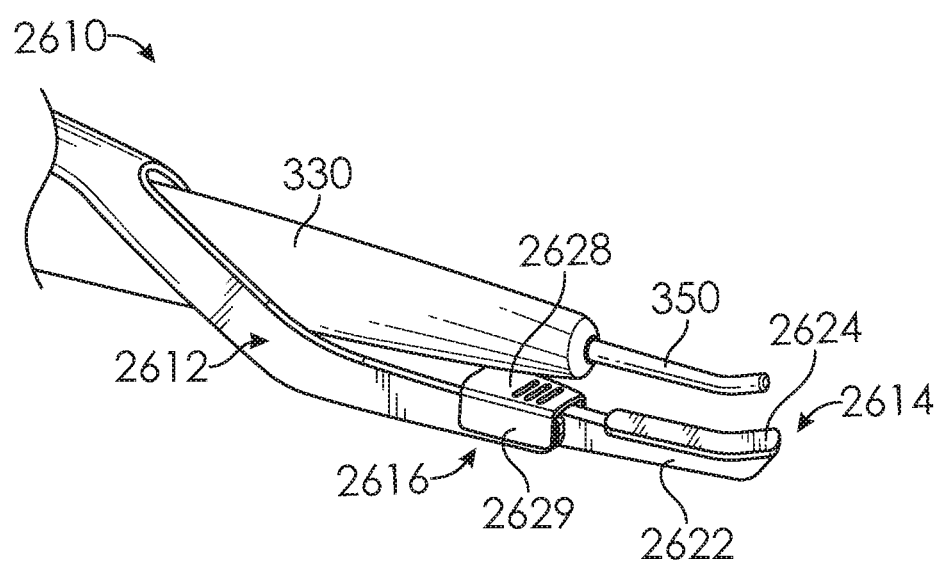
FIG. 79A depicts an enlarged perspective view of a twenty-third exemplary surgical instrument having a second modular multi-position coupling associated with a clamp arm assembly in a closed configuration.
Figure 79B:
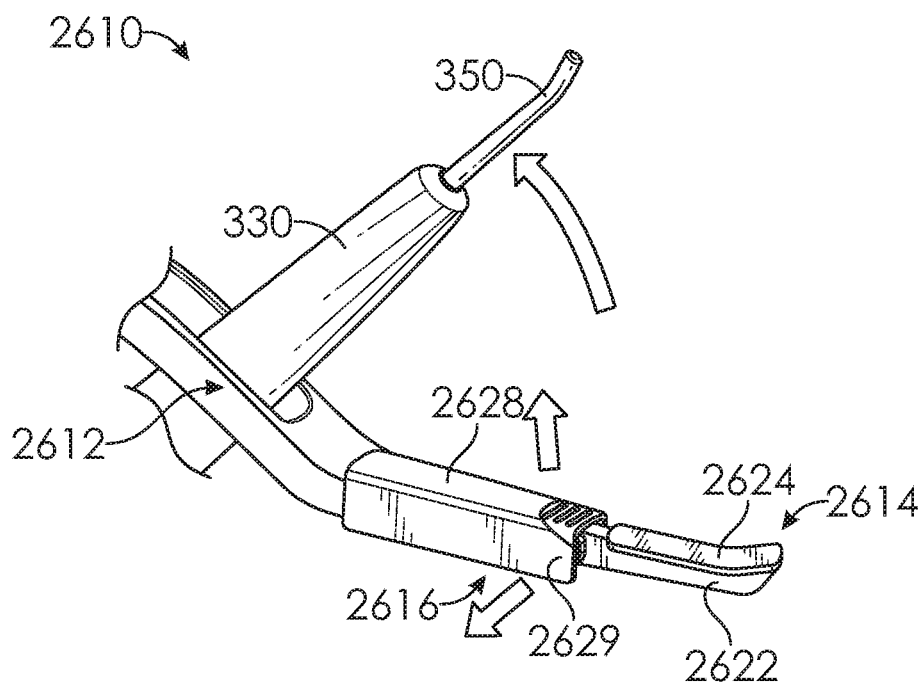
FIG. 79B depicts the enlarged perspective view of the surgical instrument similar to FIG. 79A, but showing the clamp arm assembly in an opened configuration and in a first use position with a latch cover being removed from a locked position.
Figure 79C:
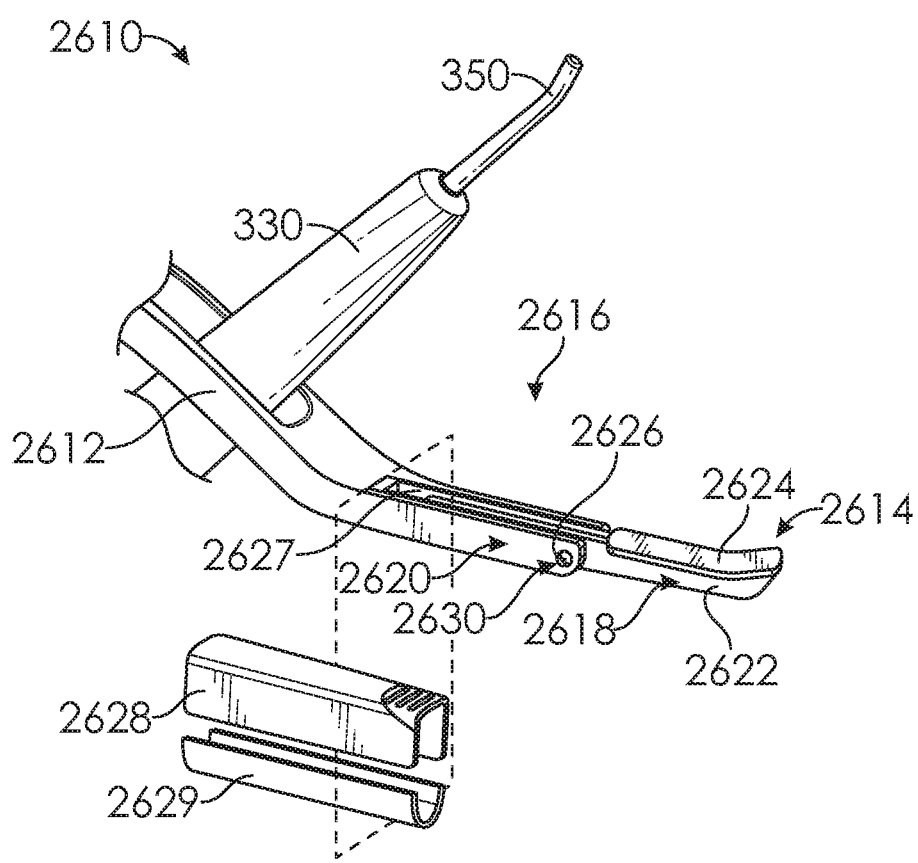
FIG. 79C depicts the enlarged perspective view of the surgical instrument similar to FIG. 79B, but showing the latch cover removed and the clamp arm assembly in an unlocked position.
Figure 79D:
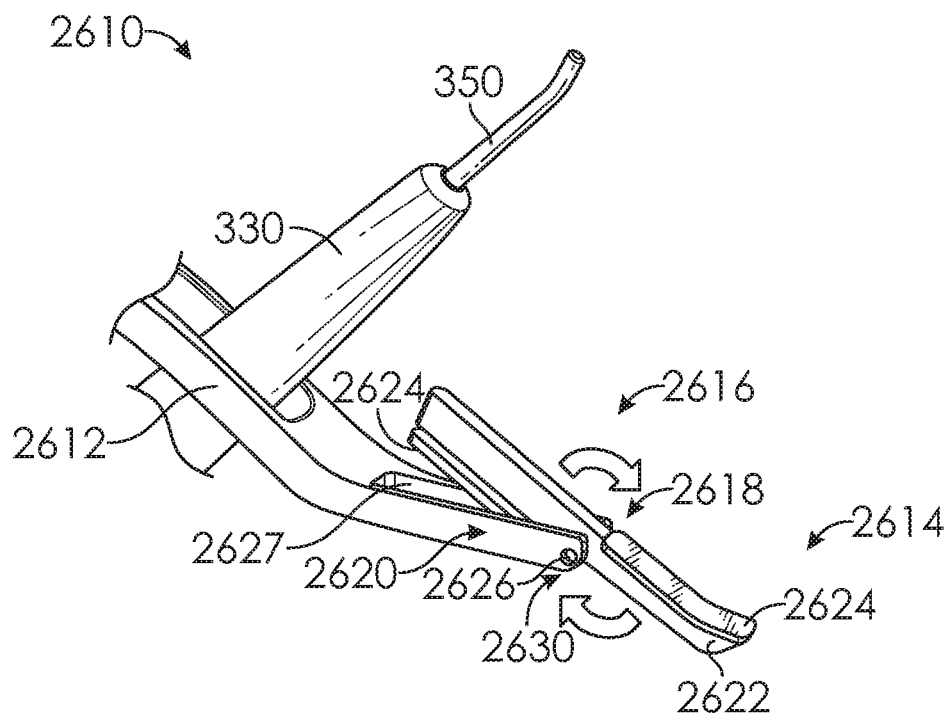
FIG. 79D depicts the enlarged perspective view of the surgical instrument similar to FIG. 79C, but showing the clamp arm assembly being rotated from the first use position to a second use position.
Figure 79E:
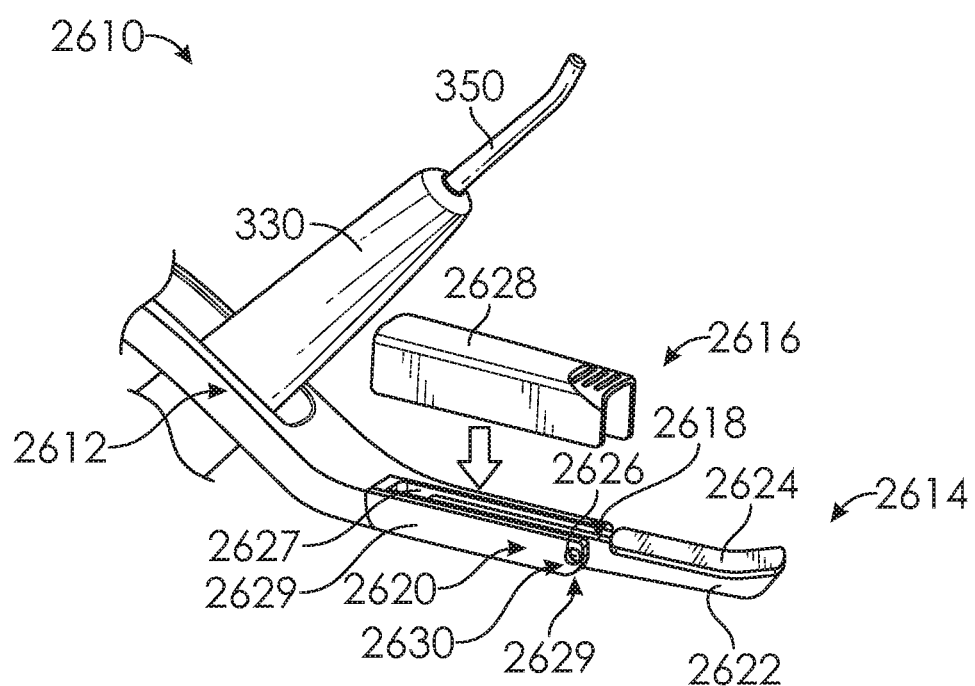
FIG. 79E depicts the enlarged perspective view of the surgical instrument similar to FIG. 79D, but showing the latch cover reconnected to the locked position to secure the clamp arm assembly in the second use position.
Figure 80:
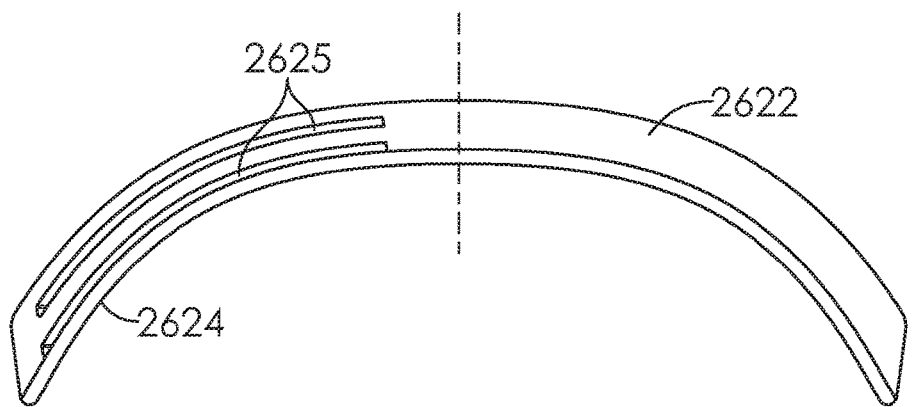
FIG. 80 depicts a bottom view of the clamp arm assembly of FIG. 79A.
Figure 81:
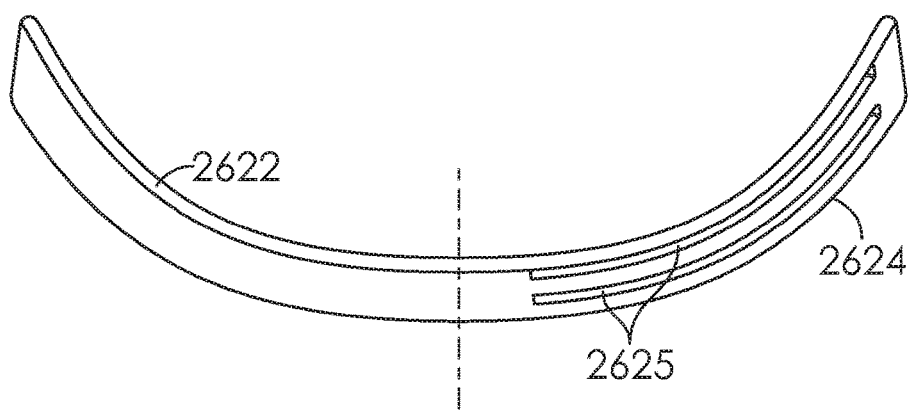
FIG. 81 depicts a top view of the clamp arm assembly of FIG. 79A.
Figure 82:
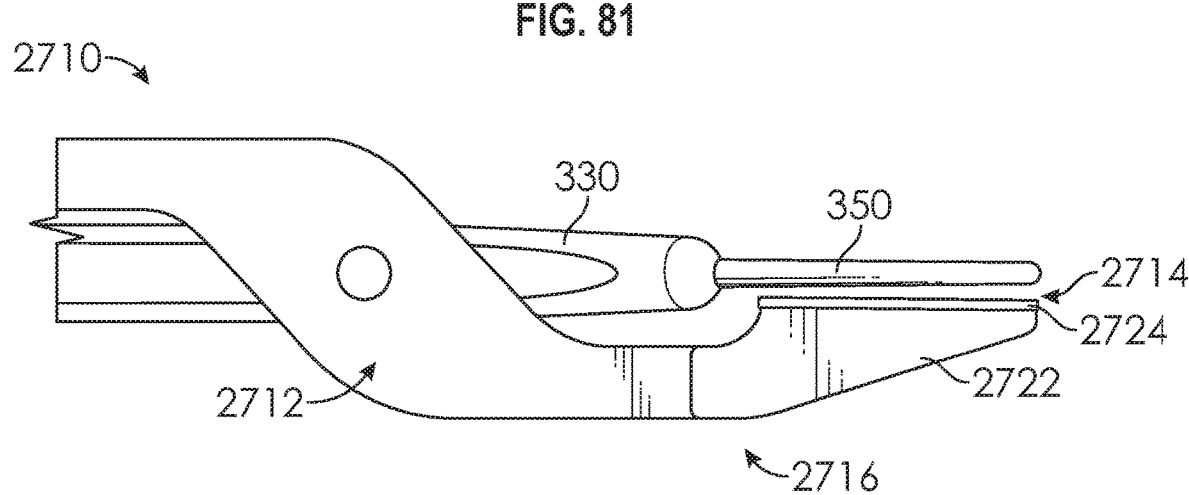
Figure 83:
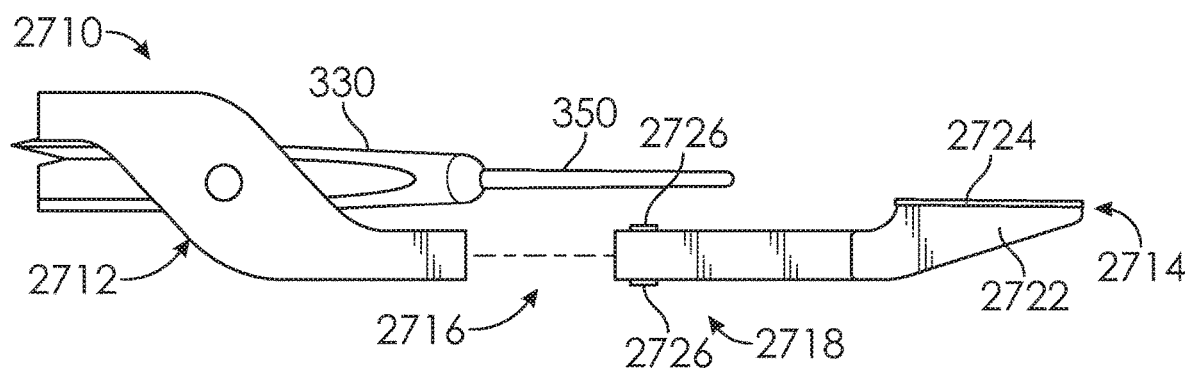
Figure 84:
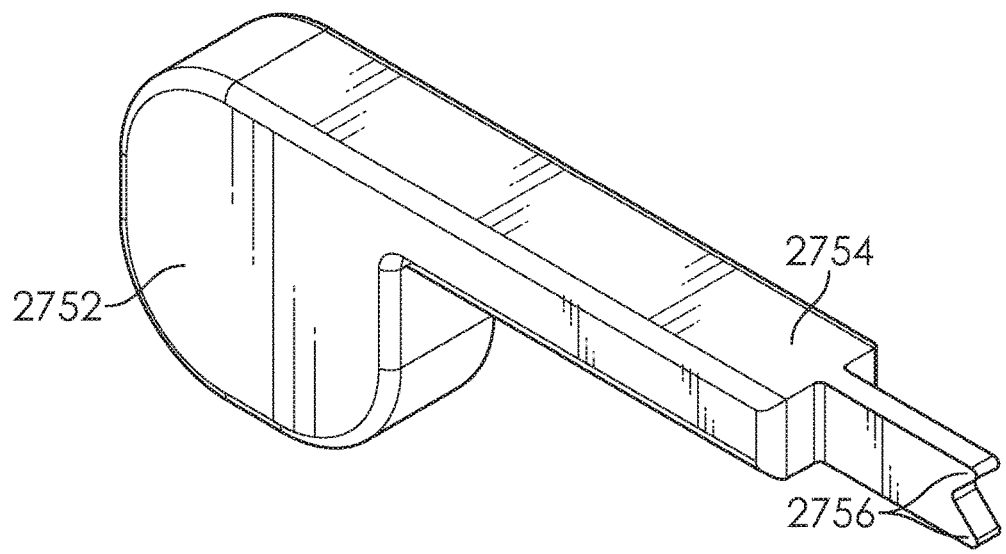
Figure 85:
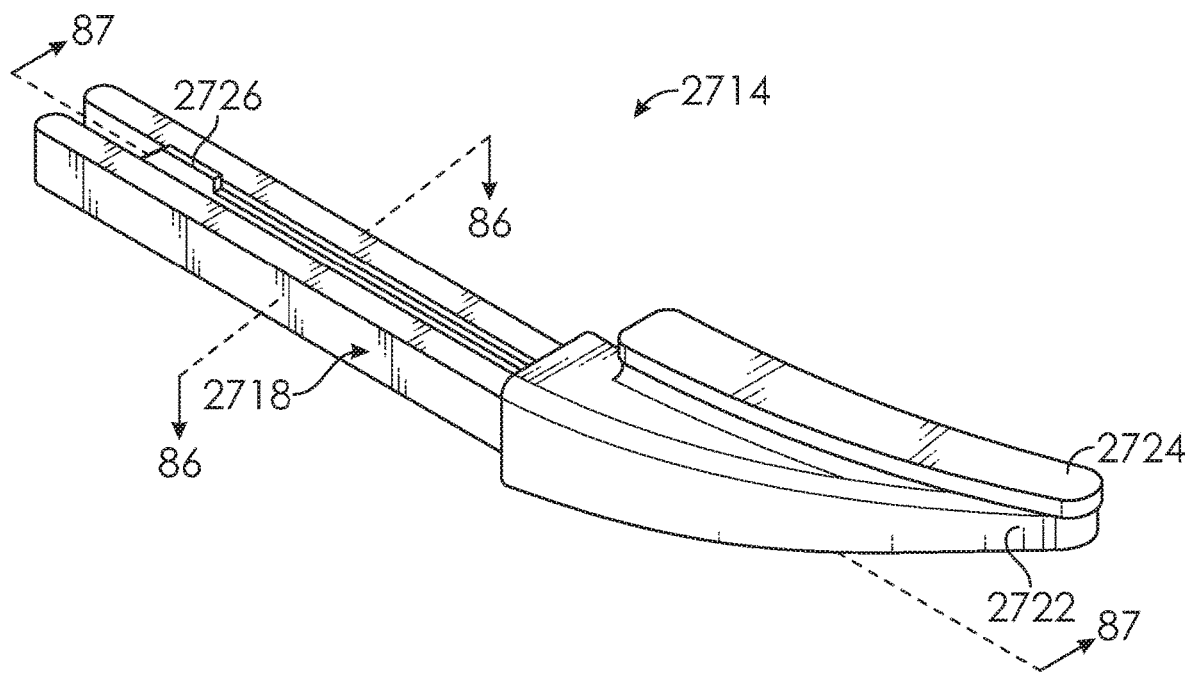
Figure 86:
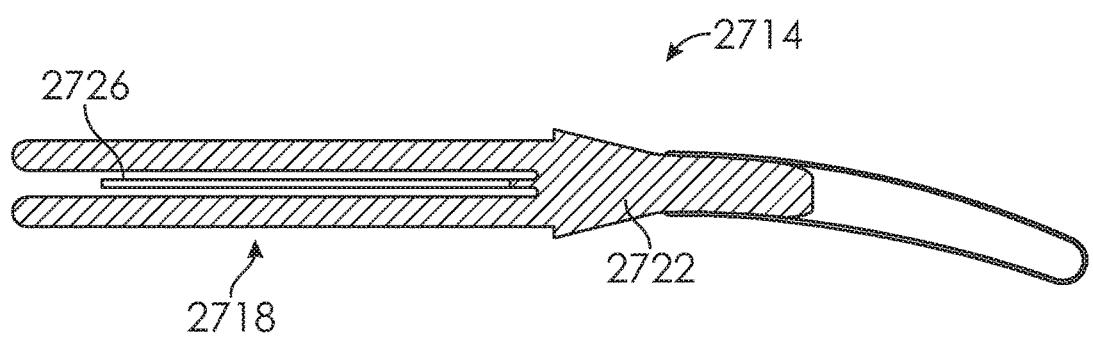
Figure 87:
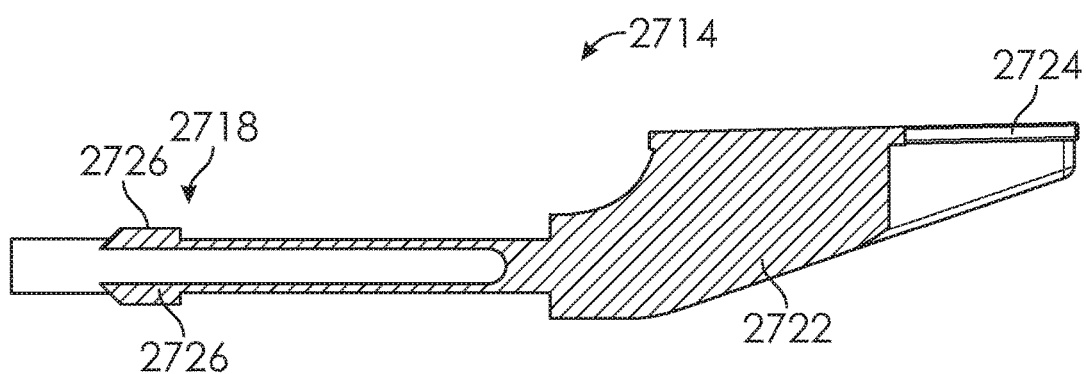
Figure 88:
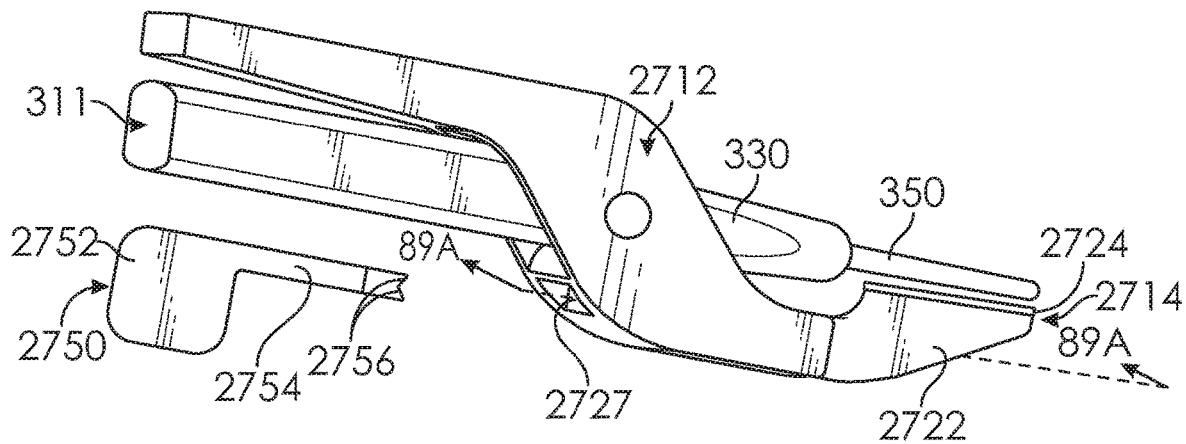

Clamp body connection (2618) shown in greater detail in FIGS. 79C and 79D includes a transverse pin (2626) transversely extending through a central portion of clamp body (2622), whereas clamp actuator connection (2620) includes a pin bore (2630) transversely extending through a distal, bifurcated end portion thereof across a gap (2627). Pin bore (2630) is configured to rotatably receive transverse pin (2626) such that transverse pin (2626) and clamp arm assembly (2614) selectively rotate between a first use position and a second use position. Alternatively or in addition, transverse pin (2626) may be configured to transversely slide between a locked position and an unlocked position such that transverse pin (2626) inhibits selective rotation of clamp arm assembly (2614) in the locked position and allows selective rotation of clamp arm assembly (2614) in the unlocked position.

Modular multi-position coupling (2616) further includes an upper latch cover (2628) and a lower latch cover (2629) removably connected together and configured to releaseably secure clamp arm assembly (2614) in either the first use position or the second use position. More particularly, upper and lower latch covers (2628, 2629) engaged to clamp arm actuator (2612) collectively inhibit selective rotation of clamp arm assembly (2614) from either the first use portion or the second use position for use in the surgical procedure. However, with upper and lower latch covers (2628, 2629) disengaged from clamp arm actuator (2612), clamp arm assembly (2614) is selectively rotatably about transverse pin (2626). Thereby, the operator rotates clamp arm assembly (2614) from the first use position once a first clamp pad is used to the second use position such that a second clamp pad faces ultrasonic blade (350) for another use.

In use, with respect to FIGS. 79A-79E, the operator disengages upper and lower latch covers (2628, 2629) from distal bifurcated portion of clamp arm actuator (2612) such that clamp arm assembly is selectively rotatable about a transverse axis along transverse pin (2626). The operator then rotates clamp arm assembly (2614) from the first use position to a second use position and engages upper and lower latch covers (2628, 2629) to clamp arm actuator (2612) to secure clamp arm assembly (2614) in the second use position for another use. In order to position the second clamp pad (2624) in a similar position to the first clamp pad (2624), clamp body (2622) is U-shaped and symmetric about the transverse axis shown in FIGS. 80 and 81.

W. Twenty-Fourth Exemplary Ultrasonic Surgical Instrument with a Modular Inner Release Coupling FIGS. 82-89B illustrate a twenty-fourth exemplary surgical instrument (2710) having handle assembly (311), shaft assembly (330), a clamp arm actuator (2712), a clamp arm assembly (2714), and a modular inner release coupling (2716). With respect to FIGS. 82 and 83, Clamp arm assembly (2714) is removably connected to clamp arm actuator (2712) with modular inner release coupling (2716), which includes a clamp body connection (2718) on clamp arm assembly (2714) and a clamp actuator connection (2720) on clamp arm actuator (2712). Clamp arm assembly (2714) includes a clamp body (2722) and a clamp pad (2724). Clamp pad (2724) is connected to clamp body (2722) such that clamp pad (2724) faces ultrasonic blade (350) for receiving and clamping tissue therebetween. Selective movement of clamp arm actuator (2712) relative to shaft assembly (330) from an opened configuration to a closed configuration respectively moves clamp arm assembly (2714) from an opened position configured to receive tissue to a closed position configured to clamp the tissue. While not shown with respect to surgical instrument (2710), clamp arm assembly (2714) may further include one or more electrodes configured to deliver RF energy to tissue for affecting the tissue, such as coagulating vessels in use.

Modular inner release coupling (2716) of the present example is generally contained within clamp arm actuator (2712) while connected to clamp arm assembly (2714) to inhibit inadvertent removably of clamp arm assembly (2714). FIG. 95 shows a modular connection tool (2750) configured to access modular inner release coupling (2716) for removal of clamp arm assembly (2714) discussed below in greater detail. In the present example, modular connection tool (2750) has a grip body (2752) configured to be manipulated by the operator and a release key (2754) extending rigidly therefrom. An end portion of release key (2754) is configured to manipulate at least a portion of modular inner release coupling (2716) for removal. More particularly, in the present example, release key (2754) has an upper wedge (2756) and an opposing lower wedge (2756) configured to manipulate clamp body connection (2718) for removing clamp arm assembly (2714) from clamp actuator arm (2712). In addition, modular connection tool (2750) may also include an integrated circuit and/or memory, such as an Electrically Erasable Programmable Read Only Memory (EEPROM), configured to pair with surgical instrument (2710) for verifying proper installation of clamp arm assembly (2714), authentication of modular connection tool (2750), and procure output drive and diagnostic parameters. In another example, a variety of modular connection tools (2750) may be provided with surgical instrument (2710) with each respective modular connection tool (2750) being configured for a particular use, such as use with an ultrasonic instrument and/or an RF bipolar instrument.

With respect to FIGS. 85-89A, clamp body connection (2718) includes a pair of upper and lower biased projection tabs (2726) extending proximally from the proximal portion of clamp arm assembly (2714), whereas clamp actuator connection (2720) includes an elongate, longitudinal aperture (2727) having a pair of upper and lower shoulders (2728) extending transversely through upper and lower surfaces of clamp arm actuator (2712). Upper and lower shoulders (2728) respectively receive upper and lower biased projection tabs (2726) thereagainst to thereby removably connect clamp arm assembly (2714) to clamp arm actuator (2712).

Figure 89A:
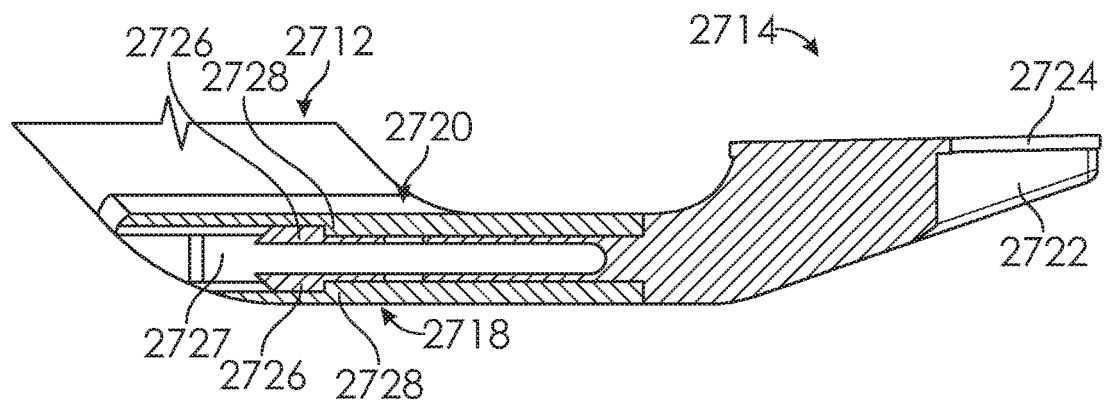
Figure 89B:
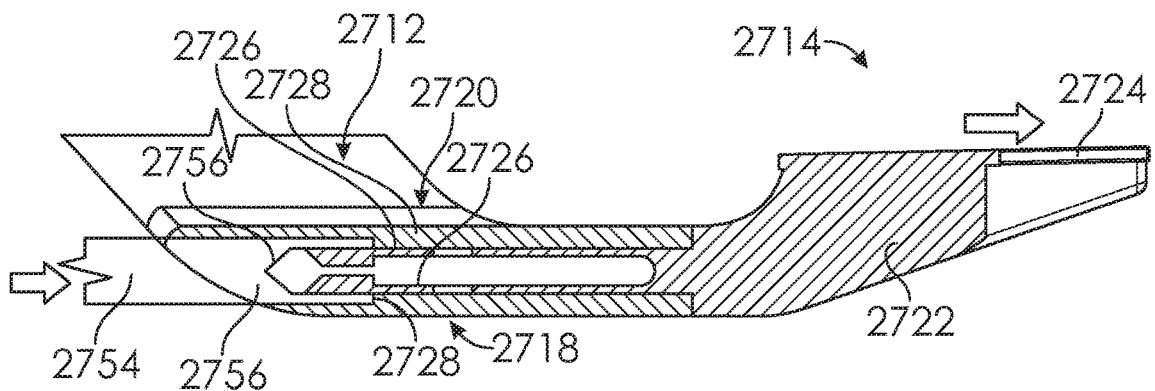

In use, with respect to FIGS. 89A and 89B, the operator distally inserts release key (2754) through a proximal portion of longitudinal aperture (2727) such that upper and lower wedges (2756) respectively engage upper and lower biased projection tabs (2726). Upper and lower wedges (2756) direct upper and lower biased projection tabs (2726) toward each other until each is transversely clear of upper and lower shoulders (2728), respectively. Once clear, the operator distally translates clamp arm assembly (2714) relative to clamp arm actuator (2712) from a distal portion of longitudinal aperture (2727). A replacement clamp arm assembly (2714) is positioned into clamp arm actuator (2712) and snapped therein in order to capture replacement clamp arm assembly (2714) for use.

X. Twenty-Fifth Exemplary Ultrasonic Surgical Instrument with a Modular Helical Coupling FIGS. 90A-94C illustrate a twenty-fifth exemplary surgical instrument (2810) having a clamp arm actuator (2812), a clamp arm assembly (2814), and a modular helical coupling (2816). With respect to FIGS. 90A and 90B, clamp arm assembly (2814) is removably connected to clamp arm actuator (2812) with modular helical coupling (2816), which includes a clamp body connection (2818) on clamp arm assembly (2814) and a clamp actuator connection (2820) on clamp arm actuator (2812). Clamp arm assembly (2814) includes a clamp body (2822) and a clamp pad (2824). Clamp pad (2824) is connected to clamp body (2822) such that clamp pad (2824) faces ultrasonic blade (350) for receiving and clamping tissue therebetween. Selective movement of clamp arm actuator (2812) relative to shaft assembly (330) from an opened configuration to a closed configuration respectively moves clamp arm assembly (2814) from an opened position configured to receive tissue to a closed position configured to clamp the tissue. While not shown with respect to surgical instrument (2810), clamp arm assembly (2814) may further include one or more electrodes configured to deliver RF energy to tissue for affecting the tissue, such as coagulating vessels in use.

Figure 91:
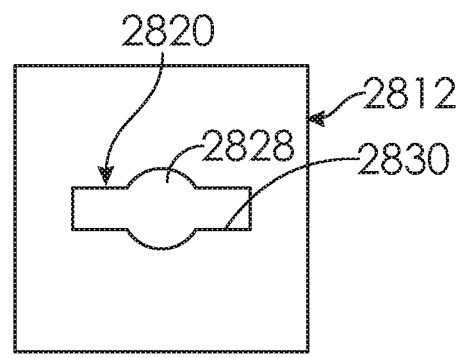

With respect to FIGS. 90B and 91, clamp body connection (2818) includes a helical connector (2826) extending proximally extending from a proximal portion thereof, whereas clamp actuator connection (2820) includes a helical hole (2828) within a distal portion thereof. Helical hole (2828) is configured to rotatably receive helical connector (2826) in order to removably connect clamp arm assembly (2814) to clamp arm actuator (2812). Helical connector (2826) also includes a keyed end (2829) configured to be received within a distal keyed hole (2830) of helical hole (2828) for proper alignment while introducing helical connector (2826) into helical hole (2828). For removal, the operator rotates clamp arm assembly (2814) relative to clamp arm actuator (2812) until clamp arm assembly (2814) is removed therefrom.

FIGS. 92 and 93 show a modular connection tool (2850) containing a replacement clamp arm assembly (2814). Modular connection tool (2850) includes a tool housing (2852) having a proximal access hole (2854). Keyed end (2829) is positioned in access hole (2854) such that the operator faces proximal access hole (2854) toward clamp arm actuator (2812) for connecting replacement clamp arm assembly (2814) to clamp arm actuator (2812).

In use, as shown in FIGS. 94A-94C, the operator inserts helical connector (2826) into helical hole (2828) rotates modular connection tool (2850) containing clamp arm assembly (2814) relative to clamp arm actuator (2812). Such rotation effectively withdraws clamp arm assembly (2814) through access hole (2854) until connected to clamp arm actuator (2812) and from tool housing (2852) for use. The used clamp arm assembly (2814) as well as modular connection tool (2850) may thus be discarded.

Y. Twenty-Sixth Exemplary Ultrasonic Surgical Instrument with a Modular Body Insert Coupling FIGS. 95-100 illustrate a twenty-sixth exemplary surgical instrument (2910) having shaft assembly (330), a clamp arm actuator (2912), a clamp arm assembly (2914), and a modular body insert coupling (2916). Clamp arm assembly (2914) is removably connected to clamp arm actuator (2912) with modular body insert coupling (2916), which includes a clamp body connection (2918) on clamp arm assembly (2914) and a clamp actuator connection (2920) on clamp arm actuator (2912). Clamp arm assembly (2914) includes a clamp body (2922) and a clamp pad (2924). Clamp pad (2924) is connected to clamp body (2922) such that clamp pad (2924) faces ultrasonic blade (350) for receiving and clamping tissue therebetween. Selective movement of clamp arm actuator (2912) relative to shaft assembly (330) from an opened configuration to a closed configuration respectively moves clamp arm assembly (2914) from an opened position configured to receive tissue to a closed position configured to clamp the tissue. In addition, clamp arm assembly (2914) further includes an RF electrode (2925) extending along clamp pad (2924). RF electrode (2925) is operatively connected to an RF energy source and configured to deliver RF energy to tissue for affecting the tissue, such as coagulating vessels in use.

Clamp body connection (2918) includes a lower longitudinal tab (2926), which longitudinal extends along a lower surface of clamp body (2922), and a proximal aperture (2927) extending through a proximal end portion of clamp body (2922). Clamp actuator connection (2920) includes an upper longitudinal slot (2928), which extends along an upper surface of clamp arm actuator (2912) and a distal pin (2929), which distally extends from a distal portion of clamp arm actuator (2912). Upper longitudinal slot (2928) and proximal aperture (2927) are configured to proximally and respectively receive lower longitudinal tab (2926) and distal pin (2929) to releasably capture clamp arm assembly (2914) to clamp arm actuator (2912). In one example, this releasable capture of clamp arm assembly (2914) is an annular slot (2930) about distal pin (2929) that receives a resiliently deflectable portion of clamp body (2922) for releaseably connecting clamp arm assembly (2914) to clamp arm actuator (2912).

Furthermore, in the present example, distal pin (2929) and proximal aperture (2927) collectively define an electrical connection (2930). Distal pin (2929) is electrically connected to the RF energy source and configured to transmit electrical signals through proximal aperture (2927), which is electrically connected to RF electrode (2925).

In use, the operator distally translates clamp arm assembly (2914) with sufficient force to overcome the resilient capture of the deflectable portion of clamp body (2922) in annular slot (2930). The operator continues this distal translation until the used clamp arm assembly (2914) is removed from clamp arm actuator (2912). A replacement clamp arm assembly (2914) is positioned into clamp arm actuator (2912) and snapped therein in order to capture replacement clamp arm assembly (2914) for use.

One exemplary method of manufacturing clamp arm assembly (2914) is shown in FIG. 100. First, clamp pad (2924) is positioned against RF electrode (2925). Second, clamp body (2922) is overmolded, such as in plastic, to clamp pad (2924) and RF electrode (2925). The overmolding continues until lower longitudinal tab (2926) is further formed with clamp body (2922). Thereby, the plastic overmold forms lower longitudinal tab (2926), clamp body (2922), and affixes clamp pad (2924) with RF electrode (2925) to manufacture clamp arm assembly (2914). Of course, alternative methods of manufacturing clamp arm assembly (2914) may be used. The invention is thus not intended to be unnecessarily limited to the overmolded clamp arm assembly (2914).

Z. Twenty-Seventh Exemplary Ultrasonic Surgical Instrument with Planar Compression and a Variety of Modular Couplings FIGS. 101 and 102 illustrate a twenty-seventh exemplary surgical instrument (3010) having a handle assembly (3002), a shaft assembly (3004), an ultrasonic blade (3006), a clamp arm actuator (3012), a clamp arm assembly (3014), and a first modular side load coupling (3016). Clamp arm assembly (3014) is removably connected to clamp arm actuator (3012) with modular side load coupling (3016), which includes a clamp body connection (3018) on clamp arm assembly (3014) and a clamp actuator connection (3020) on clamp arm actuator (3012). Clamp arm assembly (3014) includes a clamp body (3022) and a clamp pad (3024). Clamp pad (3024) is connected to clamp body (3022) such that clamp pad (3024) faces ultrasonic blade (3006) for receiving and clamping tissue therebetween. Selective movement of clamp arm actuator (3012) relative to shaft assembly (3004) from an opened configuration to a closed configuration respectively moves clamp arm assembly (3014) from an opened position configured to receive tissue to a closed position configured to clamp the tissue. More particularly, handle assembly (3002) is connected to clamp arm actuator (3012) such that selective pivotal movement therebetween yields transverse movement between clamp arm assembly (3014) and ultrasonic blade (3006). Clamp arm assembly (3014) and ultrasonic blade (3006) thereby remain in parallel planes throughout movement for a generally equal distribution of compression along relatively planar layers of tissue compressed therebetween in use. While not shown with respect to surgical instrument (3010), clamp arm assembly (3014) may further include one or more electrodes configured to deliver RF energy to tissue for affecting the tissue, such as coagulating vessels in use.

Clamp body connection (3018) includes lateral aperture (3026) extending laterally through the proximal portion of clamp arm assembly (3014), whereas clamp actuator connection (3020) includes a dowel pin (3028) extending transversely from a distal portion of clamp arm actuator (3012). Lateral aperture (3026) receives dowel pin (3028) such that clamp arm actuator (3014) removably connects to clamp arm assembly (3014).

In use, the operator laterally removes clamp body (3022) from clamp arm actuator (3014) until clamp body (3022) is clear of dowel pin (3028). A replacement clamp arm assembly (3014) is positioned on dowel pin (3028) of clamp arm actuator (3012) and connected thereto in order to capture replacement clamp arm assembly (3014) for use.

FIG. 103 shows clamp actuator (3012) with a second modular side load coupling (3116) similar to first modular side load coupling (3014) (see FIG. 102). However, rather than clamp arm assembly (3014) (see FIG. 102) as discussed above, an alternative clamp arm assembly (3114) has a unitary construction of a clamp pad (3124) with a clamp pad connection (3118) configured to removable connection to clamp actuator connection (3020). More particularly, clamp pad connection includes a pair of lateral apertures (3126) configured to receive dowel pin (3028) for removable connection as discussed above. In addition, the operator may select a desirable lateral aperture (3126) through which to position dowel pin (3028) for adjusting an operable length of clamp arm assembly (3114) in use.

FIG. 104 shows clamp actuator (3012) with a third modular side load coupling (3216) similar to first modular side load coupling (3014) (see FIG. 102). However, rather than clamp arm assembly (3014) (see FIG. 102) as discussed above, another alternative clamp arm assembly (3214) has core a clamp pad (3124) at least partially surrounded by a clamp body (3222), such as in a U-shaped transverse cross-section. A clamp body connection (3218) has a transversely extending dowel pin (3226) with a snap head (3227), whereas a clamp actuator connection (3220) has a lateral aperture (3228) laterally extending therethrough. Lateral aperture (3228) is configured to receive dowel pin (3226) such that snap head (3227) resiliently snaps through to removably connect clamp arm actuator (3012) to clamp arm assembly (3214) for use.

FIG. 105 shows clamp actuator (3012) with a fourth modular side load coupling (3316) similar to third modular side load coupling (3216) (see FIG. 104). However, rather than clamp arm assembly (3214) (see FIG. 104) with clamp body connection (3218), a clamp arm assembly (3314) has an outer clamp pad (3324) laterally connected to an inner clamp body (3322). A clamp pad connection (3318) has dowel pin (3226) with snap head (3227) configured to removably connect to lateral aperture (3328) for use.

With respect to FIG. 106, still additional alternatives of a clamp arm actuator (3412) and a clamp arm assembly (3414) cooperate with a modular transverse load coupling (3416) for removably connecting clamp arm assembly (3414) to clamp arm actuator (3412). Modular transverse load coupling (3416) includes a clamp body connection (3418) on clamp arm assembly (3414) and a clamp actuator connection (3420) on clamp arm actuator (3412). Clamp arm assembly (3414) includes a clamp body (3422) and a clamp pad (3424). Clamp pad (3424) is connected to clamp body (3422) such that clamp pad (3024) faces ultrasonic blade (3006) for receiving and clamping tissue therebetween. Selective movement of clamp arm actuator (3012) relative to shaft assembly (not shown) from an opened configuration to a closed configuration respectively moves clamp arm assembly (3014) from an opened position configured to receive tissue to a closed position configured to clamp the tissue.

Clamp body connection (3418) includes a U-shaped outer surface (3426) of clamp body (3422), whereas clamp actuator connection (3420) includes a longitudinal channel (3428) extending longitudinal along clamp arm actuator (3412). Longitudinal channel (3428) transversely receives outer surface (3426) of clamp body (3422) with a friction fit such that clamp arm assembly (3414) removably connects to clamp arm actuator (3412).

In use, the operator transversely removes clamp body (3422) from longitudinal channel (3428) in clamp arm actuator (3014) until clamp body (3422) is clear of longitudinal channel (3428). A replacement clamp arm assembly (3414) is positioned transversely into longitudinal channel (3428) of clamp arm actuator (3012) and frictionally connected therein in order to capture replacement clamp arm assembly (3414) for use.

AA. Alternative Modular Connection Tools and Transverse Clamp Pad Connection

FIGS. 107 and 108 respectively show alternative modular connection tools (3510, 3510') having grip bodies (3512, 3512'). Each grip body (3512, 3512') includes a storage support (3514, 3514') configured to receive and support at least a replacement clamp pad (3516) and, in some examples, additional replacement components of a clamp arm assembly. In addition, modular connection tool (3510) also includes an electrical connection (3518) configured to communicate to a controller (not shown) of a surgical instrument (3520) (see FIG. 109) that modular connection tool (3510) is accurately positioned relative to surgical instrument (3510) (see FIG. 109) for connecting clamp pad (3516) to a clamp actuator arm (3522) (see FIG. 109).

Surgical instrument (3520) shown in FIG. 109 includes a handle assembly (3524), a shaft assembly (3526), and an ultrasonic blade (3528) in addition to clamp actuator arm (3522). With clamp actuator arm (3522) in an open position relative to ultrasonic blade (3528), modular connection tool (3510) is introduced therebetween with a clamp pad connection (3530) as shown in FIG. 109 and FIG. 111A. The operator selectively clamps modular connection tool (3510) between clamp actuator arm (3522) and ultrasonic blade (3528) as shown in FIG. 110 in order to compress clamp pad connection (3530) against a clamp actuator connection (3532) as shown in FIG. 111B for removable connection as fourth modular pad coupling (3533). In the present example, clamp pad connection (3530) has a T-shaped tab (3534) and clamp actuator connection (3532) has a T-shaped aperture (3536). T-shaped aperture (3536) is configured to receive T-shaped tab (3534), which resiliently deflects for introduction and connection into T-shaped aperture (3536). For removal, the operator may pry T-shaped tab (3534) from T-shaped aperture (3536) or apply one of modular connection tools (3510, 3510') shown in FIGS. 107 and 108 to clamp pad (3516) in order to withdraw T-shaped tab (3534) from T-shaped aperture (3536).

IV. Exemplary Ultrasonic Surgical Instrument with Optimal Gap Setting Mechanism In some instances, it may be beneficial for an ultrasonic surgical instrument to provide the operator with an indication that a predetermined gap has been established between ultrasonic blade (150) and clamp pad (222) of end effector (12) during spot coagulation. Improving the ability of ultrasonic surgical instruments, such as surgical instrument (10, 301, 610, 710, 810, 910, 1010, 1110, 1210, 1310, 1410, 1510, 1610, 1710, 1810, 1910, 2010, 2110, 2210, 2310, 2410, 2510, 2610, 2710, 2810, 2910, 3010) discussed above, to form the predetermined gap at end effector (12) may be desirable when providing ultrasonic and/or RF energy to a patient's tissue, such as performing a spot coagulation on a patient's tissue. Furthermore, it may be desirable for ultrasonic surgical instruments to be able to maintain the predetermined gap between ultrasonic blade (150) and clamp pad (222) for an extended period. Providing this ability may improve an operator's capability to move clamp pad (222) toward ultrasonic blade (150) to an intermediate position with the predetermined gap formed at end effector (12). This may be beneficial to ensure end effector (12) is not excessively urged to a closed position or unproductively urged towards the intermediate position but remaining in an open position. Providing a surgical instrument that is able to achieve and maintain the predetermined gap at end effector (12) may approve the operator's ability to successfully perform a spot coagulation of a patient's tissue.

In ultrasonic surgical instruments, such as instrument (10, 301, 610, 710, 810, 910, 1010, 1110, 1210, 1310, 1410, 1510, 1610, 1710, 1810, 1910, 2010, 2110, 2210, 2310, 2410, 2510, 2610, 2710, 2810, 2910, 3010) described above, it may be beneficial to include a spacer, whether a physical component or electrical, that is attached or removably inserted onto handle assembly (110), clamp arm assembly (210), and/or shaft assembly (330) to thereby inhibit movement of clamp arm assembly (210) for maintaining the predetermined gap in use and/or provide an indication to the operator that the predetermined gap is formed at end effector (12). It may be desirable to provide the spacer in a manner that allows the operator to freely transition the spacer from an unactuated position, where the spacer is not actively operational to set the predetermined gap at end effector (12), to an actuated position where the spacer is actively operable to form the predetermined gap between ultrasonic blade (150) and clamp pad (222) as the ultrasonic surgical instrument (10, 301, 610, 710, 810, 910, 1010, 1110, 1210, 1310, 1410, 1510, 1610, 1710, 1810, 1910, 2010, 2110, 2210, 2310, 2410, 2510, 2610, 2710, 2810, 2910, 3010) is engaged. This may provide the operator with the selective ability to activate the spacer when the predetermined gap in end effector (12) is desired. It may further be desirable for the spacer to inhibit ultrasonic blade (150) and clamp pad (222) from the closed position. The following description provides various examples of an ultrasonic surgical instrument cooperatively configured to provide a predetermined gap at an end effector.

It should be understood that spacers and urging mechanisms described below may be readily incorporated into in any of the various surgical instruments (10, 301, 610, 710, 810, 910, 1010, 1110, 1210, 1310, 1410, 1510, 1610, 1710, 1810, 1910, 2010, 2110, 2210, 2310, 2410, 2510, 2610, 2710, 2810, 2910, 3010) described above and in any of the various surgical procedures described in the various references described herein. Other suitable ways in which the below-described surgical instruments, spacers and urging mechanisms may be used will be apparent to those of ordinary skill in the art in view of the teachings herein. It should be understood that the handle body, shaft assembly, and clamp arm actuator may be configured and operable in accordance with those assemblies in surgical instrument (10, 301, 610, 710, 810, 910, 1010, 1110, 1210, 1310, 1410, 1510, 1610, 1710, 1810, 1910, 2010, 2110, 2210, 2310, 2410, 2510, 2610, 2710, 2810, 2910, 3010) described above except for the differences explicitly noted herein. Like reference numerals below are directed to like features described above.

A. Exemplary Surgical Instrument with Spacer Mechanism i. Cover Spacer with Sliding Adjuster FIG. 112 shows an exemplary cover spacer (5050) and a surgical instrument (5000), which is similar in operation to surgical instrument (3010) (see FIG. 101) discussed above in greater detail. Cover spacer (5050) includes an adjuster body (5052), a blocker (5054), and a pair of openings (5056, 5058). Adjuster body (5052) is configured to be selectively maneuvered towards surgical instrument (5000) to move cover spacer (5050) from a disengaged position, as seen in FIG. 112, to an engaged position as shown in FIG. 114A. Openings (5056, 5058) are sized and configured to receive a clamp arm (5044) and an ultrasonic blade (5042) therein, respectively, when cover spacer (5050) is in the engaged position.

With cover spacer (5050) in the disengaged position, an end effector (5040) of surgical instrument (5000) is configured to move an ultrasonic blade (5042) and a clamp arm (5044) to a closed position. In other words, end effector (5040) is able to move to the closed position with cover spacer (5050) disengaged from surgical instrument (5000). However, with cover spacer (5050) in the engaged position, clamp arm (5044) and ultrasonic blade (5042) are received within openings (5056, 5058) and blocker (5054) is positioned between ultrasonic blade (5042) and clamp arm (5044), as seen in FIG. 114A. In this instance, blocker (5054) is configured to inhibit the actuation of clamp arm actuator (5030) towards handle body (5010) to a closed configuration by blocking clamp arm (5044) from moving relative to ultrasonic blade (5042) to the closed position.

In the present example, as seen in FIGS. 114A and 114B, adjuster body (5052) is configured to be slidably translated proximally onto a distal end (5001) of surgical instrument (5000) to thereby engage cover spacer (5050) onto surgical instrument (5000). With cover spacer (5050) in the engaged position, openings (5056, 5058) slidably receive clamp arm (5044) and ultrasonic blade (5042), respectively, to position blocker (5054) between ultrasonic blade (5042) and clamp arm (5044). In this instance, blocker (5054) is configured to inhibit clamp arm actuator (5030) from moving relative to handle body (5010) to the closed configuration. As best seen in FIG. 113, blocker (5054) is an intermediate wall separating openings (5056, 5058) and is configured to have a thickness (5055) that corresponds with a predetermined gap (5060) to be formed between ultrasonic blade (5042) and clamp arm (5044). With cover spacer (5050) in the engaged position, cover spacer (5050) is configured to maintain predetermined gap (5060) between ultrasonic blade (5042) and clamp arm (5044). Alternatively, adjuster body (5052) is further configured to be slidably translated distally from distal end (5001) of surgical instrument (5000) to thereby disengage cover spacer (5050) from surgical instrument (5000). With cover spacer (5050) in the disengaged position, clamp arm (5044) and ultrasonic blade (5042) are not contained within openings (5056, 5058) and blocker (5054) is not positioned between end effector (5040).

V. Pad Liner Formation

FIGS. 115-119 illustrate an instrument (9000), similar to instrument (10), with like elements having like numbering. In some versions of instrument (9000), clamp pad assembly (220) includes a pad liner (9002) applied to an outer surface (9004) of clamp pad (222). Pad liner (9002) may be formed using a hydrophobic or "non-stick" type of material such as a Teflon® or another Polytetrafluoroethylene (PTFE) formula or any other type of material. When coupled with clamp pad (222), pad liner (9002) presents an outer pad surface (9006) oriented to press against tissue when clamp pad (222) is clamped into ultrasonic blade (150).

Pad liner (9002) may be applied to clamp pad (222) by pressing a blank (9008) onto clamp pad (222) with sufficient pressure to couple blank (9008) with clamp pad (222). The coupling may be accomplished by way of insert molding or overmolding or any other mechanism for molding or connecting blank (9008) to clamp pad (222).

As shown in FIGS. 115-119, in some versions, blank (9008) may be coupled with clamp pad (222) using a form (9010). Form (9010) includes a top portion (9012) which defines a first cavity (9014) and a bottom portion (9016) which defines a second cavity (9018). In some versions of form (9010), first cavity (9014) is sized to receive a portion of clamp pad (222) and second cavity is sized to receive blank (9008). The portion of clamp pad (222) received within first cavity (9014) may be an electrode (9020). Electrode (9020) of clamp pad (222) may include undercuts or dovetail features which may receive the material of blank (9008) when blank (9008) is pressed together with electrode (9020). When top portion (9012) and bottom portion (9016) are combined and pressed together in the direction of Arrow 9000A and 9000B (FIG. 118), electrode (9020) in first cavity (9014) and blank (9008) in second cavity (9018) are pressed together to mold or couple blank (9008) with electrode (9020). The material of blank (9008) flows into any undercuts or dovetails or other features of electrode (9020) to provide a robust connection therebetween.

High definition features may be machined into electrode (9020) to allow for a robust connection between the material of blank (9008) and electrode (9020). As shown in FIG. 119, top portion (9012) may include one or more posts (9022) which extend to abut electrode (9020) when electrode (9020) is disposed within first cavity (9014). Posts (9022) cooperate with electrode (9020) to define one or more pockets (9024) for receiving the material of blank (9008) therein when top portion (9012) is pressed together with bottom portion (9016). Similarly, electrode (9020) may include one or more undercuts (9026) for receiving the material of blank (9008) therein when top portion (9012) is pressed together with bottom portion (9016). Pockets (9024) and undercuts (9026) help to facilitate a robust connection between the material of blank (9008) and electrode (9020) and allow for using alternative or non-traditional geometries of blank (9008) for increased attachment and stability.

VI. Exemplary Surgical Instrument with Multi-Point Alignment Feature

FIGS. 120-123 illustrate an exemplary ultrasonic surgical instrument (10010). Instrument (10010) in the present example includes a first modular assembly (10100) and a second modular assembly (10200) that are configured to connect in order to form instrument (10010) with an end effector (10012). End effector (10012) comprises an ultrasonic blade (10150) and a clamp pad (10222) of a clamp pad assembly (10220). Selected portions of second modular assembly (10200) may actuate relative to first modular assembly (10100) in order to actuate end effector (10012) from an open configuration to a closed configuration. The ability to selectively attach and detach second modular assembly (10200) with first modular assembly (10100) may provide benefits of reusability of either modular assembly (10100, 10200). Additionally, moving components of second modular assembly (10200) may be housed within static components of second modular assembly (10200), which may provide additional advantages, some of which are described herein while others will be apparent to one having ordinary skill in the art in view of the teachings herein.

First modular assembly (10100) includes a handle assembly (10110), a body assembly (10130) extending distally from handle assembly (10110), and an ultrasonic blade (10150) extending distally from body assembly (10130). Handle assembly (10110) includes a body (10112), a finger grip ring (10124), a pair of buttons (10126) distal to finger grip ring (10124), and an ultrasonic transducer assembly (30) housed within body (10112). Body assembly (10130) includes an outer sheath (10132) extending distally from body (10112), and a waveguide (10140) extending within and through outer sheath (10132). Waveguide (10140) may attach to transducer assembly (30) and be supported by portions outer sheath (10132) in the same or similar manner as described above with respect to instrument (10). Ultrasonic blade (10150) may be unitarily connected to waveguide (10140), and also extend distally from waveguide (10140). Waveguide (10140) is operable to connect to ultrasonic transducer assembly (30) in order to provide acoustic communication between ultrasonic blade (10150) and transducer assembly (30) in the same or similar manner as described above with respect to instrument (10).

Also, in the same or similar manner as described above with respect to instrument (10), end effector (10012) is configurable to also provide RF energy to tissue in addition to or instead of ultrasonic energy. Various ways in which instrument (10010) may be configured and operable to provide both ultrasonic and RF electrosurgical modes of operation are described in various references cited herein; while other ways in which instrument (10010) may be configured and operable to provide both ultrasonic and RF electrosurgical modes of operation will be apparent to those of ordinary skill in the art in view of the teachings herein.

Second modular assembly (10200) includes a clamp arm assembly (10210) and a clamp pad assembly (10220). Clamp arm assembly (10210) and clamp pad assembly (10220) are dimensioned to mesh with each other such that rotation of one assembly (10210, 10220) causes rotation of the other assembly (10210, 10220). Clamp arm assembly (10210) includes an elongated arm (10212), a thumb grip ring (10214), and a camming protrusion (10216). Thumb grip ring (10214) and elongated arm (10212) together provide a scissor grip type configuration in combination with body (10112) and finger grip ring (10124). Camming protrusion (10216) interacts with clamp pad assembly (10220) in order to rotate clamp pad assembly (10220) in response to rotation of clamp arm assembly (10210).

Clamp pad assembly (10220) includes a clamp pad (10222) facing ultrasonic blade (10150), a pair of tissue stops (10223) located adjacent to ultrasonic blade (10150) and proximal to clamp pad (10222), and clamp body (10224) defining a camming recess (10226). In some versions, clamp pad assembly (10220) further includes one or more electrodes that is/are operable to apply RF electrosurgical energy to tissue. Various references herein provide examples of how a clamp pad assembly may incorporate one or more electrodes that is/are operable to apply RF electrosurgical energy to tissue, while other examples of how clamp pad assembly (10220) may incorporate one or more electrodes that is/are operable to apply RF electrosurgical energy to tissue will be apparent to those of ordinary skill in the art in view of the teachings herein.

Camming protrusion (10216) is dimensioned to rotate within camming recess (10226) while also contacting camming recess (10226). Camming protrusion (10216) and camming recess (10226) are located between pivot couplings (10218, 10228), which respectively connect clamp arm assembly (10210) and clamp pad assembly (10220) with body assembly (10130). In use, when an operator rotates elongated arm (10212) about pivot coupling (10218), camming protrusion (10216) rotates away from body assembly (10130) about pivot coupling (10218). Because camming protrusion (10216) is housed within camming recess (10226), upward movement of camming protrusion (10216) about pivot coupling (10218) causes upward movement of camming recess (10226) about pivot coupling (10228). Upward movement of camming recess (10226) about pivot coupling (10228) rotates clamp body (10224) such that clamp pad (10222) rotates toward ultrasonic blade (10150). Therefore, closure of elongated arm (10212) of clamp arm assembly (10210) toward handle assembly (10110) leads to closure of clamp pad (10222) toward ultrasonic blade (10150). It should therefore be understood that when first modular assembly (10100) and second modular assembly (10200) are connected, an operator may squeeze thumb grip ring (10214) toward body (10112) to thereby clamp tissue between clamp pad assembly (10220) and ultrasonic blade (10150) to compress tissue against ultrasonic blade (10150). When ultrasonic blade (10150) is activated during such compression, clamp pad assembly (10220) and ultrasonic blade (10150) cooperate to transect and/or seal the compressed tissue.

Referring to FIGS. 122 and 123, instrument (10010) further comprises alignment features (10300). In the present example, instrument (10010) includes multiple alignment features (10300). Alignment features (10300) are configured to connect with an inner surface (10302) of outer sheath (10132) of body assembly (10130) as shown in FIG. 123. Alignment features (10300) further are configured to contact clamp body (10224) of clamp arm assembly (10210). An additional alignment feature (10304) is located on pivot coupling (10228) in the form of an adjustable spacer (10306). Spacer (10306) is configured to also contact clamp body (10224) and guide clamp body (10224) into contact with alignment features (10300) on the opposite side of clamp body (10224). Spacer (10306) can be set to a desired position to thereby control the degree of impingement or contact between clamp body (10224) and alignment features (10300) on one side and clamp body (10224) and spacer (10306) on the other side. Once alignment feature (10304) in the form of spacer (10306) is in its desired position, it may be secured in place by spot welding or other securing features as will be apparent to those of ordinary skill in the art in view of the teachings herein. In some instances where instrument (10010) is configured for multi-use, alignment feature (10304) is secured using a selective securing feature such as a release button, thumb screw, or other structure that will be apparent to those of ordinary skill in the art in view of the teachings herein that permits attaching and removing portions of clamp arm assembly (10210) and/or clamp pad assembly (10220).

With the above-described configuration for instrument (10010), alignment features (10300, 10304) work together to provide the ability to control jaw offset and cross jaw between clamp body (10224) and blade (10150). Additionally, in some versions, one or more alignment features (10300, 10304) are comprised of conductive material and are electrically connected with an RF source to deliver RF energy to clamp body (10224) through the contact of clamp body (10224) with alignment features (10300, 10304). In this manner, the need to directly wire the clamp body (10224) is reduced or avoided entirely. In one version of assembling instrument (10010) having alignment features (10300, 10304), alignment features (10300) can be machined at the shroud and assembled to instrument (10010) based on the position of a hole for blade (10150).

The foregoing components and operabilities of instrument (10010) are merely illustrative. Instrument (10010) may be configured in numerous other ways as will be apparent to those of ordinary skill in the art in view of the teachings herein. By way of example only, at least part of instrument (10010) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. Nos. 9,023, 071; 8,461,744; 9,381,058; U.S. Pub. No. 2012/0116265, now abandoned; U.S. Pat. Nos. 9,393,037; 9,095,367; and/or U.S. Pub. No. 2015/0080925, entitled "Alignment Features for Ultrasonic Surgical Instrument," published Mar. 19, 2015, , now abandoned, the disclosure of which is incorporated by reference herein.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body assembly; (b) an ultrasonic waveguide extending through the body assembly; (c) an ultrasonic blade connected to a distal end of the ultrasonic waveguide; (d) a clamp arm assembly configured to move from an opened position for receiving a tissue toward a closed position for clamping the tissue relative to the ultrasonic blade, wherein the clamp arm assembly includes: (i) a clamp body, and (ii) a clamp pad connected to the clamp body facing the ultrasonic blade; (e) a clamp arm actuator operatively connected to the clamp arm assembly and configured to selectively move from a first position toward a second position relative to the body to thereby respectively direct the clamp arm assembly from the opened position toward the closed position; and (f) a modular coupling operatively connected to the clamp arm assembly such that at least the clamp pad of the clamp arm assembly is configured to be disconnected relative to the ultrasonic blade for replacement thereof.

Example 2

The surgical instrument of Example 1, wherein the modular coupling includes a clamp actuator connection positioned on the clamp arm actuator and a clamp body connection positioned on the clamp body, wherein the clamp actuator connection is configured to removably connect to the clamp body connection such that the clamp arm assembly is removable from the clamp arm actuator for replacing the clamp arm assembly.

Example 3

The surgical instrument of Example 2, wherein the clamp actuator connection comprises one of a biased projection tab or an aperture and the clamp body connection comprises the other of the biased projection tab or the aperture, wherein the aperture is configured to removably receive the biased projection tab for removable connection therebetween.

Example 4

The surgical instrument of Example 3, wherein the clamp body connection is the biased projection tab extending from the clamp body and the clamp actuator connection is the aperture extending through at least a portion of the clamp arm actuator.

Example 5

The surgical instrument of Example 2, wherein the clamp actuator connection comprises one of a threaded stud or a threaded aperture and the clamp body connection comprises the other of the threaded stud or the threaded aperture, wherein the threaded aperture is configured to threadably receive the threaded stud for removable connection therebetween.

Example 6

The surgical instrument of Example 5, wherein the clamp body connection is the threaded stud extending from the clamp body and the clamp actuator connection is the threaded aperture extending through at least a portion of the clamp arm actuator.

Example 7

The surgical instrument of Example 2, wherein the clamp actuator connection comprises one of a male lure lock or a female luer lock and the clamp body connection comprises the other of the male luer lock or the female luer lock, wherein the female luer lock is configured to removably receive the male luer lock for removable connection therebetween.

Example 8

The surgical instrument of Example 7, wherein the clamp body connection is the male luer lock extending from the clamp body and the clamp actuator connection is the female luer lock extending through at least a portion of the clamp arm actuator.

Example 9

The surgical instrument of Example 2, wherein the clamp actuator connection comprises one of a bayonet tab or a bayonet slot and the clamp body connection comprises the other of the bayonet tab or the bayonet slot, wherein the bayonet slot is configured to removably receive bayonet tab for removable connection therebetween.

Example 10

The surgical instrument of Example 9, wherein the clamp body connection is the bayonet tab extending from the clamp body and the clamp actuator connection is the bayonet slot extending through at least a portion of the clamp arm actuator.

Example 11

The surgical instrument of Example 2, wherein the clamp actuator connection comprises a radial capture lock and the clamp body connection comprises an outer surface of the clamp body, wherein the radial capture lock is configured to selectively move from a locked configuration toward an unlocked configuration, wherein the radial capture lock in the locked configuration is biased radially inwardly against the outer surface of the clamp body for removable connection therewith, and wherein the radial capture lock in the unlocked configuration is directed radially outwardly from the outer surface of the clamp body for removal of the clamp body therefrom.

Example 12

The surgical instrument of Example 2, wherein the clamp actuator connection comprises one of a helical projection or a helical aperture and the clamp body connection comprises the other of the helical projection or the helical aperture, wherein the helical aperture is configured to removably receive the helical projection for removable connection therebetween.

Example 13

The surgical instrument of Example 12, wherein the clamp body connection is the helical projection extending from the clamp body and the clamp actuator connection is the helical aperture extending through at least a portion of the clamp arm actuator.

Example 14

The surgical instrument of Example 2, wherein the clamp actuator connection comprises one of a longitudinal tab or a longitudinal slot and the clamp body connection comprises the other of longitudinal tab or the longitudinal slot, wherein the longitudinal slot is configured to removably receive the longitudinal tab for removable connection therebetween.

Example 15

The surgical instrument of Example 14, wherein the clamp body connection is the longitudinal tab extending from the clamp body and the clamp actuator connection is the longitudinal slot extending through at least a portion of the clamp arm actuator.

Example 16

The surgical instrument of Example 2, wherein the clamp actuator connection comprises one of a pin tab or an aperture and the clamp body connection comprises the other of the pin tab or the aperture, wherein the aperture is configured to removably receive the pin tab for removable connection therebetween.

Example 17

The surgical instrument of Example 16, wherein the clamp actuator connection is the pin tab extending from the clamp arm actuator and the clamp body connection is the aperture extending through at least a portion of the clamp body.

Example 18

The surgical instrument of Example 2, wherein the modular connection further includes a latch lock configured to selectively move from a locked configuration toward an unlocked configuration, wherein the clamp actuator connection comprises one of a catch groove or a catch member and the clamp body connection comprises the other of the catch groove or the catch member, wherein the catch groove is configured to removably receive the catch member for removable connection therebetween with that the latch lock in the locked configuration, and wherein the latch lock is configured to release the catch member in the unlocked configuration for removal form the catch groove.

Example 19

The surgical instrument of Example 18, wherein the clamp body connection is the catch member extending from the clamp body and the clamp actuator connection is the clamp groove extending through at least a portion of the clamp arm actuator.

Example 20

The surgical instrument of Example 19, wherein the latch lock is slidably connected to the clamp arm actuator to selectively move from the locked configuration to the unlocked configuration.

Example 21

The surgical instrument of Example 1, wherein the clamp arm assembly includes another clamp pad, wherein the modular coupling includes a clamp actuator connection positioned on the clamp arm actuator and a clamp body connection positioned on the clamp body, wherein the clamp actuator connection is configured to removably connect to the clamp body connection such that the clamp arm assembly selectively movable relative to the clamp arm actuator from a first use position to a second use position, wherein one of the clamp pads faces the ultrasonic blade in the first use position for use, and wherein the other of the clamp pads faces the ultrasonic blade in the second use position for use.

Example 22

The surgical instrument of Example 21, wherein the clamp arm assembly is configured to be selectively moveable along a longitudinal axis and about the longitudinal axis from the first use position to the second use position.

Example 23

The surgical instrument of Example 21, wherein the clamp arm assembly is configured to rotate about a transverse axis from the first use position to the second use position.

Example 24

The surgical instrument of Example 1, wherein the clamp arm assembly further includes a clamp pad cap, wherein the modular coupling includes a clamp cap connection positioned on the clamp pad cap and a clamp body connection positioned on the clamp body, wherein the clamp pad connection is configured to removably connect to the clamp body connection such that the clamp pad is removably secured between the clamp pad cap and the clamp body for replacing the clamp arm assembly.

Example 25

The surgical instrument of Example 24, wherein the clamp body of the clamp arm assembly extends from the clamp arm actuator with the clamp pad and the clamp cap being removable therefrom upon disconnecting the clamp cap from the clamp body.

Example 26

The surgical instrument of Example 1, wherein the modular coupling includes a longitudinal tab and a longitudinal slot, wherein the clamp pad has the longitudinal tab or the longitudinal slot positioned thereon and the clamp body has the other of the longitudinal tab or the longitudinal slot positioned thereon, and wherein the longitudinal slot is configured to removably receive the longitudinal tab for removable connection therebetween.

Example 27

The surgical instrument of Example 26, wherein the longitudinal tab extends from the clamp pad and longitudinal slot extends through at least a portion of the clamp body.

Example 28

The surgical instrument of Example 27, wherein the clamp body of the clamp arm assembly extends from the clamp arm actuator with the clamp pad being removable therefrom upon disconnecting the clamp pad from the clamp body.

Example 29

The surgical instrument of Example 1 wherein the clamp arm assembly and the clamp arm actuator are configured to be selectively moved to a release configuration, wherein the modular coupling is configured to release the clamp arm assembly relative to the clamp arm actuator in the release configuration for replacement of the clamp arm assembly.

Example 30

The surgical instrument of any of Example 1 through Example 29, wherein the clamp arm actuator is releasably connected to the body assembly.

Example 31

The surgical instrument of any of Example 1 through Example 30, further comprising a modular connection tool configured to engage at least a portion of the clamp arm assembly or at least a portion of the modular coupling to thereby connect or disconnect the at least the portion of the clamp arm assembly relative to the ultrasonic blade.

Example 32

The surgical instrument of any of Example 1 through Example 31, wherein the clamp arm actuator further includes an RF electrode.

Example 33

The surgical instrument of any of Example 1 through Example 32, wherein the modular coupling further includes an electronic connection configured to communicate electrical signals therealong.

Example 34

A method of forming a surgical instrument comprising clamping a pad liner and an electrode of a surgical instrument together to couple the pad liner to the electrode.

Example 35

The method of Example 34, wherein the clamping is performed using a form.

Example 36

The method of Example 34, wherein the electrode includes an undercut for receiving a portion of the pad liner therein.

Example 37

A surgical instrument, comprising: (a) a body assembly; (b) an ultrasonic waveguide extending through the body assembly; (c) an ultrasonic blade connected to a distal end of the ultrasonic waveguide; (d) a clamp arm assembly configured to move from an opened position for receiving a tissue toward a closed position for clamping the tissue relative to the ultrasonic blade, wherein the clamp arm assembly includes: (i) a clamp body, and (ii) a clamp pad connected to the clamp body facing the ultrasonic blade; (e) a clamp arm actuator operatively connected to the clamp arm assembly and configured to selectively move from a first position toward a second position relative to the body to thereby respectively direct the clamp arm assembly from the opened position toward the closed position; and (f) at least one alignment feature connected to the body assembly and contacting the clamp arm assembly, wherein the at least one alignment feature is configured to control jaw offset and cross jaw between the clamp body and the ultrasonic blade.

Example 38

A surgical instrument, comprising: (a) a body assembly; (b) an ultrasonic waveguide extending through the body assembly; (c) an ultrasonic blade connected to a distal end of the ultrasonic waveguide; (d) a clamp arm assembly configured to move from an opened position for receiving a tissue toward a closed position for clamping the tissue relative to the ultrasonic blade, wherein the clamp arm assembly includes: (i) a clamp body, (ii) a clamp pad connected to the clamp body facing the ultrasonic blade, and (iii) an electrode, wherein the electrode is operable to apply electrical energy to tissue; (e) a clamp arm actuator operatively connected to the clamp arm assembly and configured to selectively move from a first position toward a second position relative to the body to thereby respectively direct the clamp arm assembly from the opened position toward the closed position; and (f) a modular coupling operatively connected to the clamp arm assembly such that at least one of the clamp pad or the electrode of the clamp arm assembly is configured to be modularly disconnected from the clamp pad.

VIII. Miscellaneous

While various examples herein describe two or more modular components being releasably coupled together, it should be understood that some variations may eliminate such modularity and releasable couplings. For instance, some versions of instrument (10) may provide first modular assembly (100) and second modular assembly (200) as a single combined unit that does not permit second modular assembly (200) to be removed form first modular assembly (100). In some such versions, coupling member (300) would either me omitted (with some other feature being used to provide permanent coupling between first modular assembly (100) and second modular assembly (200)); or coupling member (300) may be modified such that coupling member (300) may not be manipulated to decouple second modular assembly (200) from first modular assembly (100). Similarly, some versions of instrument (301) may prevent clamp arm assembly (400) from being removed from shaft assembly (330). For instance, latch member (412) may be omitted and clamp arm assembly (400) may be permanently coupled with shaft assembly (330).

It should be understood that the various teachings herein may be readily combined with the various teachings of U.S. Pub. No. 2017/0105754, entitled "Surgical Instrument with Dual Mode End Effector and Side-Loaded Clamp Arm Assembly," filed on Apr. 20, 2017, issued as U.S. Pat. No. 11,045,275 on Jun. 9, 2021, the disclosure of which is incorporated by reference herein. Various suitable ways in which the teachings herein may be combined with the teachings of U.S. Pub. No. 2017/0105754, issued as U.S. Pat. No. 11,045,275 on Jun. 9, 2021, will be apparent to those of ordinary skill in the art.

It should be understood that the various teachings herein may be readily combined with the various teachings of U.S. Pub. No. 2017/0105755, entitled "Surgical Instrument with Dual Mode End Effector and Compound Lever with Detents," published on Apr. 20, 2017, issued as U.S. Pat. No. 10,893,914 on Jan. 19, 2021, the disclosure of which is incorporated by reference herein. Various suitable ways in which the teachings herein may be combined with the teachings of U.S. Pub. No. 2017/0105755, issued as U.S. Pat. No. 11,020,200 on Jun. 1, 2021, will be apparent to those of ordinary skill in the art.

It should be understood that the various teachings herein may be readily combined with the various teachings of U.S. Pub. No. 2017/0105788, entitled "Surgical Instrument with Dual Mode End Effector and Modular Clamp Arm Assembly," published Apr. 20, 2017, issued as U.S. Pat. No. 10,893,914 on Jan. 19, 2021, the disclosure of which is incorporated by reference herein. Various suitable ways in which the teachings herein may be combined with the teachings of U.S. Pub. No. 2017/0105788, issued as U.S. Pat. No. 10,893,914 on Jan. 19, 2021, will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/798,680, entitled "Surgical Instrument with Removable Clamp Arm Assembly," filed on Oct. 31, 2017, issued as U.S. Pat. No. 11,116,531 on Sep. 14, 2021, the disclosure of which is incorporated by reference herein. Various suitable ways in which the teachings herein may be combined with the teachings of U.S. patent application Ser. No. 15/798,680, issued as U.S. Pat. No. 11,116,531 on Sep. 14, 2021, will be apparent to those of ordinary skill in the art in view of the teachings herein.

In addition to the foregoing, the teachings herein may be readily combined with the teachings of U.S. patent application Ser. No. 15/798,720, entitled "Surgical Instrument with Selectively Actuated Gap-Setting Features for End Effector, " filed on Oct. 31, 2017, issued as U.S. Pat. No. 11,116,532 on Sep. 14, 2021, the disclosure of which is incorporated by reference herein. Various suitable ways in which the teachings herein may be combined with the teachings of U.S. patent application Ser. No. 15/798,720 , issued as U.S. Pat.

No. 11,116,532 on Sep. 14, 2021, will be apparent to those of ordinary skill in the art in view of the teachings herein.

In addition to the foregoing, the teachings herein may be readily combined with the teachings of U.S. patent application Ser. No. 15/798,835, entitled "Surgical Instrument with Spot Coagulation Control Algorithm," filed on Oct. 31, 2017, issued as U.S. Pat. No. 11,039,848 on Jun. 22, 2021, the disclosure of which is incorporated by reference herein. Various suitable ways in which the teachings herein may be combined with the teachings of U.S. patent application No. 15/798,835, issued as U.S. Pat. No. 11,039,848 on Jun. 22, 2021, will be apparent to those of ordinary skill in the art in view of the teachings herein.

In addition to the foregoing, the teachings herein may be readily combined with the teachings of U.S. patent application Ser. No. 15/798,902, entitled "Surgical Instrument with Removable Portion to Facilitate Cleaning," filed on Oct. 31, 2017, issued as U.S. Pat. No. 10,736,648 on Aug. 11, 2020,the disclosure of which is incorporated by reference herein. Various suitable ways in which the teachings herein may be combined with the teachings of U.S. patent application Ser. No. 15/798,902, issued as U.S. Pat. No. 10,736,648 on Aug. 11, 2020, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body assembly;
   (b) an ultrasonic waveguide extending through the body assembly;
   (c) an ultrasonic blade connected to a distal end of the ultrasonic waveguide;
   (d) a clamp arm assembly configured to move from an opened position for receiving a tissue toward a closed position for clamping the tissue relative to the ultrasonic blade, wherein the clamp arm assembly includes:
      (i) a clamp body configured to removably connect to the body assembly, and
      (ii) a clamp pad connected to the clamp body facing the ultrasonic blade;
   (e) a clamp arm actuator configured to removably connect to the clamp arm assembly and configured to selectively move from a first position toward a second position relative to the body assembly to thereby respectively direct the clamp arm assembly from the opened position toward the closed position; and
   a modular coupling operatively connected to the clamp arm assembly such that at least the clamp body and the clamp pad of the clamp arm assembly are configured to be connected relative to the ultrasonic blade in a connected state and disconnected relative to the ultrasonic blade in a disconnected state for replacement thereof, wherein the modular coupling includes a plurality of alignment release features respectively on each of the body assembly, the clamp body, and the clamp arm actuator, wherein the clamp body is configured to be connected to each of the body assembly and the clamp arm actuator in the connected state, wherein the clamp body is configured to be disconnected from each of the body assembly and the clamp arm actuator when the plurality of alignment release features respectively on the body assembly, the clamp body, and the clamp arm actuator, is in a predetermined alignment relative to each other and thereby in the disconnected state, wherein the clamp arm assembly is configured to pivot via the clamp arm actuator in a first direction from the closed position, through the open position, and to a predetermined position, wherein the plurality of alignment release features respectively on the body assembly, the clamp body, and the clamp arm actuator, is in the predetermined alignment with the clamp arm assembly in the predetermined position and in the disconnected state.

2. The surgical instrument of claim 1, wherein the clamp arm assembly includes another clamp pad, wherein the clamp arm assembly is selectively movable relative to the clamp arm actuator from a first use position to a second use position, wherein one of the clamp pads faces the ultrasonic blade in the first use position for use, and wherein the other of the clamp pads faces the ultrasonic blade in the second use position for use.

3. The surgical instrument of claim 1, wherein the clamp arm assembly further includes a clamp pad cap, wherein the clamp pad is configured to be removably secured between the clamp pad cap and the clamp body for replacing the clamp pad.

4. The surgical instrument of claim 1, wherein the clamp pad has a longitudinal tab or a longitudinal slot positioned thereon and the clamp body has the other of the longitudinal tab or the longitudinal slot positioned thereon, and wherein the longitudinal slot is configured to removably receive the longitudinal tab for removable connection therebetween.

5. The surgical instrument of claim 1, wherein the modular coupling further includes an electronic connection configured to communicate electrical signals therealong.

6. The surgical instrument of claim 1, wherein the plurality of alignment release features includes a first slot, a second slot, and a shoulder.

7. The surgical instrument of claim 6, wherein the shoulder is configured to be secured within the second slot in the connected state, and wherein the shoulder in the predetermined alignment with the second slot is configured to be released through the second slot in the disconnected state.

8. The surgical instrument of claim 7, wherein the first slot is positioned on the clamp arm actuator.

9. The surgical instrument of claim 7, wherein the shoulder is positioned on the clamp body, and wherein the second slot is positioned on the body assembly.

10. The surgical instrument of claim 9, wherein the shoulder is positioned on the body assembly, and wherein the second slot is positioned on the clamp arm assembly.

11. The surgical instrument of claim 10, wherein the plurality of alignment features further includes a first pin, and wherein the first pin is configured to be positioned within the first slot in the connected state, and wherein the first pin in the predetermined alignment with the first slot is configured to be released through the first slot in the disconnected state.

12. The surgical instrument of claim 11, wherein the first pin is positioned on the clamp arm assembly, and wherein the first slot is positioned on the clamp arm actuator.

13. The surgical instrument of claim 10, wherein the clamp arm assembly further includes a second pin, and wherein the second slot extends through the second pin.

14. A surgical instrument, comprising:
(a) a body assembly;
(b) an ultrasonic waveguide extending through the body assembly;
(c) an ultrasonic blade connected to a distal end of the ultrasonic waveguide;
(d) a clamp arm assembly configured to move from an opened position for receiving a tissue toward a closed position for clamping the tissue relative to the ultrasonic blade, wherein the clamp arm assembly includes:
(i) a clamp body,
(ii) a coupling connected to the clamp body and configured to movably secure the clamp body relative to the body assembly, and
(iii) a clamp pad connected to the clamp body facing the ultrasonic blade;
(e) a clamp arm actuator operatively connected to the clamp arm assembly and configured to selectively move from a first position toward a second position relative to the body to thereby respectively direct the clamp arm assembly from the opened position toward the closed position;
(f) a first alignment feature connected to the body assembly and contacting the clamp arm assembly, wherein the first alignment feature is longitudinally offset from the coupling and configured to control jaw offset and cross jaw between the clamp body and the ultrasonic blade; and
(g) a second alignment feature connected to the body assembly and contacting the clamp arm assembly, wherein the first alignment feature is proximally offset from the coupling and the second alignment feature is distally offset from the coupling such that the first and second alignment features are configured to control jaw offset and cross jaw between the clamp body and the ultrasonic blade.

15. The surgical instrument of claim 14, further comprising a third alignment feature positioned at the coupling feature, wherein the third alignment feature is configured to urge the clamp body laterally toward the first and second alignment features, and wherein at least one of the first, second, and third alignment feature is laterally adjustable to further control jaw offset and cross jaw between the clamp body and the ultrasonic blade.

16. A surgical instrument, comprising:
(a) a body assembly;
(b) an ultrasonic waveguide extending through the body assembly;
(c) an ultrasonic blade connected to a distal end of the ultrasonic waveguide;
(d) a clamp arm assembly configured to move from an opened position for receiving a tissue toward a closed position for clamping the tissue relative to the ultrasonic blade, wherein the clamp arm assembly includes:
(i) a clamp body,
(ii) a clamp pad removably connected to the clamp body facing the ultrasonic blade, and
(iii) an electrode having an electrod surface facing the ultrasonic blade and removably connected to the clamp body, wherein the electrode is operable to apply electrical energy to tissue;
(e) a clamp arm actuator operatively connected to the clamp arm assembly and configured to selectively move from a first position toward a second position relative to the body to thereby respectively direct the clamp arm assembly from the opened position toward the closed position; and (f) a modular coupling operatively connected to the clamp arm assembly such that the electrode of the clamp arm assembly is configured to be modularly disconnected from the clamp body.

17. The surgical instrument of claim 16, wherein the modular coupling has a body coupling portion on the clamp body and an electrode coupling portion on the electrode, and wherein the body coupling portion of the clamp body is configured to removably connect to the electrode coupling portion of the electrode to thereby removably secure clamp pad relative to clamp body.

18. The surgical instrument of claim 17, wherein the body coupling portion of the clamp body is configured to removably connect to the electrode coupling portion of the electrode to thereby removably capture the clamp pad between the electrode and the clamp body.

19. A surgical instrument, comprising:
(a) a body assembly;
(b) an ultrasonic waveguide extending through the body assembly;
(c) an ultrasonic blade connected to a distal end of the ultrasonic waveguide;
(d) a clamp arm assembly configured to move from an opened position for receiving a tissue toward a closed position for clamping the tissue relative to the ultrasonic blade, wherein the clamp arm assembly includes:
  (i) a clamp body, and
  (ii) a clamp pad connected to the clamp body facing the ultrasonic blade;

(e) a clamp arm actuator operatively connected to the clamp arm assembly and configured to selectively move from a first position toward a second position relative to the body to thereby respectively direct the clamp arm assembly from the opened position toward the closed position; and (f) a modular coupling operatively connected to the clamp arm assembly such that at least the clamp pad of the clamp arm assembly is configured to be disconnected relative to the ultrasonic blade for replacement thereof, wherein the modular coupling includes a radial capture lock positioned on the clamp arm actuator, wherein the radial capture lock has a variable portion and is configured to selectively move from a locked configuration toward an unlocked configuration, wherein the radial capture lock in the locked configuration is biased radially inwardly against the clamp body for removable connection therewith, and wherein the radial capture lock in the unlocked configuration is directed radially outwardly from the clamp body for removal of the clamp body therefrom, wherein the variable portion of the radial capture lock in the locked configuration defines a relatively small diameter for radially engaging the clamp body, and wherein the variable portion of the radial capture lock in the unlocked configuration defines a relatively large diameter for radially disengaging the clamp body.

20. The surgical instrument of claim 19, wherein the variable portion includes a spring.

* * * * *